United States Patent
Vandyck et al.

(10) Patent No.: US 10,995,064 B2
(45) Date of Patent: May 4, 2021

(54) SULFAMOYL-ARYLAMIDES AND THE USE THEREOF AS MEDICAMENTS FOR THE TREATMENT OF HEPATITIS B

(71) Applicant: JANSSEN SCIENCES IRELAND UC, Little Island (IE)

(72) Inventors: Koen Vandyck, Paal-Beringen (BE); Stefaan Julien Last, Lint (BE); Geert Rombouts, Borsbeek (BE); Wim Gaston Verschueren, Berchem (BE); Pierre Jean-Marie Bernard Raboisson, Rosieres (BE)

(73) Assignee: JANSSEN SCIENCES IRELAND UC, Co Cork (IE)

( * ) Notice: Subject to any disclaimer, the term of this patent is extended or adjusted under 35 U.S.C. 154(b) by 0 days.

(21) Appl. No.: 15/681,309

(22) Filed: Aug. 18, 2017

(65) Prior Publication Data
US 2018/0127361 A1  May 10, 2018

Related U.S. Application Data

(63) Continuation of application No. 14/423,981, filed as application No. PCT/EP2013/067829 on Aug. 28, 2013, now abandoned.

(30) Foreign Application Priority Data

Sep. 19, 2012 (EP) .................... 12185055
Oct. 31, 2012 (EP) .................... 12190837
Feb. 28, 2013 (EP) .................... 13157230
May 28, 2013 (EP) .................... 13169574
Aug. 23, 2013 (EP) .................... 12182076

(51) Int. Cl.
*A61K 31/4164* (2006.01)
*A61K 31/426* (2006.01)
(Continued)

(52) U.S. Cl.
CPC ............ *C07C 311/37* (2013.01); *A61K 31/18* (2013.01); *A61K 31/337* (2013.01); *A61K 31/34* (2013.01); *A61K 31/341* (2013.01); *A61K 31/351* (2013.01); *A61K 31/397* (2013.01); *A61K 31/401* (2013.01); *A61K 31/4164* (2013.01); *A61K 31/426* (2013.01); *A61K 31/44* (2013.01); *A61K 31/4453* (2013.01); *A61K 31/4468* (2013.01); *A61K 31/495* (2013.01); *A61K 31/5375* (2013.01); *A61K 31/55* (2013.01); *A61K 45/06* (2013.01); *C07C 311/14* (2013.01); *C07C 311/16* (2013.01); *C07C 311/20* (2013.01); *C07C 311/51* (2013.01); *C07D 205/04* (2013.01); *C07D 207/14* (2013.01); *C07D 207/273* (2013.01); *C07D 207/36* (2013.01); *C07D 211/28* (2013.01); *C07D 211/56* (2013.01); *C07D 211/76* (2013.01); *C07D 211/96* (2013.01); *C07D 213/42* (2013.01); *C07D 213/81* (2013.01); *C07D 213/82* (2013.01); *C07D 223/06* (2013.01); *C07D 233/84* (2013.01); *C07D 233/90* (2013.01); *C07D 277/56* (2013.01); *C07D 295/13* (2013.01); *C07D 295/26* (2013.01); *C07D 305/08* (2013.01); *C07D 307/22* (2013.01); *C07D 307/60* (2013.01); *C07D 307/68* (2013.01); *C07D 309/14* (2013.01); *C07D 333/38* (2013.01); *C07D 333/48* (2013.01); *C07D 491/107* (2013.01);
(Continued)

(58) Field of Classification Search
CPC ................ C07D 207/36; C07D 277/36; A61K 31/4164; A61K 31/426
USPC ............... 548/204, 205, 333.5, 338.1, 346.1; 514/369, 398, 400
See application file for complete search history.

(56) References Cited

U.S. PATENT DOCUMENTS 3,843,662 A   10/1974   Holland
4,569,940 A   2/1986    Watts
(Continued)

FOREIGN PATENT DOCUMENTS

CA   2950807 A1   12/2013
CN   1390201 A    1/2003
(Continued)

OTHER PUBLICATIONS

Carver et al., "Polyfunctionalisation of Imidazole via Sequential Imidazolyl Anion Formation", Tetrahedron. (1997), 53 (42), pp. 14481-14496. (Year: 1997).*

(Continued)

*Primary Examiner* — Matthew P Coughlin
*Assistant Examiner* — Sagar Patel

(57) ABSTRACT

Inhibitors of HBV replication of Formula (I)

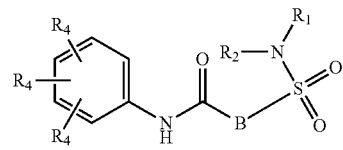

including stereochemically isomeric forms, and salts, hydrates, solvates thereof, wherein B, $R_1$, $R_2$ and $R_4$ have the meaning as defined herein.
The present invention also relates to processes for preparing said compounds, pharmaceutical compositions containing them and their use, alone or in combination with other HBV inhibitors, in HBV therapy.

10 Claims, No Drawings

(51) Int. Cl.

| | |
|---|---|
| *C07D 207/36* | (2006.01) |
| *C07D 277/36* | (2006.01) |
| *C07C 311/37* | (2006.01) |
| *C07C 311/14* | (2006.01) |
| *A61K 31/18* | (2006.01) |
| *A61K 31/337* | (2006.01) |
| *A61K 31/341* | (2006.01) |
| *A61K 31/351* | (2006.01) |
| *A61K 31/44* | (2006.01) |
| *A61K 31/4453* | (2006.01) |
| *A61K 31/4468* | (2006.01) |
| *C07C 311/16* | (2006.01) |
| *C07C 311/20* | (2006.01) |
| *C07C 311/51* | (2006.01) |
| *C07D 211/96* | (2006.01) |
| *C07D 305/08* | (2006.01) |
| *C07D 307/22* | (2006.01) |
| *C07D 205/04* | (2006.01) |
| *C07D 207/273* | (2006.01) |
| *C07D 213/42* | (2006.01) |
| *C07D 307/60* | (2006.01) |
| *C07D 213/81* | (2006.01) |
| *C07D 213/82* | (2006.01) |
| *C07D 333/38* | (2006.01) |
| *C07D 333/48* | (2006.01) |
| *C07D 233/90* | (2006.01) |
| *C07D 491/107* | (2006.01) |
| *C07D 207/14* | (2006.01) |
| *C07D 493/08* | (2006.01) |
| *C07D 277/56* | (2006.01) |
| *C07D 211/28* | (2006.01) |
| *C07D 295/13* | (2006.01) |
| *C07D 211/56* | (2006.01) |
| *C07D 211/76* | (2006.01) |
| *C07D 295/26* | (2006.01) |
| *C07D 307/68* | (2006.01) |
| *A61K 31/34* | (2006.01) |
| *A61K 31/397* | (2006.01) |
| *A61K 31/495* | (2006.01) |
| *A61K 31/5375* | (2006.01) |
| *A61K 31/55* | (2006.01) |
| *C07D 223/06* | (2006.01) |
| *C07D 233/84* | (2006.01) |
| *C07D 309/14* | (2006.01) |
| *A61K 31/401* | (2006.01) |
| *A61K 45/06* | (2006.01) |

(52) U.S. Cl.
CPC ........ *C07D 493/08* (2013.01); *C07C 2601/02* (2017.05); *C07C 2601/04* (2017.05); *C07C 2601/08* (2017.05); *C07C 2601/14* (2017.05); *C07C 2602/08* (2017.05); *C07C 2602/10* (2017.05)

(56) References Cited

U.S. PATENT DOCUMENTS

| | | | |
|---|---|---|---|
| 4,962,101 A | 10/1990 | DiNinno et al. | |
| 4,995,898 A * | 2/1991 | Nasu | A01N 43/50 514/227.8 |
| 5,272,167 A | 12/1993 | Girijavallabhan et al. | |
| 5,308,826 A | 5/1994 | Chin et al. | |
| 5,314,880 A | 5/1994 | Whittaker et al. | |
| 5,571,821 A | 11/1996 | Chan et al. | |
| 5,585,327 A | 12/1996 | Chin et al. | |
| 5,607,929 A | 3/1997 | Nicol et al. | |
| 5,708,034 A | 1/1998 | Kleemann et al. | |
| 5,723,411 A | 3/1998 | Stevenson | |
| 5,756,524 A | 5/1998 | Riordan et al. | |
| 5,795,907 A | 8/1998 | Kalindjian et al. | |
| 5,912,260 A | 6/1999 | Kalindjian et al. | |
| 5,919,970 A | 7/1999 | Song et al. | |
| 5,939,423 A | 8/1999 | Karlin et al. | |
| 6,025,367 A | 2/2000 | Forbes et al. | |
| 6,265,408 B1 | 7/2001 | Forbes et al. | |
| 6,476,025 B1 | 11/2002 | Gutterer | |
| 6,650,463 B2 | 11/2003 | Obikawa et al. | |
| 6,668,527 B2 | 12/2003 | Duplantier et al. | |
| 6,780,389 B2 | 8/2004 | Karl et al. | |
| 7,115,595 B2 | 10/2006 | Sunagawa et al. | |
| 7,186,735 B2 | 3/2007 | Strobel et al. | |
| 7,338,956 B2 | 3/2008 | Strobel et al. | |
| 7,368,457 B2 | 5/2008 | Josien | |
| 7,384,967 B2 | 6/2008 | Polisetti et al. | |
| 7,541,373 B2 | 6/2009 | Polisetti et al. | |
| 7,544,700 B2 | 6/2009 | Halazy et al. | |
| 7,576,688 B2 | 8/2009 | Lehtinen | |
| 7,595,322 B2 | 9/2009 | Morgan et al. | |
| 7,608,723 B2 | 10/2009 | Boyce et al. | |
| 7,750,158 B2 | 7/2010 | Shankar et al. | |
| 7,786,104 B2 | 8/2010 | DuBois et al. | |
| 7,790,726 B2 | 9/2010 | Zhang et al. | |
| 7,838,525 B2 | 11/2010 | Jones et al. | |
| 7,888,373 B2 | 2/2011 | Morgan et al. | |
| 7,994,168 B2 | 8/2011 | Lennig et al. | |
| 8,071,779 B2 | 12/2011 | Lampe et al. | |
| 8,084,457 B2 | 12/2011 | Choidas et al. | |
| 8,097,728 B2 | 1/2012 | Gu et al. | |
| 8,101,620 B2 | 1/2012 | Morgan et al. | |
| 8,153,650 B2 | 4/2012 | Dubois et al. | |
| 8,153,803 B2 | 4/2012 | Kazantsev | |
| 8,207,195 B2 | 6/2012 | Navratil et al. | |
| 8,227,489 B2 | 7/2012 | Dubois et al. | |
| 8,273,754 B2 | 9/2012 | Ali et al. | |
| 8,299,096 B2 | 10/2012 | Navratil et al. | |
| 8,299,114 B2 | 10/2012 | Dubois et al. | |
| 8,354,425 B2 | 1/2013 | Dubois et al. | |
| 8,394,820 B2 | 3/2013 | Dubois et al. | |
| 8,399,491 B2 | 3/2013 | Dubois et al. | |
| 8,404,747 B2 | 3/2013 | Kazantsev et al. | |
| 8,410,141 B2 | 4/2013 | Murata et al. | |
| 8,410,147 B2 | 4/2013 | Peterson et al. | |
| 8,536,168 B2 | 9/2013 | Dai et al. | |
| 8,609,668 B2 | 12/2013 | Cuconati et al. | |
| 8,629,274 B2 | 1/2014 | Hartman et al. | |
| 8,722,742 B2 | 5/2014 | Reyes et al. | |
| 8,808,702 B2 | 8/2014 | Reddy et al. | |
| 8,889,716 B2 | 11/2014 | Prime et al. | |
| 8,993,771 B2 | 3/2015 | Hartman | |
| 9,051,296 B2 | 6/2015 | Yamagishi et al. | |
| 9,061,008 B2 | 6/2015 | Hartman et al. | |
| 9,066,932 B2 | 6/2015 | Hartman et al. | |
| 9,115,101 B2 | 8/2015 | Bodil van Niel et al. | |
| RE45,670 E | 9/2015 | Polisetti et al. | |
| 9,156,839 B2 | 10/2015 | Vandyck et al. | |
| 9,169,212 B2 | 10/2015 | Hartman et al. | |
| 9,181,288 B2 | 11/2015 | Hartman et al. | |
| 9,205,079 B2 | 12/2015 | Hartman | |
| 9,339,510 B2 | 5/2016 | Hartman et al. | |
| 9,400,280 B2 | 7/2016 | Hartman | |
| 9,458,176 B2 | 10/2016 | Takaishi et al. | |
| 9,505,722 B2 | 11/2016 | Hartman et al. | |
| 9,567,299 B2 | 2/2017 | Vandyck et al. | |
| 9,579,313 B2 | 2/2017 | Hartman | |
| 9,676,747 B2 | 6/2017 | Hartman et al. | |
| 10,071,961 B2 | 9/2018 | Vandyck et al. | |
| 2002/0049236 A1 | 4/2002 | Duplantier et al. | |
| 2003/0114443 A1 | 6/2003 | Imamura et al. | |
| 2004/0039009 A1 | 2/2004 | Jagtap et al. | |
| 2004/0110802 A1 | 6/2004 | Thorarensen et al. | |
| 2005/0009871 A1 | 1/2005 | Ramesh et al. | |
| 2005/0054850 A1 | 3/2005 | Wu et al. | |
| 2005/0129833 A1 | 6/2005 | Kincaid et al. | |
| 2005/0148632 A1 | 7/2005 | Tokumasu et al. | |
| 2005/0221272 A1 | 10/2005 | Housman et al. | |

(56) References Cited

U.S. PATENT DOCUMENTS

| | | |
|---|---|---|
| 2005/0239833 A1 | 10/2005 | Kazantsev et al. |
| 2006/0040984 A1 | 2/2006 | Luckhurst et al. |
| 2006/0100228 A1 | 5/2006 | Shankar et al. |
| 2006/0100257 A1 | 5/2006 | Muto et al. |
| 2006/0122236 A1 | 6/2006 | Wood et al. |
| 2007/0142440 A1 | 6/2007 | Burgdorf et al. |
| 2007/0161578 A1 | 7/2007 | Hwa et al. |
| 2009/0018118 A1 | 1/2009 | Urleb et al. |
| 2009/0036420 A1 | 2/2009 | Galley et al. |
| 2009/0105218 A1 | 4/2009 | Ulven et al. |
| 2009/0163545 A1 | 6/2009 | Goldfarb |
| 2009/0259044 A1 | 10/2009 | Kazantsev |
| 2009/0325959 A1 | 12/2009 | Vittitow et al. |
| 2009/0325960 A1 | 12/2009 | Fulcher et al. |
| 2010/0008968 A1 | 1/2010 | Lampe et al. |
| 2010/0016310 A1 | 1/2010 | Ingraham |
| 2010/0022517 A1 | 1/2010 | Richards et al. |
| 2010/0087415 A1 | 4/2010 | Whitten et al. |
| 2010/0113421 A1 | 5/2010 | Williams |
| 2010/0204210 A1 | 8/2010 | Sorensen |
| 2011/0009622 A1 | 1/2011 | Makoto et al. |
| 2011/0064695 A1 | 3/2011 | Qiu et al. |
| 2011/0064696 A1 | 3/2011 | Or et al. |
| 2011/0065686 A1 | 3/2011 | Mazola Reyes et al. |
| 2011/0184019 A1 | 7/2011 | Zitzmann et al. |
| 2011/0189771 A1 | 8/2011 | Block et al. |
| 2011/0275630 A1 | 11/2011 | Matulenko et al. |
| 2011/0301158 A1 | 12/2011 | Polisetti et al. |
| 2013/0005756 A1 | 1/2013 | Navratil et al. |
| 2013/0131059 A1 | 5/2013 | Lampe et al. |
| 2013/0131106 A1 | 5/2013 | Lampe et al. |
| 2013/0142827 A1 | 6/2013 | Block et al. |
| 2013/0203733 A1 | 8/2013 | Kazantsev et al. |
| 2013/0251673 A1 | 9/2013 | Hartman et al. |
| 2013/0267517 A1 | 10/2013 | Guo et al. |
| 2013/0303552 A1 | 11/2013 | Xu et al. |
| 2014/0178337 A1 | 6/2014 | Hartman et al. |
| 2014/0179665 A1 | 6/2014 | Hartman et al. |
| 2014/0275167 A1 | 9/2014 | Hartman et al. |
| 2015/0152073 A1 | 6/2015 | Hartman et al. |
| 2015/0174115 A1 | 6/2015 | Hartman |
| 2015/0175602 A1 | 6/2015 | Brown et al. |
| 2015/0197493 A1 | 7/2015 | Hartman |
| 2015/0197533 A1 | 7/2015 | Hartman et al. |
| 2015/0216938 A1 | 8/2015 | Hartman |
| 2015/0225355 A1 | 8/2015 | Hartman |
| 2015/0252057 A1 | 9/2015 | Guo et al. |
| 2015/0259324 A1 | 9/2015 | Hartman et al. |
| 2015/0266890 A1 | 9/2015 | Vandyck et al. |
| 2015/0274652 A1 | 10/2015 | Hartman |
| 2015/0274653 A1 | 10/2015 | Vandyck et al. |
| 2016/0000812 A1 | 1/2016 | Hartman et al. |
| 2016/0002155 A1 | 1/2016 | Vandyck et al. |
| 2016/0051512 A1 | 2/2016 | Vandyck et al. |
| 2016/0083383 A1 | 3/2016 | Guo et al. |
| 2016/0115125 A1 | 4/2016 | Vandyck et al. |
| 2016/0115149 A1 | 4/2016 | Vandyck et al. |
| 2016/0158214 A1 | 6/2016 | Hartman |
| 2016/0176817 A1 | 6/2016 | Vandyck et al. |
| 2016/0272599 A1 | 9/2016 | Hartman et al. |
| 2016/0347741 A1 | 12/2016 | Vandyck et al. |
| 2017/0002025 A1 | 1/2017 | Vendeville et al. |
| 2017/0015629 A1 | 1/2017 | Hartman et al. |
| 2017/0114018 A1 | 4/2017 | Hartman |
| 2017/0158634 A1 | 6/2017 | Vandyck et al. |
| 2017/0182021 A1 | 6/2017 | Hartman |
| 2017/0334882 A1 | 11/2017 | Hartman et al. |

FOREIGN PATENT DOCUMENTS

| | | | |
|---|---|---|---|
| CN | 101039919 A | 9/2007 | |
| CN | 102093320 A | 6/2011 | |
| CN | 102206172 A | 10/2011 | |
| EP | 0232067 A2 | 8/1987 | |
| EP | 0742200 A1 | 11/1996 | |
| EP | 2280001 A4 | 1/2012 | |
| JP | 62142164 | 6/1987 | |
| JP | 2008179621 A | 7/2008 | |
| JP | 2008525406 A | 7/2008 | |
| JP | 2010535172 A | 11/2010 | |
| JP | 2015531773 A | 11/2015 | |
| JP | 2015533782 A1 | 11/2015 | |
| WO | 198403281 A1 | 8/1984 | |
| WO | WO-9207835 A1 * | 5/1992 | ............ A01N 43/50 |
| WO | 1998023285 A1 | 6/1998 | |
| WO | 199909022 A1 | 2/1999 | |
| WO | 1999038845 A1 | 8/1999 | |
| WO | 199948492 A1 | 9/1999 | |
| WO | 199965906 A1 | 12/1999 | |
| WO | 200105390 A2 | 1/2001 | |
| WO | 200119788 A2 | 3/2001 | |
| WO | 2001025200 A1 | 4/2001 | |
| WO | 2001051487 A1 | 7/2001 | |
| WO | 200155121 A1 | 8/2001 | |
| WO | 200185694 A2 | 11/2001 | |
| WO | 2002051410 | 7/2002 | |
| WO | 2002064618 A2 | 8/2002 | |
| WO | 2003002518 A1 | 1/2003 | |
| WO | 2003007955 A2 | 1/2003 | |
| WO | 2003044016 A1 | 5/2003 | |
| WO | 2003101961 A1 | 12/2003 | |
| WO | 2004010943 A2 | 2/2004 | |
| WO | 2004011427 A2 | 2/2004 | |
| WO | 2004022060 A2 | 3/2004 | |
| WO | 2004058709 A2 | 7/2004 | |
| WO | 2004086865 A1 | 10/2004 | |
| WO | 2004099192 A2 | 11/2004 | |
| WO | 2004100947 A2 | 11/2004 | |
| WO | 2005016922 A1 | 2/2005 | |
| WO | 2005000231 A3 | 5/2005 | |
| WO | 2005044797 A1 | 5/2005 | |
| WO | 2005087217 A1 | 9/2005 | |
| WO | 2005105785 A2 | 11/2005 | |
| WO | 2005115374 A1 | 12/2005 | |
| WO | 2006002133 A1 | 1/2006 | |
| WO | 2006012642 A2 | 2/2006 | |
| WO | 2006024834 A1 | 3/2006 | |
| WO | 2006053109 A1 | 5/2006 | |
| WO | 2006067445 A2 | 6/2006 | |
| WO | 2006067446 A1 | 6/2006 | |
| WO | 2006123257 A2 | 11/2006 | |
| WO | 2006128129 A2 | 11/2006 | |
| WO | 2006128172 A2 | 11/2006 | |
| WO | 2007031791 A1 | 3/2007 | |
| WO | 2007070556 A2 | 6/2007 | |
| WO | 2008011476 A2 | 1/2008 | |
| WO | 2008022171 A1 | 2/2008 | |
| WO | 2008054605 A2 | 7/2008 | |
| WO | 2008093614 A1 | 8/2008 | |
| WO | 2008137794 A1 | 11/2008 | |
| WO | 2008154819 A1 | 12/2008 | |
| WO | 2009016088 A1 | 2/2009 | |
| WO | 2009018219 A2 | 2/2009 | |
| WO | 2009062402 A1 | 5/2009 | |
| WO | 2009086303 A2 | 7/2009 | |
| WO | 2009131065 A1 | 10/2009 | |
| WO | 2009146013 A1 | 12/2009 | |
| WO | 2010018113 A2 | 2/2010 | |
| WO | 2010043592 A1 | 4/2010 | |
| WO | 2010059658 A1 | 5/2010 | |
| WO | 2010088000 A2 | 8/2010 | |
| WO | 2010123139 A1 | 10/2010 | |
| WO | 2010138758 A1 | 12/2010 | |
| WO | 2011002635 A1 | 1/2011 | |
| WO | 2011035143 A2 | 3/2011 | |
| WO | 2011088015 A1 | 7/2011 | |
| WO | 2011088561 A1 | 7/2011 | |
| WO | 2011109237 A1 | 9/2011 | |
| WO | 2011112191 A1 | 9/2011 | |
| WO | 2011123609 A1 | 10/2011 | |
| WO | 2011140324 A1 | 11/2011 | |
| WO | 2011155898 A1 | 12/2011 | |
| WO | 2012016133 A2 | 2/2012 | |
| WO | 2012018635 A2 | 2/2012 | |

(56) References Cited

FOREIGN PATENT DOCUMENTS

| | | |
|---|---|---|
| WO | 2012033956 A1 | 3/2012 |
| WO | 2012049277 A1 | 4/2012 |
| WO | 2012075235 A1 | 6/2012 |
| WO | 2012080050 A1 | 6/2012 |
| WO | 2012117216 A1 | 9/2012 |
| WO | 2012136834 A1 | 10/2012 |
| WO | WO2013006394 A1 | 1/2013 |
| WO | 2013096744 A1 | 6/2013 |
| WO | 2013102655 A1 | 7/2013 |
| WO | 2013130703 A2 | 9/2013 |
| WO | 2013144129 A1 | 10/2013 |
| WO | 2013174962 | 11/2013 |
| WO | 2013181584 A2 | 12/2013 |
| WO | 2013184757 A1 | 12/2013 |
| WO | 2014033167 A1 | 3/2014 |
| WO | 2014033170 A1 | 3/2014 |
| WO | 2014033176 | 3/2014 |
| WO | 2014037480 A1 | 3/2014 |
| WO | 2014106019 A2 | 7/2014 |
| WO | 2014131847 A1 | 9/2014 |
| WO | 2014151958 A1 | 9/2014 |
| WO | 2014161888 A1 | 10/2014 |
| WO | 2014165128 A2 | 10/2014 |
| WO | 2014184328 A1 | 11/2014 |
| WO | 2014184350 A1 | 11/2014 |
| WO | 2014184365 A1 | 11/2014 |
| WO | 2014191301 A1 | 12/2014 |
| WO | 2014191726 A1 | 12/2014 |
| WO | 2014198880 A1 | 12/2014 |
| WO | 2015011281 A1 | 1/2015 |
| WO | 2015055764 A1 | 4/2015 |
| WO | 2015057945 A1 | 4/2015 |
| WO | 2015059212 A1 | 4/2015 |
| WO | 2015073774 A1 | 5/2015 |
| WO | 2015109130 A1 | 7/2015 |
| WO | 2015116923 A1 | 8/2015 |
| WO | 2015118057 A1 | 8/2015 |
| WO | 2015132276 A1 | 9/2015 |
| WO | 2015138895 A1 | 9/2015 |
| WO | 2015144093 A1 | 10/2015 |
| WO | 2015180631 A1 | 12/2015 |
| WO | 2016089990 A1 | 6/2016 |
| WO | 2016109663 A2 | 7/2016 |
| WO | 2016109684 A2 | 7/2016 |
| WO | 2016109689 A1 | 7/2016 |
| WO | 2016149581 A1 | 9/2016 |
| WO | 2016113273 A1 | 10/2016 |
| WO | 2016161268 A1 | 10/2016 |
| WO | 2016168619 A1 | 10/2016 |
| WO | 2016183266 A1 | 11/2016 |
| WO | 2019011323 A1 | 1/2019 |

OTHER PUBLICATIONS

STN Registry database entry: CAS RN 1359583-56-4 (Entered STN: Mar. 2, 2012) (Year: 2012).*
STN Registry database entry: CAS RN 1359596-55-6 (Entered STN: Mar. 2, 2012) (Year: 2012).*
Carver, D., S. Lindell and E. Saville-Stones, "Polyfunctionalisation of Imidazole via Sequential Imidazolyl Anion Formation", Tetrahedron. (1997), 53 (42), pp. 14481-14496 (Year: 1997).*
Online Registry Via STN Dec. 22, 2008, RN 1088200-12-7.
Online Registry Via STN, Mar. 2, 2007, RN 924514-21-6.
Online Registry Via STN, Sep. 2, 2003, RN 577752-12-6.
Bennes, et al., "Recognition-induced control and acceleration of a pyroole Diels-Alder reaction", Tetrahedron Letters, vol. 42 : pp. 2377-2380 (2001).
Berke, et al., "Capsid Assembly Modulator JNJ-56136379 Prevents de Novo Infection of Primary Human Hepatocytes with Hepatitis B Virus", Hepatology, Oct. 2016, pp. 124A, 234.
Brahmania, et al., "New Therapeutic Agents for Chronic Hepatitis B", Lancet Infec Dis, vol. 16: pp. e10-e21 (Feb. 2016).
Brezillon, et al., "Antiviral Activity of Bay 41-4109 on Hepatitis B Virus in Humanized Alb-uPA/SCID Mice", PLos ONE, vol. 6 (12): pp. e25096 (1-6) (Dec. 2011).
Cai, et al., "Identification of disubstituted sulfonamide compounds as specific inhibitors of hepatitis B virus covalently closed circular DNA formation, Antimicrobial agents and chemotherapy", pp. vol. 56(8): pp. 4277-4288 (May 29, 2012).
Campagna et al., "Sulfamoylbenzamide Derivatives Inhibit the Assembly of Hepatitis B Virus Nucleocapsids", Journal of Virology, ),vol. 87 (12): pp. 6931-6942 (Jun. 2013).
Campagna, "Sulfamoylbenzamide Derivatives are a Novel Class of Hepatities B Virus Inhibitors Targeting PGRNA Encapsidation", 2011 International Meeting on Molecular Biology of Hepatitis B Viruses, Poster Presentation, (Oct. 9-12, 2011).
Chang, et al., "NMR-spectroscopy-based Metabonomic Approach to the Analysis of Bay41-4109, a novel anti-HBV Compound, induced Hepatotoxicity in Rats", Toxicology Letters, vol. 173: pp. 161-167 (2007).
Cho, et al., "2-Amino-N-(2,6-dichloropyridin-3-yl)acetamide derivatives as a novel class of HBV capsid assembly inhibitor", Journal of Viral Hepatitis, vol. 21: pp. 843-852 (2014).
Cowie, et al., "Mortality due to viral hepatitis in the Global Burden of Disease Study 2010: new evidence of an urgent global public health priority demanding action", Antiviral Therapy,vol. 18: pp. 953-954 (2013).
Delaney, et al., "Phenylpropenamide Derivatives AT-61 and AT-130 Inhibit Replication of Wild-Tpe and Lamivudine-Resistant Strains of Hepatitis B Virus in Vitro", Antimicrobial Agents and Chemotherapy, vol. 46(9): pp. 3057-3060 (Sep. 2002).
Deres, et al., "Inhibition of Hepatitis B Virus Replication by Drug-Induced Depletion of Nucleocpsids", Science, vol. 299: pp. 893-896 (Feb. 7, 2003).
Duan, et al., 2-Phenylquinazolin-4(3H)-one, a class of potent PDE5 Inhibitors with High Selectivity Versus PDE6, Bioorganic & Medicinal Chemistry Letter, vol. 19: pp. 2777-2779 (2009).
El-Sayed, et al, "A Comparative Study of the 1-9 Reactions of Thiophene-2-Carboxanilides and related Compounds", Chemistry of Heterocyclic Compounds, vol. 34 (7): pp. 796-801 (Jan. 1, 1998).(XP000881506).
El-Sharief, et al., "Synthesis of Different Types of Chlorinated Sulphonamides with Expected Insecticidal and Bactericidal Activities", Proceedings of the Indian National Science Academy, vol. 53(1): pp. 179-188 (1987).
Ermann, et al., "Arylsulfonamide CB2 Receptor Agonists: SAR and Optimization of CB2 Selectivity", Bioorganic & Medicinal Chemistry Letters, vol. 18: pp. 1725-1729 (2008).
Foley, "An Efficient Synthesis of 2-Chloro-3-carboethoxy or 2-Chloro-3-cyano-4,5-disubstituted and 5-substituted Pyrroles", Tetrahedron Letters, vol. 35(33): pp. 5989-5992, (1994).
Gane, et al., "Phase 1a Safety and Pharmacokinetics of NVR3-778, a Potential First-in-class HBV Core Inhibitor", The Abstract of the Liver Meeting 2014 (AASLD), Abstract LB-19, Boston, MA (2014).
Gang Liu et al, discovery of Highly Potent and Selective Pan-Aurora Kinase Inhibitors with Enhanced in Vivo Antitumor Therapeutic Index, Journal of Medicinal chemistry, Mar. 1, 2012, pp. 3250-3260, vol. 55.
Geies, et al., Synthesis of some Thiazolo-[3,2-a]Pyrimidines, Phosphorus, Sulfur and Silicon, vol. 56: pp. 87-93 (1991).
Geng et al., "Small-Molecule Inhibitors for the Treatment of Hepatitis B Virus Documented in Patents", Mini-Reviews in Medicinal Chemistry, Apr. 1, 2013, pp. 749-776 (XP055105561-XP009176654), vol. 13.
Goodman, et al, "Discovery of potent, selective sulfonylfuran urea endothelial lipase inhibitors", Bioorganic & Medicinal Chemistry Letters, vol. 19:pp. 27-30 (2009).
Guo, et al., "HBc binds to the CpG island of HBV cccDNA and promotes an epigenetic permissive state", Epigenetics, vol. 6 (6): pp. 720-726 (Jun. 2011).
Hogan, et al., "Aqueous Process Chemistry: The Preparation of Aryl Sulfonyl Chlorides", Organic Process Research & Development, vol. 13: pp. 875-879 (2009).

(56) References Cited

OTHER PUBLICATIONS

Huang, et al., "Blockage of HBV Virus Replication and Inhibition of cccDNA Establishment by Core Protein Allosteric Modifiers (CpAMs)", Hepatology, vol. 64 (1 Suppl): pp. 937A-938A, ( Oct. 2016).
Hughes, et al., "Hepatitis Delta Virus", The Lancet, vol. 378: pp. 73-85, (Jul. 2, 2011).
Jayathilaka, et al, "A chemical compound that stimulated the human homologous recombination protein RAD51", Proceedings of the National Academy of Sciences on the United States of America, vol. 105 (41): pp. 15848-15853 (Oct. 14, 2008).
Katen, et al., "Assembly-Directed Antivirals Differentially Bind Quasiequivalend Pockets to Modify Hepatitis B Virus Capsid Tertiary and Quaternary Structure", Structure, vol. 21: pp. 1406-1416 (Aug. 6, 2013).
Kim, et al, "Discovery of novel HCV polymerase inhibitors using pharmacophore-based virtual screening", Bioorganic & Medicinal Chemistry Letters, vol. 21 (11): pp. 3329-3334 (Apr. 4, 2011). (XP028211474).
Klumpp, et al., "High Antiviral Activity of the HBV Core Inhibitor NVR 3-778 in the Humanized UPA/SCID Mouse Model", Journal of Hepatology, vol. 62:p. S235 (2015).
Klumpp, et al., "High-resolution crystal structure of a hepatitis B virus replication inhibitor bound to the viral core protein", PNAS, vol. 112(49): pp. 15196-15201 (Dec. 8, 2015).
Lam, et al., "HBV Corre Assembly Modulators Block Antigen Prouction When Present During Infection, but not during Persistent Infection", The Abstracts of the Liver Meeting 2016 (AASLD), vol. 64 (1 Suppl.), Boston, MA (Oct. 2016).
Lam, et al., "Inhibition of Hepatitis B Virus Replication by the HBV Core Inhibitors NVR3-778", The Abstract of the Liver Meeting 2015 (AASLD), Abstract 33: p. 223A, San Francisco, CA (Oct. 2015).
Lam, et al., "Serum HBV RNA as a Pharmacodynamic (PD) Marker of HBV Treatment Response to Core Assembly Modulator NVR 3-778 and Pegylate-Interferon Alpha", Poster Presented in the AASLD/EASL—HBV Treatment Endpoints Workshop, Poster No. 3774, Alexandria, VA (Sep. 9, 2016).
Lambeng, et al, "Arylsulfonamides as a new class of cannabinoid CB1 receptor ligands:identification of a lead and initial SAR studies", Bioorganic & Medicinal Chemistry Letters, vol. 17(1) pp. 272-277 (Dec. 22, 2006).
Lau, et al., "Peginterferon Alfa-2a, Lamivudine, and the Combination for HBeAg-Positive Chronic Hepatitis B", New England Journal of Medicine, vol. 352(26): pp. 2682-2695 (Jun. 30, 2005).
Li Bing, et al., Progress in anti Hepatitus B Virus non-nucleosidic drugs, J. Liaoning Medical University, vol. 30(1): pp. 88-91 (Dec. 31, 2009.
Liaw, et al., "Hepatitis B Virus Infection", Lancet, vol. 373: pp. 582-592 (Feb. 14, 2009).
Lucifora, et al., "Specific and Nonhepatotoxic Degradation of Nuclear Hepatitis B Virus cccDNA", Science, vol. 343: pp. 1221-1228 (Mar. 14, 2014).
Mabrouk, "Discovering best candidates for Hepatocellular Carcinoma (HCC) by in-silico techniques and tools", Int. J. Bioinformatics Research and Applications, vol. 8 (1/2): pp. 141-152 (Jan. 1, 2012).
Manzoor, et al., "Hepatitis B Virus Therapy: What's the future holding for us?", World Journal of Gastroenterology, vol. 21(44): pp. 12558-12575 (Nov. 28, 2015).
Marcellin, et al., "Peginterferon Alfa-2a Alone, Lamivudine Alone, and the Two in Combination in Patients with HBeAg-Negative Chronic Hepatitis B", The New England Journal of Medicine, vol. 351(12): pp. 1206-1217 (Sep. 16, 2014).
Mohamed, et al., "Synthesis of Different Types of Chlorinated Sulphonamides with Expected Insecticidal and Antimicrobial Activities", Acta Pharmaceutica Jugoslavica, vol. 36 (3): pp. 301-310, (1986).
Online Registr Via STN, Dec. 28, 2008, RN 1090750-88-1.
Online Registry Via STN , Aug. 13, 2012, RN 1390589-54-4.
Online Registry Via STN Feb. 2, 2007, RN 919040-39-4.
Online Registry Via STN Feb. 2, 2007, RN 919040-53-2.
Online Registry Via STN Feb. 2, 2007, RN 919040-55-4.
Online Registry Via STN Aug. 6, 2012. RN 1386725-02-5.
Online Registry Via STN Jun. 7, 2012, RN 1375909-37-7.
Online Registry Via STN Dec. 8, 2012, RN 1389720-57-3.
Online Registry Via STN Oct. 10, 2001, RN 361373-90-2.
Online Registry Via STN Dec. 11, 2007, RN 957487-45-5.
Online Registry Via STN Dec. 11, 2007, RN 957487-49-9.
Online Registry Via STN Aug. 8, 2012, RN 1389686-79-6.
Online Registry Via STN Aug. 13, 2012, RN 1390500-09-0.
Online Registry Via STN Jan. 16, 2001, RN 314043-17-9.
Online Registry Via STN Mar. 17, 2013, RN 1424462-66-7.
Online Registry Via STN Sep. 18, 2012, RN 1394742-82-5.
Online Registry Via STN 2010, RN 1253220-91-5.
Online Registry Via STN Aug. 30, 2011, RN 1325664-90-1.
Online Registry Via STN, Jan. 24, 2008, RN 296790-26-6.
Online Registry Via STN, Feb. 2, 2007, RN 9019040-48-5.
Online Registry Via STN, Feb. 2, 2007, RN 919040-37-2.
Online Registry Via STN, May 6, 2011, RN 1291044-81-9.
Online Registry Via STN, Sep. 6, 2011, RN 1328738-57-3.
Online Registry Via STN, Jul. 10, 2008, RN 1057788-44-9.
Online Registry Via STN, Oct. 7, 2008, RN 1057871-39-2.
Online Registry Via STN, Jan. 9, 201, RN 313253-89-3.
Online Registry Via STN, Mar. 10, 2010, RN 1208400-27-4.
Online Registry Via STN, Feb. 15, 2007, RN 921179-95-5.
Online Registry Via STN, Aug. 15, 2011, RN 1317923-24-2.
Online Registry Via STN, Aug. 15, 2011, RN 1318022-74-0.
Online Registry Via STN, Mar. 17, 2003, RN 499189-09-2.
Online Registry Via STN, May 18, 2011, RN 1296380-95-4.
Online Registry Via STN, Oct. 18, 2000, RN 296894-70-7.
Online Registry Via STN, Sep. 20, 2013, RN 1452780-00-5.
Online Registry Via STN, Apr. 24, 2002, RN 406926-60-1.
Online Registry Via STN, Apr. 28, 2011, RN 1286906-97-5.
Online Registry Via STN. Apr. 19, 2008, RN 930914-71-9.
Patani, et al., "Bioisoterism: A rational Approach in Drug Design", Chem. Rev., vol. 96: pp. 3147-3176 (1996).
Patel, et al., "Synthesis N-Ethylpiperazinyl Sulfonyl Group Incorporated Benzamides", Indian Journal of Heterocyclic Chemistry, vol. 15: pp. 201-202 (Oct.-Dec. 2005).
Qidong You et al, Pharmaceutical Chemistry, Chemical Industry Press, Jan. 31, 2014, pp. 32-33.
Qiu, et al, "Antihepatitis B therapy: a review of current medications and novel small molecule inhibitors", Fudamental & Clinical Pharmacology, pp. 1-18 (XP055105340) (Nov. 1, 2013).
Qiu, et al., "Design and Synthesis of Orally Bioavailable 4-Methyl Heteroaryldihydropyrimidine Based Hepatitis B Virus (HBV) Capsid Inhibitors", Journal of Medicinal Chemistry, vol. 59: pp. 7651-7666, (2016).
Schroder, et al., "Arzneimittelchemie Passage", Arzneimittelchemei Grundlagen Nerven Musklen und Gewebe, vol. XX (XX): pp. 30-33 (Jan. 1, 1976).
Shi, et al., "NMR-spectroscopy-based metanonomic approach to the analysis of Bay41-4109, a novel anti-HBV compound, induced hepatotoxcity in rats", Toxicology Letters, vol. 173: pp. 161-167 (2007).
Stalder, et al, "Selective antagonists of mouse trace amine-associated receptor 1 (mTAAR1): Discovery of EPPTB (RO5212773)", Bioorganic & Medicinal Chemistry Letters, vol. 21: pp. 1227-1231 (Dec. 21, 2010).
Stray, et al., "A Heteroaryldihydropyrimidine Activates and Can Misdirect Hepatitis B Virus Capsid Assembly", PNAS, vol. 102(23): pp. 8138-8143 (Jun. 7, 2005).
Stray, et al., "Bay 41/4109 has multiple effects on Hepatitis B virus capsid assembly", Journal of Molecular Recognition,vol. 19: pp. 542-548 (2006).
Tan, et al., Genetically Altering the Thermodynamics and Kinetics of Hepatitis B Virus Capsid Assembly has Profound Effects on Virus Replication in Cell Culture, Journal of Virology, vol. 87(6): pp. 3208-3216 (Mar. 2013).
Taylor, et al., "A Brain-Permeable Small Molecule Reduces Neuronal Cholesterol by Inhibiting Activity of Sirtuin 2 Deacetylase", ASC Chemical Biology, vol. 6: pp. 540-546 (2011).

(56) References Cited

OTHER PUBLICATIONS

The Merk Index "Infliximab", An Encyclopedia of Chemicals, Drugs and Biologicals, 14th Ed., p. 924 (2013).
The Merk Index, "Zidovudine", An Encyclopedia of Chemicals, Drugs and Biologicals, 14th Ed., p. 1885 (2013).
Thompson et al., "Toll-like receptors, RIG-I-like RNA Helicases and the Antiviral Innate Immune Response", Immunology and Cell Biology, vol. 85: pp. 435-445 (2007).
Wang, et al., "In vitro inhibition of HBV replication by a novel compound, GLS4, and its efficacy against adefovir-dipovoxil-resistant HBV mutations", Antiviral Therapy, vol. 17:pp. 793-803 (2012).
Wang, et al., "Serum hepatitis B virus RNS is encapsidated pregenome RNA that may be associated with persistence of viral infection and rebound", Journal of Hepatology, vol. 65: pp. 700-710(2016).
Wang, et al., "Synthesis and Evaluation of Benzothiazole-Based Analogues as Novel, Potent, and Selective Fatty Acid Amide Hydrolase Inhibitors", J. Med. Chem., vol. 52: pp. 170-180 (2009).
Watanabe, et al, "Ortho lithiation of N,N-dimethylbenzenesulfunamide by n-butyllithium. Condensation with electrophilic compounds", Candian Journal of Chemistry, vol. 47: pp. 1543-1546 (Oct. 30, 1968).
Weber et al., "Inhibition of Human Hepatitis B Virus (HBV) by a Novel Non-Nucleosidic Compound in a Transgenic Mouse Model", Antiviral Research, vol. 54: pp. 69-78 (2002).
Weber, et al, "Inhibition of human hepatitis B virus (HBV) by a novel non-nucleosidic compound in a transgenic mouse model", Antiviral Research, vol. 54 (2): pp. 69-78 (Jan. 1, 2002).
West, "Chapter 10 Solid Solutions", Solid State Chemistry and Its Applications, John Wiley & Sons, pp. 33-36 (1984).
Wu, et al., "Preclinical Characterization of GLS4, an Inhibitor of Hepatitis B Virus Core Particle Assembly", Antimicrobial Agents and Chemotherapy, vol. 57(11): pp. 5344-5354 (Nov. 2013).
Yang, et al., "Effects of a Hepatitis B Virus Inhibitor, NZ-4, on Capsid Formation", Antiviral Research, vol. 125: pp. 25-33 (2016).
Yang, et al., "Isothiafludine, a novel non-nucleoside compound inhibits hepatitis B virus replication through blocking pregenomic RNA encapsidation", Acta Pharmacologica Sinica, vol. 35: pp. 410-418 (2014).
Yarmolchuk et al., "Synthesis of beta-fluoro-beta-proline", Tetrahedron Letters, vol. 52: pp. 1300-1302, (2011).
Yogaratnam, et al., "Safety, Tolerability and Pharmacokentics of JNJ 56136379, a Novel HBV Capsid Assembly Modulator in Healthy Subjects", The Abstracts of the Liver Meeting 2016 (AASLD), Abstract 1881: pp. 930A-931A, Boston, MA (Oct. 2016).
Yuen, et al., "ARC-520 Produces Deep and Durable Knockdown of Viral Antigen and DNA in Phase II Study in Patients with Chronic Hepatitis B", The Abstracts of the Liver Meeting 2015, Abstract LB-10, pp. 1385A-1386A, San Francisco, CA (Oct. 2015).
Yuen, et al., "NVR 3-778, a first-in-class HBV core inhibitor, alone and in combination with PEG-Interferon (PEGIFN), In treatment-naive HBEAG-positive patients: early reductions in HBV DNA and HBEAG", The Abstracts of the International Liver Congress (EASL), Abstract LB-06: pp. S210-S211 (Oct. 2016).
Zhang, et al., "A Potent Small Molecule Inhibits Polyglutamine Aggregation in Huntington's Disease Neurons and Suppresses Neurodegeneration in Vivo", PNAS, vol. 102 (3): pp. 892-897 (2005).
Zlotnick, et al., "Core Protein: A pleiotropic Keystone in the HBV Lifecycle", Antiviral Research, vol. 121: pp. 82-93 (2015).
Zoulim, et al., "Current Treatments for Chronic Hepatitis B Virus Infections", Current Opinion in Virology, vol. 18: pp. 109-116 (2016).
Horig, et al., "From bench to Clinic and back : Perspective on the 1st IQPC translational Research conference", Journal of Translational Medicine, vol. 2(44): pp. 1-8 (Dec. 20, 2004).
Mohebbi, et al., "An Overview of Hepatitis B Virus Surface Antigen Secretion Inhibitors", Frontier in Microbiology, vol. 9: pp. 1-9 (Apr. 2018).
Schafer, et al., "Failure is an Option: Learning from unsuccessful proof-of-concepts trails", Drug Discovery Today, vol. 13 (21/22): pp. 913-916 (Nov. 2008).
Nijampatnam et al., "Recent advances in the development of HBV capsid assembly modulators", Current Opinion Chemical Biology, vol. 50; pp. 73-79 (2019).
Online Registry VIA STN Aug. 24, 2019, RN 1275589-30-4.
Online Registry VIA STN Aug. 24, 2019, RN 312756-74-4.
Online Registry VIA STN Aug. 24, 2019, RN 312756-75-5.
Online Registry VIA STN Aug. 24, 2019, RN 313225_30_8.
Online Registry VIA STN Aug. 24, 2019, RN 313254-27-2.
Basarab et al., Design of Helicobacter pylori glutamate racemase inhibitors as selective antibacterial agents : a novel pro-drug approach to increase exposure, Bioorg. Med. Chem. Lett, vol. 18; pp. 4716-4722 (Aug. 15, 2008).
Moranta et al., "Synthesis and properties of 1-alkyl-2-methyl-3-sulfonylpyrroles and 1-alkyl-2-methyl-3-sulfonylpyrrole-5-carboxylic acid derivates", J. Chem. Soc. Perkin Trans., vol. 19: pp. 3285-3292 (1998).
Online Registry VIA STN Aug. 24, 2019, RN 311800-19-8.

* cited by examiner

SULFAMOYL-ARYLAMIDES AND THE USE THEREOF AS MEDICAMENTS FOR THE TREATMENT OF HEPATITIS B

CROSS-REFERENCE TO RELATED APPLICATIONS

This application is continuation of U.S. patent application Ser. No. 14/423,981, filed on Feb. 25, 2015 which is a 35 U.S.C. § 371 nationalization of PCT application PCT/EP2013/067829, filed Aug. 28, 2013, which claims priority to European patent application EP 12182076.5, filed Aug. 28, 2012, European patent application EP 12185055.6, filed Sep. 19, 2012, European patent application EP 12190837.0, filed Oct. 31, 2012, European patent application EP 13157230.7, filed Feb. 28, 2013 and European patent application EP 13169574.4, filed May 28, 2013, all of which are incorporated herein by reference.

BACKGROUND ART

The Hepatitis B virus (HBV) is an enveloped, partially double-stranded DNA (dsDNA) virus of the Hepadnavirus family (Hepadnaviridae). Its genome contains 4 overlapping reading frames: the precore/core gene; the polymerase gene; the L, M, and S genes, which encode for the 3 envelope proteins; and the X gene.

Upon infection, the partially double-stranded DNA genome (the relaxed circular DNA; rcDNA) is converted to a covalently closed circular DNA (cccDNA) in the nucleus of the host cell and the viral mRNAs are transcribed. Once encapsidated, the pregenomic RNA (pgRNA), which also codes for core protein and Pol, serves as the template for reverse transcription, which regenerates the partially dsDNA genome (rcDNA) in the nucleocapsid.

HBV has caused epidemics in parts of Asia and Africa, and it is endemic in China. HBV has infected approximately 2 billion people worldwide of which approximately 350 million people have developed chronic infections. The virus causes the disease hepatitis B and chronic infection is correlated with a strongly increased risk for the development cirrhosis and hepatocellular carcinoma.

Transmission of hepatitis B virus results from exposure to infectious blood or body fluids, while viral DNA has been detected in the saliva, tears, and urine of chronic carriers with high titer DNA in serum.

An effective and well-tolerated vaccine exists, but direct treatment options are currently limited to interferon and the following antivirals; tenofovir, lamivudine, adefovir, entecavir and telbivudine.

In addition, heteroaryldihydropyrimidines (HAPs) were identified as a class of HBV inhibitors in tissue culture and animal models (Weber et al., Antiviral Res. 54: 69-78).

WO2013/006394, published on Jan. 10, 2013, and WO2013/096744, published on Jun. 27, 2013 relate to subclasses of Sulphamoyl-arylamides active against HBV.

Amongst the problems which HBV direct antivirals may encounter are toxicity, mutagenicity, lack of selectivity, poor efficacy, poor bioavailability and difficulty of synthesis.

There is a need for additional HBV inhibitors that may overcome at least one of these disadvantages or that have additional advantages such as increased potency or an increased safety window.

DESCRIPTION OF THE INVENTION

The present invention relates to compounds of Formula (I)

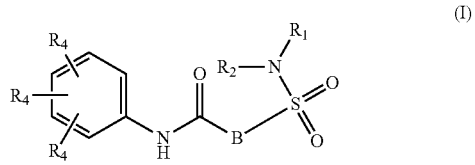

or a stereoisomer or tautomeric form thereof, wherein:

B represents a monocyclic 5 to 6 membered aromatic ring, optionally containing one or more heteroatoms each independently selected from the group consisting of O, S and N, such 5 to 6 membered aromatic ring optionally being substituted with one or more substituents each independently selected from the group consisting of hydrogen, halogen, $C_1$-$C_3$alkyl, CN, $CFH_2$, $CF_2H$ and $CF_3$;

$R_1$ represents hydrogen or $C_1$-$C_3$alkyl;

$R_2$ represents $C_1$-$C_6$alkyl, $C_1$-$C_6$alkenyl, $C_1$-$C_6$alkyl-$R_5$, $C(=O)$—$R_5$, $CFH_2$, $CF_2H$, $CF_3$, a dihydro-indenyl or tetrahydronaphtalenyl moiety optionally substituted with OH, or a 3-7 membered saturated ring optionally containing one or more heteroatoms each independently selected from the group consisting of O, S and N, such 3-7 membered saturated ring, $C_1$-$C_6$alkyl-$R_5$ or $C_1$-$C_6$alkyl optionally being substituted with one or more substituents each independently selected from the group consisting of hydrogen, halogen, $C_1$-$C_4$alkyloxy, $C_1$-$C_4$alkyloxycarbonyl, oxo, $C(=O)$—$C_1$-$C_3$alkyl, $C_1$-$C_4$alkyl, OH, CN, $CFH_2$, $CF_2H$ and $CF_3$;

Or $R_1$ and $R_2$ together with the Nitrogen to which they are attached form a 6-10 membered bicyclic or bridged ring or a 5-7 membered saturated ring, such bicyclic, bridged or saturated ring moiety optionally containing one or more additional heteroatoms each independently selected from the group consisting of O, S and N, such 5-7 membered saturated ring optionally being substituted with one or more substituents each independently selected from the group consisting of hydrogen, halogen, $C_1$-$C_4$alkyloxy, $C_1$-$C_4$alkyloxycarbonyl, oxo, $C(=O)$—$C_1$-$C_3$alkyl, $C_1$-$C_4$alkyl, OH, CN, $CFH_2$, $CF_2H$ and $CF_3$;

Each $R_4$ is independently selected from hydrogen, halogen, $C_1$-$C_4$alkyloxy, $C_1$-$C_4$alkyl, $C_1$-$C_4$alkenyl, OH, CN, $CFH_2$, $CF_2H$, $CF_3$, HC≡C or a 3-5 membered saturated ring optionally containing one or more heteroatoms each independently selected from the group consisting of O and N, such $C_1$-$C_4$alkyl optionally substituted with OH;

$R_5$ represents $C_1$-$C_6$alkyl, $CFH_2$, $CF_2H$, $CF_3$, phenyl, pyridyl or a 3-7 membered saturated ring optionally containing one or more heteroatoms each independently selected from the group consisting of O, S and N, such 3-7 membered saturated ring optionally being substituted with one or more substituents each independently selected from the group consisting of hydrogen, halogen, $C_1$-$C_4$alkyloxy, $C_1$-$C_4$alkyloxycarbonyl, oxo, $C(=O)$—$C_1$-$C_3$alkyl, $C_1$-$C_4$alkyl, OH, CN, $CFH_2$, $CF_2H$ and $CF_3$;

or a pharmaceutically acceptable salt or a solvate thereof.

The invention further relates to a pharmaceutical composition comprising a compound of Formula (I), and a pharmaceutically acceptable carrier.

The invention also relates to the compounds of Formula (I) for use as a medicament, preferably for use in the prevention or treatment of an HBV infection in a mammal.

In a further aspect, the invention relates to a combination of a compound of Formula (I), and another HBV inhibitor.

Definitions

The term "$C_{1-3}$alkyl" as a group or part of a group refers to a hydrocarbyl radical of Formula $C_nH_{2n+1}$ wherein n is a number ranging from 1 to 3. In case $C_{1-3}$alkyl is coupled to a further radical, it refers to a Formula $C_nH_{2n}$. $C_{1-3}$alkyl groups comprise from 1 to 3 carbon atoms, more preferably 1 to 2 carbon atoms. $C_{1-3}$alkyl includes all linear, or branched alkyl groups with between 1 and 3 carbon atoms, and thus includes such as for example methyl, ethyl, n-propyl, and i-propyl.

$C_{1-4}$alkyl as a group or part of a group defines straight or branched chain saturated hydrocarbon radicals having from 1 to 4 carbon atoms such as the group defined for $C_{1-3}$alkyl and butyl and the like.

$C_1$-6alkyl as a group or part of a group defines straight or branched chain saturated hydrocarbon radicals having from 1 to 6 carbon atoms such as the groups defined for $C_{1-4}$alkyl and pentyl, hexyl, 2-methylbutyl and the like.

$C_{1-4}$alkenyl as a group or part of a group defines straight or branched chain hydrocarbon radicals having from 1 to 4 carbon atoms with at least one double bond at any possible position. Examples of such alkenyls are ethenyl, propenyl, 1-butenyl, 2-butenyl. $C_{1-6}$alkenyl as a group or part of a group defines straight or branched chain hydrocarbon radicals having from 1 to 6 carbon atoms with at least one double bond.

The term "$C_{1-3}$alkyloxy" as a group or part of a group refers to a radical having the Formula $-OR^c$ wherein $R^c$ is $C_{1-3}$alkyl. Non-limiting examples of suitable $C_{1-3}$alkyloxy include methyloxy (also methoxy), ethyloxy (also ethoxy), propyloxy and isopropyloxy.

The term oxo, C(=O), or carbonyl refers to a group composed of a carbon atom double bonded to an oxygen atom.

As used herein, the term "3-7 membered saturated ring" means saturated cyclic hydrocarbon with 3, 4, 5, 6 or 7 carbon atoms and is generic to cyclopropyl, cyclobutyl, cyclopentyl, cyclohexyl and cycloheptyl.

Such saturated ring optionally contains one or more heteroatoms, such that at least one carbon atom is replaced by a heteroatom selected from N, O and S, in particular from N and O. Examples include oxetane, azetidine, tetrahydro-2H-pyranyl, piperidinyl, tetrahydrofuranyl, morpholinyl and pyrrolidinyl. Preferred are saturated cyclic hydrocarbon with 3 or 4 carbon atoms and 1 oxygen atom. Examples include oxetane and tetrahydrofuranyl.

As used herein, the term monocyclic 5 to 6 membered aromatic ring ("aryl"), means an aromatic cyclic hydrocarbon with 5 or 6 carbon atoms. A preferred example of an aryl group is phenyl.

Such saturated ring optionally contains one or more heteroatoms each independently selected from the group consisting of O, S and N ("heteroaryl") For the purposes of the invention, a heteroaryl group need only have some degree of aromatic character.

Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidinyl, tetrazolyl, furyl, thienyl, isoxazolyl, thiazolyl, isoxazolyl, and oxazolyl. A heteroaryl group can be unsubstituted or substituted with one or more suitable substituents.

As used herein, the term 6-10 membered bicyclic ring indicates a saturated bi-cyclic ring with 6-7-8-9 or 10 atoms. Such saturated bi-cyclic ring optionally contains one or more heteroatoms, such that at least one carbon atom is replaced by a heteroatom selected from N, O and S, in particular from N and O.

Examples of such 6-10 membered bicyclic ring as used herein are an 1,4-dioxa-8-azaspiro[4.5] decyl moiety indicating a group with structural formula

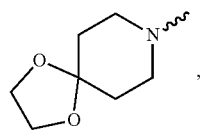

a 6-Oxa-2-azaspiro[3.4]octane moiety indicating a group with structural formula

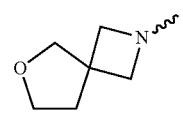

a 2-oxa-6-azaspiro[3.3]heptyl moiety indicating a group with structural formula

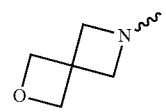

or a 6-oxa-1-azaspiro[3.3]heptyl moiety with structural formula

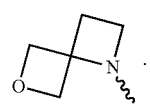

As used herein, the term 6-10 membered bridged ring indicates a saturated bridged ring with 6-7-8-9 or 10 atoms. Such saturated bi-cyclic ring optionally contains one or more heteroatoms, such that at least one carbon atom is replaced by a heteroatom selected from N, O and S, in particular from N and O. An example of such 6-10 membered bridged ring as used herein is -oxabicyclo[2.2.1] heptan represented by structure

As used herein, a dihydroindenyl moiety represents a group with structural formula

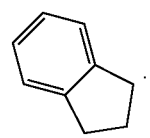

Such dihydroindenyl moiety can be optionally substituted with OH. One example as used herein, a 2-hydroxy-2,3-dihydro-1H-indenyl moiety, indicates a group with structural formula

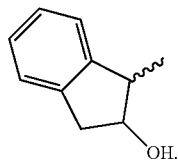

As used herein, a tetrahydronaphtalenyl moiety represents a group with structural formula

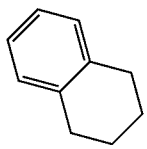

If not indicated, for any of the moieties above, the attachment to the main structure may be anywhere on such moiety as long as it is chemically stable.

It should be noted that different isomers of the various heterocycles may exist within the definitions as used throughout the specification. For example, pyrrolyl may be 1H-pyrrolyl or 2H-pyrrolyl.

The term halo and halogen are generic to fluoro, chloro, bromo or iodo. Preferred halogens are fluoro and Chloro.

It should also be noted that the radical positions on any molecular moiety used in the definitions may be anywhere on such moiety as long as it is chemically stable. For instance pyridyl includes 2-pyridyl, 3-pyridyl and 4-pyridyl; pentyl includes 1-pentyl, 2-pentyl and 3-pentyl.

Positions indicated on phenyl (e.g. ortho, meta and/or para) are indicated relative to the bond connecting the phenyl to the main structure. An example with regard to the position of $R_4$, any location is indicated relative to the nitrogen (*) connected to the main structure:

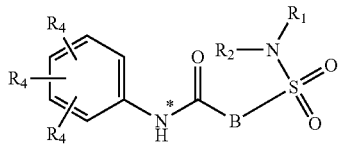

(Formula (I*))

When any variable (e.g. halogen or $C_{1-4}$alkyl) occurs more than one time in any constituent, each definition is independent.

For therapeutic use, the salts of the compounds of formula (I) are those wherein the counter ion is pharmaceutically or physiologically acceptable. However, salts having a pharmaceutically unacceptable counter ion may also find use, for example, in the preparation or purification of a pharmaceutically acceptable compound of formula (I). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; hemisulphuric, nitric; phosphoric and the like acids; or organic acids such as, for example, acetic, aspartic, dodecylsulphuric, heptanoic, hexanoic, nicotinic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The term "salts" also comprises the hydrates and the solvent addition forms that the compounds of the present invention are able to form. Examples of such forms are e.g. hydrates, alcoholates and the like.

The present compounds may also exist in their tautomeric forms for example, tautomeric forms of amide (—C(=O)—NH—) groups are iminoalcohols (—C(OH)=N—). Tautomeric forms, although not explicitly indicated in the structural formulae represented herein, are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods that may advantageously be employed are, for example, selective crystallization and chromatography, e.g. column chromatography.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

DETAILED DESCRIPTION OF THE INVENTION

Whenever used hereinafter, the term "compounds of formula (I)",

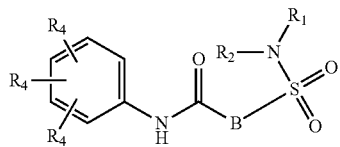

or "the present compounds" or similar term is meant to include the compounds of general formula (I), (I*), (Ia), (Ib), (Ic) and (Id), salts, stereoisomeric forms and racemic mixtures or any subgroups thereof.

Compounds for use in the prevention or treatment of an HBV infection in a mammal are disclosed as compounds per se and not limited to this use unless restricted by the claims.

The present invention relates to compounds of Formula (I)

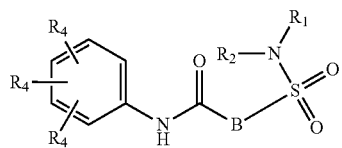

or a stereoisomer or tautomeric form thereof, wherein:

B represents a monocyclic 5 to 6 membered aromatic ring, optionally containing one or more heteroatoms each independently selected from the group consisting of O, S and N, such 5 to 6 membered aromatic ring optionally being substituted with one or more substituents each independently selected from the group consisting of hydrogen, halogen, $C_1$-$C_3$alkyl, CN, $CFH_2$, $CF_2H$ and $CF_3$;

$R_1$ represents hydrogen or $C_1$-$C_3$alkyl;

$R_2$ represents $C_1$-$C_6$alkyl, $C_1$-$C_6$alkenyl, $C_1$-$C_6$alkyl-$R_5$, C(=O)—$R_5$, $CFH_2$, $CF_2H$, $CF_3$, a dihydro-indenyl or tetrahydronaphtalenyl moiety optionally substituted with OH, or a 3-7 membered saturated ring optionally containing one or more heteroatoms each independently selected from the group consisting of O, S and N, such 3-7 membered saturated ring, $C_1$-$C_6$alkyl-$R_5$ or $C_1$-$C_6$alkyl optionally being substituted with one or more substituents each independently selected from the group consisting of hydrogen, halogen, $C_1$-$C_4$alkyloxy, $C_1$-$C_4$alkyloxycarbonyl, oxo, C(=O)—$C_1$-$C_3$alkyl, $C_1$-$C_4$alkyl, OH, CN, $CFH_2$, $CF_2H$ and $CF_3$;

Or $R_1$ and $R_2$ together with the Nitrogen to which they are attached form a 6-10 membered bicyclic or bridged ring or a 5-7 membered saturated ring, such bicyclic, bridged or saturated ring moiety optionally containing one or more additional heteroatoms each independently selected from the group consisting of O, S and N, such 5-7 membered saturated ring optionally being substituted with one or more substituents each independently selected from the group consisting of hydrogen, halogen, $C_1$-$C_4$alkyloxy, $C_1$-$C_4$alkyloxycarbonyl, oxo, C(=O)—$C_1$-$C_3$alkyl, $C_1$-$C_4$alkyl, OH, CN, $CFH_2$, $CF_2H$ and $CF_3$;

Each $R_4$ is independently selected from hydrogen, halogen, $C_1$-$C_4$alkyloxy, $C_1$-$C_4$alkyl, $C_1$-$C_4$alkenyl, OH, CN, $CFH_2$, $CF_2H$, $CF_3$, HC≡C or a 3-5 membered saturated ring optionally containing one or more heteroatoms each independently selected from the group consisting of O and N, such $C_1$-$C_4$alkyl optionally substituted with OH;

$R_5$ represents $C_1$-$C_6$alkyl, $CFH_2$, $CF_2H$, $CF_3$, phenyl, pyridyl or a 3-7 membered saturated ring optionally containing one or more heteroatoms each independently selected from the group consisting of O, S and N, such 3-7 membered saturated ring optionally being substituted with one or more substituents each independently selected from the group consisting of hydrogen, halogen, $C_1$-$C_4$alkyloxy, $C_1$-$C_4$alkyloxycarbonyl, oxo, C(=O)—$C_1$-$C_3$alkyl, $C_1$-$C_4$alkyl, OH, CN, $CFH_2$, $CF_2H$ and $CF_3$;

or a pharmaceutically acceptable salt or a solvate thereof.

In a first aspect, the invention further provides compound of Formula (I)

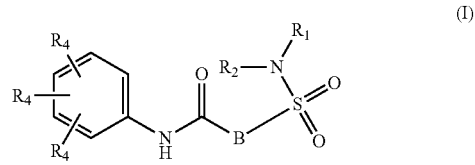

or a stereoisomer or tautomeric form thereof, wherein:

B represents a monocyclic 5 to 6 membered aromatic ring, optionally containing one or more heteroatoms each independently selected from the group consisting of O, S and N, such 5 to 6 membered aromatic ring optionally being substituted with one or more substituents each independently selected from the group consisting of hydrogen, halo, $C_1$-$C_3$alkyl, CN, $CFH_2$, $CF_2H$ and $CF_3$;

$R_1$ represents hydrogen or $C_1$-$C_3$alkyl;

$R_2$ represents $C_1$-$C_6$alkyl, $C_1$-$C_6$alkenyl, $C_1$-$C_6$alkyl-$R_5$, C(=O)—$R_5$, $CFH_2$, $CF_2H$, $CF_3$, a 2-hydroxy-2,3-dihydro-1H-indenyl moiety or a 3-7 membered saturated ring optionally containing one or more heteroatoms each independently selected from the group consisting of O, S and N, such 3-7 membered saturated ring, $C_1$-$C_6$alkyl-$R_5$ or $C_1$-$C_6$alkyl optionally being substituted with one or more substituents each independently selected from the group consisting of hydrogen, halogen, $C_1$-$C_4$alkyloxy, $C_1$-$C_4$alkyloxycarbonyl, oxo, C(=O)—$C_1$-$C_3$alkyl, $C_1$-$C_4$alkyl, OH, CN, $CFH_2$, $CF_2H$ and $CF_3$;

Or $R_1$ and $R_2$ together with the Nitrogen to which they are attached form a 1,4-dioxa-8-azaspiro[4.5]decyl moiety, a 2-oxa-6-azaspiro[3.3]heptyl moiety or a 5-7 membered saturated ring optionally containing one or more additional heteroatoms each independently selected from the group consisting of O, S and N, such 5-7 membered saturated ring optionally being substituted with one or more substituents each independently selected from the group consisting of hydrogen, halogen, $C_1$-$C_4$alkyloxy, $C_1$-$C_4$alkyloxycarbonyl, oxo, C(=O)—$C_1$-$C_3$alkyl, $C_1$-$C_4$alkyl, OH, CN, $CFH_2$, $CF_2H$ and $CF_3$;

Each $R_4$ is independently selected from hydrogen, halogen, $C_1$-$C_4$alkyloxy, $C_1$-$C_4$alkyl, $C_1$-$C_4$alkenyl, OH, CN, $CFH_2$, $CF_2H$, $CF_3$, HC≡C or a 3-5 membered saturated ring optionally containing one or more heteroatoms each independently selected from the group consisting of O and N, such $C_1$-$C_4$alkyl optionally substituted with OH;

$R_5$ represents $C_1$-$C_6$alkyl, $CFH_2$, $CF_2H$, $CF_3$, phenyl, pyridyl or a 3-7 membered saturated ring optionally containing one or more heteroatoms each independently selected from the group consisting of O, S and N, such 3-7 membered saturated ring optionally being substituted with one or more substituents each independently selected from the group consisting of hydrogen, halogen, $C_1$-$C_4$alkyloxy, $C_1$-$C_4$alkyloxycarbonyl, oxo, C(=O)—$C_1$-$C_3$alkyl, $C_1$-$C_4$alkyl, OH, CN, $CFH_2$, $CF_2H$ and $CF_3$;

or a pharmaceutically acceptable salt or a solvate thereof.

In one embodiment, at least one $R_4$ represents Fluor, and one other $R_4$ is selected from the group consisting of $C_1$-$C_3$alkyl, $C_1$-$C_3$alkenyl, $CHF_2$ or cyclopropyl.

In a sub-embodiment, one $R_4$ represents Fluor and one other $R_4$ is selected from the group consisting of methyl or $CHF_2$, preferably methyl, and wherein the location of said Fluor is on the para position and the location of said methyl or $CHF_2$ is on the meta position related to the Nitrogen(*) as indicated In Formula (I*) below.

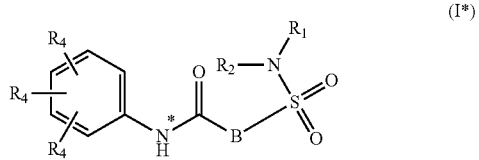

(I*)

In yet another embodiment, the invention provides compound of Formula (I) wherein at least one $R_4$ represents Fluor, and one other $R_4$ is selected from the group consisting of $C_1$-$C_3$alkyl, $C_1$-$C_3$alkenyl, $CHF_2$ or cyclopropyl; more preferably, one $R_4$ represents Fluor and one other $R_4$ is selected from the group consisting of methyl or $CHF_2$ and wherein the location of said Fluor is on the para position and the location of said methyl or $CHF_2$ is on the meta position related to the Nitrogen (*) and $R_2$ represents a 4-7 membered saturated ring containing carbon and one or more oxygen atoms, such 4-7 membered saturated ring optionally being substituted with one or more substituents each independently selected from the group consisting of hydrogen, halo, $C_1$-$C_4$alkyloxy, $C_1$-$C_4$alkyloxycarbonyl, C(=O)—$C_1$-$C_3$alkyl, $C_1$-$C_4$alkyl, OH, CN, $CFH_2$, $CF_2H$ and $CF_3$.

In yet another embodiment, compounds are disclosed wherein one $R_4$ on the para position represents Fluor and the other one $R_4$ on the meta position represents methyl and such compound is not

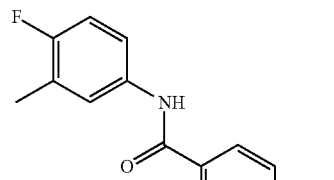

or 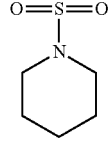

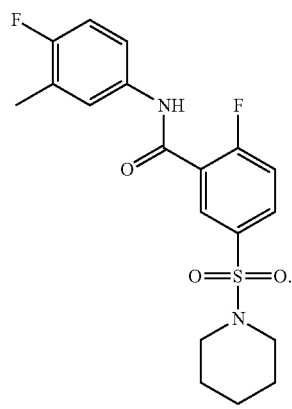

In another embodiment of the present invention, compounds according to Formula (I) are provided wherein $R_2$ represents a 4-7 membered saturated ring containing carbon and one or more oxygen atoms, such 4-7 membered saturated ring optionally being substituted with one or more substituents each independently selected from the group consisting of hydrogen, halogen, $C_1$-$C_4$alkyloxy, $C_1$-$C_4$alkyloxycarbonyl, C(=O)—$C_1$-$C_3$alkyl, $C_1$-$C_4$alkyl, OH, CN, $CFH_2$, $CF_2H$ and $CF_3$. A preferred substituent for such a 4-7 membered saturated ring containing carbon and one or more oxygen atoms is $C_1$-$C_4$alkyl. In a sub-embodiment, the saturated ring is a 4, 5 or 6 membered ring.

In another embodiment of the present invention, compounds according to Formula (I) are provided wherein $R_2$ represents a 4-7 membered saturated ring containing carbon and one or more nitrogen atoms, such 4-7 membered saturated ring optionally being substituted with one or more substituents each independently selected from the group consisting of hydrogen, halogen, $C_1$-$C_4$alkyloxy, $C_1$-$C_4$alkyloxycarbonyl, C(=O)—$C_1$-$C_3$alkyl, $C_1$-$C_4$alkyl, OH, CN, $CFH_2$, $CF_2H$ and $CF_3$. In a further embodiment, $R_2$ represents a 4-7 membered saturated ring containing carbon and one or more oxygen atoms, such 4-7 membered saturated ring optionally being substituted with one or more substituents each independently selected from the group consisting of hydrogen, halogen, $C_1$-$C_4$alkyloxy, $C_1$-$C_4$alkyloxycarbonyl, C(=O)—$C_1$-$C_3$alkyl, $C_1$-$C_4$alkyl, OH, CN, $CFH_2$, $CF_2H$ and $CF_3$ wherein such compound is not

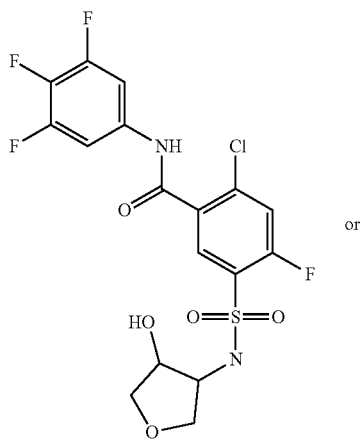

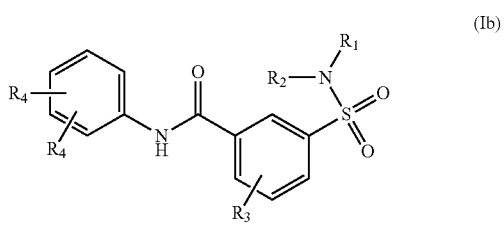

wherein $R_1$, $R_2$, $R_4$ are defined as in any one of the embodiments as described and $R_3$ is selected from the group comprising hydrogen, halogen, $C_1$-$C_3$alkyl, CN, $CFH_2$, $CF_2H$, $CF_3$. In a preferred embodiment, $R_3$ represents Fluor or hydrogen, more preferably hydrogen.

In yet another sub-embodiment, compounds are represented by Formula (Ic):

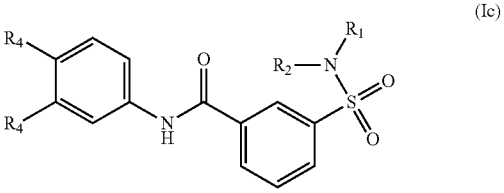

wherein $R_1$, $R_2$ and $R_4$ are defined as in any one of the embodiments as described.

In one sub-embodiment, compounds according to the present invention are represented by Formula (Id)

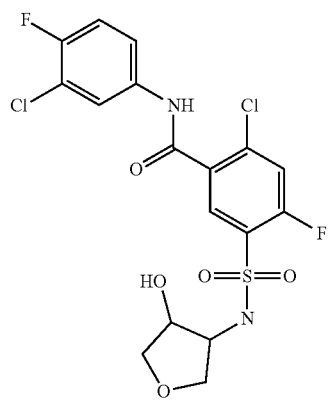

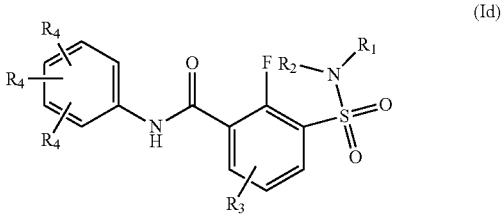

Preferably, any optional substituent on such 3-7, 4-7 and 5-7 membered saturated ring, 6-10 membered bicyclic or bridged ring, $C_1$-$C_6$alkyl-$R_5$ or $C_1$-$C_6$alkyl is independently selected from the group consisting of hydrogen, Fluoro, OH, $C_1$-$C_3$alkyl and $CF_3$, most preferably from the group consisting of hydrogen $C_1$-$C_3$alkyl, Fluoro and $CF_3$.

In another embodiment of the present invention, compounds according to Formula (I) are provided wherein B represents phenyl or thiophene, optionally being substituted with one or more substituents each independently selected from the group consisting of hydrogen, halogen, $C_1$-$C_3$alkyl, CN, $CFH_2$, $CF_2H$ and $CF_3$.

In one sub-embodiment, compounds according to the present invention are represented by Formula (Ia)

wherein $R_1$, $R_2$ and $R_4$ are defined as in any one of the embodiments described and $R_3$ is selected from the group comprising hydrogen, halogen, $C_1$-$C_3$alkyl, CN, $CFH_2$, $CF_2H$, $CF_3$.

In a preferred embodiment, the compounds according to the invention are envisioned for use in the prevention or treatment of an HBV infection in a mammal.

In one further aspect, the present invention provides compounds which can be represented by Formula (I):

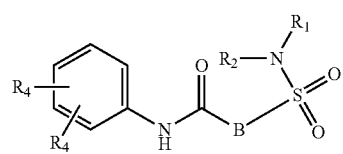

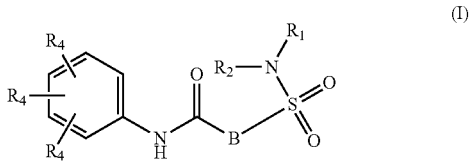

(Ia), wherein $R_1$, $R_2$ and $R_4$ are defined as in any one of the embodiments as described.

In a sub-embodiment, such compounds are represented by Formula (Ib)

or a stereoisomer or tautomeric form thereof, wherein:
B represents a monocyclic 5 to 6 membered aromatic ring, optionally containing one or more heteroatoms each independently selected from the group consisting of O, S and N, such 5 to 6 membered aromatic ring optionally being substituted with one or more substituents each independently selected from the group consisting of hydrogen, halo, $C_1$-$C_3$alkyl, CN, $CFH_2$, $CF_2H$ and $CF_3$;

$R_1$ represents hydrogen or $C_1$-$C_3$alkyl;

$R_2$ represents $C_1$-$C_6$alkyl, $C_1$-$C_3$alkyl-$R_5$, benzyl, C(=O)—$R_5$, $CFH_2$, $CF_2H$, $CF_3$ or a 3-7 membered saturated ring optionally containing one or more heteroatoms each independently selected from the group consisting of O, S and N, such 3-7 membered saturated ring or $C_1$-$C_6$alkyl optionally being substituted with one or more substituents each independently selected from the group consisting of hydrogen, halo, $C_1$-$C_4$alkyloxy, oxo, C(=O)—$C_1$-$C_3$alkyl, $C_1$-$C_4$alkyl, OH, CN, $CFH_2$, $CF_2H$ and $CF_3$;

Or $R_1$ and $R_2$ together with the Nitrogen to which they are attached form a 1,4-dioxa-8-azaspiro[4.5] moiety or a 5-7 membered saturated ring, optionally containing one or more additional heteroatoms each independently selected from the group consisting of O, S and N, such 5-7 membered saturated ring optionally being substituted with one or more substituents each independently selected from the group consisting of hydrogen, halo, $C_1$-$C_4$alkyloxy, oxo, C(=O)—$C_1$-$C_3$alkyl, $C_1$-$C_4$alkyl, OH, CN, $CFH_2$, $CF_2H$ and $CF_3$;

Each $R_4$ is independently selected from hydrogen, halo, $C_1$-$C_4$alkyloxy, $C_1$-$C_4$alkyl, OH, CN, $CFH_2$, $CF_2H$, $CF_3$, HC≡C or a 3-5 membered saturated ring optionally containing one or more heteroatoms each independently selected from the group consisting of O and N;

$R_5$ represents $C_1$-$C_6$alkyl, $CFH_2$, $CF_2H$, $CF_3$ or a 3-7 membered saturated ring optionally containing one or more heteroatoms each independently selected from the group consisting of O, S and N, such 3-7 membered saturated ring optionally being substituted with one or more substituents each independently selected from the group consisting of hydrogen, halo, $C_1$-$C_4$alkyloxy, oxo, C(=O)—$C_1$-$C_3$alkyl, $C_1$-$C_4$alkyl, OH, CN, $CFH_2$, $CF_2H$ and $CF_3$;

or a pharmaceutically acceptable salt or a solvate thereof. These compounds are especially suited for use in the prevention or treatment of an HBV infection in a mammal.

In yet a further aspect, the invention relates to compounds according to Formula (I)

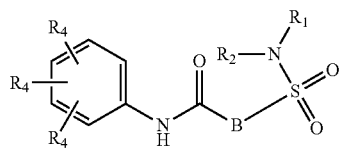

(I)

or a stereoisomer or tautomeric form thereof, wherein:

B represents a monocyclic 5 to 6 membered aromatic ring, optionally containing one or more heteroatoms each independently selected from the group consisting of 0, S and N, such 5 to 6 membered aromatic ring optionally being substituted with one or more substituents each independently selected from the group consisting of hydrogen, halo, $C_1$-$C_3$alkyl, CN, $CFH_2$, $CF_2H$ and $CF_3$;

$R_1$ represents hydrogen or $C_1$-$C_3$alkyl;

$R_2$ represents a 4-7 membered saturated ring consisting of carbon atoms and one or more heteroatoms each independently selected from the group consisting of O or S, such 4-7 membered saturated ring optionally being substituted with one or more substituents each independently selected from the group consisting of hydrogen, halo, $C_1$-$C_4$alkyloxy, oxo, C(=O)—$C_1$-$C_3$alkyl, $C_1$-$C_4$alkyl, OH, CN, $CFH_2$, $CF_2H$ and $CF_3$;

Each $R_4$ is independently selected from hydrogen, halo, $C_1$-$C_4$alkyloxy, $C_1$-$C_4$alkyl, OH, CN, $CFH_2$, $CF_2H$, $CF_3$, HC≡C or a 3-5 membered saturated ring optionally containing one or more heteroatoms each independently selected from the group consisting of O and N;

or a pharmaceutically acceptable salt or a solvate thereof.

The present invention additionally relates to compound of Formula (I)

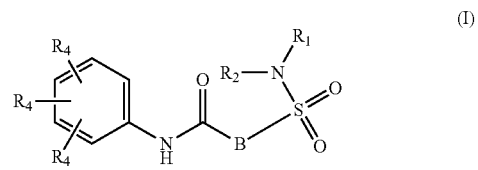

(I)

or a stereoisomer or tautomeric form thereof, or a pharmaceutically acceptable salt or a solvate thereof wherein:

B represents a monocyclic 5 to 6 membered aromatic ring, optionally containing one or more heteroatoms each independently selected from the group consisting of O, S and N, such 5 to 6 membered aromatic ring optionally being substituted with one or more substituents each independently selected from the group consisting of hydrogen, halo, $C_1$-$C_3$alkyl, CN, $CFH_2$, $CF_2H$ and $CF_3$;

$R_1$ represents hydrogen or $C_1$-$C_3$alkyl;

$R_2$ represents $C_1$-$C_6$alkyl, $C_1$-$C_3$alkyl-$R_5$, benzyl, C(=O)—$R_5$, $CFH_2$, $CF_2H$, $CF_3$ or a 3-7 membered saturated ring optionally containing one or more heteroatoms each independently selected from the group consisting of O, S and N, such 3-7 membered saturated ring or $C_1$-$C_6$alkyl optionally being substituted with one or more substituents each independently selected from the group consisting of hydrogen, halo, $C_1$-$C_4$alkyloxy, oxo, C(=O)—$C_1$-$C_3$alkyl, $C_1$-$C_4$alkyl, OH, CN, $CFH_2$, $CF_2H$ and $CF_3$;

Or $R_1$ and $R_2$ together with the Nitrogen to which they are attached form a 1,4-dioxa-8-azaspiro[4.5] moiety or a 5-7 membered saturated ring, optionally containing one or more additional heteroatoms each independently selected from the group consisting of O, S and N, such 5-7 membered saturated ring optionally being substituted with one or more substituents each independently selected from the group consisting of hydrogen, halo, $C_1$-$C_4$alkyloxy, oxo, C(=O)—$C_1$-$C_3$alkyl, $C_1$-$C_4$alkyl, OH, CN, $CFH_2$, $CF_2H$ and $CF_3$;

Each $R_4$ is independently selected from hydrogen, halo, $C_1$-$C_4$alkyloxy, $C_1$-$C_4$alkyl, OH, CN, $CFH_2$, $CF_2H$, $CF_3$, HC≡O or a 3-5 membered saturated ring optionally containing one or more heteroatoms each independently selected from the group consisting of O and N;

$R_5$ represents $C_1$-$C_6$alkyl, $CFH_2$, $CF_2H$, $CF_3$ or a 3-7 membered saturated ring optionally containing one or more heteroatoms each independently selected from the group consisting of O, S and N, such 3-7 membered saturated ring optionally being substituted with one or more substituents each independently selected from the group consisting of hydrogen, halo, $C_1$-$C_4$alkyloxy, oxo, C(=O)—$C_1$-$C_3$alkyl, $C_1$-$C_4$alkyl, OH, CN, $CFH_2$, $CF_2H$ and $CF_3$;

One sub-embodiment of the invention provides compounds which can be represented by formula (Ia)

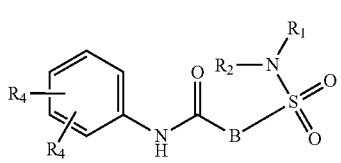

(Ia)

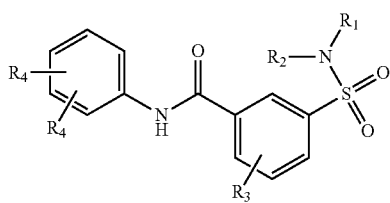

(Ib)

wherein $R_1$, $R_2$, B are defined as above and each $R_4$ is independently selected from hydrogen, halo, $C_1$-$C_4$alkyloxy, $C_1$-$C_4$alkyl, OH, CN, $CFH_2$, $CF_2H$, $CF_3$ or a 3-5 membered saturated ring optionally containing one or more heteroatoms each independently selected from the group consisting of O and N.

In one embodiment, $R_2$ represents a 3-7 membered saturated ring, containing one or more heteroatoms each independently selected from the group consisting of 0, S and N, such 3-7 membered saturated ring optionally being substituted with one or more substituents each independently selected from the group consisting of hydrogen, halo, $C_1$-$C_4$alkyloxy, oxo, $C(=O)$—$C_1$-$C_3$alkyl, $C_1$-$C_4$alkyl, OH, CN, $CFH_2$, $CF_2H$ and $CF_3$.

In yet another embodiment, $R_2$ represents a 4-7 membered saturated ring containing carbon and one or more oxygen atoms, such 4-7 membered saturated ring optionally being substituted with one or more substituents each independently selected from the group consisting of hydrogen, halo, $C_1$-$C_4$alkyloxy, $C(=O)$— $C_1$-$C_3$alkyl, $C_1$-$C_4$alkyl, OH, CN, $CFH_2$, $CF_2H$ and $CF_3$.

In another embodiment, $R_1$ and $R_2$ together with the Nitrogen to which they are attached form a 5-7 membered saturated ring, optionally containing one or more additional heteroatoms each independently selected from the group consisting of 0, S and N, such 5-7 membered saturated ring optionally being substituted with one or more substituents each independently selected from the group consisting of hydrogen, halo, $C_1$-$C_4$alkyloxy, oxo, $C(=O)$—$C_1$-$C_3$alkyl, $C_1$-$C_4$alkyl, OH, CN, $CFH_2$, $CF_2H$ and $CF_3$.

In a preferred embodiment of the invention, B represents phenyl or thiophene, optionally being substituted with one or more substituents each independently selected from the group consisting of hydrogen, halogen, $C_1$-$C_3$alkyl, CN, $CFH_2$, $CF_2H$ and $CF_3$.

In a selection of compounds according to the invention, or compounds for use in the prevention or treatment of an HBV infection in a mammal at least one $R_4$ represents Fluor, $C_1$-$C_3$alkyl, $CHF_2$ or cyclopropyl.

Preferably, at least one $R_4$ represents methyl, i-propyl or cyclopropyl. In another embodiment, one $R_4$ represents methyl, i-propyl or cyclopropyl and the other $R_4$ represents Fluor, or hydrogen. The position of $R_4$ preferably is meta and/or para (position indicated from —N~).

One specific embodiment is a compound of Formula (I) wherein one $R_4$ on the para position represents Fluor and the other one $R_4$ on the meta position represents Fluor or methyl (position indicated from —N~).

One sub-embodiment of the invention provides compounds which can be represented by formula (Ib)

wherein $R_1$, $R_2$, $R_4$ are defined as above and $R_3$ is selected from the group comprising hydrogen, halo, $C_1$-$C_3$alkyl, CN, $CFH_2$, $CF_2H$, $CF_3$. In a preferred embodiment, $R_3$ represents Fluor or hydrogen.

The invention further relates to compounds according to Formula (I)

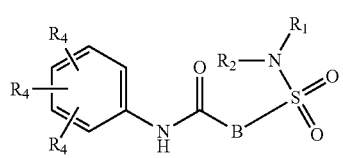

(I)

or a stereoisomer or tautomeric form thereof, wherein:

B represents a monocyclic 5 to 6 membered aromatic ring, optionally containing one or more heteroatoms each independently selected from the group consisting of 0, S and N, such 5 to 6 membered aromatic ring optionally being substituted with one or more substituents each independently selected from the group consisting of hydrogen, halo, $C_1$-$C_3$alkyl, CN, $CFH_2$, $CF_2H$ and $CF_3$;

$R_1$ represents hydrogen or $C_1$-$C_3$alkyl;

$R_2$ represents $C_1$-$C_3$alkyl-$R_6$ or a 4-7 membered saturated ring consisting of carbon atoms and one or more heteroatoms each independently selected from the group consisting of O or S, such 4-7 membered saturated ring optionally being substituted with one or more substituents each independently selected from the group consisting of hydrogen, halo, $C_1$-$C_4$alkyloxy, oxo, $C(=O)$—$C_1$-$C_3$alkyl, OH, CN, $CFH_2$, $CF_2H$ and $CF_3$, Each $R_4$ is independently selected from hydrogen, halo, $C_1$-$C_4$alkyloxy, OH, CN, $CFH_2$, $CF_2H$, $CF_3$, $HC\equiv O$ or a 3-5 membered saturated ring optionally containing one or more heteroatoms each independently selected from the group consisting of O and N;

$R_6$ represents a 4-7 membered saturated ring optionally containing one or more heteroatoms each independently selected from the group consisting of O or S, such 4-7 membered saturated ring optionally being substituted with one or more substituents each independently selected from the group consisting of hydrogen, halo, $C_1$-$C_4$alkyloxy, oxo, $C(=O)$—$C_1$-$C_3$alkyl, $C_1$-$C_4$alkyl, OH, CN, $CFH_2$, $CF_2H$ and $CF_3$;

or a pharmaceutically acceptable salt or a solvate thereof.

One sub-embodiment of the invention provides compounds which can be represented by formula (Ia)

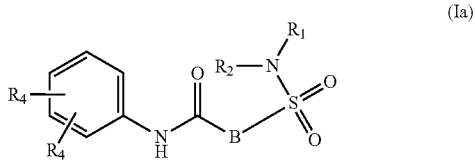

(Ia)

wherein $R_1$, $R_2$, B are defined as above and each $R_4$ is independently selected from hydrogen, halo, $C_1$-$C_4$alkyloxy, $C_1$-$C_4$alkyl, OH, CN, $CFH_2$, $CF_2H$, $CF_3$ or a 3-5 membered saturated ring optionally containing one or more heteroatoms each independently selected from the group consisting of O and N.

In one embodiment, $R_2$ represents $C_1$-$C_3$alkyl-$R_6$ or a 4-7 membered saturated ring consisting of carbon atoms and one or more heteroatoms each independently selected from the group consisting of O or S, such 4-7 membered saturated ring optionally being substituted with one or more substituents each independently selected from the group consisting of hydrogen, halo, $C_1$-$C_4$alkyloxy, oxo, $C(=O)$—$C_1$-$C_3$alkyl, $C_1$-$C_4$alkyl, OH, CN, $CFH_2$, $CF_2H$ and $CF_3$.

In a preferred embodiment for the compounds of the invention, B represents phenyl or thiophene, optionally being substituted with one or more substituents each independently selected from the group consisting of hydrogen, halogen, $C_1$-$C_3$alkyl, CN, $CFH_2$, $CF_2H$ and $CF_3$.

In a selection of compounds according to the invention at least one $R_4$ represents Fluor, $C_1$-$C_3$alkyl, $CHF_2$ or cyclopropyl. Preferably, at least one $R_4$ represents methyl, i-propyl or cyclopropyl. In another embodiment, one $R_4$ represents methyl, i-propyl or cyclopropyl and the other $R_4$ represents Fluor, or hydrogen. The position of $R_4$ preferably is meta and/or para.

One specific embodiment is a compound of Formula (I) wherein one $R_4$ on the para position represents Fluor and the other one $R_4$ on the meta position represents Fluor or methyl.

One sub-embodiment of the compounds of the invention relates to compounds according Formula (Ib)

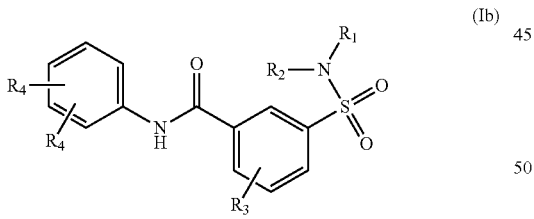

(Ib)

wherein $R_1$ represents hydrogen or $C_1$-$C_3$alkyl;

$R_2$ represents $C_1$-$C_3$alkyl-$R_6$ or a 4-7 membered saturated ring consisting of carbon atoms and one or more heteroatoms each independently selected from the group consisting of O or S, such 4-7 membered saturated ring optionally being substituted with one or more substituents each independently selected from the group consisting of hydrogen, halo, $C_1$-$C_4$alkyloxy, oxo, $C(=O)$—$C_1$-$C_3$alkyl, $C_1$-$C_4$alkyl, OH, CN, $CFH_2$, $CF_2H$ and $CF_3$, Each $R_4$ is independently selected from hydrogen, halo, $C_1$-$C_4$alkyloxy, $C_1$-$C_4$alkyl, OH, CN, $CFH_2$, $CF_2H$, $CF_3$ or a 3-5 membered saturated ring optionally containing one or more heteroatoms each independently selected from the group consisting of O and N;

$R_6$ represents a 4-7 membered saturated ring optionally containing one or more heteroatoms each independently selected from the group consisting of O or S, such 4-7 membered saturated ring optionally being substituted with one or more substituents each independently selected from the group consisting of hydrogen, halo, $C_1$-$C_4$alkyloxy, oxo, $C(=O)$—$C_1$-$C_3$alkyl, $C_1$-$C_4$alkyl, OH, CN, $CFH_2$, $CF_2H$ and $CF_3$;

$R_3$ is selected from the group comprising hydrogen, halo, $C_1$-$C_3$alkyl, CN, $CFH_2$, $CF_2H$, $CF_3$. In a preferred embodiment, $R_3$ represents Fluor or hydrogen.

In one embodiment, $R_6$ represents a 4-7 membered saturated ring consisting of carbon atoms and one or more heteroatoms each independently selected from the group consisting of O or S, such 4-7 membered saturated ring optionally being substituted with one or more substituents each independently selected from the group consisting of hydrogen, halo, $C_1$-$C_4$alkyloxy, oxo, $C(=O)$—$C_1$-$C_3$alkyl, $C_1$-$C_4$alkyl, OH, CN, $CFH_2$, $CF_2H$ and $CF_3$.

Further combinations of any of the sub- or preferred embodiments are also envisioned to be in the scope of the present invention.

Preferred compounds according to the invention are compounds or a stereoisomer or tautomeric form thereof with a formula or reference to a formula selected from the following tables 1 and 2:

TABLE 2

| Co. no. |
|---|
| 1 |
| 2 |
| 3 |
| 4 |
| 5 |
| 6 |
| 7 |
| 8 |
| 9 |
| 10 |
| 11 |
| 12 |
| 14 |
| 16 |
| 17 |
| 18 |
| 19 |
| 38 |
| 39 |
| 42 |
| 43 |
| 45 |
| 46 |
| 48 |
| 56 |
| 63 |
| 64 |
| 65 |
| 66 |
| 67 |
| 68 |
| 69 |
| 70 |
| 71 |
| 72 |
| 73 |
| 74 |
| 76 |
| 77 |
| 79 |
| 81 |
| 82 |
| 83 |
| 84 |

TABLE 2-continued

| Co. no. |
|---|
| 85 |
| 86 |
| 87 |
| 89 |
| 90 |
| 91 |
| 92 |
| 93 |
| 94 |
| 95 |
| 96 |
| 97 |
| 98 |
| 99 |
| 100 |
| 101 |
| 102 |
| 103 |
| 104 |
| 105 |
| 106 |
| 107 |
| 108 |
| 109 |
| 110 |
| 111 |
| 112 |
| 113 |
| 114 |
| 115 |
| 116 |
| 117 |
| 118 |
| 119 |
| 120 |
| 121 |
| 122 |
| 123 |
| 124 |
| 125 |
| 126 |
| 127 |
| 128 |
| 129 |
| 130 |
| 131 |
| 132 |
| 133 |
| 134 |
| 135 |
| 136 |
| 137 |
| 138 |
| 139 |
| 140 |
| 141 |
| 142 |
| 143 |
| 144 |
| 145 |
| 146 |
| 147 |
| 148 |
| 149 |
| 150 |
| 151 |
| 152 |
| 153 |
| 154 |
| 155 |
| 156 |
| 157 |
| 158 |
| 159 |
| 160 |
| 161 |
| 162 |
| 163 |
| 164 |
| 165 |
| 166 |
| 167 |
| 168 |
| 169 |
| 170 |
| 171 |
| 172 |
| 173 |
| 174 |
| 175 |
| 176 |
| 177 |
| 178 |
| 179 |
| 180 |
| 181 |
| 182 |
| 183 |
| 184 |
| 184a |
| 184b |
| 185 |
| 186 |
| 187 |
| 188 |
| 189 |
| 190 |
| 191 |
| 192 |
| 193 |
| 194 |
| 195 |
| 196 |
| 197 |
| 198 |
| 199 |
| 200 |
| 201 |
| 202 |
| 203 |
| 204 |
| 205 |
| 206 |
| 207 |
| 208 |
| 209 |
| 210 |
| 211 |
| 212 |
| 213 |
| 214 |
| 215 |
| 216 |
| 217 |
| 218 |
| 219 |
| 220 |
| 221 |
| 222 |
| 223 |
| 224 |
| 225 |
| 226 |
| 227 |
| 228 |
| 229 |
| 230 |
| 231 |
| 232 |
| 233 |
| 234 |
| 235 |
| 236 |
| 237 |
| 238 |
| 239 |

TABLE 2-continued

Co. no.

240
241
242
243 or a pharmaceutically acceptable salt or a solvate thereof.

In a further aspect, the present invention concerns a pharmaceutical composition comprising a therapeutically or prophylactically effective amount of a compound of Formula (I) as specified herein, and a pharmaceutically acceptable carrier. A prophylactically effective amount in this context is an amount sufficient to prevent HBV infection in subjects being at risk of being infected. A therapeutically effective amount in this context is an amount sufficient to stabilize HBV infection, to reduce HBV infection, or to eradicate HBV infection, in infected subjects. In still a further aspect, this invention relates to a process of preparing a pharmaceutical composition as specified herein, which comprises intimately mixing a pharmaceutically acceptable carrier with a therapeutically or prophylactically effective amount of a compound of Formula (I), as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of Formula (I) are active as inhibitors of the HBV replication cycle and can be used in the treatment and prophylaxis of HBV infection or diseases associated with HBV. The latter include progressive liver fibrosis, inflammation and necrosis leading to cirrhosis, end-stage liver disease, and hepatocellular carcinoma.

Due to their antiviral properties, particularly their anti-HBV properties, the compounds of Formula (I) or any subgroup thereof, are useful in the inhibition of the HBV replication cycle, in particular in the treatment of warm-blooded animals, in particular humans, infected with HBV, and for the prophylaxis of HBV infections. The present invention furthermore relates to a method of treating a warm-blooded animal, in particular human, infected by HBV, or being at risk of infection by HBV, said method comprising the administration of a therapeutically effective amount of a compound of Formula (I).

The compounds of Formula (I), as specified herein, may therefore be used as a medicine, in particular as medicine to treat or prevent HBV infection. Said use as a medicine or method of treatment comprises the systemic administration to HBV infected subjects or to subjects susceptible to HBV infection of an amount effective to combat the conditions associated with HBV infection or an amount effective to prevent HBV infection.

The present invention also relates to the use of the present compounds in the manufacture of a medicament for the treatment or the prevention of HBV infection. In general it is contemplated that an antiviral effective daily amount would be from about 0.01 to about 50 mg/kg, or about 0.01 to about 30 mg/kg body weight. It may be appropriate to administer the required dose as two, three, four or more sub-doses at appropriate intervals throughout the day. Said sub-doses may be formulated as unit dosage forms, for example, containing about 1 to about 500 mg, or about 1 to about 300 mg, or about 1 to about 100 mg, or about 2 to about 50 mg of active ingredient per unit dosage form.

The present invention also concerns combinations of a compound of Formula (I) or any subgroup thereof, as specified herein with other anti-HBV agents. The term "combination" may relate to a product or kit containing (a) a compound of Formula (I), as specified above, and (b) at least one other compound capable of treating HBV infection (herein designated as anti-HBV agent), as a combined preparation for simultaneous, separate or sequential use in treatment of HBV infections. In an embodiment, the invention concerns combination of a compound of Formula (I) or any subgroup thereof with at least one anti-HBV agent. In a particular embodiment, the invention concerns combination of a compound of formula (I) or any subgroup thereof with at least two anti-HBV agents. In a particular embodiment, the invention concerns combination of a compound of formula (I) or any subgroup thereof with at least three anti-HBV agents. In a particular embodiment, the invention concerns combination of a compound of formula (I) or any subgroup thereof with at least four anti-HBV agents.

The combination of previously known anti-HBV agents, such as interferon-α (IFN-α), pegylated interferon-α, 3TC, adefovir or a combination thereof, and, a compound of formula (I) or any subgroup thereof can be used as a medicine in a combination therapy.

Generic Synthesis:

Compound according to Formula (I) can be synthesized as described in general schemes 1 to 7.

A carboxylic acid chloride of general Formula II can be selectively reacted with an aniline of general formula III, for example in an organic solvent like $CH_2Cl_2$ in the presence of an organic base like triethylamine or DIPEA (N,N-diisopropylethylamine), or, as another example, by addition of the aniline III to a refluxing toluene solution of compound II, resulting in compound IV. The remaining sulfonic acid chloride functionality in compound IV is further reacted with an amine of general formula V, resulting in a compound of general Formula (I). Alternatively a compound of general Formula (I) might be obtained as described in scheme 2. This time the sulfonic acid chloride VI is reacted with an amine of general formula V, for example in an organic solvent like $CH_2Cl_2$ in the presence of an organic base like triethylamine or DIPEA or, as another example, in the presence of $Na_2CO_3$ in a mixture of $H_2O/THF$. The formed compound VII is coupled with aniline of general formula III in the presence of an activating reagent like for example HATU and an organic base like triethylamine or DIPEA.

Scheme 1

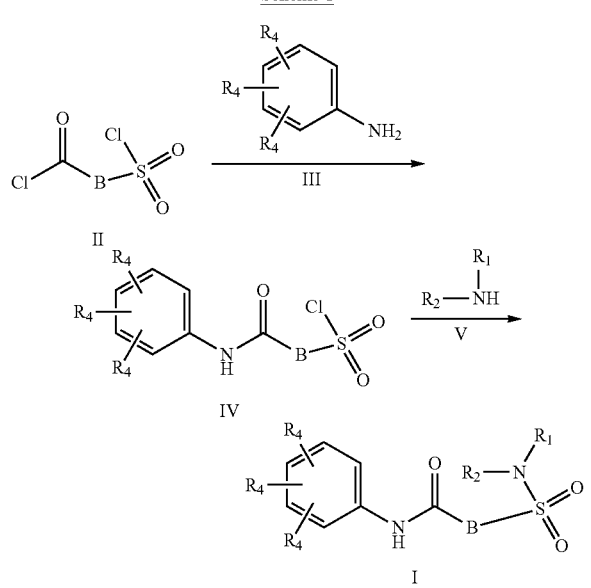

Scheme 2

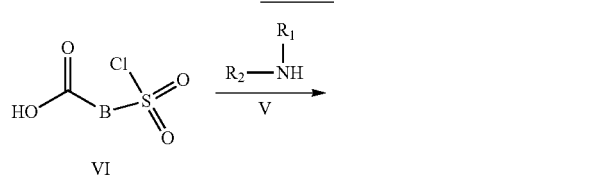

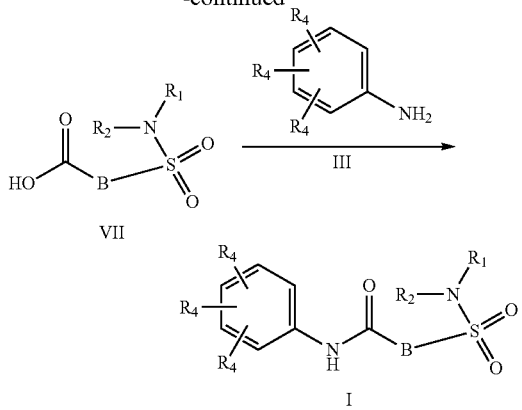

A general synthesis of compounds of formula IX and X is described in scheme 3. Intermediate IV is reacted with ammonia, resulting in a compound of formula VIII. This intermediate can be further transformed to a compound of formula IX by reacting with a carbonyl chloride, for example cyclohexane carbonyl chloride in the presence of $SiO_2$ and $H_2SO_4$ at reflux in $CHCl_3$. The compound of general formula IX can be further transformed to a compound of formula X. In case $R_1$ equals Me, this can be done by reacting IX with $TMSCHN_2$ in $MeOH/CH_2Cl_2$ Scheme 3

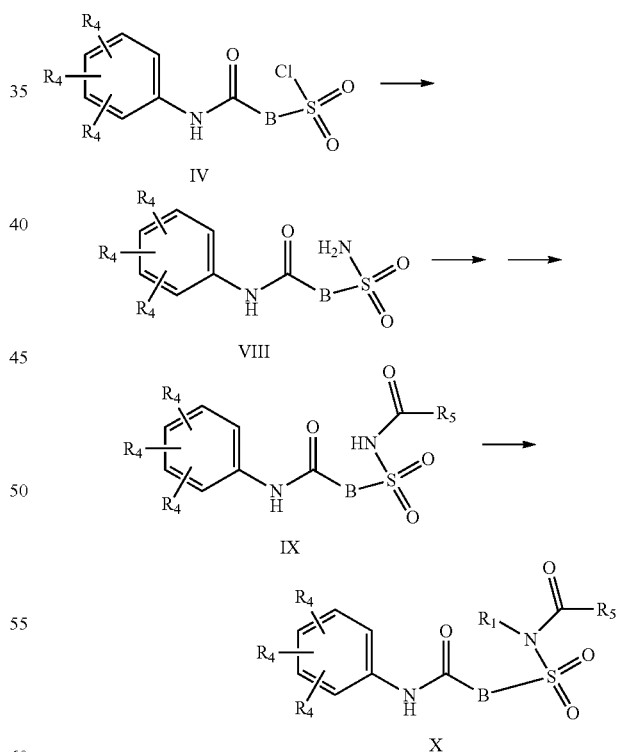

In another example, compound IV can be reacted with an amino acid XI, in the presence of a base like NaOH, resulting in compound XII as described in scheme 4. This intermediate XII can then optionally be cyclised to compound XIII for example by heating with acetic anhydride and KOAc in toluene, or converting the carboxylic acid to an acid chloride followed by cyclisation in the presence of a base like triethylamine. Suitable examples of amino acids of structure XI are derivatives of 5-aminopentanoic acid or 4-aminobutanoic acid general formula XVI. Examples of such nucleophiles (Nu) are, but are not limited to, morpholine and 1-methylpiperazine. Examples of a compound synthesized according to the route described in scheme 5, are compounds 116 and 117.

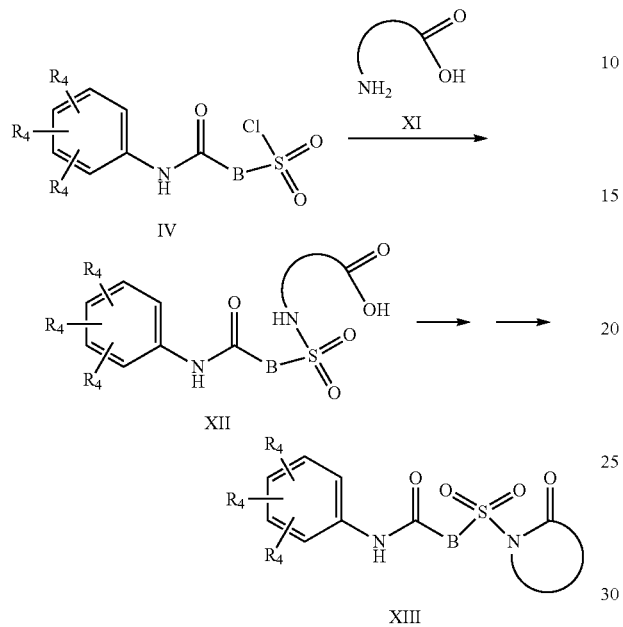

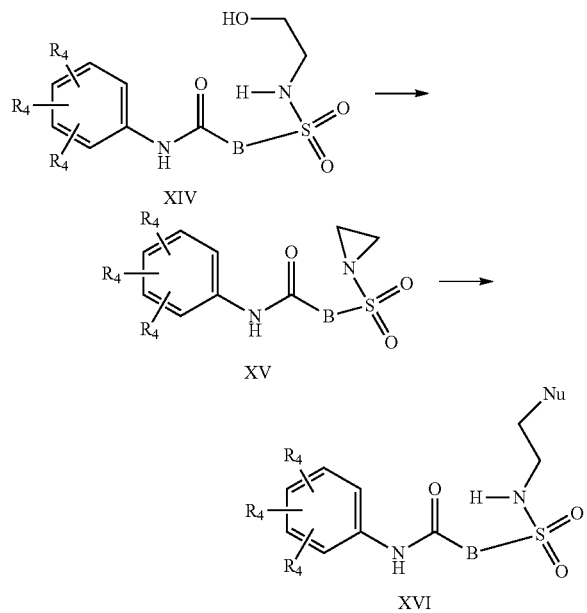

A synthetic route to compounds of general formula XVI is described in Scheme 5. A aminoethanol derivative XIV, prepared as described in scheme 1 for the compounds of general Formula (I), is transformed in a aziridine derivative XV by treatment with Diethyl diazene-1,2-dicarboxylate and $PPh_3$ in THF. The aziridine of general formula XV is reacted with a nucleophile Nu, resulting in a compound of An alternative method for the synthesis of compounds of general formula VII, is via ester XVII as described in scheme 6. Reaction of XVII with amine V, for example in an organic solvent like $CH_2Cl_2$ or THF in the presence of an organic base like for example triethylamine or DIPEA, followed by hydrolysis of the ester, for example with LiOH in THF/$H_2O$, followed by acidification, results in a compound of general formula VII. A compound of general formula VII, obtained via the route in scheme 2 or scheme 6, can be transformed to and acid chloride of formula XIX, for example by treatment with oxalyl chloride or thionyl chloride. A compound of general formula XIX can then be transformed to a compound of general Formula (I) by reaction with an aniline of general formula III.

A compound of general formula VI can be converted to a compound of general formula II, for example by treatment with oxalyl chloride in $CH_2Cl_2$.

Scheme 7

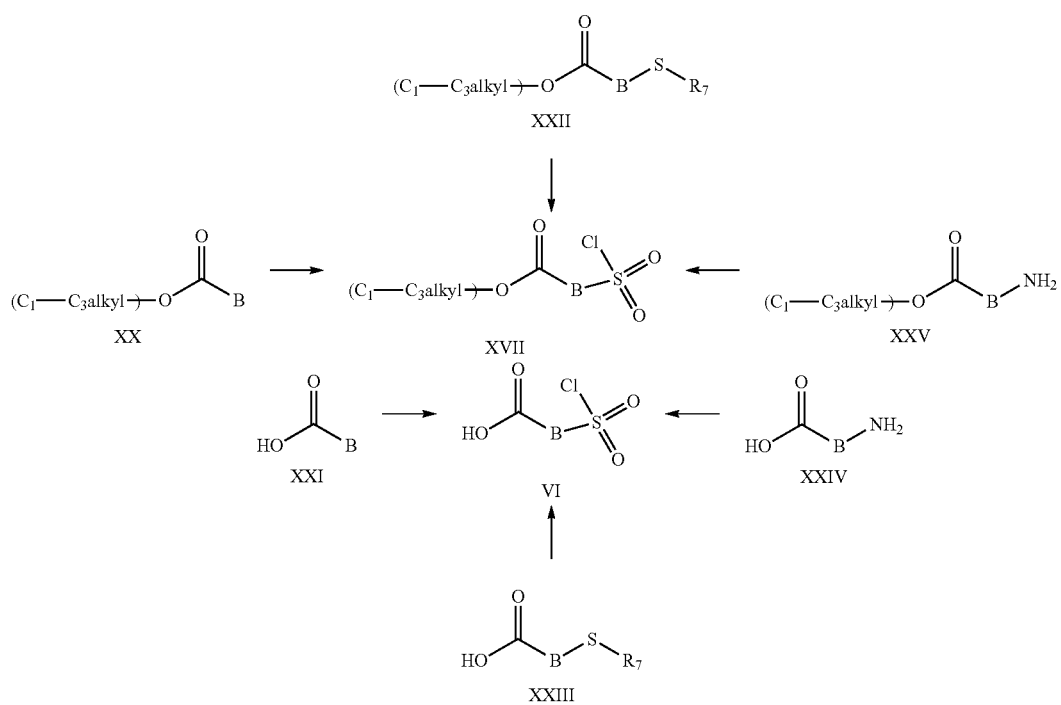

Possible synthetic routes, for compounds of general formula XVII or VI are described in scheme 7, and further exemplified in the experimental section. Chlorosulfonation of carboxylic acids XXI or carboxylic esters XX, can results in compounds of general formula VI or XVII respectively, for example by treatment with chlorosulfonic acid (for example as reviewed in Phosphorus, Sulfur, and Silicon and the Related Elements Vol. 56, Iss. 1-4, 1991). Alternatively, compounds of general formula XXV or XXIV, may be converted to compound of general formula XVII and VI respectively, by conversion to the corresponding diazonium salts (for example by $NaNO_2/HCl$), followed by conversion of the diazonium salt to a sulfonyl chloride (for example by $SO_2/CuCl$)(for example as described in Organic Process Research & Development, 13(5), 875-879; 2009). Alternatively, compounds of general formula XXII and XXIII (with $R_7$ equaling H, benzyl or methyl) may be converted to compound of general formula XVII and VI respectively, for example by treatment with $Cl_2$ or N-Chlorosuccinimide in $AcOH/H_2O$.

The substitutents represented by $R_4$ in this general synthesis section are meant to include any substituent or reactive species that is suitable for transformation into any $R_4$ subsitutent according to the present invention without undue burden for the person skilled in the art.

Compounds not specifically described in the synthesis of compounds section below can be sysnthesized according to the Schemes 1-7 above and were commercially acquired.
Synthesis of Compounds:
Lc-Ms Methods:
Method A: mobile phase A: $H_2O$ (0.1% TFA; B: $CH_3CN$ (0.05% TFA) Stop Time: 10 min; gradient time (min) [% A/% B] 0.0 [100/0] to 1 [100/0] to 5 [40/60] to 7.5 [40/60] to 8.0 [100/0]; flow: 0.8 mL/min; column temp.: 50° C., YMC-PACK ODS-AQ, 50×2.0 mm 5 µm Method B: mobile phase A: $H_2O$ (0.1% TFA; B: $CH_3CN$ (0.05% TFA) Stop Time: 10 min; gradient time (min) [% A/% B] 0.0 [90/10] to 0.8 [90/10] to 4.5 [20/80] to 7.5 [20/80] to 8.0 [90/10]; flow: 0.8 mL/min; column temp.: 50° C., YMC-PACK ODS-AQ, 50×2.0 mm 5 µm Method C: mobile phase A: $H_2O$ (0.1% TFA); B: $CH_3CN$ (0.05 TFA) Stop Time: 10 min; gradient time (min) [% A/% B] 0.0 [90/10] to 0.8 [90/10] to 4.5 [20/80] to 7.5 [20/80]; 9.5 [90/10] flow: 0.8 mL/min; column temp.: 50° C.; Agilent TC-C18, 50×2.1 mm, 5 µm Method D: mobile phase A: $H_2O$ (0.05% $NH_3.H_2O$); B: $CH_3CN$ Stop Time: 10 min; gradient time (min) [% A/% B] 0.0 [100/0] to 1 [100/0] to 5 [40/60] to 7.5 [40/60]; 8 [100/0] flow: 0.8 mL/min; column temp.: 40° C., XBridge Shield-RP18, 50*2.1 mm 5 µm Method E: mobile phase A: $H_2O$ (0.1% TFA; B: $CH_3CN$ (0.05% TFA) Stop Time: 10 min; Post Time: 0.5 min; gradient time (min) [% A/% B]0 [100/0] to 1 [100/0] to 5 [40/60] to 7.5 [15/85] to 9.5 [100/0]; flow: 0.8 mL/min; column temp.: 50° C., Agilent TC-C18, 50×2.1 mm, 5 µm Method F: The LC measurement was performed using an Acquity UPLC (Waters) system with column heater (set at 55° C.). Reversed phase UPLC (Ultra Performance Liquid Chromatography) was carried out on a bridged ethylsiloxane/silica hybrid (BEH) C18 column (1.7 µm, 2.1×50 mm; Waters Acquity) with a flow rate of 0.8 mL/min. Two mobile phases (10 mM ammonium acetate in $H_2O$/acetonitrile 95/5; mobile phase B: acetonitrile) were used to run a gradient condition from 95% A and 5% B to 5% A and 95% B in 1.3 minutes and hold for 0.3 minutes. An injection volume of 0.5 µl was used. Cone voltage was 10 V for positive ionization mode and 20 V for negative ionization mode.

Method G: The LC measurement was performed using an Acquity UPLC (Waters) with column heater (set at 55° C.).

Reversed phase UPLC (Ultra Performance Liquid Chromatography) was carried out on a Acquity UPLC HSS T3 column (1.8 μm, 2.1×100 mm; Waters Acquity) with a flow rate of 0.8 mL/min. Two mobile phases (A: 10 mM ammonium acetate in $H_2O$/acetonitrile 95/5; mobile phase B: acetonitrile) were used to run a gradient condition from 100% A and 0% B to 5% A and 95% B in 2.1 minutes and subsequently to 0% A and 100% B in 0.9 minutes to 5% A and 95% B in 0.5 min. An injection volume of 1 μl was used. Cone voltage was 30 V for positive ionization mode and 30 V for negative ionization mode.

Method H: Reversed phase HPLC was carried out on an Atlantis C18 column (3.5 μm, 4.6×100 mm) with a flow rate of 1.6 mL/min. Column heater was set at 45° C. Two mobile phases (mobile phase A: 70% methanol+30% $H_2O$; mobile phase B: 0.1% formic acid in $H_2O$/methanol 95/5) were employed to run a gradient condition from 100% B to 5% B+95% A in 9 minutes and hold these conditions for 3 minutes. An injection volume of 10 μl was used. Cone voltage was 10 V for positive ionization mode and 20 V for negative ionization mode.

Compounds 21, 49-55, 57-62 were purchased from Aurora Fine Chemicals.

Compound 1

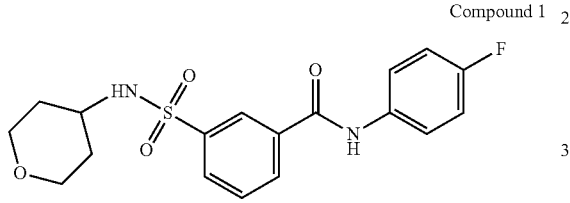

3-(chlorosulfonyl)benzoyl chloride (207 mg, 1 mmol) was dissolved in dichloromethane (3 mL) and 4-fluoroaniline (111 mg, 1.0 mmol) and triethylamine (112 mg, 1.0 mmol) in dichloromethane (2 mL) were added to the mixture at 0° C. The mixture was next stirred at 20° C. for 1 hour. To this reaction mixture containing 3-(4-fluoro-phenylcarbamoyl)benzene-1-sulfonyl chloride at 0° C., a solution of triethylamine (121 mg, 1.2 mmol) and 4-aminotetrahydropyran (88 mg, 0.861 mmol) in dichloromethane (3 mL) was added. The mixture was stirred at 20° C. for 1 hour. The solvent was removed in vacuo. The residue was purified by high performance liquid chromatography (Column: Phenomenex Synergi C18 150*20 mm*5 um. A: $H_2O$+0.1% TFA; B: MeCN). The product fractions were collected and the organic solvent was evaporated. The fraction was neutralized by saturated $NaHCO_3$. The mixture was extracted with dichloromethane. The organic layer was dried over $Na_2SO_4$ and concentrated resulting in compound 1 (85.4 mg) Method A; Rt: 4.88 min. m/z: 379.2 $(M+H)^+$ Exact mass: 378.1

Following compounds were prepared similarly as compound 1 using the corresponding amines instead of 4-aminotetrahydropyran:

Compound 2

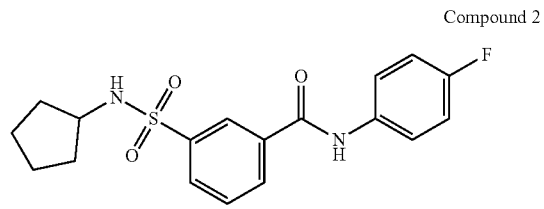 [SMILES: O=C(Nc1ccc(F)cc1)c1cccc(S(=O)(=O)NC2CCCC2)c1]

Method B; Rt: 4.27 min. m/z: 363.1 $(M+H)^+$ Exact mass: 362.1

Compound 3

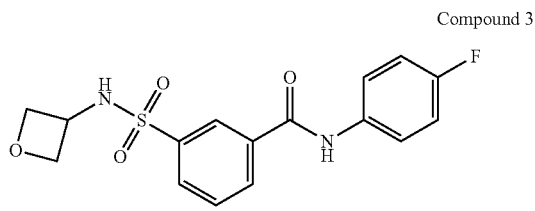 [SMILES: O=C(Nc1ccc(F)cc1)c1cccc(S(=O)(=O)NC2COC2)c1]

Method A; Rt: 4.64 min. m/z: 351.1 $(M+H)^+$ Exact mass: 350.1

Compound 4

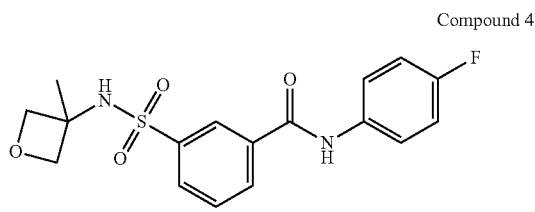 [SMILES: CC1(NS(=O)(=O)c2cccc(C(=O)Nc3ccc(F)cc3)c2)COC1]

Method A; Rt: 4.87 min. m/z: 365.1 $(M+H)^+$ Exact mass: 364.1

Compound 5

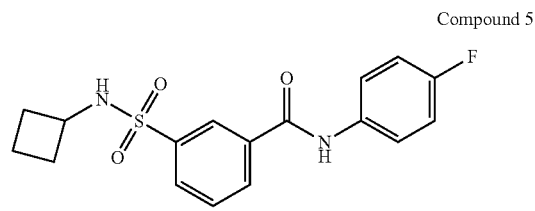 [SMILES: O=C(Nc1ccc(F)cc1)c1cccc(S(=O)(=O)NC2CCC2)c1]

Method A; Rt: 5.32 min. m/z: 349.1 $(M+H)^+$ Exact mass: 348.1

Compound 79

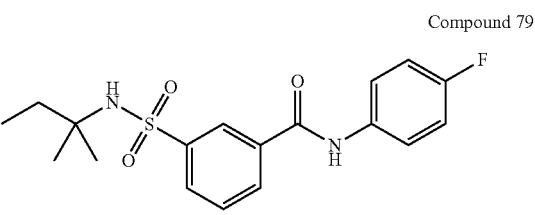 [SMILES: CCC(C)(C)NS(=O)(=O)c1cccc(C(=O)Nc2ccc(F)cc2)c1]

Method A; Rt: 5.39 min. m/z: 365.2 $(M+H)^+$ Exact mass: 364.1

$^1$H NMR (400 MHz, CHLOROFORM-d) δ ppm 8.37 (1H, t, J=1.5 Hz), 8.16 (1H, br. s.), 8.11 (1H, dm, J=8.0 Hz), 8.05 (1H, dm, J=8.0 Hz), 7.57-7.70 (3H, m), 7.08 (2H, t, J=8.7 Hz), 4.78 (1H, s), 1.55 (2H, q, J=7.5 Hz), 1.18 (6H, s), 0.84 (3H, t, J=7.5 Hz).

Compound 83

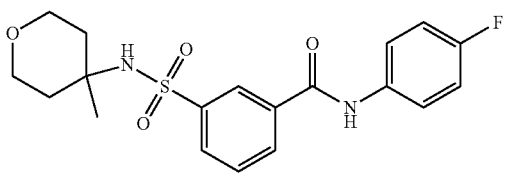

Method A; Rt: 4.20 min. m/z: 415.0 (M+Na)+ Exact mass: 392.1; Purified by silica gel chromatography (gradient eluent: petroleum ether/ethyl acetate from 100/1 to 1/1). $^1$H NMR (400 MHz, DMSO-d$_6$) δ ppm 10.57 (1H, br. s), 8.33-8.47 (1H, m), 8.19 (1H, dm, J=7.5 Hz), 8.06 (1H, dm, J=7.5 Hz), 7.72-7.85 (3H, m), 7.66-7.73 (1H, br. s), 7.12-7.31 (2H, m), 3.42-3.58 (4H, m), 1.71-1.92 (2H, m), 1.27-1.50 (2H, m), 1.06 (3H, s).

Compound 87

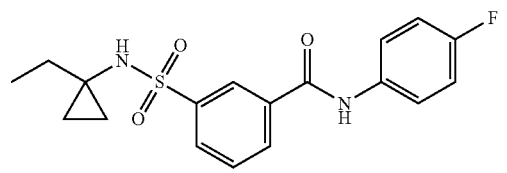

Method B; Rt: 3.94 min. m/z: 363.1 (M+H)+ Exact mass: 362.1

Purified by high performance liquid chromatography over RP-18 (eluent: CH$_3$CN in water (0.1% TFA) from 25 to 55, v/v). $^1$H NMR (400 MHz, DMSO-d$_6$), δ ppm 0.34-0.42 (m, 2H), 0.46-0.54 (m, 2H), 0.75 (t, J=7.3 Hz, 3H), 1.28 (q, J=7.3 Hz, 2H), 7.15-7.25 (m, 2H) 7.67-7.83 (m, 3H), 7.97 (d, J=8.3 Hz; 1H), 8.14-8.25 (m, 2H), 8.33 (s, 1H), 10.55 (s, 1H).

Compound 89

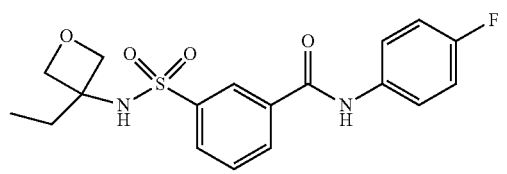

Method E; Rt: 4.83 min. m/z: 379.1 (M+H)+ Exact mass: 378.1; $^1$H NMR (400 MHz, DMSO-d$_6$), δ ppm 10.60 (s, 1H), 8.48 (br. s., 1H), 8.39 (s, 1H), 8.23 (d, J=7.8 Hz, 1H), 8.04 (d, J=7.8 Hz, 1H), 7.74-7.87 (m, 3H), 7.23 (t, J=9.0 Hz, 2H), 4.51 (d, J=6.5 Hz, 2H), 4.20 (d, J=6.5 Hz, 2H), 1.84 (q, J=7.3 Hz, 2H), J=7.3 Hz, 3H). Prepared similarly as described for compound 1, using 3-ethyloxetan-3-amine instead of 4-aminotetrahydropyran. Synthesis of 3-ethyl-oxetan-3-amine: 3-ethyloxetane-3-carboxylic acid (3.0 g, 23.1 mmol), DPPA (Diphenylphosphoryl azide, 7.61 g, 27.7 mmol), triethylamine (3.0 g, 23.1 mmol) and BnOH (2.99 g, 27.7 mmol) were dissolved in toluene (50 mL). The mixture was stirred at 110° C. overnight. The solvent was removed in vacuo. Dichloromethane (50 mL) was added. The mixture was washed with 1N HCl (20 mL). The aqueous layer was extracted with dichloromethane (20 mL). The combined organic layers were washed with brine and dried over Na$_2$SO$_4$. The solvent was removed in vacuo. The residue was purified by column chromatography over silica gel (eluent: petroleum ether/ethyl acetate from 100/1 to 60/40) resulting in benzyl 3-ethyloxetan-3-ylcarbamate (4.0 g). To a solution of benzyl 3-ethyloxetan-3-ylcarbamate (2.0 g, 8.5 mmol) and cyclohexa-1,4-diene (1.02 g, 12.75 mmol) in MeOH (20 mL) was added Pd—C (10%, 0.2 g) under N$_2$. The mixture was stirred under H$_2$ balloon at 25° C. for 4 hours. After filtration, the filtrate was concentrated resulting in 3-ethyloxetan-3-amine (860 mg), which was used as such in the next reaction.

Synthesis of Compound 6

Compound 6

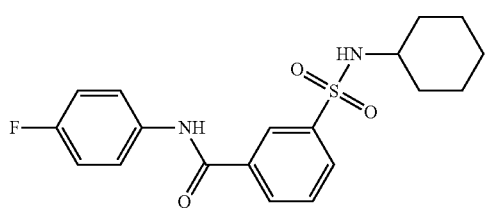

To a solution of 3-(chlorosulfonyl)benzoic acid (1 g, 4.53 mmol) in CH$_2$Cl$_2$ (20 mL) at 5° C., cyclohexanamine (0.899 g, 9.06 mmol) and triethylamine (1.38 g, 13.60 mmol) were successively added drop wise. The solution was stirred at room temperature overnight. The mixture was washed with 1N HCl (50 mL). The organic phase was dried over MgSO$_4$ and concentrated resulting in 3-(N-cyclohexylsulfamoyl) benzoic acid as a white solid (1.2 g), which was used in the next step without purification. To a solution of 3-(N-cyclohexylsulfamoyl)benzoic acid (1.2 g, 4.24 mmol) in DMF (15 mL) at 5° C., 4-fluoroaniline (0.52 g, 4.66 mmol) and DIPEA (1.64 g, 12.71 mmol) were successively added. The mixture was stirred for 20 minutes and then HATU (1.93 g, 5.08 mmol) was added. The solution was stirred at room temperature overnight. To the reaction mixture aqueous NaHCO$_3$ (50 mL) was added followed by EtOAc (50 mL). The organic layer washed with HCl (5%; 50 mL) and brine. The organic layer was dried with MgSO$_4$ and concentrated, resulting in a residue. The obtained residue was purified by a silica gel chromatography column (Petroleum ether:EtOOAc=2:1) resulting in compound 6 as a white solid (850 mg). Method B; Rt: 4.50 min. m/z: 377.2 (M+H)+ Exact mass: 376.1

Synthesis of Compound 7

Compound 7

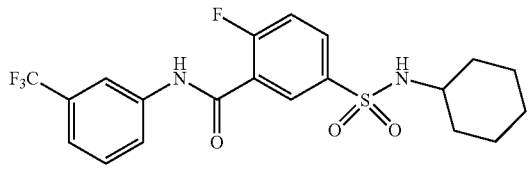

To 5-(chlorosulfonyl)-2-fluorobenzoic acid (10 g, 41.91 mmol) in EtOAc (150 mL) cyclohexanamine (12.47 g, 125.72 mmol) was added at room temperature. The reaction mixture was stirred at room temperature for 10 minutes and washed with 1N HCl (100 mL). The organic phase was dried over MgSO$_4$ and concentrated resulting in 5-(N-cyclohexylsulfamoyl)-2-fluorobenzoic acid as a white solid (10.9 g), which was used in the next steps without further purification. To a solution of 5-(N-cyclohexyl-sulfamoyl)-2-fluorobenzoic acid (1 g, 3.32 mmol) in DMF (15 mL) 3-(trifluoromethyl)-aniline (0.54 g, 3.32 mmol) and DIPEA (1.29 g, 9.96 mmol) were successively added at 5° C. The mixture was stirred for 20 minutes and then HATU (1.51 g, 3.98 mmol) was added. The solution was stirred at room temperature overnight. To the reaction mixture aqueous NaHCO$_3$ (50 mL), was added followed by EtOAc (50 mL). The organic layer was washed with HCl (5%) and brine. The organic layer was dried with MgSO$_4$, concentrated in vacuo, and the obtained residue was purified by preparative HPLC resulting in compound 7 (902 mg) as a white solid. Method B; Rt: 4.85 min. m/z: 445.2 (M+H)$^+$ Exact mass: 444.1; $^1$H NMR (400 MHz, DMSO-d$_6$) δ ppm 10.94 (1H, br. s), 8.15-8.22 (1H, m), 8.12 (1H, dd, J=6.5, 2.5 Hz), 8.03 (1H, ddd, J=9.0, 4.5, 2.5 Hz), 7.88-7.97 (1H, m), 7.83 (1H, d, J=7.5 Hz), 7.58-7.67 (2H, m), 7.46-7.54 (1H, m), 2.90-3.07 (1H, m), 1.51-1.67 (4H, m), 1.38-1.51 (1H, m), 0.96-1.27 (5H, m)

Examples of compounds prepared similar as compound 7, using the corresponding anilines instead of 3-(trifluoromethyl)aniline:

Compound 18

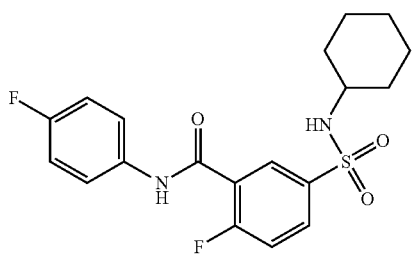

$^1$H NMR (400 MHz, DMSO-d$_6$) δ ppm 10.68 (1H, br. s), 8.08 (1H, dd, 2.5 Hz), 8.01 (1H, ddd, J=8.5, 4.5, 2.5 Hz), 7.83 (1H, br. s), 7.70-7.77 (2H, m), 7.60 (1H, app. t, J=9.0 Hz), 7.18-7.27 (2H, m), 2.90-3.07 (1H, m), 1.53-1.67 (4H, m), 1.40-1.53 (1H, m), 0.96-1.25 (5H, m). Method C; Rt: 4.21 min. m/z: 395.1 (M+H)$^+$ Exact mass: 394.1

Compound 19

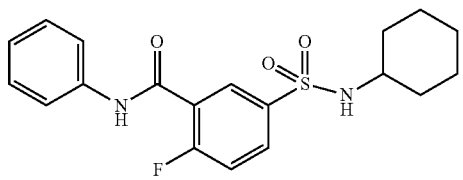

Method C; Rt: 4.17 min. m/z: 377.1 (M+H)$^+$ Exact mass: 376.1

Compound 43

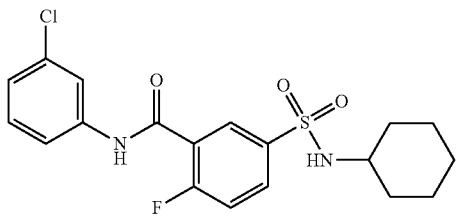

Method C; Rt: 4.53 min. m/z: 411.1 (M+H)$^+$ Exact mass: 410.1

Compound 8

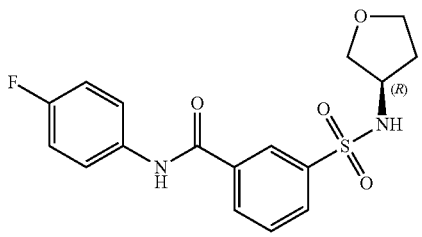

To a solution of (R)-tetrahydrofuran-3-amine (0.87 g, 9.97 mmol) in THF (20 mL) aqueous sodium hydroxide was added (4 mL, 5 N) in ice bath followed by 3-(chlorosulfonyl)benzoic acid (2.2 g, 9.97 mmol). After stirring at 25° C. for 3 hours, the reaction mixture was diluted with H$_2$O (20 mL) and extracted with EtOAc (20 mL). The aqueous layer was adjusted to pH=3 by aq. HCl (2 N) and then the resulting mixture was extracted with EtOAc (3×20 mL). The combined organic layer was washed by brine, dried over anhydrous MgSO$_4$ and concentrated in vacuo resulting in compound (R)-3-(N-(tetrahydrofuran-3-yl)sulfamoyl)benzoic acid (900 mg). To a solution of compound (R)-3-(N-(tetrahydrofuran-3-yl)sulfamoyl)benzoic acid (0.80 g, 2.95 mmol), 4-fluoroaniline (0.39 g, 3.54 mmol), and HATU (3.36 g, 8.85 mmol) in CH$_2$Cl$_2$ (10 mL) cooled in an ice bath under N$_2$ atmosphere, DIPEA (0.57 g, 0.44 mmol) was added. The resulting mixture was diluted with CH$_2$Cl$_2$ (15 mL) and washed with saturated aqueous NaHCO$_3$ (15 mL) and brine (10 mL). After drying over anhydrous MgSO$_4$ the solvent was removed in vacuo. The obtained residue was purified by preparative high performance liquid chromatography over RP-18 (eluent: CH$_3$CN in H$_2$O: from 40% to 80%, v/v; 0.05% TFA as addition). The pure fractions were collected and the volatiles were removed in vacuo. The aqueous layer was adjusted to PH=7 with Amberlite IRA-900 ion exchange resin (OH form), filtrated and lyophilized. The obtained residue was further purified by prep. SFC (Column: Chiralpak AD-3 150×4.6 mm I.D., 3 um Mobile phase: 40% of methanol (0.05% diethylamine) in CO$_2$. Flow rate: 2.5 mL/min) resulting in compound 8 (370 mg) Method A; Rt: 4.6 min. m/z: 365.2 (M+H)$^+$ Exact mass: 364.1; [α]$_D^{20}$=−13.60 (c=0.11, MeOH)$^1$H NMR (400 MHz, DMSO-d$_6$) δ ppm 10.57 (1H, br. s), 8.34-8.40 (1H, m), 8.18-8.27 (1H, m), 8.09 (1H, br. s), 7.99-8.06 (1H, m), 7.74-7.84 (3H, m), 7.13-7.33 (2H, m), 3.64-3.83 (2H, m), 3.50-3.64 (2H, m), 3.35-3.39 (1H, m), 1.80-1.99 (1H, m), 1.51-1.68 (1H, m).

Compound 9

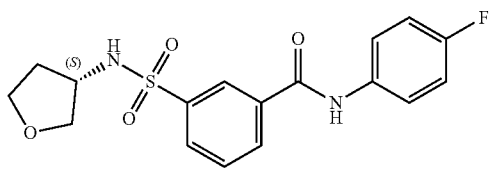

To an iced-cooled mixture of (S)-tetrahydrofuran-3-amine hydrochloride (0.500 g, 4.41 mmol) and NaOH (0.485 g, 12.138 mmol) in H$_2$O (5 mL) and THF (5 mL) 3-(chlorosulfonyl)benzoic acid (0.893 g, 4.406 mmol) was added in several portions. Then, the reaction mixture was stirred at 20° C. for 2 hours. The resulting mixture was diluted with H$_2$O (10 mL) and extracted with ethyl acetate (10 mL). The pH value of aqueous layer was adjusted to 3 by adding 1N HCl and then the mixture was extracted with ethyl acetate (3×10 mL). The combined organic layer was washed by brine (10 mL), dried over anhydrous Na$_2$SO$_4$ and concentrated under reduced pressure resulting in (S)-3-(N-(tetrahydrofuran-3-yl)sulfamoyl)benzoic acid (0.60 g). To an ice cooled mixture of (S)-3-(N-(tetrahydrofuran-3-yl)sulfamoyl)benzoic acid (600 mg, 2.212 mmol), 4-fluoroaniline (270 mg, 2.433 mmol) and HATU (1.01 g, 2.654 mmol) in DMF (5 mL) DIPEA (1.15 mL, 6.636 mmol) was added under N$_2$ atmosphere. The resulting mixture was stirred at 20° C. for 2 hour. The solvent was removed in vacuo.

The mixture was washed with saturated aqueous critic acid (10 mL), brine and dried over Na$_2$SO$_4$. The solvent was removed in vacuo. The residue was purified by column chromatography over silica gel (gradient eluent: petroleum ether/ethyl acetate from 100/0 to 10/90). The pure fractions were collected and the solvent was removed in vacuo. The residue was further purified by preparative high performance liquid chromatography over RP-18 (eluent: CH$_3$CN in H$_2$O from 40% to 80%, v/v; 0.06% NH$_4$HCO$_3$ as addition). The pure fractions were collected and the volatiles were removed in vacuo. The aqueous layer was lyophilized to dryness resulting in compound 9 (0.48 g) Method A; Rt: 4.6 min. m/z: 365.2 (M+H)$^+$ Exact mass: 364.1; $[\alpha]_D^{20}$=+15.56 (c 0.10, MeOH); $^1$H NMR (400 MHz, 80° C., DMSO-d$_6$) δ ppm 10.35 (1H, br. s), 8.32-8.48 (1H, m), 8.15-8.32 (1H, m), 8.03 (1H, br. s), 7.83-7.94 (1H, m), 7.68-7.83 (3H, m), 7.06-7.31 (2H, m), 3.70-3.87 (2H, m), 3.51-3.70 (2H, m), 3.32-3.48 (1H, m), 1.85-2.04 (1H, m), 1.59-1.78 (1H, m)

Compounds prepared similarly as described for compound 8 and 9 from the corresponding amines instead of tetrahydrofuran-3-amine:

Compound 10

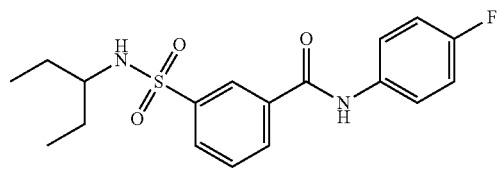

Method B; Rt: 4.24 min. m/z: 365.2 (M+H)$^+$ Exact mass: 364.1;

Compound 76

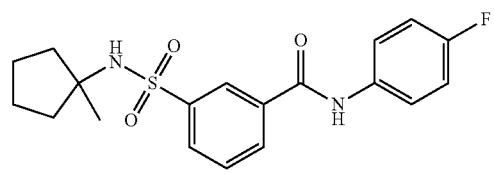

Using 1-methylcyclopentanamine instead of tetrahydrofuran-3-amine, purified using Gemini 250*20 mm*5 um (eluent: CH$_3$CN in H$_2$O (0.1% TFA) from 40% to 70%, v/v). Method B; Rt: 4.24 min. m/z: 377.2 (M+H)$^+$ Exact mass: 376.1;

Synthesis of 3-(N-cyclopentylsulfamoyl)benzoic acid

To an iced-cooled mixture of cyclopentanamine (1.93 g, 22.66 mmol) and a solution of NaOH (1.81 g, 45.32 mmol) in H$_2$O (25 mL) and THF (25 mL) was added 3-(chlorosulfonyl)benzoic acid (5.0 g, 22.66 mmol) in portions. The reaction mixture was stirred at 20° C. for 2 hours. The resulting mixture was diluted with H$_2$O (20 mL) and extracted with ethyl acetate (30 mL). The aqueous layer was separated and adjusted pH=2 by 4 N HCl and extracted with dichloromethane (3×30 mL). The combined organic layer was washed by brine (15 mL), dried over anhydrous Na$_2$SO$_4$ and concentrated under reduced pressure to afford 3-(N-cyclopentylsulfamoyl)benzoic acid (4.5 g).

Compound 11

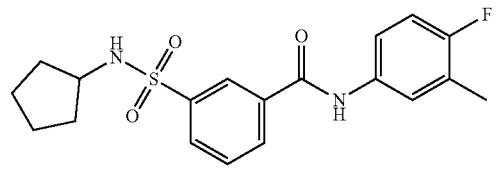

To an ice cooled mixture of 3-(N-cyclopentylsulfamoyl) benzoic acid (250 mg, 0.928 mmol), 4-fluoro-3-methylaniline (116.2 mg, 0.928 mmol), HATU (388.2 mg, 1.021 mmol) in CH$_2$Cl$_2$ (15 mL) DIPEA (359.8 mg, 2.784 mmol) was added under a N$_2$ atmosphere. The resulting mixture was stirred at 20° C. for 16 hours. The solvent was removed in vacuo. The mixture was washed with saturated aqueous critic acid (10 mL), brine and dried over Na$_2$SO$_4$. The solvent was removed in vacuo. The residue was purified by column chromatography over silica gel (gradient eluent: petroleum ether/ethyl acetate from 100/0 to 10/90). The pure fractions were collected and the solvent was removed in vacuo. The residue was further purified by preparative high performance liquid chromatography over RP-18 (eluent: CH$_3$CN in H$_2$O from 45% to 75%, v/v; 0.01% HCl as addition). The pure fractions were collected and the volatiles were removed in vacuo. The aqueous layer was adjusted to Ph=7 with Amberlite IRA-900 ion exchange resin (OH form), filtrated and lyophilized to dryness to afford compound 11 (170.0 mg). Method B; Rt: 4.31 min. m/z: 377.2 (M+H)$^+$ Exact mass: 376.1; $^1$H NMR (400 MHz, DMSO-d$_6$) δ ppm 10.47 (1H, br. s), 8.33-8.35 (1H, m), 8.17 (1H, dm, J=8.0), 7.98 (1H, dm, J=8.0), 7.78 (1H, d, J=7.0 Hz), 7.74 (1H, t, J=8.0 Hz), 7.62-7.68 (1H, m), 7.53-7.61 (1H, m), 7.13 (1H, t, J=9.0 Hz), 3.37-3.48 (1H, m), 2.23 (3H, d, J=1.8 Hz), 1.44-1.69 (4H, m), 1.12-1.45 (4H, m)

Prepared similarly as compound 11 starting from the corresponding anilines instead of 4-fluoro-3-methylaniline:

Compound 12

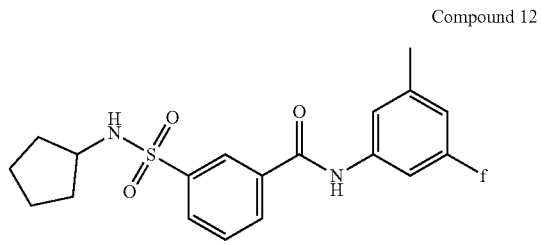

$^1$H NMR (400 MHz, DMSO-d$_6$) δ ppm 10.60 (1H, bs), 8.36 (1H, t, J=1.5 Hz), 8.19 (1H, dm, J=7.5 Hz), 8.02 (1H, dm, J=7.5 Hz), 7.81 (1H, d, J=7.5 Hz), 7.78 (1H, t, J=7.5 Hz), 7.55 (1H, dm, J=11.0 Hz), 7.38-7.46 (1H, m), 6.82 (1H, dm, J=9.5 Hz), 3.41-3.54 (1H, m), 2.34 (3H, s), 1.45-1.70 (4H, m), 1.19-1.45 (4H, m); Method B; Rt: 4.41 min. m/z: 377.2 (M+H)$^+$ Exact mass: 376.1

Compound 13

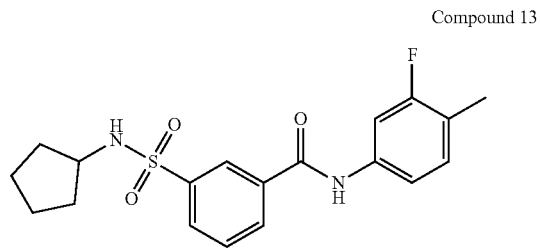 [SMILES: Cc1ccc(NC(=O)c2cccc(S(=O)(=O)NC3CCCC3)c2)cc1F]

The residue was purified by column chromatography over silica gel (gradient eluent: petroleum ether/ethyl acetate from 100/0 to 40/60). Method B; Rt: 4.41 min. m/z: 377.2 (M+H)$^+$ Exact mass: 376.1

Compound 14

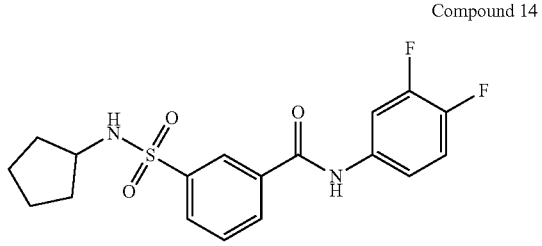 [SMILES: O=C(Nc1ccc(F)c(F)c1)c1cccc(S(=O)(=O)NC2CCCC2)c1]

Method B; Rt: 4.34 min. m/z: 381.2 (M+H)$^+$ Exact mass: 380.1

$^1$H NMR (400 MHz, DMSO-d$_6$) δ ppm 1.20-1.44 (m, 4H), 1.44-1.68 (m, 4H), 3.44 (sxt, J=6.8 Hz, 1H), 7.45 (dt, J=10.6, 9.0 Hz, 1H), 7.51-7.60 (m, 1H), 7.77 (t, J=7.8 Hz, 1H), 7.80 (d, J=7.2 Hz, 1H), 7.93 (ddd, J=13.2, 7.5, 2.5 Hz, 1H), 8.02 (d, J=7.8 Hz, 1H), 8.19 (d, J=7.7 Hz, 1H), 8.35 (t, J=1.7 Hz, 1H), 10.70 (s, 1H)

Compound 15

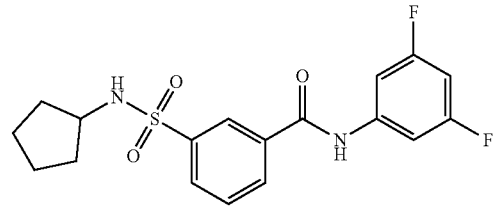

Method B; Rt: 4.43 min. m/z: 381.2 (M+H)$^+$ Exact mass: 380.1

Compound 77

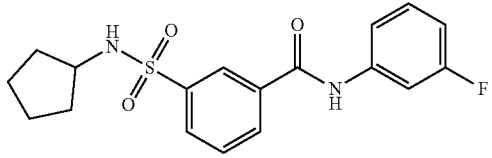

Method B; Rt: 5.45 min. m/z: 363.2 (M+H)$^+$ Exact mass: 362.1

Compound 81

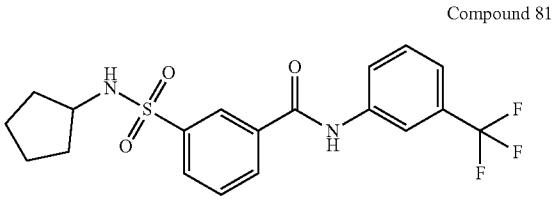 [SMILES: O=C(Nc1cccc(C(F)(F)F)c1)c1cccc(S(=O)(=O)NC2CCCC2)c1]

purified by preparative high performance liquid chromatography (column: Phenomenex Synergi 200 mm*77 mm, 10 um; mobile phase: CH$_3$CN in water (0.1% TFA) from 45% to 75%). Method A; Rt: 5.87 min. m/z: 413.2 (M+H)$^+$ Exact mass: 412.1

Compound 16

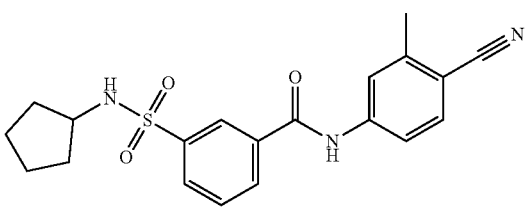

A solution of 3-(N-cyclopentylsulfamoyl)benzoic acid (500 mg, 1.73 mmol) in oxalyl dichloride (10 mL) was stirred at 45° C. for 5 hours. The solvent was removed in vacuo. The crude 3-(N-cyclopentylsulfamoyl)benzoyl chloride (600 mg) was used as such in the next step. To an ice cooled mixture of 3-(N-cyclopentylsulfamoyl)benzoyl chloride (600 mg, 1.74 mmol) and 4-amino-2-methylbenzonitrile (230 mg, 1.74 mmol) in CH$_2$Cl$_2$ (5 mL) was added pyridine (10 mL) under N$_2$ atmosphere. The resulting mixture was stirred at 20° C. for 16 hours. The solvent was removed in vacuo. The residue was purified by preparative high performance liquid chromatography over RP-18 (eluent: CH₃CN in H₂O from 50% to 80%, v/v; 0.05% TFA as addition). The pure fractions were collected and the volatiles were removed in vacuo. The aqueous layer was adjusted to PH=7 with Amberlite IRA-900 ion exchange resin (OH form), filtrated and lyophilized resulting in compound 16 (250 mg). Method B; Rt: 4.23 min. m/z: 384.2 (M+H)⁺ Exact mass: 383.1.

Compound 75

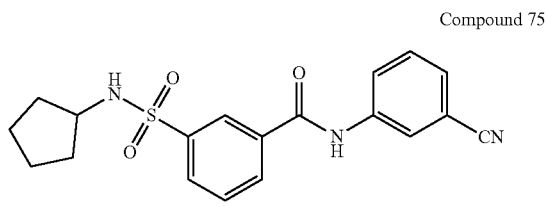 [SMILES: N#Cc1cccc(NC(=O)c2cccc(S(=O)(=O)NC3CCCC3)c2)c1]

Prepared similarly as described for compound 16 using 3-aminobenzonitrile instead of 4-amino-2-methylbenzonitrile. Method A; Rt: 5.24 min. m/z: 370.2 (M+H)⁺ Exact mass: 369.1.

Compound 80

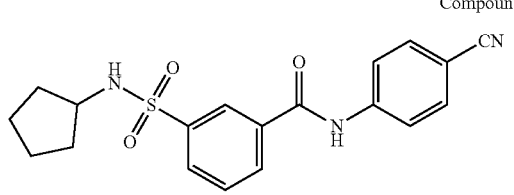

Prepared similarly as described for compound 16 using 4-aminobenzonitrile instead of 4-amino-2-methylbenzonitrile. Method A; Rt: 5.32 min. m/z: 370.2 (M+H)⁺ Exact mass: 369.1.

Compound 82

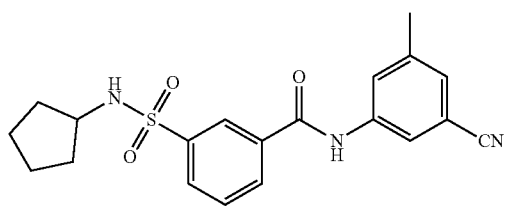

Prepared similarly as described for compound 16 using 3-amino-5-methylbenzonitrile instead of 4-amino-2-methylbenzonitrile. Method A; Rt: 5.52 min. m/z: 384.2 (M+H)⁺ Exact mass: 383.1.

Compound 17

To a solution of compound 2,4-dichloro-5-(piperidin-1-ylsulfonyl)benzoic acid (1.0 g, 2.96 mmol), m-toluidine (0.38 g, 3.55 mmol), and HATU (1.69 g, 4.44 mmol) in CH₂Cl₂ (10 mL) cooled in an ice bath, DIPEA (1.15 g, 8.88 mmol) was added under N₂ atmosphere. The resulting mixture was diluted with CH₂Cl₂ (15 mL) and washed with saturated aqueous NaHCO₃ (15 mL) and brine (10 mL), dried over anhydrous MgSO₄ and the solvent was removed in vacuo. The residue was purified by column chromatography over silica gel (gradient eluent: petroleum ether/ethyl acetate from 100/0 to 40/60). The pure fractions were collected and the solvent was removed in vacuo, resulting in compound 17 (0.65 g). Method B; Rt: 4.70 min. m/z: 427.1 (M+H)⁺ Exact mass: 426.1

Compound 46

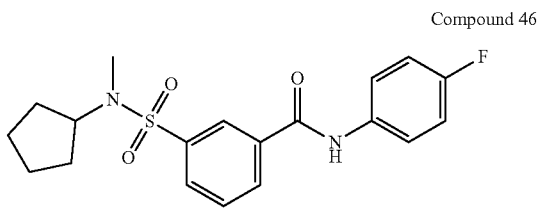 [SMILES: CN(C1CCCC1)S(=O)(=O)c1cccc(C(=O)Nc2ccc(F)cc2)c1]

To a solution of 3-(chlorosulfonyl)benzoic acid (1.10 g, 4.97 mmol) in THF (60 mL) sodium hydroxide was added (aq., 2 mL, 5N) in ice bath followed by adding N-methyl-cyclopentanamine (0.50 g, 4.97 mmol). After stirring at 25° C. for 3 hours, the reaction mixture was diluted with H₂O (50 mL) and extracted with EtOAc (50 mL). The aqueous layer was adjusted to pH=3 by HCl (2N) and extracted with EtOAc (3×50 mL). The combined organic layer was washed by brine, dried over anhydrous MgSO₄ and concentrated in vacuo resulting in 3-(N-cyclopentyl-N-methylsulfamoyl) benzoic acid (0.8 g). To a solution of 3-(N-cyclopentyl-N-methylsulfamoyl)benzoic acid (0.80 g, 2.82 mmol), 4-fluoroaniline (0.31 g, 2.82 mmol), and HATU (1.61 g, 4.24 mmol) in CH₂Cl₂ (10 mL), cooled in an icebath, DIPEA (1.09 g, 8.47 mmol) was added under N₂ atmosphere. The resulting mixture was diluted with CH₂Cl₂ (15 mL) and washed with saturated aqueous NaHCO₃ (15 mL) and brine (10 mL), dried over anhydrous MgSO₄ and the solvent was removed in vacuo. The obtained residue was purified by preparative high performance liquid chromatography over RP-18 (eluent: CH₃CN in H₂O from 30% to 80%, v/v; 0.05% TFA as addition). The pure fractions were collected and the volatiles were removed in vacuo. The aqueous layer was adjusted to Ph=7 with Amberlite IRA-900 ion exchange resin (OH form), filtrated and lyophilized to dryness resulting in compound 46 (0.73 g). Method B; Rt: 4.43 min. m/z: 377.2 (M+H)⁺ Exact mass: 376.1

Compound 56

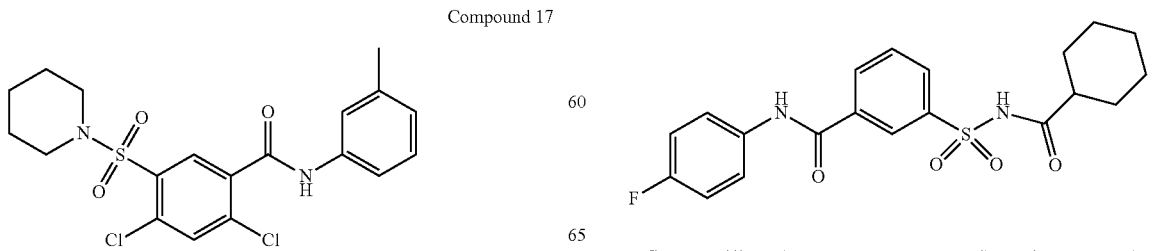

4-fluoroaniline (0.93 g, 8.366 mmol) and DIPEA (2.91 mL, 16.732 mmol) were dissolved in CH₂Cl₂ (20 mL).

3-(chlorosulfonyl)benzoyl chloride (2 g, 8.366 mmol) in CH₂Cl₂ (20 mL) was added in one portion at 0° C. The mixture was stirred for 1 hour at 0° C. The reaction mixture (40 mL) containing 3-(4-fluorophenylcarbamoyl)benzene-1-sulfonyl chloride was used to the next step without further purification. Ammonia (2.52 g, 18 mmol, 25-28% wt) was added to a solution of 3-(4-fluorophenylcarbamoyl)-benzene-1-sulfonyl chloride (obtained as above, 6 mmol) in CH₂Cl₂ (30 mL) at 0° C. The mixture was stirred for 1 hour at 20° C. 1 N HCl (30 mL) was added to the reaction mixture and the volatiles were partly removed in vacuo. The formed precipitate was filtered and co-evaporated with toluene (10 mL), resulting in N-(4-fluorophenyl)-3-sulfamoylbenzamide (1.6 g). A solution of N-(4-fluorophenyl)-3-sulfamoylbenzamide (1.8 g, 6.12 mmol) and cyclohexanecarbonyl chloride (1.79 g, 12.23 mmol) in chloroform (40 mL) with SiO₂ (180 mg) and H₂SO₄ (0.5 mL) was refluxed for 1 hour. Dichloromethane (20 mL) was added and the solid was filtered off. The filtrate was washed with water (10 mL) and dried over Na₂SO₄. The solvent was removed in vacuo. The obtained residue was purified by silica gel column chromatography (gradient eluent: petroleum ether/ethyl acetate from 100/0 to 70/30). The obtained product (1.2 g, purity 95%) was further washed with methyl t-butyl ether (10 mL) resulting in compound 56 (500 mg, 99.7% purity). Method A; Rt: 5.51 min. m/z: 405.2 (M+H)⁺ Exact mass: 404.1; ¹H NMR (400 MHz, DMSO-d₆) δ ppm 12.16 (1H, br. s), 10.62 (1H, br. s), 8.41 (1H, t, J=2.0 Hz), 8.27 (1H, dm, J=7.5 Hz), 8.09 (1H, dm, J=7.5 Hz), 7.73-7.82 (3H, m), 7.07-7.33 (2H, m), 2.11-2.31 (1H, m), 1.43-1.80 (5H, m), 0.94-1.32 (5H, m)

Compound 48

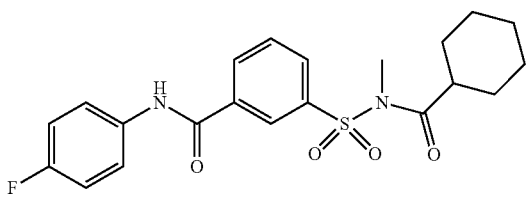

Compound 56 (600 mg) was dissolved in CH₂Cl₂ (6 mL) and MeOH (2 mL) and TMSCHN₂ (3.7 mL, 7.415 mmol, 2M in hexane) were added drop wise at 20° C. The mixture was stirred for 2 hours at 20° C. The solvent was removed in vacuo. The residue was purified by flash column (gradient eluent: petroleum ether/ethyl acetate from 100/0 to 70/30) resulting in a residue (0.41 g). The obtained product was further purified by preparative high performance liquid chromatography over RP-18 (eluent: CH₃CN in H₂O (0.1% TFA) from 20% to 50%, v/v). The pure fractions were collected and the volatiles were removed in vacuo. The precipitate was filtered and the residual water was removed by lyophilization resulting in compound 48 (300 mg). Method B; Rt: 4.60 min. m/z: 419.2 (M+H)⁺ Exact mass: 418.1; ¹H NMR (400 MHz, DMSO-d₆) δ ppm 10.62 (1H, br. s), 8.40-8.45 (1H, m), 8.28 (1H, dm, J=7.5 Hz), 8.13 (1H, dm, J=7.5 Hz), 7.66-7.95 (3H, m), 7.07-7.33 (2H, m), 3.40 (3H, s), 2.73-2.92 (1H, m), 1.42-1.77 (5H, m), 0.90-1.35 (5H, m).

Compound 63

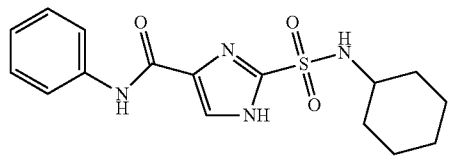

A mixture of ethyl 2-(chlorosulfonyl)-1H-imidazole-4-carboxylate (1 g, 4.19 mmol), Et₃N (1.27 g, 12.55 mmol) and cyclohexanamine (0.623 g, 6.28 mmol) in THF (25 mL) was stirred at room temperature for 15 hours. The mixture was concentrated and purified by preparative HPLC (Column: C18; Mobile phase A: purified water (0.075% TFA, V/V); Mobile phase B: acetonitrile; Flow rate: 80 mL/min; Gradient: 25-55%, 30 min) resulting in ethyl 2-(N-cyclohexylsulfamoyl)-1H-imidazole-4-carboxylate (0.6 g) as a light yellow solid. To a solution of ethyl 2-(N-cyclohexylsulfamoyl)-1H-imidazole-4-carboxylate (0.6 g, 1.99 mmol) in EtOH—H₂O (3/1; 20 mL), LiOH (0.145 g, 6.055 mmol) was added. The mixture was stirred at room temperature for 15 hours. The reaction mixture was neutralized with HCl (2M), diluted with water and then extracted into EtOAc, dried over MgSO₄, filtered and concentrated resulting in 2-(N-cyclohexylsulfamoyl)-1H-imidazole-4-carboxylic acid (400 mg) as a white solid. A mixture of 2-(N-cyclohexylsulfamoyl)-1H-imidazole-4-carboxylic acid (0.3 g, 1.098 mmol), aniline (0.102 g, 1.098 mmol), DIPEA (0.284 g, 2.196 mmol) and HATU (0.501 g, 1.317 mmol) in DMF (25 mL) was stirred at room temperature for 15 hours. The mixture was purified by preparative HPLC (Column: YMC 150×30 mm. Mobile phase A: purified water (0.075% TFA, V/V); Mobile phase B: acetonitrile; Flow rate: 30 mL/min; Gradient: 40-70%, 8 min) resulting in compound 63 (218 mg). Method B; Rt: 3.98 min. m/z: 349.2 (M+H)⁺ Exact mass: 348.1. ¹H NMR (400 MHz, METHANOL-d₄) δ ppm 1.26 (s, 5H) 1.51-1.62 (m, 1H) 1.65-1.80 (m, 4H) 3.23-3.29 (m, 1H) 7.10-7.18 (m, 1H) 7.32-7.39 (m, 2H) 7.67-7.74 (m, 2H) 7.86 (s, 1H);

Compound 64

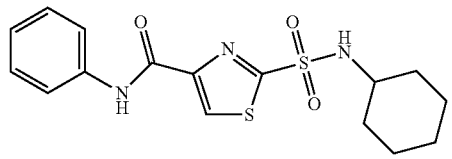

A mixture of ethyl 2-(chlorosulfonyl)thiazole-4-carboxylate (3 g, 11.73 mmol), Et₃N (3.56 g, 35.2 mmol) and cyclohexanamine (1.75 g, 17.65 mmol) in THF (100 mL) was stirred at room temperature for 15 hours. The mixture was concentrated and purified by preparative HPLC resulting in ethyl 2-(N-cyclohexylsulfamoyl)thiazole-4-carboxylate (2 g) as a white solid. To a solution of ethyl 2-(N-cyclohexylsulfamoyl)thiazole-4-carboxylate (2 g) in EtOH-THF (1/1, 60 mL) was added LiOH (0.451 g, 18.83 mmol). The mixture was stirred at room temperature for 15 hours. The reaction mixture was neutralized with HCl (2M), diluted with water and then extracted into EtOAc, dried over MgSO₄, filtered and concentrated in vacuo, resulting in 2-(N-cyclohexyl-sulfamoyl)thiazole-4-carboxylic acid (1.7 g) as a white solid. A mixture of 2-(N-cyclo-hexylsulfamoyl)

thiazole-4-carboxylic acid (1 g), aniline (0.321 g, 3.44 mmol), DIPEA (1.33 g, 10.29 mmol) and HATU (1.57 g, 4.13 mmol) in DMF (40 mL) was stirred at room temperature for 15 hours. The mixture was concentrated and purified by preparative HPLC (Column: SYNERGI 250*50 10 um; Mobile phase A: purified water (0.075% TFA, V/V); Mobile phase B: acetonitrileFlow rate: 80 mL/min Gradient: 35-65%, 30 min) resulting in compound 64 (895 mg) as a white solid. Method B; Rt: 4.45 min. m/z: 366.1 (M+H)+ Exact mass: 365.1

Compound 65

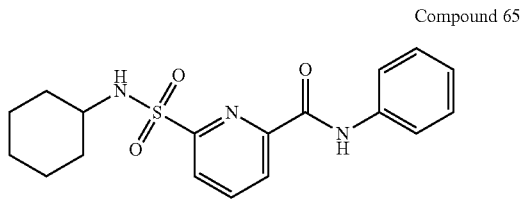 [SMILES: O=C(Nc1ccccc1)c1cccc(S(=O)(=O)NC2CCCCC2)n1]

The mixture of 6-chloro-N-phenylpicolinamide (4 g, 17.19 mmol), phenylmethanethiol (3.23 g, 25.79 mmol) and $K_2CO_3$ (4.75 g, 34.38 mmol) in DMF was stirred at 80° C. for 18 hour. The reaction mixture was diluted with EtOAc (150 mL), and washed with brine (2×200 mL). The organic layer was dried over $MgSO_4$, filtered and concentrated. The residue was purified by flash chromatography on silica gel (20% EtOAc in petroleum ether) to obtain 6-(benzylthio)-N-phenylpicolinamide (2.8 g). N-Chlorosuccinimide (3.42 g, 25.6 mmol) was added to the mixture of 6-(benzylthio)-N-phenylpicolinamide (2 g, 6.24 mmol) in acetic acid (60 mL) and water (40 mL). The reaction mixture was stirred at room temperature for 3 hours. The reaction was diluted with $CH_2Cl_2$ (100 mL). After washing with water, the organic layer was added to the mixture of cyclohexanamine (12.4 g, 125 mmol) and $Et_3N$ (50 mL) in $CH_2Cl_2$ (200 mL). The resulting mixture was stirred at room temperature for 4 hours. The reaction mixture was washed with $NH_4Cl$ (saturated), brine, dried over $MgSO_4$, filtered and concentrated. The obtained residue was purified by preparative HPLC (Column: Synergi 150*30 mm*5 um; Mobile phase A: purified water (0.075% TFA, V/V); Mobile phase B: acetonitrile; Flow rate: 30 mL/min; Gradient: 46-76% (solvent B), 8 min) resulting in compound 65 (330 mg). Method B; Rt: 4.46 min. m/z: 360.2 (M+H)+ Exact mass: 359.1. $^1$H NMR (400 MHz, DMSO-$d_6$) δ ppm 1.00-1.31 (m, 5H) 1.34-1.47 (m, 1H) 1.51-1.71 (m, 4H) 3.02-3.13 (m, 1H) 7.15-7.21 (m, 1H) 7.40-7.46 (m, 2H) 7.82-7.88 (m, 2H) 8.15 (dd, J=6.3, 2.5 Hz, 1H) 8.23-8.28 (m, 1H) 8.29-8.36 (m, 2H) 10.47 (s, 1H)

Compound 66

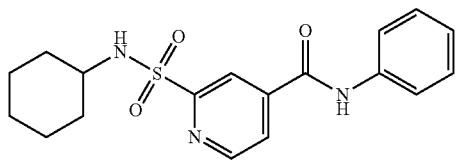

A mixture of 2-chloro-N-phenylisonicotinamide (2 g, 8.6 mmol), phenylmethanethiol (2.11 g, 17 mmol) and $K_2CO_3$ (2.35 g, 17 mmol) in DMF was stirred at 80° C. for 18 hours. The reaction was diluted with water (200 mL) and extracted with EtOAc (2×100 mL). The combined organic layers were washed with brine, dried over $MgSO_4$, filtered and concentrated. The obtained residue was purified by silica gel chromatography (0-20% EtOAc in petroleum ether) resulting in 2-(benzylthio)-N-phenylisonicotinamide (1.7 g). N-Chlorosuccinimide (2.56 g, 19.2 mmol) was added to a mixture of 2-(benzylthio)-N-phenylisonicotinamide (1.5 g, 4.68 mmol) in acetic acid (20 mL) and water (10 mL). The reaction mixture was stirred at room temperature for 4 hours. The reaction was diluted with $CH_2Cl_2$ (20 mL). After washing with water, the organic layer was added to the mixture of cyclohexanamine (4.641 g, 46.8 mmol) and $Et_3N$ (10 mL, 71.74 mmol) in $CH_2Cl_2$ (50 mL). The resulting mixture was stirred at room temperature for 4 hours. The reaction mixture was washed with $NH_4Cl$ (saturated), brine, dried over $MgSO_4$, filtered and concentrated. The obtained residue was purified by preparative HPLC (Column: C18-10 um; Mobile phase A: purified water (0.075% TFA, V/V); Mobile phase B: acetonitrile; Flow rate: 80 mL/min; Gradient: 40-70% (solvent B), 25 min) resulting in compound 66 (250 mg). Method B; Rt: 4.22 min. m/z: 360.2 (M+H)+ Exact mass: 359.1. $^1$H NMR (400 MHz, DMSO-$d_6$) δ ppm 0.96-1.08 (m, 1H) 1.08-1.24 (m, 4H) 1.40-1.52 (m, 1H) 1.53-1.67 (m, 4H) 3.11-3.22 (m, 1H) 7.14-7.21 (m, 1H) 7.37-7.44 (m, 2H) 7.78 (d, J=7.8 Hz, 2H) 7.97 (br. s, 1H) 8.12 (dd, 1.5 Hz, 1H) 8.40 (s, 1H) 8.94 (d, J=5.0 Hz, 1H) 10.75 (s, 1H)

Compound 67

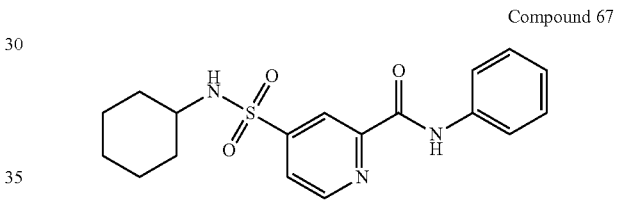

2-chloro-N-cyclohexylpyridine-4-sulfonamide (540 mg, 1.965 mmol), $PdCl_2dppf$ (100 mg, 0.137 mmol) and $Et_3N$ (5.89 mmol) in methanol (50 mL) was stirred at 50° C. for 18 hours under CO (50 Psi) atmosphere. The solvent was removed under reduced pressure. The obtained residue (700 mg) containing methyl 4-(N-cyclohexylsulfamoyl)-picolinate was used in the next step without further purification. $K_2CO_3$ (421 mg, 3.05 mmol) was added to the mixture of methyl 4-(N-cyclohexylsulfamoyl)picolinate in methanol and water. The mixture was stirred at 20° C. for 18 hour. The solvent was removed, the residue was diluted with water (50 mL) and washed with EtOAc (2×50 mL). The aqueous layer was then acidified to pH=3 with 1 M HCl and extracted with EtOAc (2×50 mL). The combined organic layers were dried over $MgSO_4$, filtered and concentrated resulting in 4-(N-cyclohexylsulfamoyl)picolinic acid (380 mg). HATU (0.76 g, 2.0 mmol) was then added to a mixture of 4-(N-cyclohexylsulfamoyl)-picolinic acid (380 mg, 1.34 mmol), aniline (251 mg, 2.7 mmol) and DIPEA (0.517 g, 4.0 mmol) in DMF (50 mL) at room temperature The resulting mixture was stirred at room temperature for 18 hour. The mixture was diluted with water (200 mL), and extracted with EtOAc. The organic layers were washed with brine, dried over $MgSO_4$, filtered and concentrated in vacuo. The obtained residue was purified by silica gel chromatography (10-20% EtOAc in petroleum ether) resulting in compound 67 as a white solid (330 mg). Method B; Rt: 4.58 min. m/z: 360.2 (M+H)+ Exact mass: 359.1. $^1$H NMR (300 MHz, DMSO-$d_6$) δ ppm 0.93-1.26 (m, 5H) 1.37-1.50 (m, 1H) 1.50-1.69 (m, 4H) 2.98-3.12 (m, 1H) 7.15 (t, J=7.2 Hz, 1H) 7.32-7.45 (m, 2H)

7.86-7.97 (m, 2H) 8.03 (dd, J=5.0, 1.5 Hz, 1H) 8.25 (d, J=7.3 Hz, 1H) 8.47 (d, J=1.5 Hz, 1H) 9.00 (d, J=5.0 Hz, 1H) 10.78 (s, 1H)

Compound 68

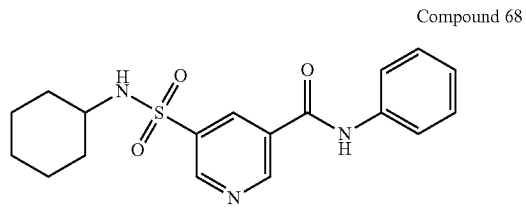 [SMILES: O=C(Nc1ccccc1)c1cncc(S(=O)(=O)NC2CCCCC2)c1]

Thionyl chloride (10 mL, 137 mmol) was added drop wise to water (60 mL) at 0-5° C. The mixture was stirred at room temperature for 16 hour. CuCl (40 mg, 0.4 mmol) was added, and the mixture (mixture A) was cooled to −5° C. To a mixture of 5-amino-nicotinic acid in con. HCl (35 mL), a solution of NaNO$_2$ (2.76 g, 40 mmol) in of water (40 mL) at −5° C. to 0° C., was added (mixture B). The mixture B was added portionwise to the mixture A over 30 minutes, maintaining temperature at −5° C. to 0° C. After stirring at 0° C. for 1 hour, the solid was collected by filtration, washed with water, and dried in vacuo resulting in 5-(chlorosulfonyl)nicotinic acid (1.05 g). The mixture of 5-(chlorosulfonyl)nicotinic acid (1 g, 4.5 mmol), cyclohexanamine (0.893 g, 9 mmol) and Et$_3$N (1.37 mmol, 13.5 mmol) in CH$_2$Cl$_2$ (30 mL) was stirred at room temperature for 18 hours. The solvent was removed under reduced pressure. The residue was purified by HPLC (Column: C18 10 um; Mobile phase A: purified water (0.075% TFA, V/V); Mobile phase B: acetonitrile; Flow rate: 80 mL/min; Gradient: 30-60% (solvent B), 30 min) resulting in 5-(N-cyclohexylsulfamoyl) nicotinic acid as a white solid (1 g). HATU (2.6 g, 7 mmol) was added to the mixture of 5-(N-cyclohexylsulfamoyl) nicotinic acid (1 g, 3.5 mmol), aniline (391 mg, 4.2 mmol) and DIPEA (1.36 g, 10.5 mmol) in DMF (50 mL) at room temperature The resulting mixture was stirred at room temperature for 18 hour. The mixture was diluted with of water (200 mL) and extracted with EtOAc. The organic layers were washed with brine, dried over MgSO$_4$, filtered and concentrated. The residue was purified by silica gel chromatography (10-100% EtOAc in petroleum ether) resulting in compound 68 (708 mg) as white solid. Method B; Rt: 4.58 min. m/z: 360.2 (M+H)$^+$ Exact mass: 359.1

Compound 69

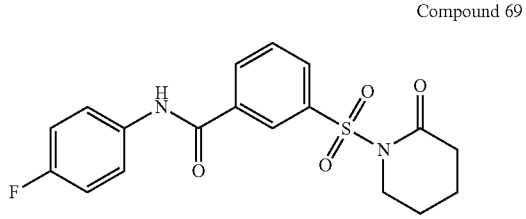 [SMILES: O=C(Nc1ccc(F)cc1)c1cccc(S(=O)(=O)N2CCCCC2=O)c1]

To an ice-cooled solution of 5-aminopentanoic acid (1.2 g, 3.44 mmol) and 1N NaOH (8 mL) in THF (16 mL) was added 3-(4-fluorophenylcarbamoyl)benzene-1-sulfonyl chloride (0.444 g, 3.78 mmol). Then the reaction mixture was stirred at 25° C. overnight. The resulting mixture was diluted with 1N HCl (10 mL) and extracted with ethyl acetate (2×30 mL). The combined organic layers were washed with brine, dried over anhydrous Na$_2$SO$_4$ and concentrated under reduced pressure. The residue was purified by silica gel column chromatography (gradient eluent: petroleum ether:ethyl acetate: from 100:0 to 65:35) resulting in 5-(3-(4-fluorophenylcarbamoyl)phenylsulfonamido) pentanoic acid (0.9 g). A mixture of 5-(3-(4-fluorophenylcarbamoyl)phenylsulfonamido) pentanoic acid (400 mg, 0.913 mmol), acetic anhydride (0.466 g, 4.57 mmol) and AcOK (1.79 g, 18.3 mmol) in toluene (25 mL) was heated by microwave irradiation at 150° C. for 30 minutes. The formed precipitate was filtered off and the filtrate was concentrated in vacuo. The residue was purified by preparative high performance liquid chromatography (eluent: CH$_3$CN in H$_2$O (0.05% HCl) from 0% to 35%, v/v). The pure fractions were collected and adjusted to pH=7 with Amberlite IRA-900 (OH)anionic exchange resin. The resin was filtered off and the filtrate was lyophilized to dryness resulting in compound 69 (200 mg). Method A; Rt: 4.97 min. m/z: 377.2 (M+H)$^+$ Exact mass: 376.1; $^1$H NMR (400 MHz, CHLOROFORM-d) δ ppm 1.78-1.87 (m, 2H), 1.90-1.99 (m, 2H), 2.44 (t, J=6.8 Hz, 2H), 3.95 (t, J=6.0 Hz, 2H), 7.08 (t, J=8.7 Hz, 2H), 7.55-7.70 (m, 3H), 8.15 (d, J=8.0 Hz, 1H), 8.20 (d, J=7.8 Hz, 1H), 8.26 (br. s., 1H), 8.49 (s, 1H)

Compound 70

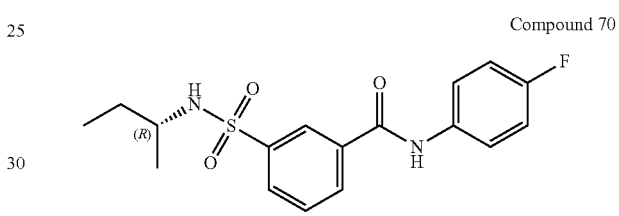

To an iced-cooled mixture of (R)-butan-2-amine (0.500 g, 6.837 mmol) and NaOH (0.547 g, 13.67 mmol) in H$_2$O (15 mL) and THF (15 mL), 3-(chlorosulfonyl)benzoic acid was added (1.508 g, 6.84 mmol) in portions. The reaction mixture was stirred at 20° C. for 2 hours. The resulting mixture was diluted with H$_2$O (15 mL) and extracted with ethyl acetate (15 mL). The aqueous layer was separated and pH was adjusted to 3 by 1 N HCl and extracted with ethyl acetate (3×10 mL). The combined organic layer was washed by brine (10 mL), dried over anhydrous Na$_2$SO$_4$ and concentrated under reduced pressure resulting in (R)-3-(N-sec-butylsulfamoyl)benzoic acid (0.73 g). To an ice cooled mixture of (R)-3-(N-sec-butylsulfamoyl)benzoic acid (730 mg), 4-fluoroaniline (347 mg, 3.121 mmol), HATU (1.294 g, 3.404 mmol) in DMF (10 mL) DIPEA (1.48 mL, 8.51 mmol) was added under N$_2$ atmosphere. The resulting mixture was stirred at 20° C. for 2 hour. The solvent was removed in vacuo. The mixture was washed with saturated aqueous critic acid (10 mL), brine and dried over Na$_2$SO$_4$. The solvent was removed in vacuo. The residue was purified by column chromatography over silica gel (gradient eluent: petroleum ether/ethyl acetate from 100/0 to 55/45). The pure fractions were collected and the solvent was removed in vacuo. The residue was purified by SFC separation (Chiralcel OJ, 20 μm; Supercritical CO$_2$: MeOH (0.2% diethylamine)). The pure fractions were collected and the solvent was removed in vacuo, resulting in compound 70 (300 mg). Method A; Rt: 5.25 min. m/z: 351.2 (M+H)$^+$ Exact mass: 350.1. [α]$_D^{20}$=-(c=0.2, MeOH). [α]$_D^{20}$=-9.9 (c 0.435 w/v %, DMF); Column: Chiralpak AD-3 150×4.6 mm I.D., 3 um; Mobile phase: methanol (0.05% diethylamine) in CO$_2$ from 5% to 40%; Flow rate: 2.5 mL/min; Rt: 7.58 min; $^1$H NMR (400 MHz, DMSO-d$_6$) δ ppm 0.70 (t, J=7.4 Hz, 3H), 0.88 (d, J=6.5 Hz, 3H), 1.30 (quin, J=7.2 Hz, 2H), 3.01-3.18

(m, 1H), 7.21 (t, J=8.8 Hz, 2H), 7.67 (br. d, J=5.5 Hz, 1H), 7.75 (t, J=7.8 Hz, 1H), 7.78 (dd, J=8.8, 5.1 Hz, 2H), 8.00 (d, J=7.8 Hz, 1H), 8.19 (d, J=7.8 Hz, 1H), 8.36 (s, 1H), 10.55 (s, 1H).

Compound 71

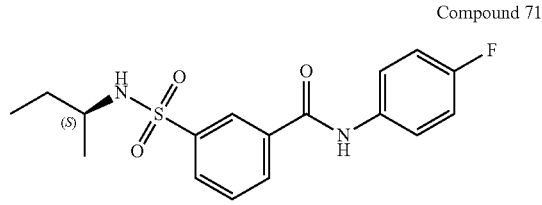

Prepared similar as described for compound 70 starting from (S)-butan-2-amine instead of (R)-butan-2-amine. Method B; Rt: 4.03 min. m/z: 351.2 (M+H)+ Exact mass: 350.1 ([α]$_D^{20}$=+(c=0.2, MeOH). [α]$_D^{20}$=+9.49 (c 0.611 w/v %, DMF), Column: Chiralpak AD-3 150×4.6 mm I.D., 3 um; Mobile phase: methanol (0.05% diethylamine) in CO$_2$ from 5% to 40%; Flow rate: 2.5 mL/min; Rt: 7.73 min. [α]$_{589}^{20}$+9.49° (c 0.61 w/v %, MeOH)

Compound 72

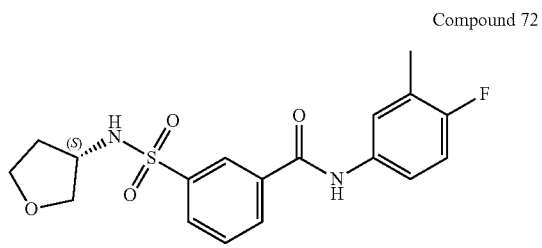

3-(chlorosulfonyl)benzoyl chloride (1200 mg, 5.0 mmol) was dissolved in dichloromethane (15 mL). A solution of 4-fluoro-3-methylaniline (625 mg, 5.0 mmol) and triethylamine (606 mg, 6.0 mmol) in dichloromethane (15 mL) was added to the mixture at 0° C. The mixture was stirred at 25° C. for 1 hour. The reaction mixture was used to the next step without further purification. To the above reaction mixture a solution of triethylamine (606 mg, 6.0 mmol) and (S)-tetrahydrofuran-3-amine (460.0 mg, 5.3 mmol) in dichloromethane (15 mL) was added at 0° C. The mixture was stirred at 25° C. for 1 hour. The solvent was removed in vacuo. The residue was purified by reversed phase high performance liquid chromatography (eluent: CH$_3$CN in water (0.1% TFA) from 25 to 55, v/v). The pure fractions were collected and the organic solvent was evaporated. The aqueous layer was neutralized with saturated aqueous NaHCO$_3$ to pH=7-8. The mixture was extracted with dichloromethane (3×15 mL). The combined organic layers were dried over Na$_2$SO$_4$ and concentrated in vacuo resulting in compound 72 (620 mg). Method A; Rt: 4.88 min. m/z: 379.2 (M+H)+ Exact mass: 378.1. $^1$H NMR (400 MHz, DMSO-d$_6$) δ ppm 1.56-1.65 (m, 1H), 1.85-1.94 (m, 1H), 2.22-2.28 (m, 3H), 3.33-3.39 (m, 1H), 3.52-3.65 (m, 2H), 3.65-3.73 (m, 1H), 3.73-3.79 (m, 1H), 7.14 (t, J=9.2 Hz, 1H), 7.56-7.62 (m, 1H), 7.67 (dd, J=7.0, 2.3 Hz, 1H), 7.78 (t, J=7.8 Hz, 1H), 8.02 (d, J=7.8 Hz, 1H), 8.10 (d, J=4.5 Hz, 1H), 8.21 (d, J=7.8 Hz, 1H), 8.37 (s, 1H), 10.49 (s, 1H)

Compound 85

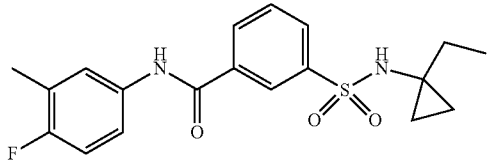

Prepared similarly as described for compound 72 using 1-ethylcyclopropanamine hydrochloride instead of (S)-tetrahydrofuran-3-amine. Compound 85 was purified by preparative high performance liquid chromatography over RP-18 (eluent: CH$_3$CN in H$_2$O (0.5% NH$_4$HCO$_3$) from 43% to 73%, v/v). Method B; Rt: 4.17 min. m/z: 377.1 (M+H)+ Exact mass: 376.1. $^1$H NMR (400 MHz, DMSO-d$_6$) δ ppm 0.35-0.45 (m, 2H), 0.49-0.58 (m, 2H), 0.77 (t, J=7.2 Hz, 3H), 1.31 (q, J=7.1 Hz, 2H), 2.26 (s, 3H), 7.15 (t, J=9.3 Hz, 1H), 7.55-7.64 (m, 1H) 7.69 (d, J=7.0 Hz, 1H), 7.76 (t, J=7.8 Hz, 1H), 7.98 (d, J=7.8 Hz, 1H), 8.16-8.25 (m, 2H), 8.35 (s, 1H), 10.50 (s, 1H).

Compound 86

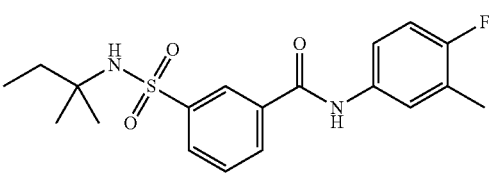

Prepared similarly as described for compound 72 using 2-methylbutan-2-aminehydro-chloride instead of (S)-tetrahydrofuran-3-amine. Purified by high performance liquid chromatography over RP-18 (eluent: CH$_3$CN in water from 47% to 77%, v/v). Method D; Rt: 5.97 min. m/z: 379.1 (M+H)+ Exact mass: 378.1. $^1$H NMR (400 MHz, DMSO-d$_6$), δ=0.73 (t, J=7.5 Hz, 3H), 1.02 (s, 6H), 1.44 (q, J=7.5 Hz, 2H), 2.23 (d, J=1.0 Hz, 3H), 7.12 (t, J=9.3 Hz, 1H), 7.52-7.61 (m, 2H), 7.64-7.77 (m, 2H), 8.01 (d, J=7.8 Hz, 1H), 8.14 (d, J=7.8 Hz, 1H), 8.36 (s, 1H). 10.45 (s, 1H).

Alternative Synthesis of Compound 72

A mixture of 3-(chlorosulfonyl)benzoyl chloride (4.61 g, 19.28 mmol) in toluene (45 mL) was refluxed under a gentle flow of nitrogen. 4-fluoro-3-methylaniline (2.19 g, 17.53 mmol) in toluene (15 mL) was added drop wise to the refluxing solution. After addition, the mixture was refluxed for another 30 minutes. The mixture was next cooled to room temperature, and a mixture of (S)-3-aminotetrahydrofuran tosylate (5 g, 19.28 mmol) and diisopropylethylamine (15 mL) in toluene (15 mL) and CH$_2$Cl$_2$ (10 mL) was added drop wise. After addition, the mixture was stirred for 4 hours at room temperature. The resulting mixture was washed with HCl (2×100 mL, 1M aq), water (2×100 mL) and NaHCO$_3$ (2×100 mL, sat. aq). The organic layer was dried on MgSO$_4$, filtered and concentrated under reduced pressure. The obtained residue was purified using silica gel chromatography (CH$_2$Cl$_2$-MeOH 100:0 to 95:5) yielding 3-(4-fluoro-3-methylphenylcarbamoyl)benzene-1-sulfonyl chloride (1.07 g) during CH$_2$Cl$_2$ elution, followed by compound 72 (2.85 g) as a white solid after removal of the solvent (dried in a vacuum oven at 55° C. for 20 hours). ([α]$_D^{20}$=−5.21 (c 0.67 w/v %, MeOH), Method F; Rt: 0.88 min. m/z: 379.1 (M+H)+ Exact mass: 378.1. The compound was crystallized from CH$_2$Cl$_2$: DSC (From 30 to 300° C. at 10° C./min): 149° C. [α]$_D^{20}$=+3.21 (c 0.65 w/v %, DMF).

Compound 73

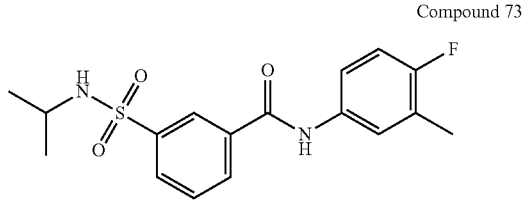 [SMILES: Cc1cc(NC(=O)c2cccc(S(=O)(=O)NC(C)C)c2)ccc1F]

To an iced-cooled solution of 3-(chlorosulfonyl)benzoic acid (50.0 g, 226.6 mmol) in ethylacetate (1000 mL) was added isopropylamine (67.0 g, 1.13 mol) in one portion. The reaction mixture was stirred at 25° C. for 3 hours. The resulting mixture was diluted with 1N HCl (500 mL) and extracted with ethyl acetate (2×500 mL). The combined organic layers were washed with brine (400 mL), dried over anhydrous Na$_2$SO$_4$ and concentrated under reduced pressure resulting 3-(N-isopropylsulfamoyl)benzoic acid (46 g). To an ice-cooled mixture of 3-(N-isopropylsulfamoyl)benzoic acid (7.0 g, 28.77 mmol), 4-fluoro-3-methylaniline (3.6 g, 28.77 mmol) and DIPEA (18.6 g, 143.91 mmol) in CH$_2$Cl$_2$ (70 mL) HATU (12.0 g, 31.56 mmol) was added under N$_2$ atmosphere. The resulting mixture was stirred at 20° for 16 hours. The solvent was removed in vacuo. The mixture was washed with saturated aqueous critic acid (30 mL), brine (20 mL) and dried over Na$_2$SO$_4$. The solvent was removed in vacuo. The residue was purified by preparative high performance liquid chromatography on SYNERGI 250*50 10 um (eluent: CH$_3$CN in H$_2$O (0.05% TFA) from 35% to 65%, v/v). The pure fractions were collected and adjusted to pH=7 with Amberlite IRA-900 (OH) anionic exchange resin. The resin was filtered off. The filtrate was lyophilized to dryness resulting in compound 73 (7.5 g). Method B; Rt: 3.44 min. m/z: 351.1 (M+H)+ Exact mass: 350.1 $^1$H NMR (400 MHz, DMSO-d$_6$) δ ppm 10.49 (1H, br. s), 8.36 (1H, t, J=1.5 Hz), 8.19 (1H, ddd, J=7.8, 1.5, 1.0 Hz), 8.01 (1H, ddd, J=7.8, 1.5, 1.0 Hz), 7.76 (1H, t, J=7.8 Hz), 7.68 (1H, dd, J=7.0, 3.0 Hz), 7.75 (1H, bs), 7.59 (1H, ddd, 4.5, 3.0 Hz), 7.15 (1H, t, J=9.0 Hz), 3.14-3.33 (1H, m), 2.25 (3H, d, J=1.5 Hz), 0.96 (6H, d, J=6.5 Hz).

Compound 74

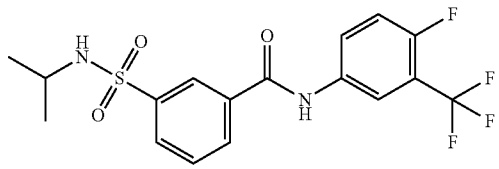

Prepared similarly as described for compound 73, using 4-fluoro-3-(trifluoromethyl)-aniline instead of 4-fluoro-3-methylaniline. Purified on HPLC Synergi 150×30 mm×5 u (eluent: CH$_3$CN in H$_2$O (0.05% HCl) from 45% to 75%, v/v). Method A; Rt: 5.62 min. m/z: 405.2 (M+H)+ Exact mass: 404.1. $^1$H NMR (400 MHz, DMSO-d$_6$) δ ppm 10.82 (1H, s), 8.39 (1H, t, J=1.5 Hz), 8.17-8.30 (2H, m), 8.07-8.17 (1H, m), 8.03 (1H, d, J=7.8), 7.73-7.83 (2H, m), 7.55 (1H, t, J=10.0 Hz), 3.20-3.33 (1H, m), 0.95 (6H, d, J=6.5 Hz).

Compound 84

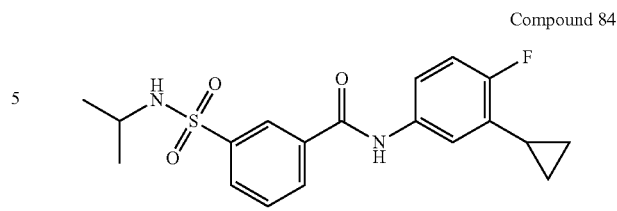

A mixture of N-(3-bromo-4-fluorophenyl)-3-(N-isopropylsulfamoyl)benzamide (prepared similarly as described for compound 73, using 3-bromo-4-fluoroaniline instead of 4-fluoro-3-methylaniline and purified via preparative high performance liquid chromatography over RP-18 (eluent: CH$_3$CN in H$_2$O (0.05% NH$_4$HCO$_3$) from 40% to 70%, v/v); 700 mg, 1.69 mmol), cyclopropylboronic acid (0.22 g, 2.529 mmol), Pd(PPh$_3$)$_4$ (0.20 g, 0.169 mmol) and Na$_2$CO$_3$ (1.43 g, 13.49 mmol) in water (7 mL), EtOH (7 mL) and toluene (7 mL) was heated by microwave irradiation for 40 minutes at 100° C. under N$_2$. The reaction mixture was filtered through celite. Water (10 mL) was added to the filtrate and the mixture was extracted with ethyl acetate (2×10 mL). The combined organic layers were washed with brine and dried over Na$_2$SO$_4$. The solvent was removed in vacuo. The residue was purified by preparative high performance liquid chromatography over RP-18 (eluent: CH$_3$CN in H$_2$O (0.1% TFA) from 20% to 50%, v/v). The pure fractions were collected and the volatiles were removed in vacuo. The aqueous layer was adjusted to pH=7 with saturated aqueous NaHCO$_3$ and extracted with ethyl acetate (2×20 mL). The combined organic layers were dried over Na$_2$SO$_4$. The solvent was removed in vacuo and the obtained residue was further purified by supercritical fluid chromatography (Column: Chiralpak AD-3 150×4.6 mm I.D., 3 um Mobile phase: methanol (0.05% diethylamine) in CO$_2$ from 5% to 40%. Flow rate: 2.5 mL/min). The pure fractions were collected and the volatiles were removed in vacuo. The residue was suspended in water (5 mL) and lyophilized to dryness resulting in compound 84 (35 mg) Method B; Rt: 4.18 min. m/z: 377.1 (M+H)+ Exact mass: 376.1; $^1$H NMR (400 MHz, chloroform-d) δ ppm 8.34 (s, 1H), 8.12 (d, J=8.0 Hz, 1H), 7.97-8.07 (m, 2H), 7.65 (t, J=8.0 Hz, 1H), 7.36-7.46 (m, 1H), 7.15-7.22 (m, 1H), 7.01 (t, J=9.3 Hz, 1H), 4.65 (d, J=7.5 Hz, 1H), 3.44-3.58 (m, 1H), 2.04-2.16 (m, 1H), 1.10 (d, J=6.5 Hz, 6H), 0.96-1.06 (m, 2H), 0.71-0.82 (m, 2H).

Compound 88

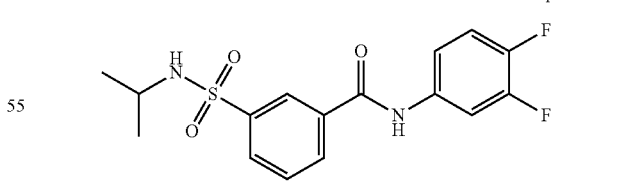

Prepared similarly as described for compound 73, using 3,4-difluoroaniline instead of 4-fluoro-3-methylaniline. Method E; Rt: 5.31 min. m/z: 355.1 (M+H)+ Exact mass: 354.1; $^1$H NMR (400 MHz, DMSO-d$_6$) δ ppm 10.71 (s, 1H), 8.36 (t, J=1.5 Hz, 1H), 8.19 (d, J=7.8 Hz, 1H), 7.98-8.08 (m, 1H), 7.94 (ddd, J=13.2, 7.5, 2.4 Hz, 1H), 7.71-7.83 (m, 2H), 7.53-7.59 (m, 1H), 7.42-7.51 (m, 1H), 3.21-3.29 (m, 1H), 0.96 (d, J=6.5 Hz, 6H).

Compound 90

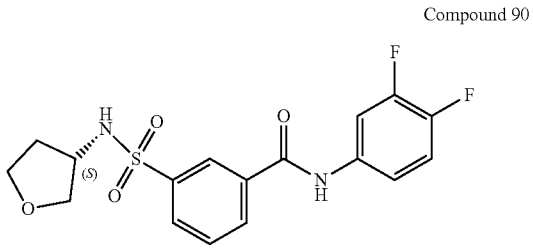

3-(chlorosulfonyl)benzoyl chloride (1200 mg, 5.0 mmol) was dissolved in dichloromethane (15 mL). A solution of 3,4-difluoroaniline (650 mg, 5.0 mmol) and triethylamine (606 mg, 6.0 mmol) in dichloromethane (15 mL) was added to the mixture at 0° C. The mixture was stirred at 25° C. for 1 hour. To the obtained reaction mixture a solution of triethylamine (606 mg, 6.0 mmol) and (S)-tetrahydrofuran-3-amine (460.0 mg, 5.3 mmol) in dichloromethane (15 mL) was added at 0° C. The mixture was stirred at 25° C. for 1 hour. The solvent was removed in vacuo. The obtained residue was purified by high performance liquid chromatography over RP-18 (eluent: $CH_3CN$ in water (0.1% TFA) from 30 to 60, v/v). The pure fractions were collected and the organic solvent was evaporated. The aqueous layer was neutralized with saturated aqueous $NaHCO_3$ to pH=7-8. The mixture was extracted with dichloromethane (3×15 mL). The combined organic layers were dried over $Na_2SO_4$ and concentrated in vacuo resulting in compound 90 (710 mg) Method A; Rt: 4.16 min. m/z: 383.0 (M+H)$^+$ Exact mass: 382.1; $^1$H NMR (400 MHz, DMSO-d$_6$) δ ppm 1.54-1.63 (m, 1H), 1.83-1.93 (m, 1H), 3.32-3.38 (m, 1H), 3.52-3.63 (m, 2H), 3.63-3.77 (m, 2H), 7.45 (dt, J=10.5, 9.0 Hz, 1H), 7.51-7.57 (m, 1H), 7.78 (t, J=7.8 Hz, 1H), 7.92 (ddd, J=13.3, 7.5, 2.5 Hz, 1H), 8.02 (d, J=7.8 Hz, 1H), 8.09 (d, J=6.5 Hz, 1H), 8.20 (d, J=7.8 Hz, 1H), 8.35 (s, 1H), 10.70 (s, 1H). SFC: Column: Chiralcel OJ-H 250×4.6 mm I.D., Sum; Flow: 2.35 mL/min; Mobile phase: methanol (0.05% diethylamine) in $CO_2$ from 5% to 40%; Rt: 5.61=+3.21 (c 0.624 w/v %, DMF)

Compound 91

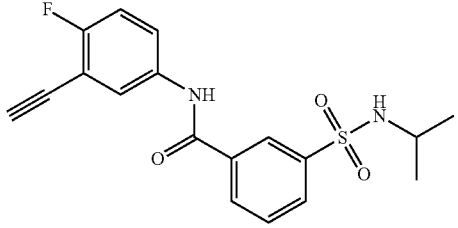

N-(3-bromo-4-fluorophenyl)-3-(N-isopropylsulfamoyl) benzamide (1.5 g, 3.61 mmol), ethynyltrimethylsilane (1.77 g, 18.06 mmol), Pd(PPh$_3$)$_2$Cl$_2$ (0.127 g, 0.181 mmol) and copper iodide (34.4 mg, 0.181 mmol) were dissolved in diisopropylamine (10 mL). The mixture was stirred at 80° C. in autoclave for 24 hours. The solvent was removed in vacuo and dichloromethane (30 mL) was added. The mixture was washed with water (20 mL) and the aqueous layer was extracted with dichloromethane (20 mL). The combined organic layers were washed with brine and dried over $Na_2SO_4$. The solvent was removed in vacuo. The obtained residue was purified by silica gel column chromatography (eluent: petroleum ether/ethyl acetate from 100/1 to 60/40) resulting in N-(4-fluoro-3-((trimethylsilyl)ethynyl)phenyl)-3-(N-isopropylsulfamoyl)benzamide (0.8 g). N-(4-fluoro-3-((trimethylsilyl)ethynyl)phenyl)-3-(N-isopropylsulfamoyl)-benzamide (0.8 g, 1.66 mmol) and TFA (4 mL) were dissolved in anhydrous $CH_2Cl_2$ (16 mL). The mixture was stirred at 25° C. overnight and next concentrated in vacuo. The obtained residue was purified by silica gel column chromatography (gradient eluent: petroleum ether/ethyl acetate from 100/0 to 75/25) resulting in compound 91 (220 mg). Method A; Rt: 5.12 min. m/z: 361.3 (M+H)$^+$ Exact mass: 360.1. $^1$H NMR (400 MHz, DMSO-d$_6$) δ ppm 10.60 (1H, s), 8.35 (1H, t, J=1.5 Hz), 8.18 (1H, d, J=8.0 Hz), 8.00 (1H, d, J=8.0 Hz), 7.97 (1H, dd, J=6.5, 3.0 Hz), 7.77-7.84 (1H, m), 7.70-7.79 (2H, m), 7.32 (1H, t, J=9.0 Hz), 4.52 (1H, s) 3.22-3.31 (1H, m), 0.94 (6H, d, J=6.5 Hz).

Compound 92

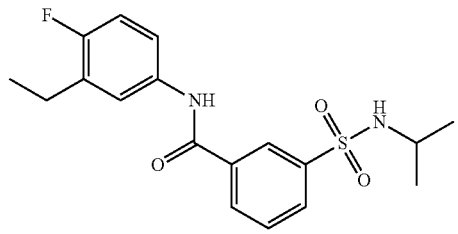

N-(4-fluoro-3-((trimethylsilyl)ethynyl)phenyl)-3-(N-isopropylsulfamoyl)benzamide (0.8 g, 1.66 mmol) and TFA (4 mL) were dissolved in anhydrous $CH_2Cl_2$ (16 mL). The mixture was stirred at 25° overnight. The mixture was concentrated resulting in crude N-(3-ethynyl-4-fluorophenyl)-3-(N-isopropylsulfamoyl)benzamide which was used as such in the next step (650 mg). To a solution of N-(3-ethynyl-4-fluorophenyl)-3-(N-isopropylsulfamoyl)benzamide (0.6 g) in MeOH (20 mL) was added Pd—C (10%, 0.2 g) under $N_2$ atmosphere. The mixture was stirred under hydrogen atmosphere (50 psi) at 25° C. for 4 hours. After filtration on celite, the solvent was removed in vacuo and the obtained residue was purified by preparative high performance liquid chromatography on reversed phase C-18 (eluent: $CH_3CN$ in $H_2O$ (0.05% HCl) from 42% to 72%, v/v). The pure fractions were collected and the volatiles were removed in vacuo. The aqueous layer was adjusted to PH=7 with Amberlite IRA-900 anionic exchange resin (OH form), filtered and lyophilized to dryness resulting in compound 92 (160 mg). Method B; Rt: 4.13 min. m/z: 365.3 (M+H)$^+$ Exact mass: 364.1; $^1$H NMR (400 MHz, DMSO-d$_6$) δ ppm 10.48 (1H, s), 8.35 (1H, t, J=1.5 Hz), 8.18 (1H, d, J=8.0 Hz), 7.99 (1H, d, J=8.0 Hz), 7.70-7.78 (2H, m), 7.65-7.70 (1H, m), 7.57-7.65 (1H, m), 7.13 (1H, t, J=9.0 Hz), 3.21-3.32 (1H, m), 2.62 (2H, q, J=7.5 Hz), 1.18 (3H, t, J=7.5 Hz), 0.94 (6H, d, J=6.5 Hz).

Compound 93

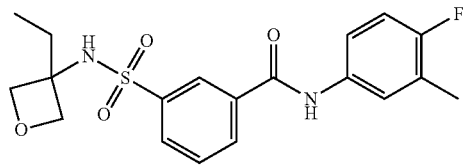

To a solution of 3-(chlorosulfonyl)benzoyl chloride (0.50 g, 2.09 mmol) in CH$_2$Cl$_2$ (10 mL), DIPEA was added (1.35 g, 10.45 mmol) followed by slow addition of 4-fluoro-3-methylaniline (0.25 g, 1.99 mmol). After stirring at 25° C. for 0.5 hour, 3-ethyloxetan-3-amine (0.21 g, 2.09 mmol) was added. After 1 hour, the resulting mixture was diluted with CH$_2$Cl$_2$ (15 mL), washed with saturated aqueous NaHCO$_3$ (15 mL) and brine (10 mL) and dried over anhydrous MgSO$_4$. The solvent was removed in vacuo and the obtained residue was purified by silica gel column chromatography (gradient eluent: petroleum ether/ethyl acetate from 100/0 to 80/20) resulting in compound 93 (70 mg). Method B; Rt: 3.79 min. m/z: 393.3 (M+H)$^+$ Exact mass: 392.1; $^1$H NMR (400 MHz, DMSO-d$_6$) δ ppm 10.50 (1H, s), 8.47 (1H, br. s), 8.38 (1H, t, J=1.5 Hz), 8.22 (1H, d, J=8.0 Hz), 8.03 (1H, d, J=8.0 Hz), 7.78 (1H, t, J=8.0 Hz), 7.68 (1H, dd, J=7.5, 2.5 Hz), 7.56-7.64 (1H, m), 7.15 (1H, t, J=9.0 Hz), 4.51 (2H, d, J=6.5 Hz), 4.19 (2H, d, J=6.5 Hz), 2.25 (3H, d, J=1.5 Hz), 1.84 (2H, q, J=7.0 Hz), 0.64 (3H, t, J=7.0 Hz).

Compound 94

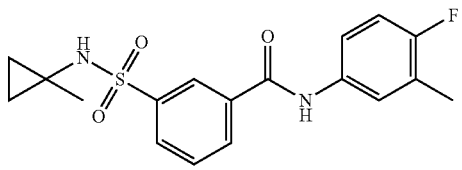

3-(chlorosulfonyl)benzoyl chloride (1200 mg, 5.0 mmol) was dissolved in dichloromethane (15 mL). A solution of 4-fluoro-3-methylaniline (625 mg, 5.0 mmol) and triethylamine (606 mg, 6.0 mmol) in dichloromethane (15 mL) was added to the mixture at 0° C. The mixture was stirred at 25° C. for 1 hour. The reaction mixture was used to the next step without further purification (crude, 30 mL). To the above reaction mixture was added a solution of triethylamine (606 mg, 6.0 mmol) and 1-methylcyclo-propanamine (425.0 mg, 5.9 mmol) in dichloromethane (15 mL) at 0° C. The mixture was stirred at 25° C. for 1 hour. The solvent was removed in vacuo. The residue was purified by high performance liquid chromatography on reversed phase (eluent: CH$_3$CN in water from 40% to 70%, v/v). The pure fractions were collected and the organic solvent was evaporated. The aqueous layer was neutralized with saturated aqueous NaHCO$_3$ to pH=7-8. The mixture was extracted with dichloromethane (3×15 mL). The combined organic layers were dried over Na$_2$SO$_4$ and concentrated in vacuo resulting in compound 94 (365 mg). Method B; Rt: 3.40 min. m/z: 363.0 (M+H)$^+$ Exact mass: 362.1; $^1$H NMR (400 MHz, DMSO-d$_6$) δ ppm 10.49 (1H, s), 8.35 (1H, t, J=1.5 Hz), 8.17-8.23 (2H, m), 7.99 (1H, d, J=8.0 Hz), 7.76 (1H, t, J=8.0 Hz), 7.68 (1H, dd, J=7.0, 2.5 Hz), 7.56-7.62 (1H, m), 7.14 (1H, t, J=9.0 Hz), 2.25 (3H, d, J=1.5 Hz), 1.06 (3H, s), 0.58-0.63 (2H, m), 0.37-0.42 (2H, m)

Compound 95

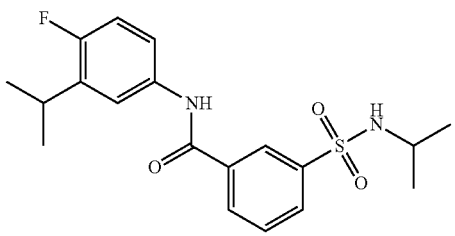

A mixture of N-(3-bromo-4-fluorophenyl)-3-(N-isopropylsulfamoyl)benzamide (800 mg, 1.93 mmol), 4,4,5,5-tetramethyl-2-(prop-1-en-2-yl)-1,3,2-dioxaborolane (0.65 g, 3.85 mmol), Pd(PPh$_3$)$_4$ (111 mg, 0.096 mmol)) and K$_2$CO$_3$ (0.53 g, 3.85 mmol) in dioxane (8 mL) and water (2 mL) was heated by microwave irradiation for 110 minutes at 120° C. under N$_2$ atmosphere. The reaction mixture was diluted with ethyl acetate (20 mL) and the catalyst was filtered off. The filtrate was concentrated in vacuo. Water (20 mL) was added and the aqueous layer was extracted with ethyl acetate (2×20 mL). The combined organic layers were washed with brine and dried over Na$_2$SO$_4$. The solvent was removed in vacuo and the obtained residue was purified by preparative high performance liquid chromatography over reversed phase C-18 (eluent: CH$_3$CN in H$_2$O (0.1% TFA) from 40% to 70%, v/v). The pure fractions were collected and the organic solvent was removed in vacuo. The aqueous layer was lyophilized to dryness resulting in N-(4-fluoro-3-(prop-1-en-2-yl)phenyl)-3-(N-iso-propylsulfamoyl)benzamide (300 mg). N-(4-fluoro-3-(prop-1-en-2-yl)phenyl)-3-(N-isopropylsulfamoyl)benzamide (180 mg) and Pd/C (wet) (20 mg) were stirred in methanol (4 mL) under a hydrogen atmosphere at 25° C. for 3 hours. The mixture was filtered over celite and the filtrate was evaporated to dryness in vacuo. The residue was purified by silica gel column chromatography (gradient eluent: petroleum ether/ethyl acetate from 100/0 to 70/30). The volatiles were removed in vacuo, resulting in compound 95 (175 mg). Method B; Rt: 4.33 min. m/z: 379.3 (M+H)$^+$ Exact mass: 378.1;

Compound 96

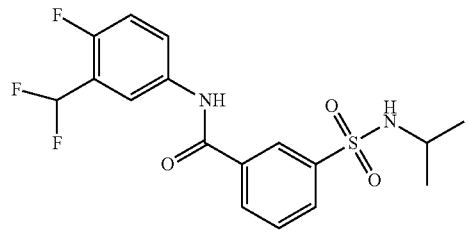

3-(difluoromethyl)-4-fluoroaniline (1.20 g, 7.448 mmol), 3-(N-isopropylsulfamoyl)-benzoic acid (0.90 g, 3.699 mmol) and DIPEA (1.93 mL, 11.10 mmol) were dissolved in CH$_2$Cl$_2$ (10 mL) and HATU (1.41 g, 3.699 mmol) was added at 0° C. The mixture was stirred at 20° C. for 2 hours. The mixture was diluted with CH$_2$Cl$_2$ (10 mL) and H$_2$O (10 mL). The organic layer was separated, washed with saturated aqueous NaHCO$_3$ (10 mL) and brine (10 mL) and dried over Na$_2$SO$_4$. The solvent was removed in vacuo and the obtained residue was purified by preparative high performance liquid chromatography over reversed phase C-18

(eluent: CH$_3$CN in H$_2$O (0.1%0 NH$_4$HCO$_3$) from 45% to 75%, v/v). The pure fractions were collected and the organic solvent was removed in vacuo. The aqueous layer was lyophilized to dryness resulting in compound 96 (0.885 g). Method A; Rt: 5.16 min. m/z: 387.3 (M+H)$^+$ Exact mass: 386.1; $^1$H NMR (400 MHz, DMSO-d$_6$) δ ppm 10.72 (1H, s), 8.38 (1H, t, J=1.5 Hz), 8.21 (1H, d, J=8.0 Hz), 8.06-8.13 (1H, m), 8.02 (1H, d, J=8.0 Hz), 7.92-8.00 (1H, m), 7.72-7.82 (2H, m), 7.40 (1H, t, J=9.5 Hz), 7.25 (1H, t, 55 Hz), 3.23-3.32 (1H, m), 0.95 (6H, d, J=6.5 Hz).

ether and acetonitrile) and dried in vacuo at 55° C. for 20 hours resulting in compound 98 (257 mg) as a white solid. Method F; Rt: 1.04 min. m/z: 382.1 (M+NH$_4$)$^+$ Exact mass: 364.1; $^1$H NMR (400 MHz, DMSO-d$_6$) δ ppm 0.71 (t, J=7.5 Hz, 3H), 0.88 (d, J=6.6 Hz, 3H), 1.31 (quin, J=7.5 Hz, 2H), 2.25 (d, J=1.8 Hz, 3H), 3.05-3.18 (m, 1H), 7.14 (t, J=9.0 Hz, 1H), 7.55-7.62 (m, 1H), 7.63-7.72 (m, 2H), 7.75 (t, J=8.0 Hz, 1H), 8.00 (d, J=8.0 Hz, 1H), 8.18 (d, J=8.0 Hz, 1H), 8.36 (t, J=1.5 Hz, 1H), 10.46 (s, 1H).

Compound 97

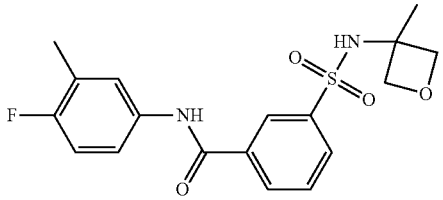

Compound 99

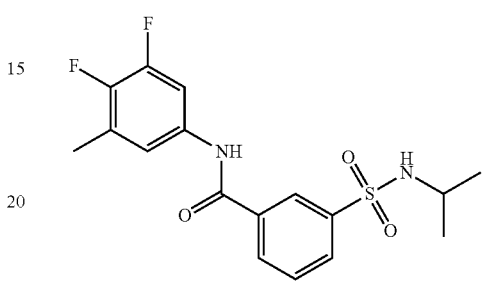

To 3-(4-fluoro-3-methylphenylcarbamoyl)benzene-1-sulfonyl chloride (500 mg, 1.53 mmol) in toluene (10 mL) at room temperature, a solution of diisopropylethylamine (0.657 mL, 141.6 mmol) and 3-methyl-3-oxetanamine hydrochloride (207 mg, 1.68 mmol) in toluene (5 mL) and dichloromethane (10 mL) was added drop wise. After 2 hours, the reaction mixture was washed with 1M hydrochloric acid (2×10 mL, saturated NaHCO$_3$ (2×10 mL) and brine (2×10 mL). The organic layer was dried on MgSO$_4$, filtered and concentrated under reduced pressure until only toluene remained. The formed white precipitate was filtered and recrystallised out of diisopropylether and acetonitrile. The crystals were dried in a vacuum oven at 55° C. for 20 hours yielding compound 97 (361 mg) as a white solid. Method F; Rt: 0.89 min. m/z: 379.0 (M+H)$^+$ Exact mass: 378.1; $^1$H NMR (400 MHz, DMSO-d$_6$) δ ppm 1.41 (s, 3 H), 2.25 (d, J=1.5 Hz, 3H), 4.14 (d, J=6.3 Hz, 2H), 4.56 (d, J=6.3 Hz, 2H), 7.14 (t, J=9.0 Hz, 1H), 7.52-7.64 (m, 1H), 7.68 (dd, J=7.0, 2.2 Hz, 1H), 7.77 (t, J=8.0 Hz, 1H), 7.99-8.06 (m, 1H), 8.20 (d, J=8.0 Hz, 1H), 8.37 (t, J=1.5 Hz, 1H), 8.50 (br. s., 1H), 10.48 (s, 1H).

Compound 98

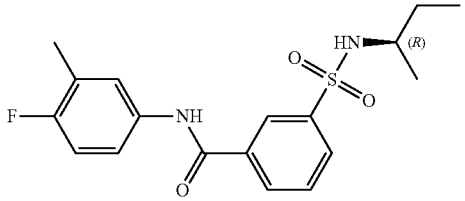

To 3-(4-fluoro-3-methylphenylcarbamoyl)benzene-1-sulfonyl chloride (500 mg, 1.53 mmol) in toluene (10 mL) at room temperature, a solution of diisopropylethylamine (0.657 mL, 141.6 mmol) and (R)-(−)-2-aminobutane (130 mg, 1.83 mmol) in toluene (5 mL) and dichloromethane (10 mL) was added drop wise. After 2 hours, the reaction mixture was washed with 1M aqueous HCl (2×10 mL), NaHCO$_3$ (2×10 mL) and brine (2×10 mL). The organic layer was dried on MgSO$_4$, filtered and concentrated under reduced pressure until only toluene remained. The formed white precipitate was filtered, recrystallised (diisopropyl- A mixture of 3-(N-isopropylsulfamoyl)benzoic acid (2.3 g, 9.615 mmol), 3-bromo-4,5-difluoroaniline (2 g, 9.615 mmol) and DIPEA (5 mL) in CH$_2$Cl$_2$ (30 mL) was cooled to 0° C. and HATU (4.39 g, 11.538 mmol) was added. The mixture was stirred for 2 hours at 20° C. The mixture was washed with 1N HCl (30 mL) and brine (30 mL) and dried over Na$_2$SO$_4$. The solvent was removed in vacuo. The residue was purified by silica gel column chromatography (gradient eluent: petroleum ether/ethyl acetate from 100/0 to 70/30) resulting in crude N-(3-bromo-4,5-difluorophenyl)-3-(N-isopropylsulfamoyl)-benzamide (4 g). A mixture of N-(3-bromo-4,5-difluorophenyl)-3-(N-isopropyl-sulfamoyl)benzamide (1 g, 2.308 mmol), methylboronic acid (1 g, 4.616 mmol), Cs$_2$CO$_3$ (2.26 g, 6.924 mmol), 2-Dicyclohexylphosphino-2',6'-dimethoxybiphenyl (95 mg, 0.231 mmol) and Tris(dibenzylideneacetone)dipalladium(0) (0.21 g, 0.231 mmol) in dioxane (15 mL) was heated by microwave irradiation for 40 minutes at 120° C. under N$_2$ atmosphere. After cooling, the mixture was filtered through celite and the filtrate was evaporated to dryness. The obtained residue was purified by silca gel column chromatography (gradient eluent: petroleum ether/ethyl acetate from 100/0 to 70/30) and further purified by preparative high performance liquid chromatography over reversed phase C-18 (eluent: CH$_3$CN in H$_2$O (0.1% TFA) from 38% to 68%, v/v). The pure fractions were collected and half of the volatiles were removed in vacuo. The mixture was adjusted to pH=7 with Amberlite IRA-900 (OH) anionic exchange resin and the resin was filtered off. The organic solvent was concentrated in vacuo and the aqueous layer was lyophilized to dryness. The obtained product was further purified by silica gel chromatography (gradient eluent: petroleum ether/ethyl acetate from 100/0 to 70/30) resulting in compound 99 (190 mg). Method A; Rt: 6.09 min. m/z: 369.2 (M+H)$^+$ Exact mass: 368.1, $^1$H NMR (400 MHz, CHLOROFORM-d) δ ppm 8.35 (1H, t, J=1.5 Hz), 8.09-8.17 (2H, m), 8.04 (1H, dt, 1.5 Hz), 7.66 (1H, t, J=8.0 Hz), 7.54 (1H, ddd, J=11.5, 6.5, 3.0 Hz), 7.14-7.22 (1H, m), 4.72 (1H, d, J=8.0 Hz), 3.43-3.60 (1H, m), 2.32 (3H, d, J=2.0 Hz), 1.10 (6H, d, J=6.5 Hz).

Compound 100

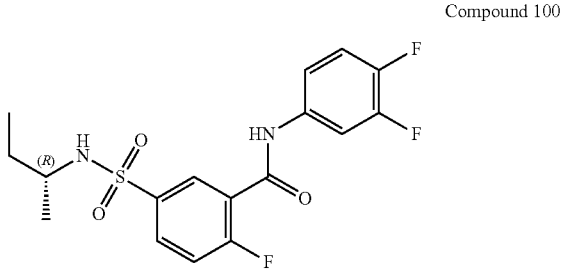

5-(chlorosulfonyl)-2-fluorobenzoic acid (7 g, 29.3 mmol) was dissolved in dichloromethane (70 mL). DMF (0.7 mL) was added, followed by drop wise addition of oxalyl chloride (4.46 g, 35.16 mmol) at 0° C. The mixture was stirred for 1 hour at 20° C. The mixture was concentrated in vacuo and the crude 5-(chlorosulfonyl)-2-fluorobenzoyl chloride was dissolved in dichloromethane (15 mL). A solution of 3,4-difluoroaniline (3.6 g, 27.87 mmol) and DIPEA (4.6 g, 35.20 mmol) in dichloromethane (60 mL) was added to the mixture at 0° C. The mixture was stirred at 25° C. for 1 hour and used to the next step directly. To the above reaction mixture, a solution of (R)-(−)-2-aminobutane (2.2 g, 29.34 mmol) and DIPEA (4.6 g, 35.20 mmol) in dichloromethane (60 mL) was added at 0° C. The resulting mixture was stirred at 25° C. for 1 hour. The mixture was concentrated in vacuo and the obtained residue was purified by high performance liquid chromatography on reversed phase (eluent: CH$_3$CN in water (0.1% TFA) from 25% to 55%, v/v). The pure fractions were collected and the organic solvent was evaporated. The aqueous solution was adjusted to pH=7 with saturated aqueous NaHCO$_3$. The mixture was extracted with dichloromethane (3×200 mL). The combined organic layers were dried over Na$_2$SO$_4$ and concentrated in vacuo. The obtained residue was suspended in water (10 mL) and the aqueous layer was lyophilized to dryness resulting in compound 100 (4.7 g). Method B; Rt: 4.70 min. m/z: 387.2 (M+H)$^+$ Exact mass: 386.1.

Compound 101

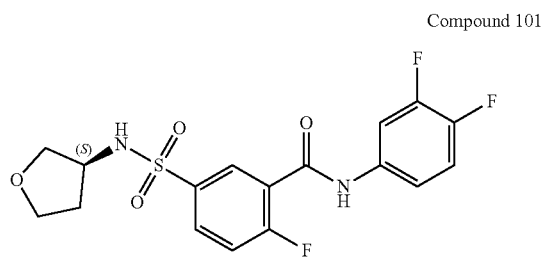

(S)-tetrahydrofuran-3-amine hydrochloride (5.17 g, 42 mmol) and NaOH (5 g, 126 mmol) were dissolved in THF (50 mL) and H$_2$O (50 mL). 5-(chlorosulfonyl)-2-fluorobenzoic acid (10 g, 42 mmol) was added at 0° C. The mixture was stirred at 20° C. for 4 hours. The mixture was washed with ethyl acetate (3×20 mL). The aqueous layer was separated and adjusted to pH=3 with 1N HCl. The aqueous layer was extracted with ethyl acetate (3×50 mL). The combined organic layers were washed with brine and dried over Na$_2$SO$_4$. The solvent was removed in vacuo resulting in (S)-2-fluoro-5-(N-(tetrahydrofuran-3-yl)sulfamoyl)benzoic acid (2.1 g). (S)-2-fluoro-5-(N-(tetra-hydrofuran-3-yl)sulfamoyl)benzoic acid (1 g, 3.457 mmol), 3,4-difluoroaniline (0.53 g, 4.15 mmol) and triethylamine (0.7 g, 6.9 mmol) were dissolved in DMF (400 mL) and HATU (1.57 g, 4.15 mmol) was added at 0° C. The mixture was next stirred at 20° C. for 6 hours. The solvent was removed in vacuo and the obtained residue was purified by silica gel chromatography (eluent: petroleum ether:ethyl acetate=5:1) resulting in compound 101 (0.8 g). Method B; Rt: 4.15 min. m/z: 401.3 (M+H)$^+$ Exact mass: 400.1 Synthesis of 3-[[(3S)-tetrahydrofuran-3-yl]sulfamoyl]benzoic acid: (3S)-tetrahydrofuran-3-amine hydrochloride (5.6 g, 45.3 mmol) and NaOH (5.2 g, 130 mmol) were dissolved in THF (50 mL) and H$_2$O (50 mL). 3-(chlorosulfonyl)-benzoic acid (10 g, 45.325 mmol) was added at 0° C. The mixture was stirred at 20° C. for 4 hours. The aqueous layer was separated and the pH was adjusted to 2 with 1N HCl. The mixture was washed with ethyl acetate (3×100 mL). The combined organic layers were concentrated in vacuo resulting in 3-[[(3S)-tetrahydrofuran-3-yl]sulfamoyl]benzoic acid (11.2 g).

Compound 102

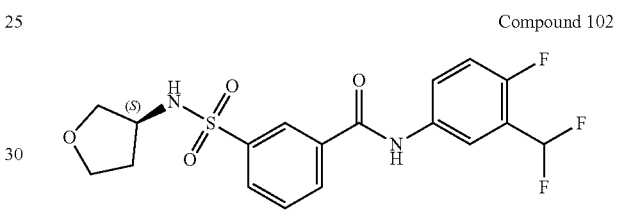

A mixture of (S)-tetrahydrofuran-3-amine hydrochloride (11.2 g, 90.7 mmol) and NEt$_3$ (50.5 mL, 362.6 mmol) in dry CH$_2$Cl$_2$ (400 mL) was stirred for 5 minutes at 20° C. 3-(chlorosulfonyl)benzoic acid (20 g, 90.7 mmol) was added and the mixture was stirred overnight at 20° C. The reaction mixture was washed with 1N HCl (100 mL), the aqueous layer was extracted with dichloromethane (2×200 mL). The combined organic layers were dried over Na$_2$SO$_4$ and the solvent was removed in vacuo, resulting in 3-[[(3S)-tetrahydrofuran-3-yl]sulfamoyl]benzoic acid (16.3 g). 3-[[(3S)-tetrahydro-furan-3-yl]sulfamoyl]benzoic acid (3 g, 11.058 mmol), 3-(difluoromethyl)-4-fluoro-aniline (2.1 g, 13.3 mmol) and triethylamine (3.3 g, 33 mmol) were dissolved in DMF (400 mL). PyBrOP (132705-51-2, 6.2 g, 13.3 mmol) was added at 0° C. The mixture was stirred at 50° C. for 12 hours. The solvent was removed in vacuo and the obtained residue was purified by reversed phase high performance liquid chromatography (mobile phase: CH$_3$CN in water (0.1% TFA) from 30% to 60%). The pure fractions were collected and neutralized with solid NaHCO$_3$. The organic solvent was removed in vacuo and the formed precipitate was filtered, washed with H$_2$O (5 mL) and dried under high vacuum. The obtained residue was suspended in water (5 mL) and lyophilized to dryness resulting in compound 102 (2.3 g). Method A; Rt: 5.32 min. m/z: 415.2 (M+H)$^+$ Exact mass: 414.1. $^1$H NMR (400 MHz, DMSO-d$_6$) δ ppm 1.53-1.68 (m, 1H) 1.82-1.99 (m, 1H) 3.27-3.42 (m, 1H) 3.51-3.90 (m, 4H) 7.26 (t, J=55 Hz, 1H) 7.36-7.51 (m, 1H) 7.80 (t, J=7.8 Hz, 1H) 7.92-8.00 (m, 1H) 8.01-8.08 (m, 1H) 8.08-8.15 (m, 2H) 8.25 (d, J=7.8 Hz, 1H) 8.40 (s, 1H) 10.75 (s, 1H).

Compound 103

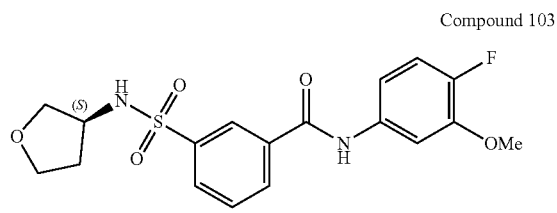

3-[[(3S)-tetrahydrofuran-3-yl]sulfamoyl]benzoic acid (400 mg, 1.47 mmol) was dissolved in DMF (0.5 mL) and CH$_2$Cl$_2$ (10 mL). (COCl)$_2$ (223 mg, 1.76 mmol) was added at 0° C. The mixture was stirred at 20° C. for 2 hours. The solvent was removed in vacuo and the obtained residue was co-evaporated with toluene (2×10 mL) resulting in crude 3-[[(3S)-tetrahydrofuran-3-yl]sulfamoyl]benzoyl chloride (400 mg). The crude product was used in the next step without purification. 3-[[(3S)-tetrahydrofuran-3-yl]-sulfamoyl]benzoyl chloride (200 mg) was dissolved in dichloromethane (5 mL). 4-fluoro-3-methoxy-aniline (78 mg, 0.552 mmol) and triethylamine (167 mg, 165 mmol) were added at 0° C. The mixture was stirred at 20° C. for 2 hours, washed with H$_2$O (5 mL) and the water layer extracted with dichloromethane (3×10 mL). The combined organic layers were concentrated in vacuo. The obtained residue was purified by reversed phase high performance liquid chromatography (mobile phase: CH$_3$CN in water (0.1% TFA) from 30% to 60%). The pure fractions were collected and neutralized with solid NaHCO$_3$. The organic solvent was removed in vacuo. The obtained precipitate was filtered, washed with H$_2$O (5 mL) and dried under high vacuum. The residue was suspended in water (5 mL) lyophilized to dryness resulting in compound 103 (140 mg). Method A; Rt: 4.98 min. m/z: 395.2 (M+H)$^+$ Exact mass: 394.1

Prepared similarly as described for compound 103:

Compound 104

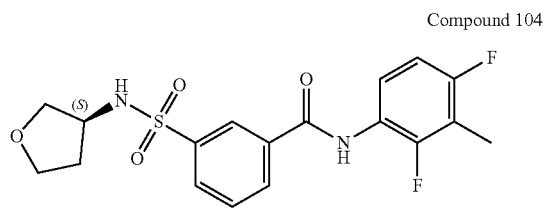

Method A; Rt: 5.17 min. m/z: 397.3 (M+H)$^+$ Exact mass: 396.1

Compound 105

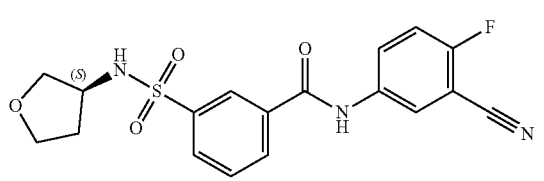

Method A; Rt: 5.10 min. m/z: 389.1 (M+H)$^+$ Exact mass: 390.2

Compound 106

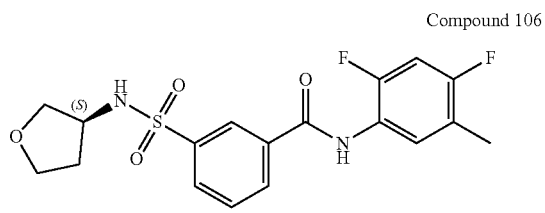

Method A; Rt: 5.18 min. m/z: 397.2 (M+H)$^+$ Exact mass: 396.1

$^1$H NMR (400 MHz, DMSO-d$_6$) δ ppm 1.54-1.69 (m, 1H) 1.82-1.98 (m, 1H) 2.24 (s, 3H) 3.35-3.40 (m, 1H) 3.52-3.66 (m, 2H) 3.66-3.83 (m, 2H) 7.32 (t, J=10.0 Hz, 1H) 7.49 (t, J=8.5 Hz, 1H) 7.79 (t, J=7.8 Hz, 1H) 8.04 (d, J=8.0 Hz, 1H) 8.07-8.18 (m, 1H) 8.23 (d, J=7.8 Hz, 1H) 8.39 (s, 1H) 10.40 (br. s, 1H)

Compound 107

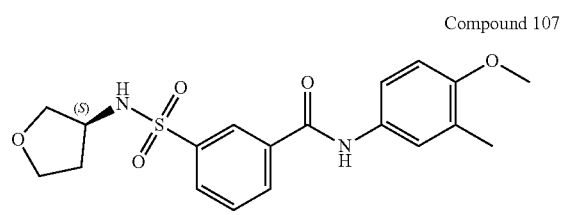

3-[[(3S)-tetrahydrofuran-3-yl]sulfamoyl]benzoic acid (270 mg, 1.0 mmol) was dissolved in dichloromethane (5 mL). 3-methyl-4-methoxyaniline (165 mg, 1.2 mmol) and triethylamine (145 mg, 1.4 mmol) were added to the mixture at 20° C. The mixture was stirred at 20° C. for 5 minutes. HATU (456 mg, 1.2 mol) was added and the mixture was further stirred at 20° C. for 8 hours. The solvent was removed in vacuo and the obtained residue was purified by high performance liquid chromatography (Column: Phenomenex Synergi C18 150*20 mm*5 um. A: H$_2$O+0.1% TFA B: MeCN from 30% to 60% B in A). The product fractions were collected and the organic solvent was evaporated in vacuo. The aqueous layer was neutralized with saturated aqueous NaHCO$_3$ and extracted with dichloromethane (2×10 mL). The combine organic layers was dried over Na$_2$SO$_4$ and concentrated in vacuo resulting in compound 107 (135 mg). Method A; Rt: 5.24 min. m/z: 391.3 (M+H)$^+$ Exact mass: 390.1

Compound 108

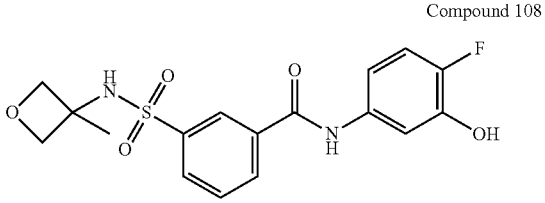 [SMILES: CC1(NS(=O)(=O)c2cccc(C(=O)Nc3ccc(F)c(O)c3)c2)COC1]

5-amino-2-fluoro-phenol (234 mg, 1.84 mmol) and 3-[(3-methyloxetan-3-yl)-sulfamoyl]benzoic acid (500 mg, 1.84 mmol) were dissolved in dichloromethane (8 mL). PyBrOP (132705-51-2, 1030 mg, 2.21 mmol) was added followed by drop wise addition of DIPEA (714 mg, 5.53 mmol) at 0° C. The mixture was stirred for 1 hour at 25° C. The mixture was washed with saturated aqueous citric acid (15 mL), saturated aqueous NaHCO$_3$ (15 mL) and brine and dried over Na$_2$SO$_4$.

The solvent was removed in vacuo. The obtained residue was purified by reversed phase preparative high-performance liquid chromatography (mobile phase: CH₃CN in water (0.05% NH₄HCO₃) from 29% to 39%). The pure fractions were collected and the volatiles were removed in vacuo. The residual aqueous layer was lyophilized to dryness re suiting in compound 108 (60 mg). Method A; Rt: 4.47 min. m/z: 381.2 (M+H)⁺ Exact mass: 380.1

Compound 109

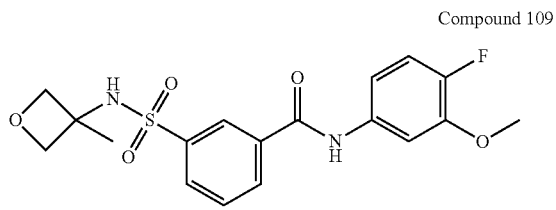 [SMILES: COc1cc(NC(=O)c2cccc(S(=O)(=O)NC3(C)COC3)c2)ccc1F]

Prepared similarly as described for compound 108, using 4-fluoro-3-methoxy-aniline instead of 5-amino-2-fluoro-phenol. Method A; Rt: 5.03 min. m/z: 395.2 (M+H)⁺ Exact mass: 394.1

Compound 110

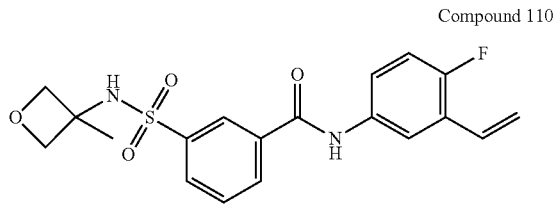 [SMILES: C=Cc1cc(NC(=O)c2cccc(S(=O)(=O)NC3(C)COC3)c2)ccc1F]

DIPEA (2.85 g, 22.08 mmol) was added to a solution of 3-[(3-methyloxetan-3-yl)-sulfamoyl]benzoic acid (3.0 g, 11.06 mmol) and HATU (4.20 g, 11.05 mmol) in DMF (100 mL) at 25° C. After 30 minutes, 3-bromo-4-fluoro-aniline (2.1 g, 11.05 mmol) was added to the solution. The reaction mixture was stirred at 25° C. overnight. The solvent was removed in vacuo and the obtained residue was purified by silica gel column chromatography (gradient eluent: petroleum ether/ethyl acetate from 10/1 to 5/1). The pure fractions were collected and the solvent was removed in vacuo resulting in N-(3-bromo-4-fluoro-phenyl)-3-[(3-methyl-oxetan-3-yl)sulfamoyl]benzamide (compound 160, 2.5 g). A mixture of N-(3-bromo-4-fluoro-phenyl)-3-[(3-methyl-oxetan-3-yl)sulfamoyl]benzamide (0.3 g, 0.68 mmol), 4,4,5,5-tetramethyl-2-vinyl-1,3,2-dioxaborolane (54.2 mg, 0.35 mmol), Pd (dppf) C₁₂ (50 mg, 0.068 mmol), KOAc (108 mg, 1.1 mmol) and Na₂CO₃ (100 mg, 0.94 mmol) in CH₃CN (10 mL) and H₂O (2 mL) was heated by microwave irradiation for 30 minutes at 130° C. under a N₂ atmosphere. The reaction mixture was filtered through Celite and the filter cake was washed with ethyl acetate (2×10 mL). The organic layer was separated from the filtrate, washed with brine and dried over Na₂SO₄. The solvent was removed in vacuo. The obtained residue was purified by reversed phase preparative high performance liquid chromatography (eluent: CH₃CN in H₂O (0.05% NH₃.H₂O) from 30% to 80%, v/v). The pure fractions were collected and the volatiles were removed in vacuo. The aqueous layer was lyophilized to dryness resulting in compound 110 (70 mg). Method B; Rt: 4.19 min. m/z: 391.3 (M+H)⁺ Exact mass: 390.1.

Compound 111

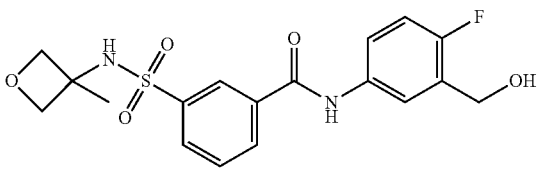

3-[(3-methyloxetan-3-yl)sulfamoyl]benzoic acid (3 g, 11.06 mmol), methyl 5-amino-2-fluoro-benzoate (2.33 g, 13.2 mmol) and DIPEA (2.84 g, 22 mmol) were dissolved in DMF (40 mL). HATU (5.02 g, 13.2 mmol) was added at 0° C. The mixture was stirred at 20° C. for 2 hours. The solvent was removed in vacuo and the obtained residue was purified by silica gel column chromatography (eluent: petroleum ether:ethyl acetate=3:1) resulting in methyl 2-fluoro-5-[[3-[(3-methyloxetan-3-yl)sulfamoyl]-benzoyl]amino]benzoate (2.3 g). Methyl 2-fluoro-5-[[3-[(3-methyloxetan-3-yl)-sulfamoyl]benzoyl]amino]benzoate (0.3 g, 0.71 mmol) was dissolved in THF (5 mL) and ethanol (5 mL). NaBH₄ (53 mg, 1.4 mmol) was added at 0° C. The mixture was stirred for 2 hours at 20° C. The solvent was removed in vacuo and the obtained residue was purified by reversed phase high performance liquid chromatography (mobile phase: CH₃CN in water (0.1% TFA) from 34% to 64%). The pure fractions were collected and neutralized with solid NaHCO₃. The organic solvent was removed in vacuo. The precipitate was filtered, washed with H₂O (5 mL) and dried under high vacuum. The residue was suspended in water (5 mL) and the aqueous layer was lyophilized to dryness resulting in compound 111 (220 mg). Method A; Rt: 4.34 min. m/z: 395.3 (M+H)⁺ Exact mass: 394.1.

Compound 127

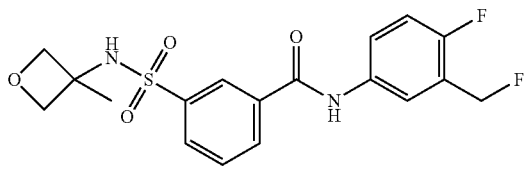

(2-fluoro-5-nitro-phenyl)methanol (4.3 g, 25.1 mmol) was dissolved in dichloromethane (50 mL). Diethylamino-sulfur trifluoride (4.5 g, 27.9 mmol) was added drop wise to the mixture at −30° C. The mixture was stirred at 10° C. for 4 hours. Methanol (10 mL) was added to the mixture and the mixture was further stirred at 10° C. for 30 minutes. The mixture was washed with brine (30 mL) and the aqueous layer was extracted with CH₂Cl₂ (2×30 mL). The combined organic layers were dried over Na₂SO₄ and concentrated in vacuo, resulting in 1-fluoro-2-(fluoromethyl)-4-nitro-benzene (3.9 g). A mixture of 1-fluoro-2-(fluoromethyl)-4-nitrobenzene (3.1 g, 17.9 mmol), iron (4.0 g, 71.6 mmol) and methanol (30 mL) was stirred at 65° for 8 hours. The mixture was filtrated and the filtrate was concentrated in vacuo, resulting in 4-fluoro-3-(fluoromethyl)aniline (1.5 g). 3-(chlorosulfonyl)benzoyl chloride (300 mg, 1.2 mmol) and triethylamine (150 mg, 1.5 mmol) were dissolved in dichloromethane (20 mL). 4-fluoro-3-(fluoromethyl)aniline (175 mg, 1.22 mmol) was added to the mixture at 0° C. The mixture was stirred at 10° C. for 30 minutes. The mixture was used to the next step without further purification.

Triethylamine (152 mg, 1.5 mmol) and 3-methyl-3-oxetan-amine (131 mg. 1.5 mmol) were added to the above obtained reaction mixture at 0° C. The mixture was stirred at 20° C. for 1 hour. The solvent was removed in vacuo and the obtained residue was purified by reversed phase high performance liquid chromatography (Column: Gemini 250*20 mm*5 um. A: H$_2$O+0.1% TFA B: MeCN. 27% to 57% B in A). The product fractions were collected and the organic solvent was removed in vacuo. The fraction was neutralized by saturated NaHCO$_3$. The mixture was extracted with dichloromethane (3×20 mL) and the combined organic layer was dried over Na$_2$SO$_4$ and concentrated in vacuo, resulting in compound 127 (91.1 mg). Method A; Rt: 4.95 min. m/z: 397.3 (M+H)$^+$ Exact mass: 396.1. $^1$H NMR (400 MHz, DMSO-d$_6$) δ ppm 1.41 (s, 3H) 4.14 (d, J=6.3 Hz, 2H) 4.56 (d, J=6.3 Hz, 2H) 5.52 (d, J=48 Hz, 2H) 7.31 (t, J=9.4 Hz, 1H) 7.72-7.89 (m, 2H) 7.92-7.97 (m, 1H) 8.03 (d, J=8.0 Hz, 1H) 8.23 (d, J=7.8 Hz, 1H) 8.39 (s, 1H) 8.55 (s, 1H) 10.67 (s, 1H).

Compound 112

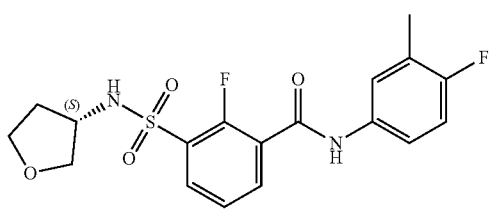

Compound 123 (255 mg, 0.592 mmol) and Pd/C (50 mg) were stirred in methanol (25 mL) under a hydrogen atmosphere for 3 hours. The reaction mixture was filtered, concentrated and the obtained residue dried in vacuo at 50° C. resulting in compound 112 as a colorless resin. (174 mg). Method G; Rt: 1.57 min. m/z: 397.1 (M+H)$^+$ Exact mass: 396.1. $^1$H NMR (400 MHz, DMSO-d$_6$) δ ppm 1.65-1.80 (m, 1H), 1.91-2.04 (m, 1H), 2.24 (d, J=1.5 Hz, 3H), 3.43 (dd, J=9.0, 4.6 Hz, 1H), 3.55-3.79 (m, 3H), 3.80-3.91 (m, 1H), 7.14 (t, J=9.2 Hz, 1H), 7.45-7.57 (m, 2H), 7.64 (dd, J=7.0, 2.4 Hz, 1H), 7.85-8.02 (m, 2H), 8.40 (d, J=6.8 Hz, 1H), 10.62 (s, 1H)

Compound 113

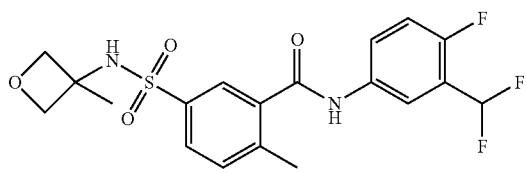

3-methyloxetan-3-amine hydrochloride (210 mg, 1.7 mmol) and NaOH (204 mg, 5.1 mmol) were dissolved in 2-methyltetrahydrofuran (5 mL) and H$_2$O (5 mL). 5-chlorosulfonyl-2-methyl-benzoic acid (400 mg, 1.7 mmol) was added at 0° C. The mixture was stirred at 20° C. for 4 hours. The aqueous layer was separated and adjusted to pH=3 by aq.HCl (1N). The mixture was extracted with ethyl acetate (3×100 mL). The combined organic layers were concentrated in vacuo resulting in 2-methyl-5-[(3-methyloxetan-3-yl)sulfamoyl]benzoic acid (250 mg). 2-methyl-5-[(3-methyloxetan-3-yl)sulfamoyl]benzoic acid (250 mg, 0.876 mmol), 3-(difluoromethyl)-4-fluoro-aniline (178 mg, 1.1 mmol) and DIPEA (232 mg, 1.8 mmol) were dissolved in DMF (5 mL). HATU (399 mg, 1.05 mmol) was added at 0° C. The mixture was stirred at 20° C. for 2 hours. The solvent was removed in vacuo and the obtained residue was purified by reversed phase high performance liquid chromatography (mobile phase: CH$_3$CN in water (0.1% TFA) from 34% to 64%). The pure fractions were collected and neutralized with solid NaHCO$_3$. The organic solvent was removed in vacuo and the formed precipitate was filtered, washed with H$_2$O (5 mL) and dried under high vacuum. The residue was suspended in water (5 mL) and the aqueous layer was lyophilized to dryness resulting in compound 113 (220 mg). Method A; Rt: 5.28 min. m/z: 429.3 (M+H)$^+$ Exact mass: 428.1. $^1$H NMR (400 MHz, DMSO-d$_6$) δ ppm 1.44 (s, 3H) 2.47 (s, 3H) 4.15 (d, J=6.3 Hz, 2H) 4.57 (d, J=6.0 Hz, 2H) 7.24 (t, J=54.5 Hz, 1H) 7.40 (t, J=9.5 Hz, 1H) 7.56 (d, J=8.0 Hz, 1H) 7.71-7.98 (m, 3H) 8.09 (d, J=4.3 Hz, 1H) 8.37 (br. s., 1H) 10.74 (br. s., 1H)

Compound 114

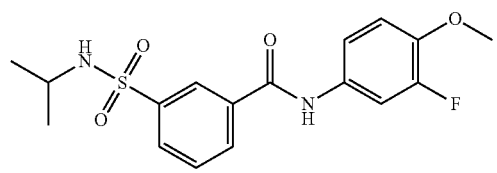

3-(isopropylsulfamoyl)benzoic acid (190 mg, 0.78 mmol) was dissolved in dichloromethane (5 mL). 3-fluoro-4-methoxyaniline (139 mg, 0.94 mmol) and triethylamine (112 mg, 1 mmol) were added to the mixture at 20° C. The mixture was stirred at 20° C. for 5 minutes. HATU (358 mg, 0.94 mmol) was added to the mixture at 20° C. The mixture was stirred at 20° C. for 8 hours. The solvent was removed in vacuo and the obtained residue was purified by high performance liquid chromatography (Column: Phenomenex Synergi C18 150*20 mm*5 um. A: H$_2$O+0.1% TFA B: MeCN 30% to 60% B in A). The product fractions were collected and the organic solvent was evaporated. The aqueous layer was neutralized with saturated aqueous NaHCO$_3$. The mixture was extracted with dichloromethane (2×10 mL). The combined organic layers were dried over Na$_2$SO$_4$ and concentrated in vacuo resulting in compound 114 (135 mg). Method A; Rt: 5.60 min. m/z: 367.2 (M+H)$^+$ Exact mass: 366.1

Compound 115

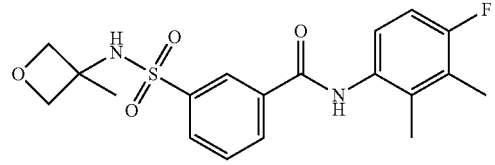

Prepared similarly as described for compound 127 using 4-fluoro-2,3-dimethyl-aniline instead of 4-fluoro-3-(fluoromethyl)aniline. Method A; Rt: 4.98 min. m/z: 393.3 (M+H)$^+$ Exact mass: 392.1.

Compound 116

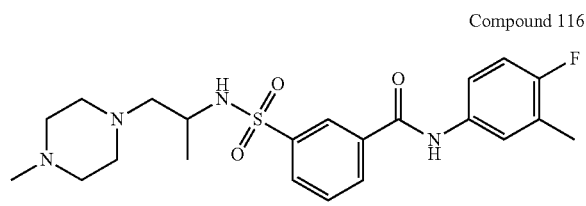

4-fluoro-3-methyl-aniline (9.04 g, 72.2 mmol) was added drop wise to a solution of 3-(chlorosulfonyl) benzoyl chloride (19.0 g, 79.47 mmol) in toluene (300 mL) at 110° C. The resultant mixture was stirred at 110° C. for 1 hour and allowed to cool to 20° C. overnight. The precipitate was filtered and recrystallized from dry toluene resulting in 3-[(4-fluoro-3-methyl-phenyl)carbamoyl]benzenesulfonyl chloride (20 g). 3-[(4-fluoro-3-methyl-phenyl)carbamoyl] benzenesulfonyl chloride (15 g, 45.77 mmol) was added drop wise at 0° C. to a solution of 2-aminopropan-1-ol (3.437 g, 45.77 mmol) and triethylamine (6.946 g) in THF (200 mL). The resultant mixture was stirred for 10 minutes and then allowed to warm to 20° C. during 2 hours. The reaction mixture was quenched with 1N HCl (50 mL). The mixture was extracted with dichloromethane (3×30 mL). The combined organic layers were washed with brine, dried over $MgSO_4$, filtered and concentrated in vacuo. The residue was purified by silica gel column chromatography (gradient eluent: petroleum ether/ethyl acetate from 100/1 to 50/50), resulting in N-(4-fluoro-3-methyl-phenyl)-3-[(2-hydroxy-1-methyl-ethyl)sulfamoyl]-benzamide (15.6 g). Diethyl diazene-1,2-dicarboxylate (4.91 g, 28.19 mmol) was added drop wise to a solution of N-(4-fluoro-3-methyl-phenyl)-3-[(2-hydroxy-1-methyl-ethyl)sulfamoyl]benzamide (7.8 g, 21.29 mmol) and $PPh_3$ (6.14 g, 23.41 mmol) in THF (500 mL) at −70° C. under Argon. The resultant mixture was stirred for 1 hour and then allowed to warm to 20° C. overnight. The reaction mixture was quenched with 1N HCl (300 mL). The mixture was extracted with dichloromethane (4×400 mL) and the combined organic layers were washed with brine, dried over $MgSO_4$, filtered and concentrated in vacuo. The obtained residue was purified by silica gel column chromatography (gradient eluent: petroleum ether/ethyl acetate from 100/1 to 60/40) resulting in N-(4-fluoro-3-methyl-phenyl)-3-(2-methylaziridin-1-yl)sulfonyl-benzamide (6.5 g). A mixture of N-(4-fluoro-3-methyl-phenyl)-3-(2-methylaziridin-1-yl)sulfonyl-benzamide (300 mg, 0.861 mmol) and 1-methylpiperazine (862 mg, 8.61 mmol) in 1,4-dioxane (3 mL) was heated by microwave irradiation at 150° C. for 30 minutes. The volatiles were removed in vacuo. The obtained residue was purified by silica gel column chromatography (gradient eluent: petroleum ether/ethyl acetate from 100/1 to 1/100). The pure fractions were collected and the solvent was removed in vacuo. The obtained residue was purified by preparative high-performance liquid chromatography (column: Luna 150*30 mm*5 u, mobile phase: $CH_3CN$ in water (0.1% $NH_4HCO_3$) from 44% to 74%). The pure fractions were collected, concentrated in vacuo and the residual aqueous solution was lyophilized to dryness resulting in compound 116 (250 mg). Method A; Rt: 4.26 min. m/z: 449.4 $(M+H)^+$ Exact mass: 448.2

Compound 117

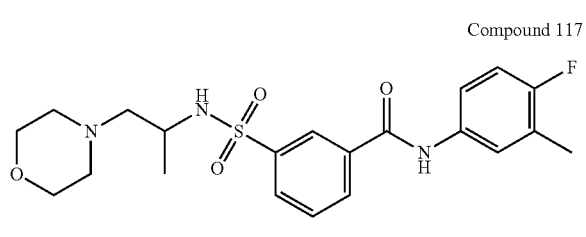 [SMILES: Cc1cc(NC(=O)c2cccc(S(=O)(=O)NC(C)CN3CCOCC3)c2)ccc1F]

Prepared similarly as described for compound 116 using morpholine instead of 1-methylpiperazine. Method A; Rt: 4.45 min. m/z: 436.3 $(M+H)^+$ Exact mass: 435.2

Compound 118

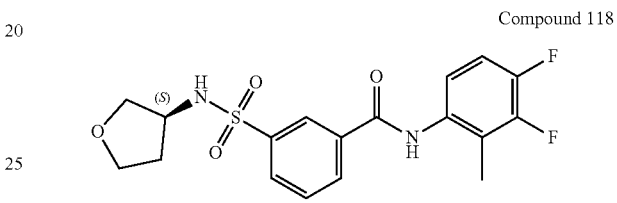

To a stirred solution of 3,4-difluoro-2-methyl-aniline (369 mg, 2.6 mmol), 3-[[(3S)-tetrahydrofuran-3-yl]sulfamoyl] benzoic acid (700 mg, 2.58 mmol) and N,N-diisopropylethylamine (1.35 ml, 7.74 mmol) in DMF (10 mL), Pybrop (132705-51-2, 1.82 g, 3.9 mmol) was added at 0° C. The resulting mixture was stirred overnight at 18° C. The mixture was concentrated in vacuo, ethyl acetate (15 mL) was added and the organic layer was washed with 1N HCl (15 ml) and saturated aqueous $NaHCO_3$ (15 mL). After drying over $Na_2SO_4$ and concentration in vacuo, the crude residue was purified by reversed phase preparative high-performance liquid chromatography (eluent: $CH_3CN$ in $H_2O$ (0.05% $NH_3.H_2O$) from 37% to 37%, v/v). The pure fractions were collected and the volatiles were removed in vacuo. The aqueous layer was lyophilized to dryness, resulting in compound 118 (238 mg). Method D; Rt: 5.01 min. m/z: 396.9 $(M+H)^+$ Exact mass: 396.1

Compound 119

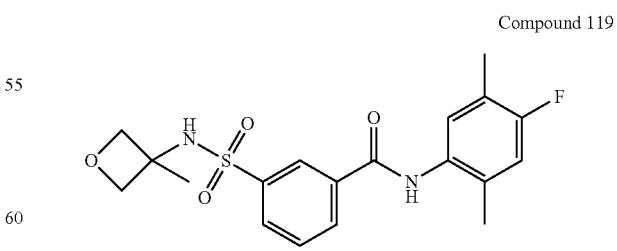

Prepared similarly as described for compound 127 using 4-fluoro-2,5-dimethyl-aniline instead of 4-fluoro-3-(fluoromethyl)aniline, and DIPEA instead of $NEt_3$. Method A; Rt: 5.27 min. m/z: 393.3 $(M+H)^+$ Exact mass: 392.1

Compound 120

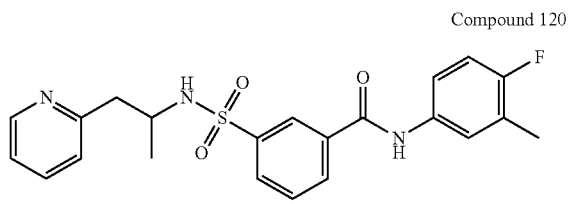 [SMILES: Cc1cc(NC(=O)c2cccc(S(=O)(=O)NC(C)Cc3ccccn3)c2)ccc1F]

A mixture of 1-(2-pyridyl)propan-2-amine (207.8 mg, 1.53 mmol) and DIPEA (0.532 mL, 3.05 mmol) were dissolved in $CH_2Cl_2$ (10 mL). 3-[(4-fluoro-3-methyl-phenyl)carbamoyl]benzenesulfonyl chloride (500 mg, 1.53 mmol) was added portion wise at 0° C. and the mixture was stirred at 0° C. for 1 hour. The mixture was washed with saturated citric acid (10 mL), saturated aqueous $NaHCO_3$ (10 mL), brine and dried over $Na_2SO_4$. The solvent was removed in vacuo and the obtained residue was purified by silica gel column chromatography (gradient eluent: petroleum ether/ethyl acetate from 100/1 to 1/100). The pure fractions were collected and the solvent was removed in vacuo. The obtained solid was suspended in water (10 mL) and acetonitrile (10 mL) and the solution was lyophilized to dryness resulting in compound 120 (550 mg). Method B; Rt: 3.36 min. m/z: 428.3 $(M+H)^+$ Exact mass: 427.1. $^1H$ NMR (400 MHz, DMSO-$d_6$) δ ppm 0.95 (d, J=6.5 Hz, 3H) 2.26 (d, J=1.5 Hz, 3H) 2.69 (dd, J=13.6, 7.3 Hz, 1H) 2.80 (dd, J=13.6, 7.0 Hz, 1H) 3.64-3.74 (m, 1H) 7.08-7.19 (m, 3H) 7.55-7.64 (m, 2H) 7.64-7.71 (m, 2H) 7.84-7.89 (m, 1H) 7.89-7.95 (m, 1H) 8.12-8.17 (m, 1H) 8.25 (t, J=1.5 Hz, 1H) 8.32-8.36 (m, 1H) 10.45 (s, 1H).

Compound 224

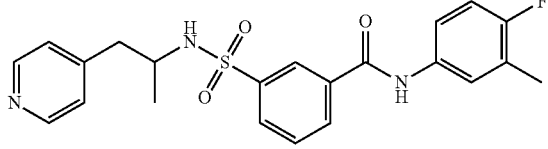

Compound 224 was prepared similarly as described for compound 223, using 1-(4-pyridyl)propan-2-amine instead of 1-(2-pyridyl)propan-2-amine. Compound 224 was purified by preparative high-performance liquid chromatography (column: Luna 150*30 mm*4 u, mobile phase: $CH_3CN$ in water (0.05% $NH_4HCO_3$) from 40% to 70%). Method A; Rt: 4.6 min. m/z: 428.3 $(M+H)^+$ Exact mass: 427.1.

Synthesis of 5-chlorosulfonyl-2-methyl-benzoyl chloride and 3-[(4-fluoro-3-methyl-phenyl)carbamoyl]-4-methyl-benzenesulfonyl chloride 5-(chlorosulfonyl)-2-methylbenzoic acid (10 g, 42.61 mmol) was dissolved in dichloromethane (200 mL). N,N-dimethylformamide (166 4, 2.13 mmol) was added and the mixture was stirred at room temperature under a nitrogen atmosphere. Oxalyl chloride (18.3 mL, 213 mmol) was added in four portions over one hour.

The resulting mixture was stirred for one hour at room temperature. The mixture was concentrated in vacuo and co-evaporated twice using toluene (2×100 mL) yielding 5-chlorosulfonyl-2-methyl-benzoyl chloride as a yellow oil which was used as such. 5-chlorosulfonyl-2-methyl-benzoyl chloride (10.7 g, 42.3 mmol) was dissolved in toluene (220 mL) and this was heated to reflux and stirred under a gentle flow of nitrogen.

4-fluoro-3-methylaniline (4.76 g, 38.1 mmol) in toluene (80 mL) was added drop wise using a syringe pump (0.8 mL/min). The resulting mixture was stirred for 30 minutes while heating was continued. Then the mixture was cooled to room temperature. A precipitation was formed and collected on a glass filter. The obtained solid was dried in vacuo at 55° C., yielding 3-[(4-fluoro-3-methyl-phenyl)carbamoyl]-4-methyl-benzenesulfonyl chloride (10.4 g) as a solid which was used as such in the next step.

Compound 121

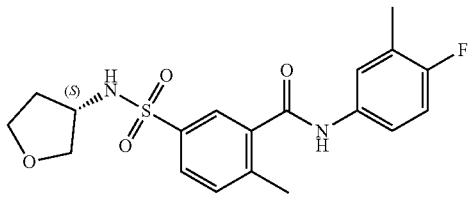

A solution of (S)-3-aminotetrahydrofuran tosylate (0.76 g, 2.93 mmol) and diisopropylethylamine (1.26 mL, 7.31 mmol) in dichloromethane (10 mL) was added drop wise to a solution of 3-[(4-fluoro-3-methyl-phenyl)carbamoyl]-4-methyl-benzenesulfonyl chloride (1 g, 2.93 mmol) in dichloromethane (10 mL). The resulting mixture was stirred for 1 hour at room temperature. The mixture was quenched using HCl (aq/14.6 mL, 14.6 mmol). The layers were separated and the water layer was extracted with dichloromethane (2×20 mL). The combined organics were concentrated in vacuo and purified using silica gel column chromatography (gradient elution: EtOAc-heptane 0:100 to 100:0). The desired fractions were concentrated in vacuo and dried in vacuo at 55° C. yielding compound 121 as a bright white solid. Method F; Rt: 0.90 min. m/z: 393.2 $(M+H)^+$ Exact mass: 392.1. $^1H$ NMR (400 MHz, DMSO-$d_6$) δ ppm 1.58-1.69 (m, 1H), 1.85-1.98 (m, 1H), 2.24 (d, J=1.3 Hz, 3H), 2.45 (s, 3H), 3.38 (dd, J=8.8, 4.4 Hz, 1H), 3.53-3.65 (m, 2H), 3.66-3.76 (m, 2H), 7.13 (t, J=9.2 Hz, 1H), 7.46-7.59 (m, 2H), 7.66 (dd, J=7.0, 2.2 Hz, 1H), 7.75-7.87 (m, 2H), 7.96 (br. s., 1H), 10.46 (s, 1H).

Compound 122

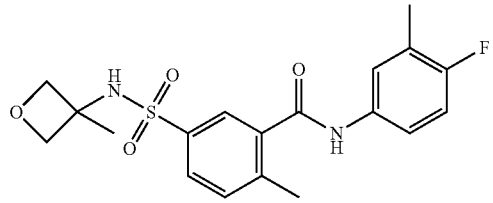

A solution of 3-methyl-3-oxetanamine hydrochloride (0.4 g, 3.22 mmol) and diisopropylethylamine (1.26 mL, 7.31 mmol) in of dichloromethane (10 mL) was added drop wise to a solution of 3-[(4-fluoro-3-methyl-phenyl)carbamoyl]-4-methyl-benzenesulfonyl chloride (1 g, 2.93 mmol) in dichloromethane (10 mL). The resulting mixture was stirred for 1 hour at room temperature. The mixture was quenched using HCl (aq/14.63 mL, 14.63 mmol). The layers were separated and the water layer was extracted using dichloromethane (2×20 mL). The combined organic layers were concentrated in vacuo and purified using column chromatography (gradient elution: EtOAc-heptane 0:100 to 100:0). The desired fractions were concentrated in vacuo and dried in a vacuum oven at 55° C. yielding compound 122 as a bright white solid. Method F; Rt: 0.90 min. m/z: 410.2 (M+NH$_4$)$^+$ Exact mass: 392.1. $^1$H NMR (400 MHz, DMSO-d$_6$) δ ppm 1.43 (s, 3H), 2.19-2.29 (m, 3H), 2.44 (s, 3H), 4.14 (d, J=6.4 Hz, 2H), 4.56 (d, J=6.2 Hz, 2H), 7.13 (t, J=9.1 Hz, 1H), 7.42-7.57 (m, 2H), 7.59-7.71 (m, 1H), 7.74-7.90 (m, 2H), 8.36 (s, 1H), 10.46 (s, 1H).

Compound 123

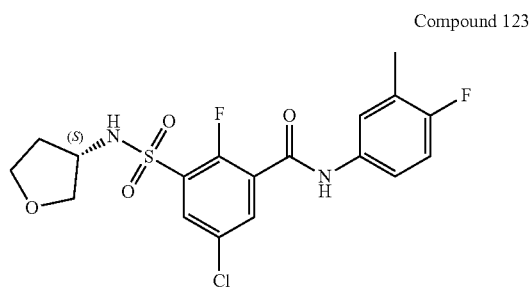

Compound 123 was prepared similarly as described for compound 121 starting from 5-chloro-3-chlorosulfonyl-2-fluoro-benzoic acid (commercial from Enamine EN300-35191) via 5-chloro-3-chlorosulfonyl-2-fluoro-benzoyl chloride ($^1$H NMR (400 MHz, CHLOROFORM-d) δ ppm 8.23 (dd, J=5.4, 2.8 Hz, 1H), 8.37 (dd, J=5.5, 2.6 Hz, 1H)). After silica gel column chromatography (gradient elution: EtOAc-heptane 10:90 to 100:0) compound 123 was crystallised by addition of H$_2$O to a hot iPrOH solution of compound 123, resulting in compound 123 as white solid (3153 mg). Method G; Rt: 1.81 min. m/z: 431.0 (M+H)$^+$ Exact mass: 430.1. $^1$H NMR (400 MHz, DMSO-d$_6$) δ ppm 1.65-1.79 (m, 1H), 1.93-2.06 (m, 1H), 2.25 (d, J=1.8 Hz, 3H), 3.44 (dd, J=9.0, 4.4 Hz, 1H), 3.62 (td, J=8.0, 5.9 Hz, 1H), 3.69 (dd, J=8.9, 6.3 Hz, 1H), 3.71-3.79 (m, 1H), 3.84-3.98 (m, 1H), 7.15 (t, J=9.1 Hz, 1H), 7.45-7.55 (m, 1H), 7.61 (dd, J=6.9, 2.3 Hz, 1H), 7.91 (dd, J=5.7, 2.6 Hz, 1H), 8.07 (dd, J=5.2, 2.8 Hz, 1H), 8.57 (d, J=6.8 Hz, 1H), 10.68 (s, 1H)

Compound 124

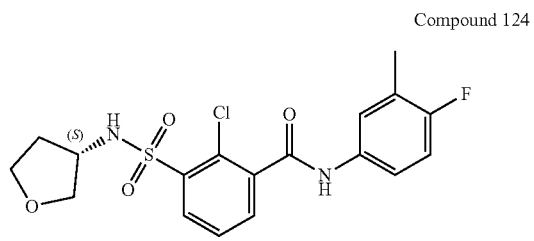

Compound 125 (167 mg, 0.371 mmol) and Pd/C (25 mg) were stirred in methanol (19 mL) under hydrogen atmosphere during 80 minutes. The reaction mixture was filtered and concentrated. The obtained residue was purified by preparative SFC (Stationary phase: Chiralpak Diacel AD 30×250 mm), Mobile phase: CO$_2$, MeOH with 0.2% iPrNH$_2$), the desired fractions were collected, evaporated, dissolved in MeOH and evaporated again resulting in compound 124 (67 mg). Method G; Rt: 1.61 min. m/z: 430.0 (M+NH$_4$)$^+$ Exact mass: 412.1. $^1$H NMR (400 MHz, DMSO-d$_6$) δ ppm 1.68-1.83 (m, 1H), 1.89-2.03 (m, 1H), 2.24 (d, J=1.5 Hz, 3H), 3.45 (dd, J=8.9, 4.7 Hz, 1H), 3.56-3.69 (m, 2H), 6 3.70-3.86 (m, 2H), 7.14 (t, J=9.1 Hz, 1H), 7.45-7.55 (m, 1H), 7.60-7.69 (m, 2H), 7.82 (dd, J=7.6, 1.7 Hz, 1H), 8.09 (dd, J=7.8, 1.7 Hz, 1H), 8.34 (s, 1H), 10.62 (s, 1H)

Compound 125

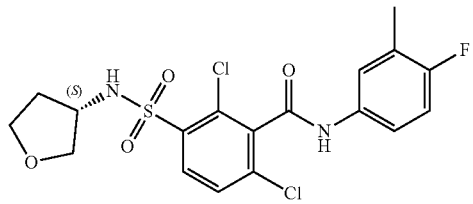

Compound 125 was prepared similarly as described for compound 126 starting from 2,6-dichloro-3-chlorosulfonyl-benzoic acid instead of 3-chlorosulfonyl-2-methyl-benzoic acid. Method G; Rt: 1.77 min. m/z: 464.0 (M+NH$_4$)$^+$ Exact mass: 446.0. $^1$H NMR (400 MHz, CHLOROFORM-d) δ ppm 1.75-1.86 (m, 1H), 2.04-2.16 (m, 1H), 2.30 (d, J=1.8 Hz, 3H), 3.57-3.65 (m, 1H), 3.66-3.76 (m, 2H), 3.82-3.95 (m, 2H), 5.45 (d, J=7.5 Hz, 1H), 7.01 (t, J=8.9 Hz, 1H), 7.30-7.38 (m, 1H), 7.47-7.56 (m, 2H), 7.83 (s, 1H), 8.05 (d, J=8.6 Hz, 1H).

Compound 126

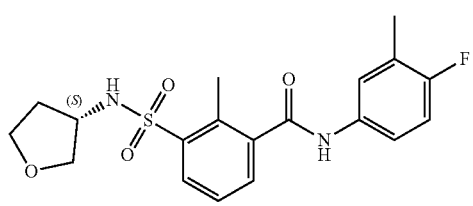

3-chlorosulfonyl-2-methyl-benzoic acid (commercial from Enamine EN300-109516; 508.4 mg, 2.17 mmol) was dissolved in dichloromethane (50 mL). DMF (1 drop) and oxalylchloride (1375 mg, 10.83 mmol) were added and the mixture was stirred for 4 hours under an inert atmosphere. The reaction mixture was concentrated resulting in 3-chlorosulfonyl-2-methyl-benzoyl chloride as a yellow oil (554 mg) which was used as such in the next step. $^1$H NMR (400 MHz, CHLOROFORM-d) δ ppm 2.92-3.01 (m, 3H), 7.60 (t, J=7.9 Hz, 1H), 8.27-8.41 (m, 2H). 4-Fluoro-3-methylaniline (227 mg, 1.98 mmol) dissolved in dichloromethane (10 mL) was added drop wise, over 5 minutes, to a solution of 3-chlorosulfonyl-2-methyl-benzoyl chloride (550 mg, 2.17 mmol) in toluene (50 mL) at reflux. The reaction mixture was refluxed for 30 minutes and next cooled in an icebath. A solution of (S)-3-aminotetrahydrofuran tosylate (564 mg, 2.17 mmol) and DIPEA (0.85 ml, 4.94 mmol) dissolved in dichloromethane (10 mL) was added and the obtained mixture was stirred for 30 minutes. The resulting mixture was washed with HCl (2×100 mL/1M aq), water (2×100 mL) and NaHCO$_3$ (2×100 mL/sat. aq). The organic layer was dried over MgSO$_4$, filtered and concentrated in vacuo. The obtained residue was purified using silica gel column chromatography (CH$_2$Cl$_2$-MeOH 100:0 to 90:10) and repurified by applying a gradient from 10 till 100% EtOAc in heptane. The product fractions were concentrated and dried overnight in vacuo at 50° C. yielding compound 126 as colourless oil (16.6 mg). Method G; Rt: 1.65 min. m/z: 393.1 (M+H)+ Exact mass: 392.1. ¹H NMR (400 MHz, CHLOROFORM-d) δ ppm 1.73-1.87 (m, 1H), 2.06-2.20 (m, 1H), 2.30 (d, J=1.8 Hz, 3H), 2.69 (s, 3H), 3.54-3.63 (m, 1H), 3.65-3.78 (m, 2H), 3.83-3.97 (m, 2H), 4.99 (d, J=8.1 Hz, 1H), 7.01 (t, J=8.9 Hz, 1H), 7.31-7.44 (m, 2H), 7.51 (dd, J=6.7, 2.5 Hz, 1H), 7.58-7.69 (m, 2H), 8.06 (dd, J=8.0, 1.2 Hz, 1H)

Procedure S1:

A solution of 3-[(4-fluoro-3-methyl-phenyl)carbamoyl] benzenesulfonyl chloride (0.50 g, 1.52 mmol, 1 eq) in toluene (10 mL) was added to a flask containing an amine (1.1 eq). DIPEA (657 μL, 3.81 mmol, 2.5 eq) was added and the reaction mixture was stirred for 1 hour. Next, 1M HCl (5 mL) was added to the reaction mixture.

Procedure S2:

A tube was charged with 3-[(4-fluoro-3-methyl-phenyl) carbamoyl]-benzenesulfonyl chloride (250 mg, 0.76 mmol) and an amine (1.1 eq) and CH₂Cl₂ (5 mL) was added. The solution was stirred, DIPEA (329 μL, 1.9 mmol, 2.5 eq) was added and the mixture was further stirred for 30 minutes. Then, HCl (1M aq/5 mL) was added and the mixture was stirred for 5 minutes more.

Procedure S3:

To a solution of 3-[(4-fluoro-3-methyl-phenyl)carbamoyl] benzenesulfonyl chloride (0.50 g, 1.52 mmol, 1 eq) and DIPEA (657 μL, 3.81 mmol, 2.5 eq) in CH₂Cl₂ (10 mL), an amine (1.1 eq) was added. The reaction mixture was stirred for 1 hour. Next, 1M HCl (5 mL) was added to the reaction mixture.

Procedure S4:

3-[(4-fluoro-3-methyl-phenyl)carbamoyl]benzenesulfonyl chloride (250 mg, 0.76 mmol) and DIPEA (329 μL, 1.9 mmol, 2.5 eq) dissolved in CH₂Cl₂ (5 mL) were added to a tube containing an amine (1.1 eq). The reaction mixture was stirred for 3 hours. 1M HCl (5 mL) was added.

Workup W1:

A precipitate was formed. The precipitate was filtered off, rinced with diisopropylether and dried in a vacuum oven at 55° C.

Workup W2:

The organic layer was separated and concentrated in vacuo. The obtained residue was purified by silica gel column chromatography using a heptane to EtOAc gradient as eluent.

Workup W3:

The layers were separated and the organic layer was loaded on a silica gel column for purification (with gradient elution: CH₂Cl₂-methanol 100:0 to 97:3).

Workup W4:

The organic layer was separated and loaded on a silica gel column. The mixture was purified using gradient elution from heptane to EtOAc.

Compound 128

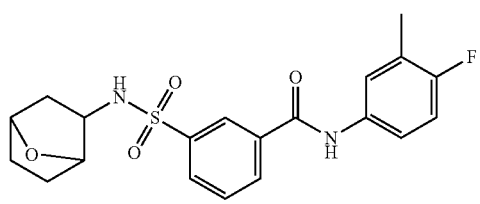

Synthesis following procedure S4 with 7-oxabicyclo [2.2.1]heptan-2-amine. as amine, workup W4. Method F; Rt: 0.94 min. m/z: 422.1 (M+NH₄)+ Exact mass: 404.1. ¹H NMR (400 MHz, DMSO-d₆) δ ppm 1.22-1.48 (m, 5H), 1.68 (dd, J=12.5, 7.9 Hz, 1H), 2.25 (d, J=1.8 Hz, 3H), 3.25-3.29 (m, 1H), 4.14 (d, J=4.8 Hz, 1H), 4.44 (t, J=4.8 Hz, 1H), 7.14 (t, J=9.2 Hz, 1H), 7.54-7.63 (m, 1H), 7.68 (dd, J=7.2, 2.3 Hz, 1H), 7.74-7.80 (m, 1H), 7.86 (d, J=6.8 Hz, 1H), 7.98-8.03 (m, 1H), 8.20 (dt, J=7.8, 1.4 Hz, 1H), 8.35 (t, J=1.5 Hz, 1H), 10.46 (s, 1H).

Compound 129

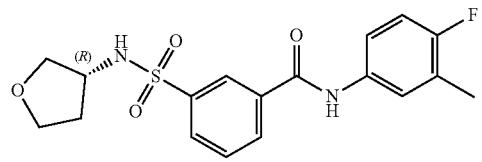

Synthesis following procedure S3 with R-(+)-3-aminotetrahydrofuran toluene-4-sulfonate as amine, workup W2.

Method F; Rt: 0.89 min. m/z: 396.1 (M+NH₄)+ Exact mass: 378.1. ¹H NMR (400 MHz, DMSO-d₆) ppm 1.56-1.65 (m, 1H), 1.85-1.94 (m, 1H), 2.25 (d, J=1.8 Hz, 3H), 3.36 (dd, J=9.0, 4.4 Hz, 1H), 3.52-3.65 (m, 2H), 3.65-3.73 (m, 1H), 3.73-3.79 (m, 1H), 7.14 (t, J=9.2 Hz, 1H), 7.56-7.62 (m, 1H), 7.67 (dd, J=7.0, 2.3 Hz, 1H), 7.78 (t, J=7.8 Hz, 1H), 7.99-8.05 (m, 1H), 8.08 (bs, 1H), 8.20-8.23 (m, 1H), 8.37 (t, J=1.7 Hz, 1H), 10.47 (s, 1H), $[\alpha]_D^{20}$=+5.8 (c 0.61 w/v %, MeOH)

Compound 130

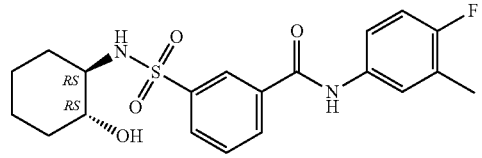

Method F; Rt: 0.95 min. m/z: 424.2 (M+NH₄)+ Exact mass: 406.1.

Synthesis following procedure S3 with racemic trans-2-aminocyclohexanol hydrochloride as amine, workup W2.

Compound 131

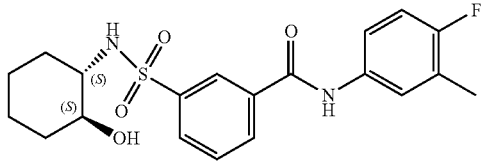

Synthesis following procedure S3 with (1S,2S)-trans-2-aminocyclohexanol hydrochloride as amine, workup W2.

Method F; Rt: 0.95 min. m/z: 424.2 (M+NH₄)+ Exact mass: 406.1.

¹H NMR (400 MHz, DMSO-d₆) δ ppm 1.01-1.23 (m, 4H), 1.41-1.58 (m, 2H), 1.59-1.70 (m, 1H), 1.71-1.83 (m, 1H), 2.25 (d, J=1.3 Hz, 3H), 2.77-2.90 (m, 1H), 3.15-3.27 (m, 1H), 4.50 (d, J=4.6 Hz, 1H), 7.14 (t, J=9.2 Hz, 1H), 7.54-7.64 (m, 2H), 7.64-7.69 (m, 1H), 7.72 (t, J=7.9 Hz, 1H), 8.04 (d, J=7.7 Hz, 1H), 8.16 (d, J=7.9 Hz, 1H), 8.39 (s, 1H), 10.43 (s, 1H)

Compound 132

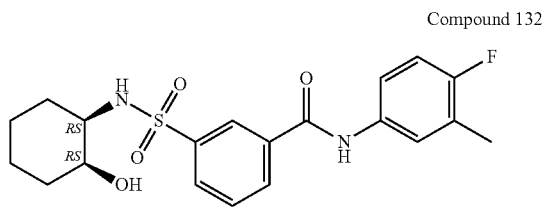 [SMILES: Cc1cc(NC(=O)c2cccc(S(=O)(=O)N[C@@H]3CCCC[C@@H]3O)c2)ccc1F]

Synthesis following procedure S3 with racemic cis-2-aminocyclohexanol hydrochloride as amine, workup W2. Method F; Rt: 0.96 min. m/z: 424.1 (M+NH$_4$)$^+$ Exact mass: 406.1. $^1$H NMR (400 MHz, DMSO-d$_6$) δ ppm 1.01-1.26 (m, 4H), 1.26-1.36 (m, 1 H), 1.38-1.62 (m, 3H), 2.25 (d, J=1.8 Hz, 3H), 3.03-3.14 (m, 1H), 3.57 (br. s., 1H), 4.52 (d, J=4.2 Hz, 1H), 7.14 (t, J=9.1 Hz, 1H), 7.46 (d, J=7.9 Hz, 1H), 7.56-7.62 (m, 1H), 7.68 (dd, J=7.0, 2.6 Hz, 1H), 7.73 (t, J=7.8 Hz, 1H), 8.05 (dt, J=8.1, 1.2 Hz, 1H), 8.14-8.19 (m, 1H), 8.39 (t, J=1.7 Hz, 1H), 10.43 (s, 1H)

Compound 133

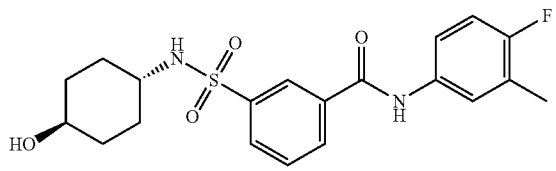

Synthesis following procedure S3 with trans-4-aminocyclohexanol hydrochloride as amine, workup W2.

Method F; Rt: 0.84 min. m/z: 424.2 (M+NH$_4$)$^+$ Exact mass: 406.1.

$^1$H NMR (400 MHz, DMSO-d$_6$) δ ppm 1.01-1.31 (m, 4H), 1.57 (d, J=10.3 Hz, 2H), 1.69 (d, J=12.5 Hz, 2H), 2.25 (d, J=1.8 Hz, 3H), 2.84-3.01 (m, 1H), 3.22-3.29 (m, 1H), 4.46 (d, J=4.4 Hz, 1H), 7.14 (t, J=9.1 Hz, 1H), 7.53-7.64 (m, 1H), 7.68 (dd, J=7.0, 2.2 Hz, 1H), 7.72-7.79 (m, 2H), 7.95-8.04 (m, 1H), 8.18 (dt, J=7.7, 1.3 Hz, 1H), 8.36 (t, J=1.7 Hz, 1H), 10.46 (s, 1H)

Compound 134

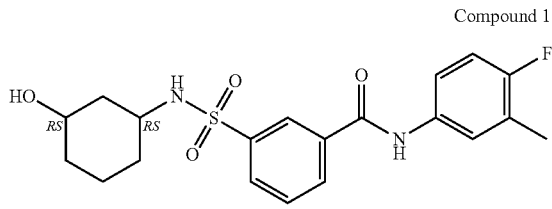

Method F; Rt: 0.89 min. m/z: 424.2 (M+NH$_4$)$^+$ Exact mass: 406.1.

Synthesis following procedure S3 with 3-amino-cyclohexanol as amine, workup W2. Compound 134 was separated in it's isomers by preparative SFC (Stationary phase: Chiralpak Daicel IC 20×250 mm), Mobile phase: CO$_2$, iPrOH with 0.4% iPrNH$_2$), the desired fractions were collected, evaporated, dissolved in MeOH and evaporated again, yielding 134a, 134b, 134c, 134d. SFC Columns: ID-H 250 mm×4.6 mm Flow: 3 ml/min Mobile phase: 25% iPrOH (containing 0.2% iPrNH$_2$) hold 18.0 min. Temperature: 30° C.; Rt: 134 a (10.0 min), 134b (11.1 min), 134c (13.6 min), 134d (14.7 min). Cis: Enantiomers 134a and 134b N-(4-fluoro-3-methyl-phenyl)-3-[[(1R,3S)-3-hydroxycyclohexyl]sulfamoyl]benzamide or N-(4-fluoro-3-methyl-phenyl)-3-[[(1S,3R)-3-hydroxycyclohexyl]sulfamoyl]benzamide. $^1$H NMR (400 MHz, DMSO-d$_6$) δ ppm 0.84-1.14 (m, 4H), 1.48-1.60 (m, 2H), 1.60-1.72 (m, 1H), 1.72-1.82 (m, 1H), 2.26 (d, J=1.8 Hz, 3H), 2.93-3.07 (m, 1H), 3.20-3.30 (m, 1H), 4.58 (d, J=4.6 Hz, 1H), 7.14 (t, J=9.1 Hz, 1H), 7.55-7.64 (m, 1H), 7.69 (dd, J=7.0, 2.2 Hz, 1H), 7.76 (t, J=7.8 Hz, 1H), 7.83 (br. s., 1H), 7.96-8.06 (m, 1H), 8.13-8.24 (m, 1H), 8.38 (t, J=1.7 Hz, 1H), 10.47 (s, 1H)

Trans: enantiomers 134c and 134d N-(4-fluoro-3-methyl-phenyl)-3-[[(1R,3R)-3 hydroxycyclohexyl]sulfamoyl]benzamide or N-(4-fluoro-3-methyl-phenyl)-3-[[(1S,3S)-3-hydroxycyclohexyl]sulfamoyl]benzamide $^1$H NMR (400 MHz, DMSO-d$_6$) δ ppm 1.08-1.20 (m, 1H), 1.25-1.42 (m, 4H), 1.42-1.58 (m, 3H), 2.25 (d, J=1.8 Hz, 3H), 3.36-3.45 (m, 1H), 3.71-3.89 (m, 1H), 4.38 (d, J=3.5 Hz, 1H), 7.14 (t, J=9.1 Hz, 1H), 7.51 (br. s., 1H), 7.56-7.63 (m, 1H), 7.69 (dd, J=7.2, 2.3 Hz, 1H), 7.73-7.78 (m, 1H), 7.97-8.05 (m, 1H), 8.19 (dt, J=7.9, 1.2 Hz, 1H), 8.37 (t, J=1.7 Hz, 1H), 10.47 (br. s., 1H)

Compound 135

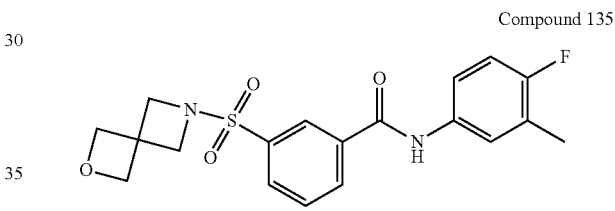

Synthesis following procedure S3 with 2-oxa-6-azaspiro[3.3]heptane as amine, workup W2. Method F; Rt: 0.91 min. m/z: 389.1 (M−H)$^−$ Exact mass: 390.1. $^1$H NMR (400 MHz, DMSO-d$_6$) δ ppm 2.26 (d, J=1.8 Hz, 3H), 3.95 (s, 4H), 4.44 (s, 4H), 7.15 (t, J=9.2 Hz, 1H), 7.57-7.65 (m, 1H), 7.68 (dd, J=7.0, 2.4 Hz, 1H), 7.85 (t, J=7.8 Hz, 1H), 8.01 (dt, J=8.0, 1.3 Hz, 1H), 8.28-8.38 (m, 2H), 10.51 (s, 1H).

Compound 136

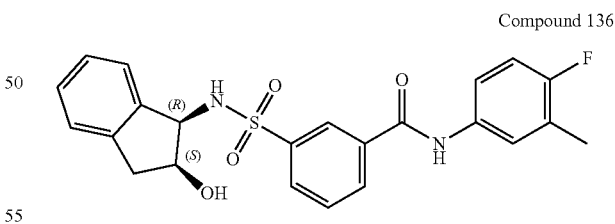

Synthesis following procedure 51 with (1R,2S)-(+)-cis-1-aminoindan-2-ol as amine, workup W1. Method G; Rt: 1.79 min. m/z: 439.0 (M−H)$^−$ Exact mass: 440.1. $^1$H NMR (400 MHz, DMSO-d$_6$) δ ppm 2.25 (d, J=1.8 Hz, 3H), 2.72 (d, J=15.0 Hz, 1H), 2.93 (dd, J=16.1, 4.6 Hz, 1H), 4.15 (qd, J=4.7, 1.8 Hz, 1H), 4.69 (dd, J=8.7, 4.7 Hz, 1H), 4.96 (d, J=4.4 Hz, 1H), 6.87 (d, J=7.3 Hz, 1H), 7.04-7.10 (m, 1H), 7.10-7.21 (m, 3H), 7.55-7.64 (m, 1H), 7.68 (dd, J=7.0, 2.4 Hz, 1H), 7.77 (t, J=7.8 Hz, 1H), 7.93 (d, J=9.0 Hz, 1H), 8.15 (dt, J=8.1, 1.2 Hz, 1H), 8.21 (dd, J=7.7, 1.5 Hz, 1H), 8.48 (t, J=1.7 Hz, 1H), 10.44 (s, 1H)

Compound 137

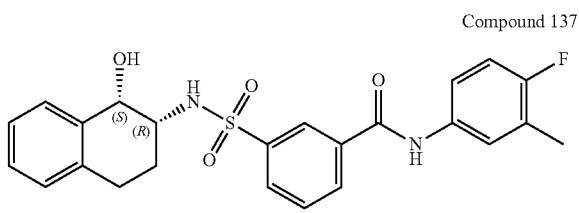

Synthesis following procedure S4 with (1S,2R)-2-amino-tetralin-1-ol hydrochloride as amine, workup W4. Method F; Rt: 1.03 min. m/z: 472.2 (M+NH$_4$)$^{-1}$ Exact mass: 454.1. $^1$H NMR (400 MHz, DMSO-d$_6$) δ ppm 1.35-1.46 (m, 1H), 1.96 (qd, J=11.8, 6.2 Hz, 1H), 2.25 (d, J=1.5 Hz, 3H), 2.62 (ddd, J=17.2, 10.9, 6.3 Hz, 1H), 2.70-2.82 (m, 1H), 3.34-3.45 (m, 1H), 4.39 (br. s., 1H), 5.29 (d, J=5.7 Hz, 1H), 7.04 (d, J=6.8 Hz, 1H), 7.09-7.24 (m, 4H), 7.55-7.63 (m, 1H), 7.62-7.70 (m, 2H), 7.75 (t, J=7.8 Hz, 1H), 8.06-8.13 (m, 1H), 8.19 (d, J=8.1 Hz, 1H), 8.43 (t, J=1.5 Hz, 1H), 10.44 (s, 1H), [α]$_D^{20}$: +66° (c 0.55 w/v %, DMF). DSC (From 30 to 300° C. at 10° C./min): 170° C.

Compound 138

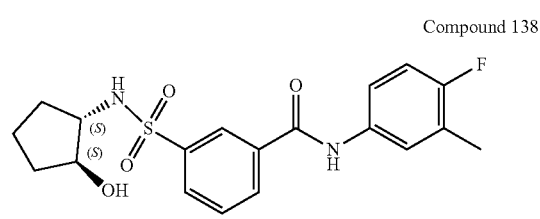

Synthesis following procedure 51 with trans-(1S,2S)-2-aminocyclopentanol hydrochloride as amine, workup W1. Method F; Rt: 0.88 min. m/z: 410.4 (M+NH$_4$)$^+$ Exact mass: 392.1. $^1$H NMR (400 MHz, DMSO-d$_6$) δ ppm 1.16-1.29 (m, 1H), 1.29-1.40 (m, 1H), 1.50 (quin, J=7.4 Hz, 2H), 1.61-1.78 (m, 2H), 2.25 (d, J=1.8 Hz, 3H), 3.16-3.26 (m, 1H), 3.74-3.82 (m, 1H), 4.67 (d, J=4.4 Hz, 1H), 7.14 (t, J=9.2 Hz, 1H), 7.55-7.63 (m, 1H), 7.65-7.72 (m, 2H), 7.75 (t, J=7.8 Hz, 1H), 7.98-8.04 (m, 1H), 8.18 (dt, J=7.9, 1.3 Hz, 1H), 8.36 (t, J=1.7 Hz, 1H), 10.45 (s, 1H)

Compound 139

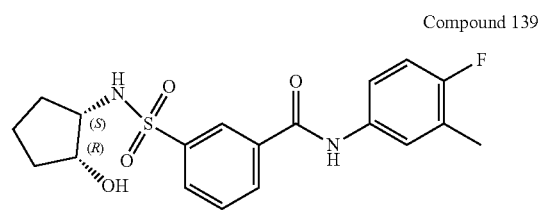

Synthesis following procedure 51 with cis-(1R,2S)-2-aminocyclopentanol hydrochloride as amine, workup W1. Method F; Rt: 0.92 min. m/z: 410.1 (M+NH$_4$)$^+$ Exact mass: 392.1. $^1$H NMR (400 MHz, DMSO-d$_6$) δ ppm 1.25-1.51 (m, 4H), 1.51-1.67 (m, 2H), 2.25 (d, J=1.5 Hz, 3H), 3.21-3.28 (m, 1H), 3.72-3.79 (m, 1H), 4.63 (d, J=4.0 Hz, 1H), 7.14 (t, J=9.2 Hz, 1H), 7.42 (d, J=8.1 Hz, 1H), 7.55-7.63 (m, 1H), 7.68 (dd, J=7.3, 2.4 Hz, 1H), 7.73 (t, J=7.8 Hz, 1H), 8.06 (dt, J=8.1, 1.2 Hz, 1H), 8.17 (d, J=8.1 Hz, 1H), 8.40 (t, J=1.5 Hz, 1H), 10.43 (s, 1H)

Compound 172

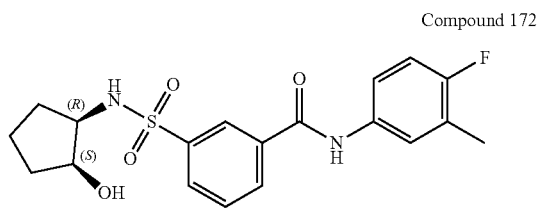

Synthesis following procedure S2 with cis-(1S,2R)-2-aminocyclopentanol hydrochloride as amine. The formed precipitate was collected on a glassfilter and rinsed with CH$_2$Cl$_2$ (2×5 mL). The precipitate was further purified using silica gel column chromatography (gradient elution: EtOAc-heptane 0:100 to 100:0). Drying in vacuo at 55° C. resulted in compound 172 as a bright white powder. Method G; Rt: 1.65 min. m/z: 392.9 (M+H)$^+$ Exact mass: 392.1. DSC (From 30 to 300° C. at 10° C./min): 145° C.

Compound 173

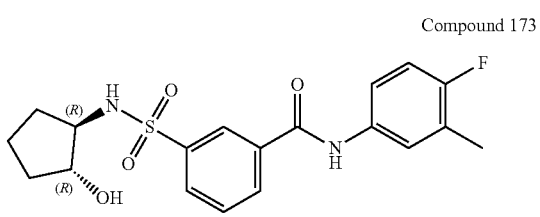

Synthesis following procedure S4 (reaction time=20 hours instead of 3 hours) with trans-(1R,2R)-2-aminocyclopentanol as amine, workup W4. Method F; Rt: 0.87 min. m/z: 410.1 (M+NH$_4$)$^+$ Exact mass: 392.1.

Compound 140

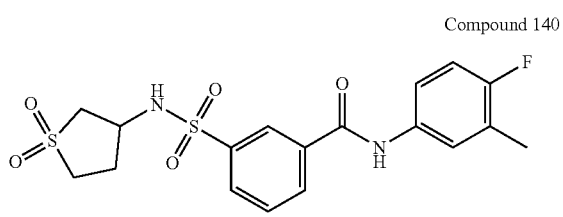 [SMILES: Cc1cc(NC(=O)c2cccc(S(=O)(=O)NC3CCS(=O)(=O)C3)c2)ccc1F]

Synthesis following procedure 51 with 1,1-dioxothiolan-3-amine hydrochloride as amine, workup W1. Method F; Rt: 0.85 min. m/z: 444.2 (M+NH$_4$)$^+$ Exact mass: 426.1. $^1$H NMR (400 MHz, DMSO-d$_6$) δ ppm 1.90-2.04 (m, 1H), 2.16-2.24 (m, 1H), 2.25 (d, J=1.8 Hz, 3H), 2.81 (dd, J=13.4, 7.0 Hz, 1H), 3.08 (ddd, J=13.1, 9.1, 7.5 Hz, 1H), 3.15-3.26 (m, 2H), 3.94-4.06 (m, 1H), 7.15 (t, J=9.2 Hz, 1H), 7.55-7.63 (m, 1H), 7.68 (dd, J=7.2, 2.3 Hz, 1H), 7.79 (t, J=7.8 Hz, 1H), 8.01-8.07 (m, 1H), 8.23 (dt, J=7.7, 1.3 Hz, 1H), 8.38 (t, J=1.7 Hz, 1H), 8.40 (br. s., 1H), 10.48 (s, 1H)

Compound 141

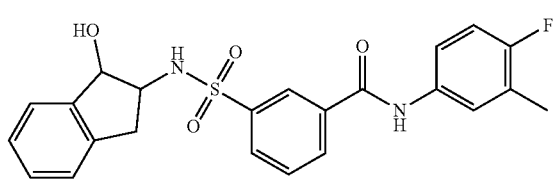

Synthesis following procedure S4 with 2-aminoindan-1-ol hydrochloride as amine, workup W4. Method F; Rt: 0.98 and 1.01 min. m/z: 458.1 (M+NH$_4$)$^+$ Exact mass: 440.1. Compound 141 was separated in it's isomers by preparative SFC (Stationary phase: Chiralcel Diacel OD 20×250 mm), Mobile phase: CO$_2$, MeOH with 0.2% iPrNH$_2$), the desired fractions were collected, evaporated, dissolved in MeOH and evaporated again. SFC, Column: OD-H (Diacel) 250 mm×4.6 mm Flow: 5 mL/min, Mobile phase: 30% MeOH (containing 0.2% iPrNH$_2$) hold 4.00 min, up to 50% in 1 min and hold 2.00 min @ 50% Temperature: 40° C. Rt: 141a (1.8 min), 141b (2.1 min), 141c (2.5 min), 141d (2.7 min).

141a, 141c: N-(4-fluoro-3-methyl-phenyl)-3-[[(1S,2S)-1-hydroxyindan-2-yl]-sulfamoyl]benzamide or N-(4-fluoro-3-methyl-phenyl)-3-[[(1R,2R)-1-hydroxyindan-2-yl]sulfamoyl]benzamide. $^1$H NMR (400 MHz, DMSO-d$_6$) δ ppm 2.25 (d, J=1.5 Hz, 3H), 2.43-2.55 (m, 1H), 2.83 (dd, J=15.7, 7.8 Hz, 1H), 3.59-3.70 (m, 1H), 4.83 (d, J=6.8 Hz, 1H), 5.58 (br. s., 1H), 7.03-7.27 (m, 5H), 7.56-7.65 (m, 1H), 7.68 (dd, J=7.0, 2.4 Hz, 1H), 7.78 (t, J=7.8 Hz, 1H), 8.05-8.11 (m, 1H), 8.16 (br. s., 1H), 8.22 (d, J=8.1 Hz, 1H), 8.43 (t, J=1.7 Hz, 1H), 10.47 (br. s., 1H) Method F; Rt: 0.98 m/z: 458.3 (M+NH$_4$)$^+$ Exact mass: 440.1.

141b, 141d: N-(4-fluoro-3-methyl-phenyl)-3-[[(1R,2S)-1-hydroxyindan-2-yl]sulfamoyl]benzamide or N-(4-fluoro-3-methyl-phenyl)-3-[[(1S,2R)-1-hydroxyindan-2-yl]sulfamoyl]benzamide. $^1$H NMR (600 MHz, ACETONE-d$_6$, −14° C.) δ ppm 2.25 (d, J=1.9 Hz, 3H), 2.80-2.90 (m, 2H), 3.94-3.99 (m, 1H), 4.72 (d, J=5.3 Hz, 1H), 4.87 (d, J=3.8 Hz, 1H), 6.96 (d, J=5.0 Hz, 1H), 7.08 (t, J=9.2 Hz, 1H), 7.14-7.19 (m, 2H), 7.21 (td, J=7.3, 1.2 Hz, 1H), 7.29 (d, J=7.3 Hz, 1H), 7.65-7.70 (m, 1H), 7.74 (dt, J=6.8, 3.1 Hz, 1H), 7.79 (t, J=7.8 Hz, 1H), 8.19 (ddd, J=7.8, 1.8, 1.1 Hz, 1H), 8.27 (ddt, J=7.8, 1.8, 0.9, 0.9 Hz, 1H), 8.54 (q, J=1.6 Hz, 1H), 10.09 (s, 1H) Method F; Rt: 1.00 m/z: 458.2 (M+NH$_4$)$^+$ Exact mass: 440.1.

Compound 142

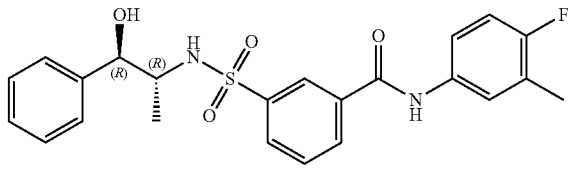

Synthesis following procedure S4 with (1R,2R)-2-amino-1-phenyl-propan-1-ol as amine, workup W4. Method F; Rt: 1.00 min. m/z: 460.1 (M+NH$_4$)$^+$ Exact mass: 442.1. $^1$H NMR (400 MHz, DMSO-d$_6$) δ ppm 0.76 (d, J=6.8 Hz, 3H), 2.25 (d, J=1.3 Hz, 3H), 3.37-3.46 (m, 1H), 4.56 (d, J=4.6 Hz, 1H), 5.41 (br. s., 1H), 7.14 (t, J=9.2 Hz, 1H), 7.18-7.23 (m, 1H), 7.23-7.32 (m, 4H), 7.49 (br. s., 1H), 7.56-7.64 (m, 1H), 7.64-7.72 (m, 2H), 7.88-7.96 (m, 1H), 8.15 (d, J=7.9 Hz, 1H), 8.31 (t, J=1.5 Hz, 1H), 10.42 (s, 1H).

Compound 143

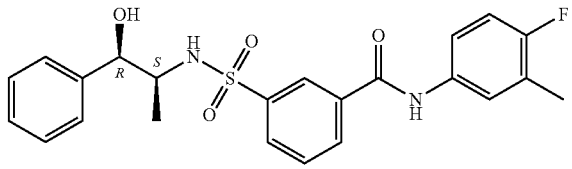

Synthesis following procedure S1 with (1R,2S)-(−)-norephedrine as amine, workup W1. Method F; Rt: 1.01 min. m/z: 460.1 (M+NH$_4$)$^+$ Exact mass: 442.1. $^1$H NMR (400 MHz, DMSO-d$_6$) δ ppm 0.79 (d, J=6.8 Hz, 3H), 2.25 (d, J=1.8 Hz, 3H), 3.33-3.37 (m, 1H), 4.48 (t, J=4.6 Hz, 1H), 5.42 (d, J=4.6 Hz, 1H), 7.10-7.27 (m, 6H), 7.55-7.63 (m, 1H), 7.64-7.71 (m, 2H), 7.78 (d, J=8.4 Hz, 1H), 7.91 (dt, J=8.2, 1.2 Hz, 1H), 8.12-8.18 (m, 1H), 8.30 (t, J=1.7 Hz, 1H), 10.42 (s, 1H)

Compound 144

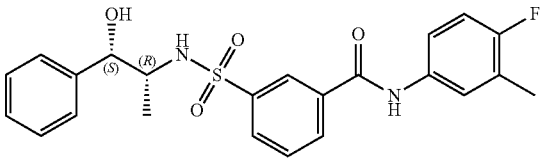

Synthesis following procedure S1 with (1s, 2R)-(+)-norephedrine as amine, workup W1. Method F; Rt: 1.01 min. m/z: 460.2 (M+NH$_4$)$^+$ Exact mass: 442.1.

$^1$H NMR (400 MHz, DMSO-d$_6$) δ ppm 0.79 (d, J=6.8 Hz, 3H), 2.25 (d, J=1.8 Hz, 3H), 3.32-3.38 (m, 1H), 4.48 (t, J=4.6 Hz, 1H), 5.42 (d, J=4.8 Hz, 1H), 7.10-7.27 (m, 6H), 7.56-7.63 (m, 1H), 7.65-7.71 (m, 2H), 7.78 (d, J=8.4 Hz, 1H), 7.89-7.94 (m, 1H), 8.15 (dt, J=7.8, 1.3 Hz, 1H), 8.30 (t, J=1.7 Hz, 1H), 10.42 (s, 1H)

Compound 145

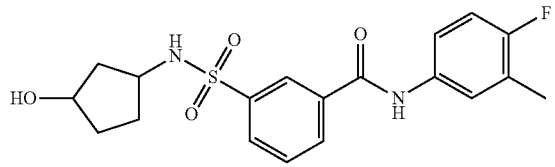

Synthesis following procedure S4 with 3-aminocyclopentanol as amine, after completion, the reaction mixture was directly loaded on a silica gel column for purification, using a heptane to EtOAc gradient yielding compound 145 as a 83 (145a, 145b): 17 (145c, 145d) mixture of diastereomers. Method F; Rt: 0.82 and 0.86 min. m/z: 410.2 (M+NH$_4$)$^+$ Exact mass: 392.1. Compound 145 was separated in it's isomers by preparative SFC (Stationary phase: Chiralpak Diacel AD 30×250 mm), Mobile phase: CO$_2$, MeOH with 0.4% iPrNH$_2$), the desired fractions were collected, evaporated, dissolved in MeOH and evaporated again yielding compound 145a (238 mg) and 145b (236 mg) and a mixture of compound 145c and 145d. The mixture of 145c and 145d was further purified by Preparative SFC (Stationary phase: Chiralpak Diacel AD 30×250 mm), Mobile phase: CO$_2$, EtOH with 0.4% iPrNH$_2$), the desired fractions were collected, evaporated, dissolved in MeOH and evaporated again yielding 145c (29 mg) and 145d (27 mg). 145a and 145b: N-(4-fluoro-3-methyl-phenyl)-3-[[(1R,3S)-3-hydroxycyclopentyl]sulfamoyl]benzamide or N-(4-fluoro-3-methyl-phenyl)-3-[[(1S,3R)-3-hydroxycyclopentyl]sulfamoyl]benzamide.

Method F; Rt: 0.85 min. m/z: 410.2 (M+NH$_4$)$^+$ Exact mass: 392.1.

$^1$H NMR (400 MHz, DMSO-d$_6$) δ ppm 1.21 (ddd, J=13.3, 7.8, 6.1 Hz, 1H), 1.36-1.64 (m, 4H), 1.84-1.95 (m, 1H), 2.25 (d, J=1.1 Hz, 3H), 3.37-3.47 (m, 1H), 3.85-3.96 (m, 1H), 4.25-5.00 (1H, br. s), 7.14 (t, J=9.2 Hz, 1H), 7.35-7.75 (1H, br. s), 7.54-7.63 (m, 1H), 7.68 (dd, J=7.0, 2.2 Hz, 1H), 7.75 (t, J=7.8 Hz, 1H), 8.01 (d, J=7.9 Hz, 1H), 8.19 (d, J=7.7 Hz, 1H), 8.36 (s, 1H), 10.46 (br. s., 1H)

145c and 145d: N-(4-fluoro-3-methyl-phenyl)-3-[[(1S,3S)-3-hydroxycyclopentyl]-sulfamoyl]benzamide or N-(4-fluoro-3-methyl-phenyl)-3-[[(1R,3R)-3-hydroxycyclopentyl]sulfamoyl]benzamide. Method F; Rt: 0.82 min. m/z: 410.2 (M+NH$_4$)$^+$ Exact mass: 392.1.

$^1$H NMR (400 MHz, DMSO-d$_6$) δ ppm 1.17-1.35 (m, 2H), 1.41 (ddd, J=13.4, 8.0, 5.7 Hz, 1H), 1.56 (ddd, J=13.2, 7.3, 2.6 Hz, 1H), 1.69-1.83 (m, 2H), 2.25 (d, J=1.8 Hz, 3H), 3.59-3.72 (m, 1H), 3.99-4.09 (m, 1H), 4.43 (d, J=3.5 Hz, 1H), 7.14 (t, J=9.2 Hz, 1H), 7.55-7.63 (m, 1H), 7.68 (dd, J=7.0, 2.2 Hz, 1H), 7.73-7.84 (m, 2H), 7.96-8.02 (m, 1H), 8.20 (dt, J=7.9, 1.2 Hz, 1H), 8.36 (t, J=1.7 Hz, 1H), 10.48 (br. s., 1H) 145a: [α]$_D^{20}$: +5.2° (c 0.56 w/v %, DMF); 145b: [α]$_D^{20}$: −5.4° (c 0.60 w/v %, DMF); 145c: [α]$_D^{20}$: −3.5° (c 0.46 w/v %, DMF); 145d: [α]$_D^{20}$: +2.5° (c 0.44 w/v %, DMF)

Compound 146

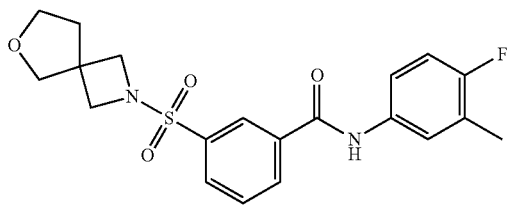

Synthesis following procedure S2 with 6-oxa-2-azaspiro[3.4]octane oxalate as amine, after completion, the reaction mixture was directly loaded on a silica gel column for purification, using a heptane to EtOAc gradient yielding compound 146. Method F; Rt: 0.93 min. m/z: 422.3 (M+NH$_4$)$^+$ Exact mass: 404.1. $^1$H NMR (400 MHz, DMSO-d$_6$) ppm 1.81 (t, J=6.9 Hz, 2H), 2.26 (d, J=1.8 Hz, 3H), 3.46 (s, 2H), 3.57 (t, J=6.9 Hz, 2H), 3.72-3.80 (m, 4H), 7.15 (t, J=9.1 Hz, 1H), 7.58-7.64 (m, 1H), 7.69 (dd, J=7.0, 2.2 Hz, 1H), 7.87 (t, J=7.8 Hz, 1H), 8.04 (dt, J=8.0, 1.3 Hz, 1H), 8.32-8.41 (m, 2H), 10.53 (s, 1H).

Compound 147

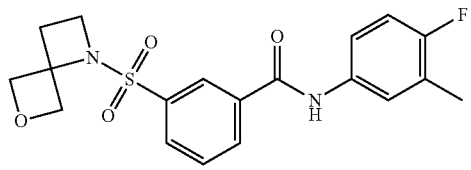

Synthesis following procedure S2 with 6-oxa-1-azaspiro[3.3]heptane as amine, after completion, the reaction mixture was directly loaded on a silica gel column for purification, using a heptane to EtOAc gradient yielding compound 147. Method F; Rt: 0.92 min. m/z: 408.2 (M+NH$_4$)$^+$ Exact mass: 390.1. $^1$H NMR (400 MHz, DMSO-d$_6$) δ ppm 2.25 (d, J=1.8 Hz, 3H), 2.53 (t, J=7.3 Hz, 2H), 3.73 (t, J=7.4 Hz, 2H), 4.53 (d, J=7.9 Hz, 2H), 5.01 (d, J=7.9 Hz, 2H), 7.15 (t, J=9.1 Hz, 1H), 7.56-7.64 (m, 1H), 7.68 (dd, J=7.0, 2.2 Hz, 1H), 7.82 (t, J=7.8 Hz, 1H), 8.05-8.11 (m, 1H), 8.29 (dt, J=7.8, 1.3 Hz, 1H), 8.40 (t, J=1.7 Hz, 1H), 10.51 (s, 1H)

Compound 148

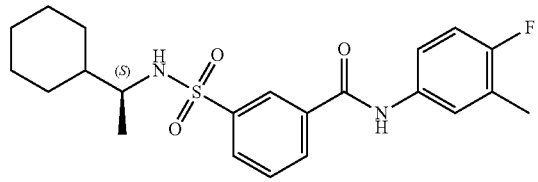

Synthesis following procedure S4 with (S)-(+)-1-cyclohexylethylamine as amine, workup W4. Method F; Rt: 1.23 min. m/z: 436.2 (M+NH$_4$)$^+$ Exact mass: 418.2

Compound 149

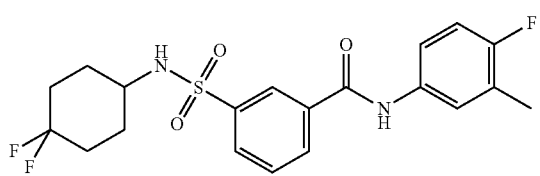

Synthesis following procedure S4 with 4,4-difluorocyclohexylamine as amine, workup W4. Method F; Rt: 1.06 min. m/z: 444.5 (M+NH$_4$)$^+$ Exact mass: 426.1.

Compound 150

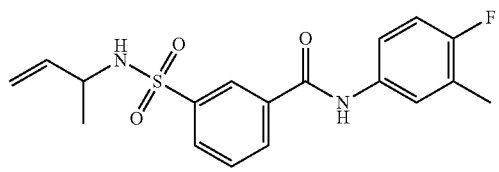

Synthesis following procedure S4 with 3-buten-2-amine, hydrochloride as amine, workup W4. Method F; Rt: 1.01 min. m/z: 380.3 (M+NH$_4$)$^+$ Exact mass: 362.1. $^1$H NMR (400 MHz, DMSO-d$_6$) δ ppm 1.03 (d, J=6.8 Hz, 3H), 2.25 (d, J=1.8 Hz, 3H), 3.74-3.87 (m, 1H), 4.87 (dt, J=10.5, 1.4 Hz, 1H), 5.00 (dt, J=17.3, 1.4 Hz, 1H), 5.61 (ddd, J=17.3, 10.5, 6.1 Hz, 1H), 7.14 (t, J=9.2 Hz, 1H), 7.55-7.63 (m, 1H), 7.68 (dd, J=7.2, 2.3 Hz, 1H), 7.74 (t, J=7.8 Hz, 1H), 7.93 (d, J=7.9 Hz, 1H), 7.96-8.01 (m, 1H), 8.18 (dt, J=7.7, 1.3 Hz, 1H), 8.35 (t, J=1.7 Hz, 1H), 10.45 (s, 1H).

Compound 151

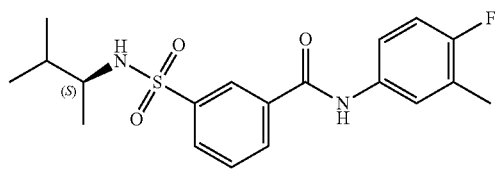

Synthesis following procedure S4 (stirred for 20 hours instead of 3 hours) with (S)-(+)-2-amino-3-methylbutane as amine, workup W4. Method F; Rt: 1.11 min. m/z: 396.2 (M+NH$_4$)$^+$ Exact mass: 378.1. $^1$H NMR (400 MHz, CHLOROFORM-d) δ ppm 0.81 (d, J=6.8 Hz, 6H), 0.95 (d, J=6.8 Hz, 3H), 1.57-1.67 (m, 1H), 2.28 (d, J=1.8, 3H), 3.13-3.28

(m, 1H), 4.85 (d, J=8.6 Hz, 1H), 6.98 (t, J=9.0 Hz, 1H), 7.36-7.46 (m, 1H), 7.49-7.57 (m, 1H), 7.61 (t, J=7.8 Hz, 1H), 8.00 (dt, J=7.9, 1.5 Hz, 1H), 8.12 (dt, J=7.9, 1.5 Hz, 1H), 8.25 (s, 1H), 8.39 (t, J=1.9 Hz, 1H).

Compound 152

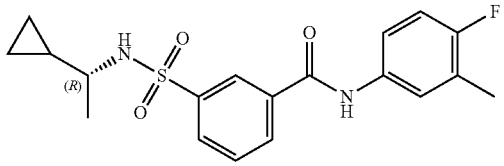

Synthesis following procedure S4 (stirred for 20 hours instead of 3 hours) with (1R)-1-cyclopropylethylamine as amine, workup W4. ¹H NMR (400 MHz, CHLOROFORM-d) δ ppm −0.05-0.05 (m, 1H), 0.09-0.16 (m, 1H), 0.20-0.36 (m, 1H), 0.38-0.51 (m, 1H), 0.69-0.81 (m, 1H), 1.13 (d, J=6.6 Hz, 3H), 2.27 (d, J=1.8 Hz, 3H), 2.63-2.85 (m, 1H), 5.10 (d, J=6.8 Hz, 1H), 6.98 (t, J=8.9 Hz, 1H), 7.37-7.45 (m, 1H), 7.52 (dd, J=6.6, 2.4 Hz, 1H), 7.60 (t, J=7.8 Hz, 1H), 7.98-8.02 (m, 1H), 8.08-8.13 (m, 1H), 8.25 (s, 1H), 8.38 (t, J=1.7 Hz, 1H). Method F; Rt: 1.07 min. m/z: 394.2 (M+NH₄)⁺ Exact mass: 376.1.

Compound 174

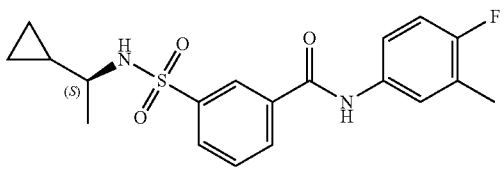

Synthesis following procedure S4 (stirred for 20 hours instead of 3 hours) with (1R)-1-cyclopropylethylamine as amine, workup W4. The obtained residue was recrystallised from disopropylether/acetonitrile. The precipitate was collected and dried in vacuo at 55° C., resulting in compound 174. ¹H NMR (400 MHz, DMSO-d₆) δ ppm −0.11-−0.01 (m, 1H), 0.07-0.23 (m, 2H), 0.29-0.38 (m, 1H), 0.70-0.82 (m, 1H), 0.99 (d, J=6.6 Hz, 3H), 2.21-2.30 (m, 3H), 2.66 (quin, J=6.8 Hz, 1H), 7.14 (t, J=9.1 Hz, 1H), 7.56-7.64 (m, 1H), 7.68 (dd, J=7.0, 2.4 Hz, 1H), 7.75 (t, J=7.8 Hz, 1H), 7.85 (br. s., 1H), 7.93-8.07 (m, 1H), 8.18 (d, J=7.9 Hz, 1H), 8.37 (t, J=1.7 Hz, 1H), 10.46 (br. s., 1H)

Compound 153

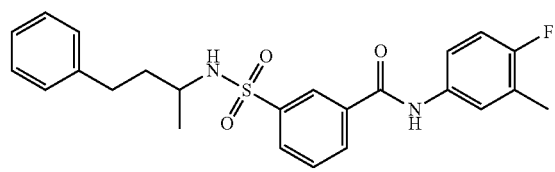

Synthesis following procedure S4 (stirred for 20 hours instead of 3 hours) with 3-amino-1-phenylbutane as amine, workup W4. Method F; Rt: 1.19 min. m/z: 458.2 (M+NH₄)⁺ Exact mass: 440.2. ¹H NMR (400 MHz, CHLOROFORM-d) δ ppm 1.06 (d, J=6.6 Hz, 3H), 1.62-1.76 (m, 2H), 2.25 (d, J=1.8 Hz, 3H), 2.44-2.64 (m, 2H), 3.30-3.43 (m, 1H), 5.05 (d, J=8.4 Hz, 1H), 6.96 (t, J=8.9 Hz, 1H), 7.00-7.04 (m, 2H), 7.09-7.17 (m, 1H), 7.17-7.25 (m, 2H), 7.36-7.42 (m, 1H), 7.50 (dd, J=6.8, 2.4 Hz, 1H), 7.57 (t, J=7.8 Hz, 1H), 7.95 (m, J=7.8, 1H), 8.10 (m, J=7.8 Hz, 1H), 8.25 (s, 1H), 8.37 (t, J=1.5 Hz, 1H)

Compound 154

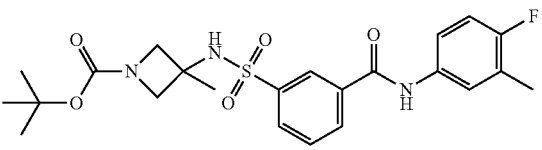

3-[(4-fluoro-3-methyl-phenyl)carbamoyl]benzenesulfonyl chloride (500 mg, 1.53 mmol) and DIPEA (657 μL, 3.8 mmol, 2.5 eq) dissolved in CH₂Cl₂ (15 mL) were added to a tube containing 3-amino-1-Boc-3-methyl-azetidine (1.1 eq). The reaction mixture was stirred for 20 hours. 1M HCl (5 mL) was added and the mixture was stirred for 5 minutes. The organic layer was separated and loaded on a silica gel column. The mixture was purified using gradient elution from heptane to EtOAc, resulting in compound 154 (721 mg). Method F; Rt: 1.11 min. m/z: 478.2 (M+H)⁺ Exact mass: 477.2.

Compound 155

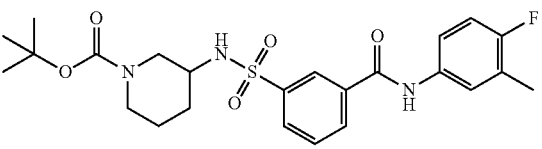

Prepared as described for compound 154 using 1-Boc-3-aminopiperidine instead of 3-amino-1-Boc-3-methyl-azetidine. Method F; Rt: 1.13 min. m/z: 492.1 (M+H)⁺ Exact mass: 491.2.

Compound 156

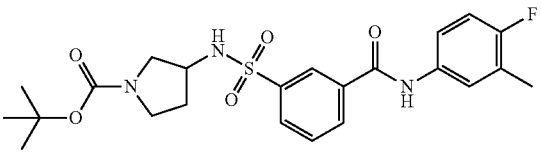

Prepared as described for compound 154 using (+/−)-3-amino-1-N-Boc-pyrrolidine instead of 3-amino-1-Boc-3-methyl-azetidine. Method F; Rt: 1.08 min. m/z: 478.2 (M+H)⁺ Exact mass: 477.2 ¹H NMR (400 MHz, CHLOROFORM-d) δ ppm 1.36 (s, 9H), 1.71-1.92 (m, 1H), 1.92-2.15 (m, 1H), 2.28 (d, J=1.8 Hz, 3H), 3.10-3.24 (m, 1H), 3.24-3.44 (m, 3H), 3.81-3.94 (m, 1H), 5.50-6.00 (m, 1H), 6.98 (t, J=9.0 Hz, 1H), 7.40-7.48 (m, 1H), 7.52-7.71 (m, 2H), 7.93-8.03 (m, 1H), 8.04-8.17 (m, 1H), 8.31 (br. s., 1H), 8.45-8.88 (m, 1H).

Compound 157

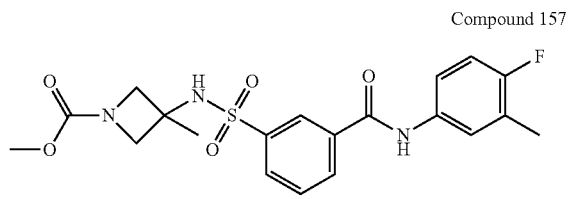

Compound 154 (721 mg, 1.51 mmol) was dissolved in CH$_2$Cl$_2$ (10 mL) and HCl (6M in iPrOH, 2.5 mL) was added. The mixture was stirred overnight and the volatiles were removed in vacuo, resulting in N-(4-fluoro-3-methyl-phenyl)-3-[(3-methylazetidin-3-yl)sulfamoyl]benzamide hydrochloride as a white solid (0.57 g). To N-(4-fluoro-3-methyl-phenyl)-3-[(3-methylazetidin-3-yl)sulfamoyl]benzamide hydrochloride (150 mg) in CH$_2$Cl$_2$ (10 mL), DIPEA (263 μL, 1.5 mmol) and methyl chloroformate (444, 0.57 mmol) were added. The mixture was concentrated under a gentle flow of nitrogen at 55° C. until only 2 mL remained. This residue was purified using silica gel column chromatography (gradient elution: EtOAc-heptane 0:100 to 100:0). The desired fractions were concentrated under reduced pressure and the obtained product was dried in a vacuum oven at 55° C. yielding compound 157 (74.2 mg) as a bright white powder. Method F; Rt: 0.93 min. m/z: 436.1 (M+H)$^+$ Exact mass: 435.1. $^1$H NMR (400 MHz, DMSO-d$_6$) δ ppm 1.36 (s, 3H), 2.25 (d, J=1.5 Hz, 3H), 3.52 (s, 3H), 3.56-3.68 (m, 2H), 3.83-3.93 (m, 2H), 7.14 (t, J=9.2 Hz, 1H), 7.57-7.62 (m, 1H), 7.68 (dd, J=6.8, 2.4 Hz, 1H), 7.77 (t, J=7.9 Hz, 1H), 8.01 (m, J=7.9 Hz, 1H), 8.21 (m, J=7.9 Hz, 1H), 8.37 (t, J=1.5 Hz, 1H), 8.48 (bs, 1H), 10.49 (s, 1H)

Compound 158

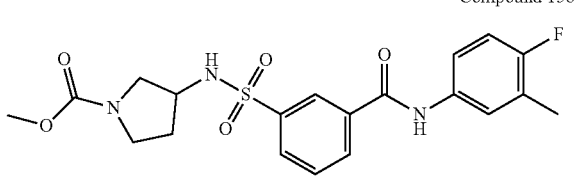

Prepared similarly as described for compound 157, starting from compound 156 instead of compound 154, via intermediate N-(4-fluoro-3-methyl-phenyl)-3-(pyrrolidin-3-yl-sulfamoyl)benzamide hydrochloride. Method F; Rt: 0.91 min. m/z: 436.2 (M+H)$^+$ Exact mass: 435.1. $^1$H NMR (400 MHz, DMSO-d$_6$) δ ppm 1.61-1.77 (m, 1H), 1.80-1.98 (m, 1H), 2.25 (d, J=1.5 Hz, 3H), 3.00-3.12 (m, 1H), 3.14-3.27 (m, 1H), 3.26-3.39 (m, 2H), 3.50-3.58 (m, 3H), 3.67-3.76 (m, 1H), 7.14 (t, J=9.2 Hz, 1H), 7.57-7.63 (m, 1H), 7.68 (dd, J=7.2, 2.3 Hz, 1H), 7.78 (t, J=7.8 Hz, 1H), 7.97-8.04 (m, 1H), 8.04-8.18 (m, 1H), 8.18-8.25 (m, 1H), 8.37 (t, J=1.5 Hz, 1H), 10.48 (s, 1H)

Compound 159

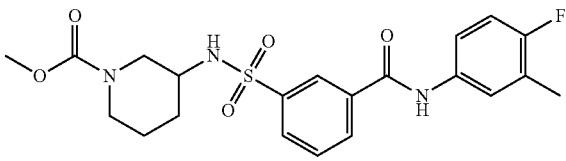

Prepared similarly as described for compound 157, starting from compound 155 instead of compound 154, via intermediate N-(4-fluoro-3-methyl-phenyl)-3-(3-piperidyl-sulfamoyl)benzamide hydrochloride. Method F; Rt: 0.96 min. m/z: 467.1 (M+NH$_4$)$^+$ Exact mass: 449.1. The racemic compound 159 was separated by Preparative SFC (Stationary phase: Chiralpak Daicel IC 20×250 mm), Mobile phase: CO$_2$, MeOH with 0.2% iPrNH$_2$), the desired fractions were collected, evaporated, dissolved in methanol and evaporated again, resulting in enantiomer 159a and 159b.

Columns: ID-H (Daicel) 250 mm×4.6 mm; Flow: 3 mL/min; Mobile phase: 20% EtOH (containing 0.2% iPrNH$_2$) hold 15.00 min; Temperature: 30° C.; Rt: 9.6 min (159a), Rt: 11.0 min (159b)

Compound 160

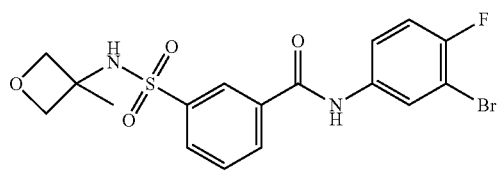

Method B; Rt: 4 min. m/z: 443.1 (M+H)$^+$ Exact mass: 442.0

$^1$H NMR (400 MHz, DMSO-d$_6$) δ ppm 1.41 (s, 3H) 4.14 (d, J=6.3 Hz, 2H) 4.56 (d, J=6.0 Hz, 2H) 7.42 (t, J=8.8 Hz, 1H) 7.74-7.82 (m, 2H) 8.04 (s, 1H) 8.15-8.24 (m, 2H) 8.37 (t, J=1.5 Hz, 1H) 8.54 (br. s, 1H) 10.67 (br. s, 1H).

Compound 161

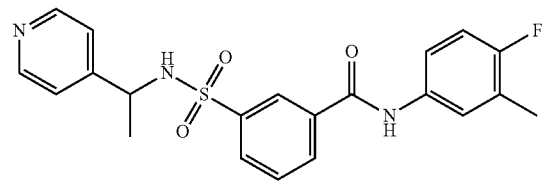

1-pyridin-4-yl-ethylamine (220 mg, 1.8 mmol) and 3-[(4-fluoro-3-methyl-phenyl)-carbamoyl]benzenesulfonyl chloride (500 mg, 1.53 mmol) were dissolved in CH$_2$Cl$_2$ (10 mL). DIPEA (6.2 mmol) was added at 0° C. and the mixture was stirred at 25° C. for 4 hours. The mixture was washed with water (20 mL) and the aqueous layer was extracted with CH$_2$Cl$_2$ (3×20 mL). The combined organic layers were washed with brine and dried over Na$_2$SO$_4$. The solvent was removed in vacuo and the obtained residue was purified by reversed phase high performance liquid chromatography (mobile phase: CH$_3$CN in water (0.1% TFA) from 30% to 60%).

The pure fractions were collected and neutralized with solid NaHCO$_3$. The organic solvent was removed in vacuo and the formed precipitate was filtered, washed with H$_2$O (5 mL) and dried under high vacuum. The obtained residue was suspended in water (5 mL) and the aqueous layer was lyophilized to dryness, resulting in compound 161 (410 mg). Method A; Rt: 4.34 min. m/z: 414.3 (M+H)$^+$ Exact mass: 413.1. $^1$H NMR (400 MHz, DMSO-d$_6$) δ ppm 1.23 (d, J=7.0 Hz, 3H) 2.26 (d, J=1.5 Hz, 3H) 4.34-4.50 (m, 1H) 7.15 (t, J=9.3 Hz, 1H) 7.20-7.24 (m, 2H) 7.56-7.66 (m, 2H) 7.68 (dd, J=7.0, 2.3 Hz, 1H) 7.86 (m, J=7.8 Hz, 1H) 8.13 (m, J=7.8 Hz, 1H) 8.26 (t, J=1.3 Hz, 1H) 8.32-8.39 (m, 2H) 8.55 (d, J=8.3 Hz, 1H) 10.41 (s, 1H).

Compound 162

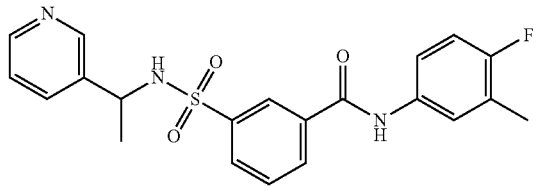

Prepared similarly as described for compound 161, using 1-(3-pyridyl)ethanamine instead of 1-pyridin-4-yl-ethylamine. Method D; Rt: 5.16 min. m/z: 414.3 (M+H)+ Exact mass: 413.1.

Compound 163

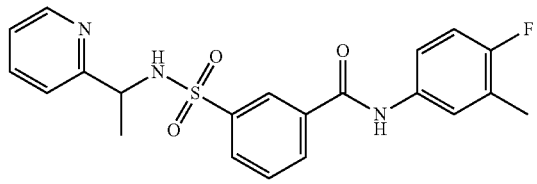

Prepared similarly as described for compound 161, using 1-(2-pyridyl)ethanamine instead of 1-pyridin-4-yl-ethylamine. Method A; Rt: 4.60 min. m/z: 414.3 (M+H)+ Exact mass: 413.1.

Compound 164

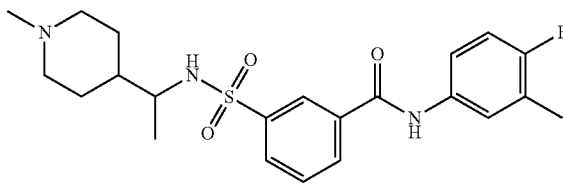

Prepared similarly as described for compound 161, using 1-(1-methyl-4-piperidyl)ethanamine instead of 1-pyridin-4-yl-ethylamine. Method B; Rt: 3.35 min. m/z: 434.4 (M+H)+ Exact mass: 433.2.

Compound 165

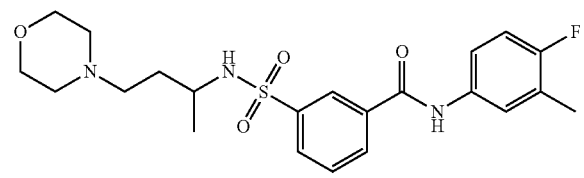

Prepared similarly as described for compound 161, using 4-morpholinobutan-2-amine instead of 1-pyridin-4-yl-ethylamine. Method B; Rt: 3.33 min. m/z: 450.3 (M+H)+ Exact mass: 449.2.

Compound 166

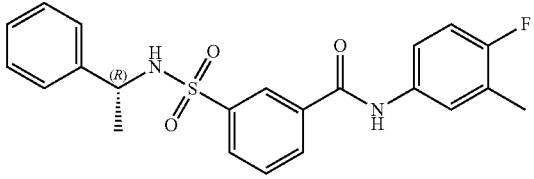

Prepared similarly as described for compound 161, using (R)-1-phenylethanamine instead of 1-pyridin-4-yl-ethylamine. The impure compound was purified by preparative high-performance liquid chromatography (column: Luna 150*30 mm*5 u, mobile phase: CH$_3$CN in water (0.1% NH$_4$HCO$_3$) from 40% to 70%, flow rate: 35 ml/min). Method B; Rt: 4.45 min. m/z: 413.3 (M+H)+ Exact mass: 412.1. $[\alpha]_D^{20}$: +55° (c 0.12 w/v, methanol).

Compound 167

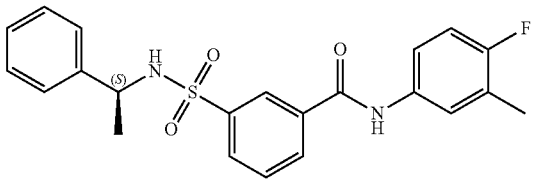

Prepared similarly as described for compound 166, using (S)-1-phenylethanamine instead of (R)-1-phenylethanamine. Method B; Rt: 4.45 min. m/z: 413.3 (M+H)+ Exact mass: 412.1. $[\alpha]_D^{20}$: -57° (c 0.12 w/v, methanol).

Compound 168

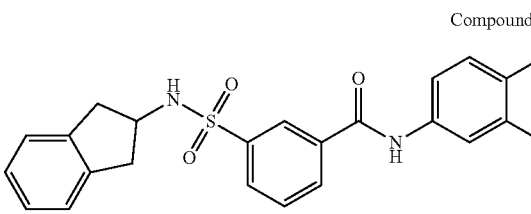

Synthesis following procedure S4 (20 hours reaction time instead of 3 hours) with 2-aminoindane as amine, workup W4. The obtained residue was recrystallised from Diisopropylether/acetonitrile, resulting in compound 168. Method F; Rt: 1.14 min. m/z: 442.2 (M+NH$_4$)+ Exact mass: 424.1. $^1$H NMR (400 MHz, DMSO-d$_6$) δ ppm 2.25 (d, J=1.8 Hz, 3H), 2.72 (dd, J=15.6, 7.0 Hz, 2H), 2.96 (dd, J=15.8, 7.5 Hz, 2H), 3.95 (quin, J=7.3 Hz, 1H), 7.08-7.17 (m, 5H), 7.57-7.63 (m, 1H), 7.68 (dd, J=6.9, 2.3 Hz, 1H), 7.79 (t, J=7.8 Hz, 1H), 8.03-8.12 (m, 1H), 8.13-8.28 (m, 2H), 8.41 (t, J=1.7 Hz, 1H), 10.49 (br. s., 1H)

Compound 169

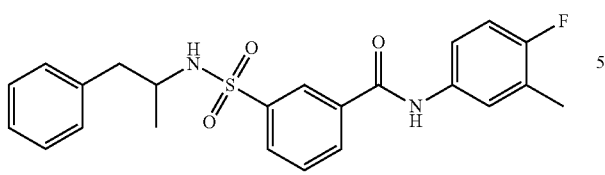

Prepared similarly as described for compound 166, using 1-phenylpropan-2-amine instead of (R)-1-phenylethanamine. Method B; Rt: 4.60 min. m/z: 427.3 (M+H)+ Exact mass: 426.1.

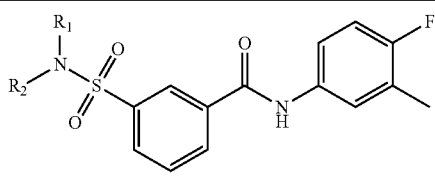

| # | R1,R2-N structure | Amine used | Synthetic/ work up Procedure | LC-MS method | Rt (min.) | [M + NH4]+ or [M + H]+ | Exact mass |
|---|---|---|---|---|---|---|---|
| 170 | 2-cyclopropylethyl-NH- | 2-cyclopropyl-ethanamine | S4/W4 | H | 8.63 | 377.1 | 376.1 |
| 171 | 4-hydroxy-tetrahydrofuran-3-yl-NH- | 4-aminotetra-hydrofuran-3-ol | S4/W4 | F | 0.79 | 412.1 | 394.1 |
| 175 | (1R,2R)-2-hydroxyindan-1-yl-NH- | (1R,2R)-1-amino-2,3-dihydro-1H-inden-2-ol | S4*/W4 | F | 0.97 | 458.1 | 440.1 |
| 176 | (1S,2S)-2-hydroxyindan-1-yl-NH- | (1S,2S)-1-Amino-2,3-dihydro-1H-inden-2-ol | S4*/W4 | F | 1.01 | 458.1 | 440.1 |
| 177 | (1S,2R)-2-hydroxyindan-1-yl-NH- | (1S,2R)-(−)-Cis-1-amino-2-indanol | S4*/W4 | F | 0.97 | 458.4 | 440.1 |
| 178 | (1R,2R)-1-hydroxytetralin-2-yl-NH- | (1R,2R)-2-aminotetralin-1-ol hydrochloride | S4*/W4 | F | 1.01 | 472.2 | 454.1 |

-continued

| # | R1R2N- group | Amine used | Synthetic/ work up Procedure | LC-MS method | Rt (min.) | [M + NH4]+ or [M + H]+ | Exact mass |
|---|---|---|---|---|---|---|---|
| 179 | 4-amino-1-methyl-pyrrolidin-2-one group | 4-Amino-1-methyl-pyrrolidin-2-one | S4*/W4 | F | 0.81 | 406.1 | 405.1 |
| 180 | 5-amino-1-methyl-piperidin-2-one group | 5-Amino-1-methyl-piperidin-2-one | S4*/W4 | F | 0.81 | 420.2 | 419.1 |
| 181 | 3-amino-1-methylpyrrolidin-2-one group | 3-Amino-1-methylpyrrolidin-2-one | S4*/W4 | F | 0.84 | 423.1 | 405.1 |
| 182 | 3-amino-1-N-boc-azetidine group | 3-Amino-1-N-boc-azetidine | S4*/W4 | F | 1.06 | 481.2 | 463.2 |
| 183 | 1-(trifluoromethyl)cyclopropanamine group | 1-(trifluoromethyl)cyclopropanamine | S4*/W4 | F | 1.03 | 434.1 | 416.1 |

S4*: reaction time 20 hours instead of 3 hours

Compound 175. $^1$H NMR (400 MHz, DMSO-$d_6$) δ ppm 2.25 (d, J=1.5 Hz, 3H), 2.62 (dd, J=15.7, 6.5 Hz, 1H), 3.07 (dd, J=15.7, 6.7 Hz, 1H), 4.11 (quin, J=6.2 Hz, 1H), 4.50 (dd, J=7.9, 6.2 Hz, 1H), 5.14 (d, J=5.7 Hz, 1H), 6.92 (d, J=7.5 Hz, 1H), 7.06-7.24 (m, 4H), 7.55-7.65 (m, 1H), 7.69 (dd, J=7.0, 2.4 Hz, 1H), 7.77 (t, J=7.8 Hz, 1H), 8.05-8.15 (m, 1H), 8.19-8.26 (m, 1H), 8.31 (d, J=8.4 Hz, 1H), 8.47 (t, J=1.7 Hz, 1H), 10.45 (s, 1H) Compound 178. $^1$H NMR (400 MHz, DMSO-$d_6$) δ ppm 1.51-1.72 (m, 1H), 1.86-1.99 (m, 1H), 2.22-2.31 (m, 3H), 2.60-2.74 (m, 1H), 2.74-2.85 (m, 1H), 3.26-3.41 (m, 1H), 4.38 (t, J=6.2 Hz, 1H), 5.32-5.39 (m, 1H), 6.96-7.09 (m, 1H), 7.11-7.21 (m, 3H), 7.28-7.37 (m, 1H), 7.51-7.65 (m, 1H), 7.69 (dd, J=7.0, 2.4 Hz, 1H), 7.72-7.82 (m, 2H), 8.05-8.12 (m, 1H), 8.17-8.24 (m, 1H), 8.43 (t, J=1.7 Hz, 1H), 10.48 (s, 1H) Compound 179. $^1$H NMR (400 MHz, DMSO-$d_6$) δ ppm 1.99 (dd, J=5.1, 16.7 Hz, 1H), 2.25 (d, J=1.8 Hz, 3H), 2.35 (dd, J=8.4, 16.7 Hz, 1H), 2.66 (s, 3H), 3.10 (dd, J=10.1, 4.6 Hz, 1H), 3.47 (dd, J=10.3, 7.3 Hz, 1H), 3.80-3.92 (m, 1H), 7.14 (t, J=9.2 Hz, 1H), 7.53-7.63 (m, 1H), 7.68 (dd, J=7.0, 2.2 Hz, 1H), 7.74-7.86 (m, 1H), 7.97-8.08 (m, 1H), 8.15-8.32 (m, 2H), 8.37 (s, 1H), 10.48 (s, 1H). Racemic compound 179 was separated in enantiomers 179a and 179b by Preparative SFC (Stationary phase: Chiralpak Diacel AD 30×250 mm), Mobile phase: CO$_2$, iPrOH with 0.4% iPrNH$_2$) The collected fractions were concentrated in vacuo resulting in compound 179a and 179b. Columns: AD-H (diacel) 250 mm×4.6 mm; Flow: 5 mL/min; Mobile phase: 30% iPrOH (containing 0.2% iPrNH$_2$) hold 4.00 min, up to 50% in 1 min and hold 2.00 min @ 50%; Temperature: 40° C. Rt: 2.2 min (179a); 2.9 min (179b). 179a: +6.1° (589 nm, c 0.6225 w/v %, MeOH, 20° C.). 179b: −6.1° (589 nm, c 0.506 w/v %, MeOH, 20° C.).

Compound 180. $^1$H NMR (400 MHz, DMSO-$d_6$) δ ppm 1.55-1.79 (m, 2H), 2.01-2.36 (m, 5H), 2.68 (s, 3H), 3.06 (dd, J=12.3, 6.8 Hz, 1H), 3.25-3.30 (m, 1H), 3.46-3.58 (m, 1H), 7.14 (t, J=9.1 Hz, 1H), 7.52-7.63 (m, 1H), 7.64-7.71 (m, 1H), 7.78 (t, J=7.8 Hz, 1H), 8.01-8.09 (m, 1H), 8.11-8.27 (m, 2H), 8.39 (t, J=1.7 Hz, 1H), 10.47 (s, 1H)

Compound 181. $^1$H NMR (400 MHz, DMSO-$d_6$) δ ppm 1.59 (dq, J=12.4, 9.3 Hz, 1H), 1.93-2.16 (m, 1H), 2.25 (d, J=1.5 Hz, 3H), 2.69 (s, 3H), 3.06-3.24 (m, 2H), 4.00 (t, J=9.1 Hz, 1H), 7.14 (t, J=9.2 Hz, 1H), 7.54-7.64 (m, 1H), 7.65-7.71 (m, 1H), 7.74 (t, J=7.8 Hz, 1H), 7.99-8.09 (m, 1H), 8.25 (br. s, 1H), 8.11-8.20 (m, 1H), 8.44 (t, J=1.7 Hz, 1H), 10.42 (s, 1H).

Compound 182. ¹H NMR (400 MHz, DMSO-d₆) δ ppm 1.12-1.52 (m, 9H), 2.26 (d, J=1.3 Hz, 3H), 3.40-3.60 (m 2H), 3.80-4.00 (m, 2H), 4.02-4.19 (m, 1H), 7.15 (t, J=9.2 Hz, 1H), 7.57-7.66 (m, 1H), 7.70 (dd, J=7.0, 2.2 Hz, 1H), 7.80 (t, J=7.8 Hz, 1H), 8.01 (m, J=8.1 Hz, 1H), 8.26 (m, J=7.9 Hz, 1H), 8.38 (t, J=1.0 Hz, 1H), 8.51 (d, J=8.4 Hz, 1H), 10.50 (s, 1H).

Compound 183. ¹H NMR (400 MHz, CHLOROFORM-d) δ ppm 1.19-1.43 (m, 4H), 2.28 (d, J=1.8 Hz, 3H), 5.74 (br. s., 1H), 6.99 (t, J=8.8 Hz, 1H), 7.37 (m, J=8.4, 3.7 Hz, 1H), 7.45-7.54 (m, 1H), 7.64 (t, J=7.8 Hz, 1H), 7.88 (br. s, 1H), 8.03 (m, J=8.1 Hz, 1H), 8.10 (m, J=7.9 Hz, 1H), 8.29-8.38 (m, 1H)

Compound 184

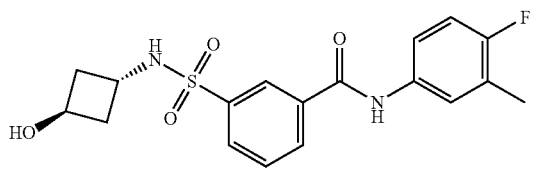

Synthesis following procedure S4 with 3-aminocyclobutanol as amine, 1 hour reaction time instead of 3 hour, workup W4. Method F; Rt: 0.81 min. m/z: 396.2 (M+NH₄)⁺ Exact mass: 378.1. SFC: Columns: Diacel AD-H (250 mm×4.6 mm); Flow: 5 mL/min Mobile phase: 30% MeOH (containing 0.2% iPrNH₂) hold 4.00 min, up to 50% in 1 min and hold 2.00 min at 50%; Temperature: 40° C.; Rt: 184a (2.5 min), 184b (3.4 min). The diastereomeric mixture of compound 184 was separated in diastereoisomers (Prep SFC (Stationary phase: Chiralpak Diacel AD 30×250 mm), Mobile phase: CO₂, MeOH with 0.4% iPrNH₂). The obtained fractions were concentrated under reduced pressure and dried in vacuo at 55° C., resulting in compound 184a and 184b.

Compound 184a

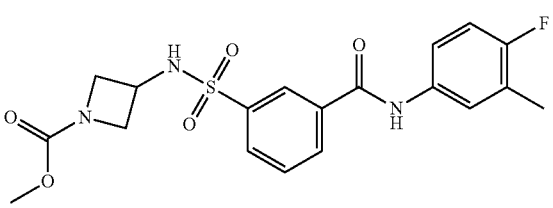

¹H NMR (600 MHz, DMSO-d₆) δ ppm 1.84-1.91 (m, 2H), 1.92-1.98 (m, 2H), 2.25 (d, J=1.8 Hz, 3H), 3.77 (quin, J=6.9 Hz, 1H), 4.10-4.14 (m, 1H), 4.93 (d, J=4.9 Hz, 1H), 7.14 (t, J=9.2 Hz, 1H), 7.59 (ddd, J=8.8, 4.6, 2.7 Hz, 1H), 7.68 (dd, J=7.1, 2.7 Hz, 1H), 7.76 (t, J=7.8 Hz, 1H), 7.96 (ddd, J=7.8, 1.9, 1.1 Hz, 1H), 8.06 (br. s, 1H), 8.20 (dt, J=7.8, 1.5 Hz, 1H), 8.33 (t, J=1.8 Hz, 1H), 10.49 (br. s., 1H).

Compound 184b

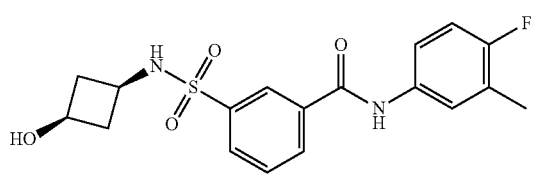

¹H NMR (600 MHz, DMSO-d₆) δ ppm 1.54-1.60 (m, 2H), 2.19-2.24 (m, 2H), 2.25 (d, J=1.8 Hz, 3H), 3.09-3.19 (m, 1H), 3.62-3.68 (m, 1H), 5.00 (d, J=5.6 Hz, 1H), 7.14 (t, J=9.2 Hz, 1H), 7.59 (ddd, J=8.5, 4.5, 2.8 Hz, 1H), 7.68 (dd, J=7.0, 2.2 Hz, 1H), 7.75 (t, J=7.8 Hz, 1H), 7.97 (ddd, J=7.8, 1.9, 1.0 Hz, 1H), 8.02 (br. s., 1H), 8.19 (ddd, J=7.8, 1.8, 1.1 Hz, 1H), 8.34 (t, J=1.6 Hz, 1H), 10.48 (s, 1H)

Compound 185

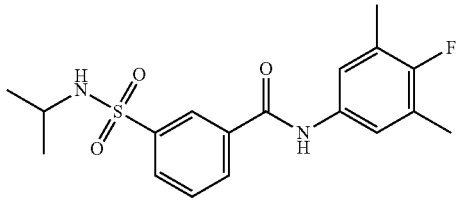

Prepared similarly as described for compound 157, starting from compound 182 instead of compound 154, via intermediate 3-(azetidin-3-ylsulfamoyl)-N-(4-fluoro-3-methyl-phenyl)benzamide hydrochloride. Method F; Rt: 0.89 min. m/z: 439.2 (M+NH₄)⁺ Exact mass: 421.1. ¹H NMR (400 MHz, DMSO-d₆) δ ppm 2.25 (d, J=1.8 Hz, 3H), 3.45-3.60 (m, 5H), 3.85-4.05 (m, 2H), 4.07-4.17 (m, 1H), 7.15 (t, J=9.1 Hz, 1H), 7.53-7.64 (m, 1H), 7.65-7.71 (m, 1H), 7.78 (t, J=7.8 Hz, 1H), 7.94-8.03 (m, 1H), 8.23 (m, J=7.9 Hz, 1H), 8.33 (t, J=1.7 Hz, 1H), 8.44-8.63 (br. s, 1H), 10.49 (s, 1H).

Compound 186

3-(isopropylsulfamoyl)benzoic acid (250 mg, 1.03 mmol), 4-fluoro-3,5-dimethyl-aniline (157 mg, 1.13 mmol) and DIPEA (398 mg, 3.08 mmol) were mixed in acetonitrile (10 mL) at room temperature under a nitrogen atmosphere. HATU (430 mg, 1.13 mmol) was added and the mixture was stirred overnight. EtOAc (100 mL) was added and the mixture was washed with 1M HCl, sat NaHCO₃ and brine. After drying over MgSO₄ and evaporation to dryness in vacuo, the obtained residue was crystallized from MeOH (10 mL) to provide a white solid (216 mg). Method F; Rt: 1.04 min. m/z: 382.2 (M+NH₄)⁺ Exact mass: 364.1. ¹H NMR (400 MHz, DMSO-d₆) δ ppm 0.96 (d, J=6.6 Hz, 6H), 2.23 (d, J=2.0 Hz, 6H), 3.23-3.29 (m, 1H), 7.48 (d, J=6.6 Hz, 2H), 7.66-7.80 (m, 2H), 7.95-8.04 (m, 1H), 8.18 (d, J=7.9 Hz, 1H), 8.35 (t, J=1.7 Hz, 1H), 10.37 (s, 1H).

Compound 187

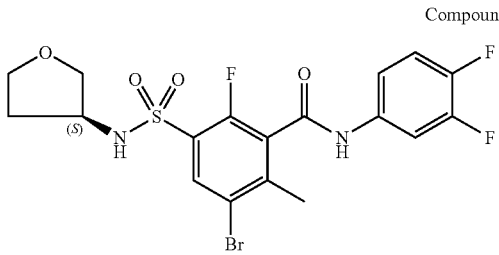

A solution of 2-fluoro-6-methylbenzoic acid (10 g, 0.0649 mol) in HOAc (300 mL) was stirred on a water-bath containing a bit of ice. At ~15° C., HNO₃ (65%, 32.7 mL) was added dropwise. After addition, H₂O (30 mL) was added slowly. After addition, Br₂ (3.7 mL) was added dropwise. A solution of silver nitrate (14.33 g, 0.0844 mol) in H₂0 (100 mL) was added dropwise over a period of 30 minutes. After addition, the reaction mixture was stirred at room temperature for 3 hours 30 minutes. The reaction mixture was poured into H₂O (850 mL), and EtOAc (300 mL) was added. The mixture was stirred vigorously for 5 minutes. Both upper liquid layers were decanted from a residue. The separated water layer was combined with the residue, and extracted with EtOAc. Both upper liquid layers were decanted from the residue. The separated water layer was combined with the residue, and extracted again with EtOAc. The organic layers were combined, washed with saturated NaCl and dried with Na₂SO₄, filtered off, evaporated, and co-evaporated with toluene. The obtained solid residue was stirred in a small amount of diisopropylether, filtered off, washed with diisopropylether, resulting in 3-bromo-6-fluoro-2-methyl-benzoic acid (4 g). The filtrate was evaporated. The residue was stirred in heptane, filtered off, washed with heptanes (3×), and dried at 50° C. in vacuo, resulting in a mixture of bromo-6-fluoro-2-methyl-benzoic acid and 2-fluoro-6-methylbenzoic acid (12 g, 1/0.4 ratio). 3-bromo-6-fluoro-2-methyl-benzoic acid (4 g, 0.0172 mol) was added portionwise to stirring chlorosulfonic acid (25 mL). The resulting solution was stirred at 115° C. for 2 hours, left standing at room temperature overnight and next stirred at 115° C. for 3 hours more. The reaction mixture was allowed to reach room temperature, and added dropwise to a stirring mixture of crushed ice (150 g) and H₂O (50 mL). The product was extracted with EtOAc (2×). The combined organic layers were washed with brine, dried with Na₂SO₄, filtered off, and evaporated, resulting in a crude mixture containing 5-bromo-3-chlorosulfonyl-2-fluoro-6-methyl-benzoic acid (4.4 g) (Na₂CO₃, 1.407 g, 0.0133 mol) was dissolved in water (25 mL). A solution of (S)-3-aminotetrahydrofuran (2.312 g, 0.0265 mol) in THF (20 mL) was added, and the reaction mixture was cooled to 0° C. on an ice-bath. A solution of crude 5-bromo-3-chlorosulfonyl-2-fluoro-6-methyl-benzoic acid (4.4 g) in THF (30 mL) was added dropwise at 0° C. After addition, the reaction mixture was stirred at 0° C. for 1 hour, and at room temperature for 2 hours. The mixture was concentrated till ~35 mL remained, then left standing for 70 hours. The solid was filtered off and washed with H₂O (2×). The filtrate was washed with Et₂O. The separated waterlayer was acidified with 1N HCl (30 mL), and the product was extracted with 2-MeTHF. The separated waterlayer was acidified further till pH~2 and extracted with 2-MeTHF. The organic layer was washed with brine, dried with Na₂SO₄ and filtered, resulting in crude 5-bromo-2-fluoro-6-methyl-3-[[(3S)-tetrahydrofuran-3-yl]sulfamoyl]benzoic acid (6.5 g). To a stirring solution of crude 5-bromo-2-fluoro-6-methyl-3-[[(3S)-tetrahydrofuran-3-yl]sulfamoyl]benzoic acid (1.3 g) in CH₃CN (30 mL) under N₂-atm triethylamine (1.42 mL, 0.0102 mol), 3,4-difluoroaniline (0.446 mL, 4.42 mmol) and HATU (1.55 g, 4.08 mmol) were successively added. The reaction mixture was stirred at room temperature for 16 hours. The volatiles were evaporated and the obtained residue was purified by silica gel chromatography (heptane-EtOAc 100/0 to 0/100], resulting in compound 187 (0.45 g). An impure fraction was further purified by Preparative HPLC (Stationary phase: RP XBridge Prep C18 OBD-10 μm, 30×150 mm), Mobile phase: 0.25% NH₄HCO₃ solution in water, CH₃CN), resulting in more compound 187 (0.048 g)

Method F; Rt: 1.06 min. m/z: 491.0 (M−H)⁻ Exact mass: 492.0. ¹H NMR (400 MHz, DMSO-d₆) δ ppm 1.66-1.76 (m, 1H), 1.94-2.05 (m, 1H), 2.41 (s, 3H), 3.43 (dd, J=8.9, 4.5 Hz, 1H), 3.58-3.65 (m, 1H), 3.68 (dd, J=8.9, 6.3 Hz, 1H), 3.71-3.78 (m, 1H), 3.83-3.92 (m, 1H), 7.36-7.42 (m, 1H), 7.43-7.52 (m, 1H), 7.85 (ddd, J=12.8, 7.5, 2.4 Hz, 1H), 8.02 (d, J=6.8 Hz, 1H), 8.55 (s, 1H), 11.09 (s, 1H)

Compound 188

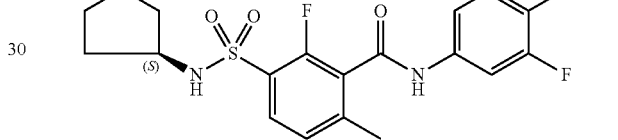

Compound 187 (0.45 g, 0.912 mmol) was dissolved in MeOH (20 mL) and THF (30 mL). To the resulting solution, triethylamine (0.254 mL, 1.82 mmol) was added and the mixture was stirred with 10% Pd/C (0.2 g) under hydrogen atmosphere at room temperature. After 3 hours, the catalyst was filtered off over dicalite, and washed with MeOH (3×) and THF (1×). The volatiles were removed in vacuo and the obtained residue was dissolved in hot MeOH (10 mL) and hot H₂O (10 mL) was added. The volume was concentrated till~15 mL, and left standing for 1 hour. The precipitated product was filtered off, washed with H₂O (3×), and dried at 50° C. in vacuo, resulting in compound 188 (245 mg). Method F; Rt: 0.93 min. m/z: 413.2 (M−H)⁻ Exact mass: 414.1. ¹⁹F NMR (377 MHz, DMSO-d₆) δ ppm −143.7-−143.2 (m, 1° F.), −137.1-−136.5 (m, 1° F.), −114.8 (d, J=7.9 Hz, 1° F.). ¹H NMR (400 MHz, DMSO-d₆) δ ppm 1.66-1.77 (m, 1H), 1.91-2.03 (m, 1H), 2.39 (s, 3H), 3.43 (dd, J=9.0, 4.6 Hz, 1H), 3.57-3.70 (m, 2H), 3.70-3.77, (m, 1H), 3.78-3.86 (m, 1H), 7.35 (d, J=8.1 Hz, 1H), 7.39-7.52 (m, 2H), 7.79 (t, J=7.8 Hz, 1H), 7.87 (ddd, J=12.9, 7.5, 2.1 Hz, 1H), 8.32 (br. s., 1H), 11.00 (s, 1H).

Compound 189

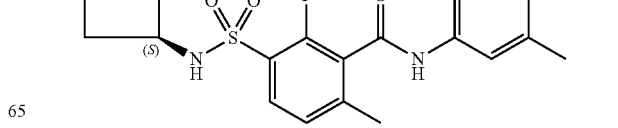

Compound 189 was prepared similarly as described for compound 188, using 4-fluoro-3-methylaniline instead of 3,4-difluoroaniline. Method F; Rt: 0.94 min. m/z: 409.2 (M−H)⁻ Exact mass: 410.1. ¹⁹F NMR (377 MHz, DMSO-d₆) δ ppm −122.40 (dtd, J=9.3, 4.6, 4.6, 2.1 Hz, 1° F.), −114.96 (d, J=7.2 Hz, 1° F.). ¹H NMR (400 MHz, DMSO-d₆) δ ppm 1.67-1.77 (m, 1H), 1.92-2.03 (m, 1H), 2.24 (d, J=1.5 Hz, 3H), 2.38 (s, 3H), 3.43 (dd, J=8.8, 4.6 Hz, 1H), 3.58-3.64 (m, 1H), 3.65-3.70 (m, 1H), 3.70-3.77 (m, 1H), 3.78-3.86 (m, 1H), 7.14 (dd, J=9.1 Hz, 1H), 7.34 (d, J=8.1 Hz, 1H), 7.45-7.53 (m, 1H), 7.63 (dd, J=7.0, 2.4 Hz, 1H), 7.77 (dd, J=7.9 Hz, 1H), 8.30 (br. s., 1H), 10.72 (s, 1H). Differential scanning calorimetry From 30 to 300° C. at 10° C./min: Peak at 157.0° C.

Compound 190

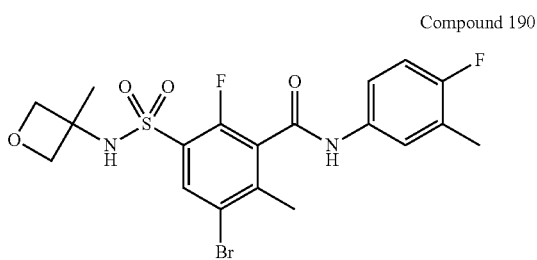 [SMILES: Cc1cc(NC(=O)c2c(C)c(Br)cc(S(=O)(=O)NC3(C)COC3)c2F)ccc1F]

Na₂CO₃ (1.60 g, 0.0151 mol) was dissolved in water (25 mL). A solution of 3-methyloxetan-3-amine (2.63 g, 0.0302 mol) in THF (20 mL) was added, and the reaction mixture was cooled to 0° C. on an ice-bath. A solution of crude 5-bromo-3-chlorosulfonyl-2-fluoro-6-methyl-benzoic acid (5 g) in THF (30 mL) was added dropwise at 0° C. After addition, the reaction mixture was stirred vigorously at 0° C. for 30 minutes, and at room temperature for 2 hours. The organic volatiles were evaporated, and the remaining~30 mL was washed with Et₂O (50 mL). The separated waterlayer was acidified with 1N HCl (40 mL), and the product was extracted with 2-MeTHF (2×). The combined organic layers were washed with brine, dried with Na₂SO₄, filtered off, evaporated, and co-evaporated with CH₃CN, resulting in crude 5-bromo-2-fluoro-6-methyl-3-[(3-methyloxetan-3-yl)sulfamoyl]benzoic acid (3.6 g) To a solution of crude 5-bromo-2-fluoro-6-methyl-3-[(3-methyloxetan-3-yl)sulfamoyl]benzoic acid (0.72 g, 0.00188 mol) in CH₃CN (15 mL) under N₂-atm was successively added NEt₃ (0.786 mL, 0.00565 mol), 4-fluoro-3-methylaniline (0.313 g, 0.00245 mol), and HATU (0.86 g, 0.00226 mol). The reaction mixture was stirred at room temperature for 20 hours. More 4-fluoro-3-methylaniline (0.1 g) and HATU (0.3 g) were added, and the reaction was continued for 20 hours. The volatiles were evaporated. The residue was purified by silica gel Chromatography (heptane-EtOAc 100/0 to 0/100). The desired fractions were combined and evaporated. The residue was stirred in diisopropylether, filtered off, washed with diisopropylether (3×), and dried at 50° C., resulting in compound 190 (0.38 g). m/z: 486.9 (M−H)⁻ Exact mass: 488.0. ¹⁹F NMR (377 MHz, DMSO-d₆) δ ppm −122.15-−121.89 (m, 1° F.), −116.05 (d, J=6.4 Hz, 1° F.). ¹H NMR (400 MHz, DMSO-d₆) δ ppm 1.47 (s, 3H), 2.25 (d, J=1.5 Hz, 3H), 2.40 (s, 3H), 4.22 (d, J=6.6 Hz, 2H), 4.62 (d, J=6.4 Hz, 2H), 7.16 (dd, J=9.2 Hz, 1H), 7.44-7.51 (m, 1H), 7.61 (dd, J=6.9, 2.3 Hz, 1H), 8.01 (d, J=6.8 Hz, 1H), 8.86 (br. s., 1H), 10.81 (s, 1H)

Synthesis of 2-fluoro-6-methyl-3-[(3-methyloxetan-3-yl)sulfamoyl]benzoic acid

A solution of 5-bromo-2-fluoro-6-methyl-3-[(3-methyloxetan-3-yl)sulfamoyl]benzoic acid (0.9 g) and triethylamine (0.98 mL, 7.1 mmol) in MeOH (30 mL) was stirred with Pd/C 10% (0.1 g) at room temperature under a hydrogen atmosphere. After the calculated amount of hydrogen was taken up, the catalyst was filtered off. The filtrate was concentrated in vacuo, and co-evaporated with CH₃CN. The obtained residue containing 2-fluoro-6-methyl-3-[(3-methyloxetan-3-yl)sulfamoyl]benzoic acid was used as such. Method F; Rt: 0.38 min. m/z: 302.0 (M−H)⁻ Exact mass: 303.1

Compound 191

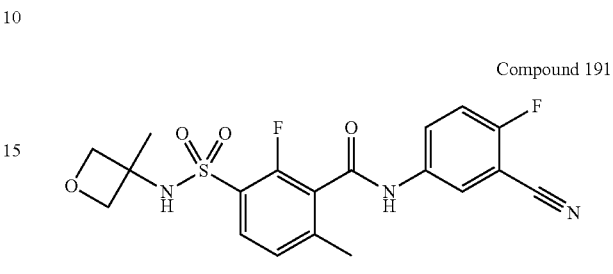

Triethylamine (0.206 mL, 0.00149 mol) was added to a stirring mixture of 2-fluoro-6-methyl-3-[(3-methyloxetan-3-yl)sulfamoyl]benzoic acid (0.15 g, 0.000495 mol) and CH₃CN (10 mL) under N₂-atm. To the resulting solution was added HATU (0.207 g, 0.545 mmol). After stirring for 5 minutes, 5-amino-2-fluorobenzonitrile, (79.9 mg, 0.569 mmol) was added, and the reaction mixture was stirred at room temperature for 20 hours. The reaction was next continued at 50° C. for 4 hours. The volatiles were evaporated and the obtained residue was dissolved in CH₂Cl₂ (2.5 mL) and purified by silica gel Chromatography (heptane-EtOAc 100/0 to 0/100) followed by repurification with CH₂Cl₂-MeOH 100/0 to 98/2 as eluent. The desired fractions were combined and evaporated, and co-evaporated with EtOAc. The residue was dried further at 50° C. in vacuo, resulting in compound 191 (63 mg). Method F; Rt: 0.88 min. m/z: 420.1 (M−H)⁻ Exact mass: 421.1. ¹H NMR (400 MHz, DMSO-d₆) δ ppm 1.46 (s, 3H), 2.40 (s, 3H), 4.19 (d, J=6.6 Hz, 2H), 4.62 (d, J=6.2 Hz, 2H), 7.36 (d, J=8.1 Hz, 1H), 7.58 (t, J=9.1 Hz, 1H), 7.80 (t, J=7.9 Hz, 1H), 7.96 (ddd, J=9.1, 4.8, 2.8 Hz, 1H), 8.22 (dd, J=5.7, 2.6 Hz, 1H), 8.64 (s, 1H), 11.16 (s, 1H). ¹⁹F NMR (377 MHz, DMSO-d₆) δ ppm −115.10 (d, J=7.9 Hz, 1° F.), −113.61 (dt, J=8.9, 5.2 Hz, 1° F.).

Synthesis of 3-chloro-4,5-difluoro-aniline 3-chloro-4,5-difluorobenzoic acid (commercial from astatech, 25.5 g, 0.132 mol) was dissolved in tert-butyl alcohol (200 mL) at 50° C. Et₃N (20.2 mL, 0.146 mol) was added. Diphenylphosphoryl azide, 30.0 mL, 0.139 mol) was added slowly, and the reaction mixture was stirred and refluxed for 18 hours. The volatiles were evaporated, and co-evaporated with EtOAc. The residue was stirred in Et₂O (300 mL)/Sat. NaHCO₃ (300 mL)/H₂O (50 mL) for 15 minutes. The separated organic layer was dried with MgSO₄, filtered off, and evaporated. The solid residue was stirred in diisopropylether (20 mL), filtered off, washed with diisopropylether (3×) and dried at 50° C., resulting in tert-butyl N-(3-chloro-4,5-difluoro-phenyl)carbamate (8.5 g). The filtrate was concentrated in vacuo. The residue was stirred in CH₂Cl₂ (20 mL)+heptanes (20 mL), filtered off, washed with CH₂Cl₂-heptane 1/1 (2×) and heptanes (2×), and dried at 50° C. in vacuo, resulting in more tert-butyl N-(3-chloro-4,5-difluoro-phenyl)carbamate, 11.8 g). tert-butyl N-(3-chloro-4,5-difluoro-phenyl)carbamate (8.5 g, 0.0322 mol) was added portion wise to stirring HCl (40 mL, 0.16 mol, 4

M in dioxane). The mixture was stirred at room temperature for 2 hours, then left standing for 65 hours. Stirring was continued for another 2 hours. The formed precipitate was filtered off, washed with dioxane (4×) and dried at 50° C. in vacuo, resulting in 3-chloro-4,5-difluoro-aniline hydrochloride (5.95 g). A mixture of 3-chloro-4,5-difluoro-aniline hydrochloride (1 g, 0.005 mol), NaOH (1M in $H_2O$, 10 mL, 0.01 mol) and toluene (15 mL) was stirred at room temperature for 1 hour. The separated organic layer was dried with $MgSO_4$, filtered off, and evaporated. The obtained 3-chloro-4,5-difluoro-aniline (0.81 g) was used as such.

Compound 192

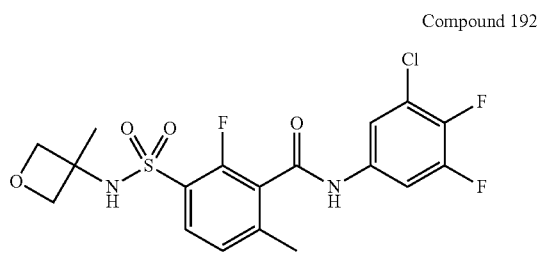 [SMILES: Cc1ccc(S(=O)(=O)NC2(C)COC2)c(F)c1C(=O)Nc1cc(F)c(F)c(Cl)c1]

Compound 192 was prepared similarly as described for compound 191, using 3-chloro-4,5-difluoro-aniline hydrochloride instead of 5-amino-2-fluorobenzonitrile. $^{19}$F NMR (377 MHz, DMSO-$d_6$) d ppm −144.93 (br. s., 1° F.), −134.02-−133.17 (m, 1° F.), −115.09 (d, J=7.9 Hz, 1° F.). $^1$H NMR (400 MHz, DMSO-$d_6$) δ ppm 1.45 (s, 3H), 2.38 (s, 3H), 4.18 (d, J=6.4 Hz, 2H), 4.61 (d, J=6.2 Hz, 2H), 7.35 (d, J=8.1 Hz, 1H), 7.71-7.83 (m, 3H), 8.64 (br. s., 1H), 11.14 (br. s., 1H). Method F; Rt: 1.05 min. m/z: 447.1 (M−H)$^-$ Exact mass: 448.0.

Compound 193

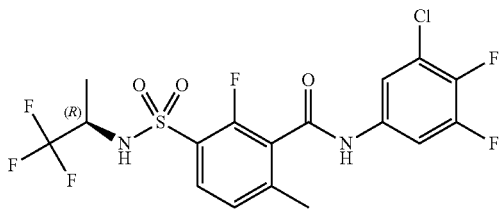

Oxalyl chloride (12.3 mL, 0.143 mol) was added dropwise to a stirring solution of 5-bromo-3-chlorosulfonyl-2-fluoro-6-methyl-benzoic acid (9.5 g) and DMF (0.111 mL) in $CH_2Cl_2$ (100 mL). After addition, the reaction mixture was stirred at room temperature for 2 hours and 30 minutes. The volatiles were removed in vacuo, and co-evaporated with toluene. The obtained residue containing 5-bromo-3-chlorosulfonyl-2-fluoro-6-methyl-benzoyl chloride was used as such. A solution of 5-bromo-3-chlorosulfonyl-2-fluoro-6-methyl-benzoyl chloride (1.75 g) in toluene (20 mL) was stirred at reflux under $N_2$-flow. A solution of 3-chloro-4,5-difluoroaniline (0.818 g, 0.005 mol) in toluene (10 mL) was added dropwise. After addition, the reaction mixture was refluxed for 45 minutes, then allowed to reach room temperature, and left standing for 18 hours. A precipitate (0.51 g) was filtered off, washed with toluene (2×), and dried at 50° C. in vacuo. (R)-1,1,1-trifluoro-2-propylamine (0.181 g, 0.0016 mol) was dissolved in $CH_3CN$ (5 mL) under $N_2$-atm. 5-bromo-3-[(3-chloro-4,5-difluoro-phenyl) carbamoyl]-2-fluoro-4-methyl-benzenesulfonyl chloride (0.51 g) was added, then DIPEA (0.461 mL, 0.00267 mol). The mixture was stirred in a sealed tube at 80° C. for 20 hours. The reaction mixture was allowed to reach room temperature, and left standing for 2 hours. The mixture was filtered and the filtrate was evaporated. The residue was dissolved in $CH_2Cl_2$ (2 mL), and purified by silica gel chromatography [heptane-EtOAc 100/0 to 0/100]. The fractions containing the desired compound were combined and evaporated, and co-evaporated with EtOH, resulting in crude 5-bromo-N-(3-chloro-4,5-difluoro-phenyl)-2-fluoro-6-methyl-3-[[(1R)-2,2,2-trifluoro-1-methyl-ethyl]sulfamoyl]benzamide (0.12 g). To a solution of 5-bromo-N-(3-chloro-4,5-difluoro-phenyl)-2-fluoro-6-methyl-3-[[(1R)-2,2,2-trifluoro-1-methyl-ethyl]sulfamoyl]benzamide (0.1 g) in EtOH (11 mL) was added $H_2O$ (3.5 mL), then $K_2CO_3$ aq. sat. sol., (1.25 mL) and next Palladium(0)tetrakis(triphenylphosphine) (26.1 mg, 0.023 mmol). The mixture was stirred 150° C. by microwave irradiation for 45 minutes. The reaction mixture was combined with a similar reaction mixture starting from 20 mg 5-bromo-N-(3-chloro-4,5-difluoro-phenyl)-2-fluoro-6-methyl-3-[[(1R)-2,2,2-trifluoro-1-methyl-ethyl]sulfamoyl]benzamide) allowed to reach room temperature and left standing for 15 minutes. The upper layer was isolated by means of a separation funnel, and evaporated. The obtained residue was purified by silica gel chromatography (heptane-EtOAc 100/0 to 0/100, also $CH_2Cl_2$-MeOH 100/0 to 98/2), followed by separation by preparative HPLC (Stationary phase: RP Vydac Denali C18 −10 μm, 200 g, 5 cm), Mobile phase: 0.25% $NH_4HCO_3$ solution in water, $CH_3CN$), resulting in compound 193 (11.4 mg). Method F; Rt: 1.17 min. m/z: 473.0 (M−H)$^-$ Exact mass: 474.0. $^1$H NMR (400 MHz, DMSO-$d_6$) δ ppm 1.17 (d, J=6.8 Hz, 3H), 2.38 (s, 3H), 4.00-4.15 (m, 1H), 7.35 (d, J=8.4 Hz, 1H), 7.71-7.78 (m, 2H), 7.82 (t, J=7.8 Hz, 1H), 9.00 (br. s., 1H), 11.13 (s, 1H). $^{19}$F NMR (377 MHz, DMSO-$d_6$) d ppm −145.3 to −144.5 (m, 1° F.), −134.4 to −132.8 (m, 1° F.), −114.9 (br. s., 1° F.), −76.0 (d, J=7.2 Hz, 3° F.).

Compound 194

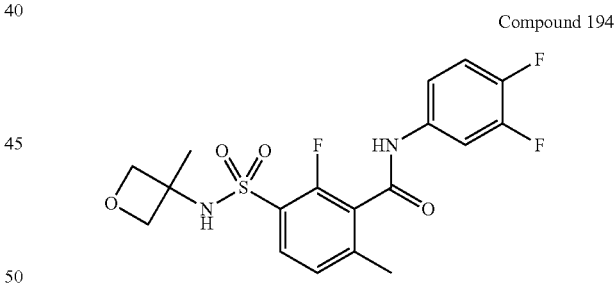

2-fluoro-6-methyl-3-[(3-methyloxetan-3-yl)sulfamoyl] benzoic acid (0.15 g, 0.473 mmol) was dissolved in DMF (5 mL) and triethylamine (0.2 mL) and HATU (233 mg, 0.61 mmol) were added to the reaction mixture. The reaction mixture was stirred for 10 minutes and 3,4-difluoroaniline (123 mg, 0.945 mmol) was added. The reaction mixture was stirred at room temperature for 42 hours. The reaction mixture was poured into ice water (50 mL). The mixture was extracted with Me-THF (3×20 mL). The combined organic extracts were washed with brine, dried ($Na_2SO_4$) and concentrated. The residue was purified using silica gel column chromatography (ethyl acetate in heptane from 0 to 100% and methanol in dichloromethane from 0 to 2%) to afford compound 194 (79 mg) as a white powder which was dried in vacuum oven overnight. Method F; Rt: 0.94 min. m/z: 413.2 (M−H)$^-$ Exact mass: 414.1. $^1$H NMR (400 MHz, DMSO-$d_6$) δ ppm 1.45 (s, 3H), 2.39 (s, 3H), 4.18 (d, J=6.6 Hz, 2H), 4.62 (d, J=6.2 Hz, 2H), 7.35 (d, J=8.1 Hz, 1H), 7.39-7.51 (m, 2H), 7.79 (t, J=7.8 Hz, 1H), 7.87 (ddd, J=12.9, 7.4, 2.0 Hz, 1H), 8.64 (br. s., 1H), 11.00 (s, 1H)

Compound 195

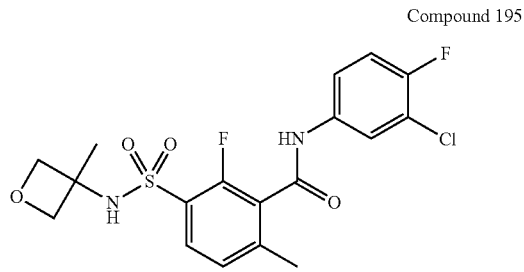 [SMILES: Cc1ccc(S(=O)(=O)NC2(C)COC2)c(F)c1C(=O)Nc1ccc(F)c(Cl)c1]

Compound 195 (98 mg) was prepared similarly as described for compound 194, using 3-chloro-4-fluoroaniline instead of 3,4-difluoroaniline. Method F; Rt: 0.99 min. m/z: 429.1 (M–H⁻)⁻ Exact mass: 430.1. $^1$H NMR (400 MHz, DMSO-$d_6$) δ ppm 1.45 (s, 3H), 2.39 (s, 3H), 4.18 (d, J=6.4 Hz, 2H), 4.62 (d, J=6.2 Hz, 2H), 7.35 (d, J=8.1 Hz, 1H), 7.45 (t, J=9.0 Hz, 1H), 7.60 (ddd, J=9.0, 4.3, 2.5 Hz, 1H), 7.79 (t, J=7.9 Hz, 1H), 8.02 (dd, J=6.8, 2.6 Hz, 1H), 8.63 (br. s., 1H), 10.99 (s, 1H)

Compound 196

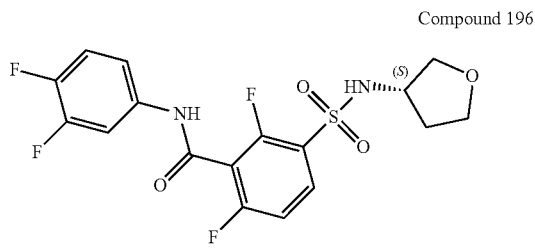

Sodium carbonate (2.07 g, 19.48 mmol) was dissolved in distilled water (30 mL). To this was added (S)-3-aminotetrahydrofuran (3.4 g, 38.97 mmol) at once followed by THF (30 mL). The obtained solution was stirred and cooled in an ice bath. 3-(chlorosulfonyl)-2,6-difluorobenzoic acid (5 g, 19.48 mmol) was dissolved in THF (40 mL) and this was added drop wise to the stirring solution. The resulting mixture was stirred for 30 minutes while cooling was continued. Then the mixture was stirred for 3 hours at room temperature. The mixture was concentrated in vacuo until only water remained. Water (20 mL) was added and the mixture was acidified with HCl (1M/aq; 40 mL). This was extracted using Me-THF (3×50 mL). The combined organics were washed with of brine (50 mL), dried on Na₂SO₄, filtered and concentrated in vacuo yielding 2,6-difluoro-3-[[(3S)-tetrahydrofuran-3-yl]sulfamoyl]benzoic acid as a yellow powder (5.9 g). Method F, Rt: 0.33 min. m/z: 306.0 (M–H)⁻ Exact mass: 307.0. 2,6-difluoro-3-[[(3S)-tetrahydrofuran-3-yl]sulfamoyl]benzoic acid (1 g, 2.99 mmol) was dissolved in N,N-dimethylformamide (5 mL). HATU (1.42 g, 3.74 mmol) was added followed by diisopropylethylamine (1.55 mL, 8.98 mmol). The resulting mixture was stirred for 30 minutes at room temperature. Then, 3,4-difluoroaniline (0.77 g, 5.99 mmol) was added. The resulting mixture was stirred for 24 hours and next poured in water (50 mL) and extracted using Me-THF (3×50 mL). The combined organics were washed with brine, dried on Na₂SO₄, filtered and concentrated in vacuo. The obtained residue was purified by silica gel column chromatography using gradient elution from heptane to EtOAc. (100:0 to 0:100). The desired fractions were concentrated in vacuo and dried in a vacuum oven at 55° C. for 24 hours yielding compound 196. Method F, Rt: 0.92 min. m/z: 417.1 (M–H)⁻ Exact mass: 418.1. $^1$H NMR (400 MHz, DMSO-$d_6$) δ ppm 1.64-1.79 (m, 1H), 1.92-2.07 (m, 1H), 3.43 (dd, J=9.0, 4.6 Hz, 1H), 3.56-3.79 (m, 3H), 3.80-3.92 (m, 1H), 7.32-7.43 (m, 1H), 7.44-7.54 (m, 2H), 7.84 (ddd, J=12.7, 7.4, 2.5 Hz, 1H), 8.01 (td, J=8.6, 6.2 Hz, 1H), 8.49 (br. s., 1H), 11.21 (br. s., 1H)

Compound 197 to 201 were prepared as described for compound 196, using the corresponding aniline instead of 3,4-difluoroaniline:

Compound 197

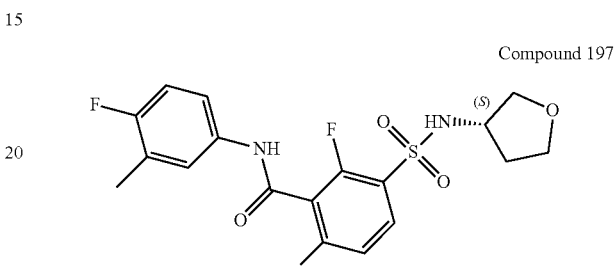

4-fluoro-3-methylaniline was used as aniline. $^1$H NMR (400 MHz, DMSO-$d_6$) δ ppm 1.64-1.76 (m, 1H), 1.91-2.05 (m, 1H), 2.25 (d, J=1.8 Hz, 3H), 3.42 (dd, J=8.9, 4.7 Hz, 1H), 3.56-3.78 (m, 3H), 3.79-3.88 (m, 1H), 7.16 (t, J=9.1 Hz, 1H), 7.41-7.51 (m, 2H), 7.60 (dd, J=7.0, 2.2 Hz, 1H), 7.97 (td, J=8.6, 6.2 Hz, 1H), 8.49 (br. s, 1H), 10.93 (s, 1H). Method F, Rt: 0.93 min. m/z: 413.2 (M–H)⁻ Exact mass: 414.1

Compound 198

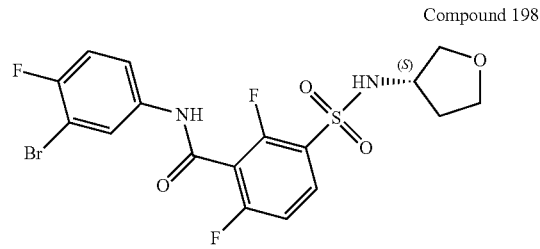

3-bromo-4-fluoroaniline was used as aniline. Method G, Rt: 1.74 min. m/z: 478.8 (M–H)⁻ Exact mass: 480.0. $^1$H NMR (400 MHz, DMSO-$d_6$) δ ppm 1.67-1.77 (m, 1H), 1.93-2.05 (m, 1H), 3.43 (dd, J=9.0, 4.6 Hz, 1H), 3.57-3.78 (m, 3H), 3.80-3.89 (m, 1H), 7.43 (t, J=8.7 Hz, 1H), 7.49 (m, J=8.7, 8.7 Hz, 1H), 7.61 (ddd, J=9.0, 4.4, 2.6 Hz, 1H), 8.00 (td, J=8.6, 6.2 Hz, 1H), 8.11 (dd, J=6.3, 2.5 Hz, 1H), 8.49 (br. s., 1H), 11.19 (br. s., 1H)

Compound 199

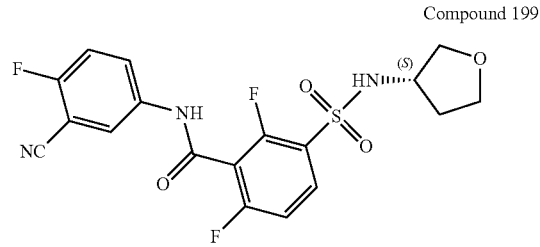

5-amino-2-fluorobenzonitrile was used as aniline

Method G, Rt: 1.56 min. m/z: 423.9 (M−H)⁻ Exact mass: 425.1. ¹H NMR (400 MHz, DMSO-d₆) δ ppm 1.65-1.80 (m, 1H), 1.94-2.06 (m, 1H), 3.43 (dd, J=9.0, 4.6 Hz, 1H), 3.57-3.78 (m, 3H), 3.80-3.91 (m, 1H), 7.49 (t, J=8.5 Hz, 1H), 7.59 (t, J=9.1 Hz, 1H), 7.94 (ddd, J=9.2, 4.8, 2.6 Hz, 1H), 8.02 (td, J=8.6, 6.2 Hz, 1H), 8.19 (dd, J=5.7, 2.9 Hz, 1H), 8.50 (br. s., 1H), 11.37 (br. s., 1H).

Compound 200

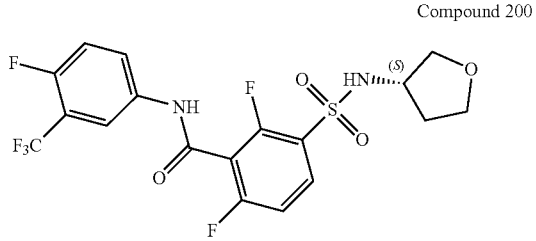

4-fluoro-3-(trifluoromethyl)aniline was used as aniline

Method F, Rt: 1.02 min. m/z: 467.1 (M−H)− Exact mass: 468.1. ¹H NMR (400 MHz, DMSO-d₆) δ ppm 1.72 (ddt, J=12.6, 7.2, 5.6, 5.6 Hz, 1H), 1.93-2.08 (m, 1H), 3.43 (dd, J=9.0, 4.6 Hz, 1H), 3.58-3.79 (m, 3H), 3.80-3.91 (m, 1H), 7.49 (t, J=8.4 Hz, 1H), 7.58 (t, J=9.7 Hz, 1H), 7.93 (s, 1H), 8.02 (td, J=8.6, 6.2 Hz, 1H), 8.16 (dd, J=6.4, 2.6 Hz, 1H), 8.50 (br. s., 1H), 11.35 (br. s., 1H)

Compound 201

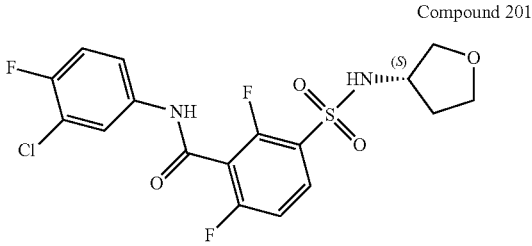

3-chloro-4-fluoroaniline was used as aniline.

Method F, Rt: 0.97 min. m/z: 433.1 (M−H)− Exact mass: 434.0. ¹H NMR (400 MHz, DMSO-d₆) δ ppm 1.72 (ddt, J=12.5, 7.2, 5.6, 5.6 Hz, 1H), 1.92-2.12 (m, 1H), 3.43 (dd, J=8.8, 4.6 Hz, 1H), 3.55-3.79 (m, 3H), 3.80-3.91 (m, 1H), 7.35-7.52 (m, 2H), 7.53-7.67 (m, 1H), 7.90-8.12 (m, 2H), 8.49 (br. s., 1H), 11.20 (br. s., 1H)

Compound 202 and 203 were prepared similarly as described for compound 196, using isopropyl amine instead of (S)-3-aminotetrahydrofuran and for compound 203, using 3-(trifluoromethyl)aniline instead of 3,4-difluoroaniline.

Compound 202

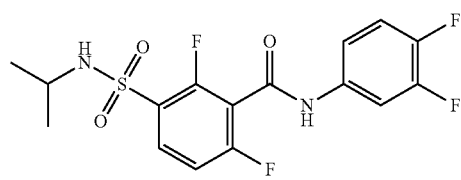

Method G, Rt: 1.80 min. m/z: 388.9 (M−H)− Exact mass: 390.1.

¹H NMR (400 MHz, DMSO-d₆) δ ppm 1.03 (d, J=6.6 Hz, 8H), 3.34-3.46 (m, 1H), 7.36-7.53 (m, 3H), 7.84 (ddd, J=12.7, 7.4, 2.5 Hz, 1H), 8.00 (td, J=8.6, 6.2 Hz, 1H), 8.09 (br. s., 1H), 11.20 (br. s., 1H)

Compound 203

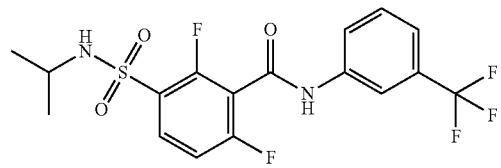

Method G, Rt: 1.82 min. m/z: 421.1 (M−H)− Exact mass: 422.1. ¹H NMR (400 MHz, DMSO-d₆) δ ppm 1.04 (d, J=6.6 Hz, 6H), 3.34-3.46 (m, 1H), 7.47 (t, J=8.6 Hz, 1H), 7.54 (d, J=7.9 Hz, 1H), 7.65 (t, J=7.9 Hz, 1H), 7.87 (d, J=8.4 Hz, 1H), 8.01 (td, J=8.6, 6.2 Hz, 1H), 8.11 (d, J=7.5 Hz, 1H), 8.15 (s, 1H), 11.32 (s, 1H).

Compound 204

Compound 204 (0.19 g) was prepared starting from compound 190 (0.34 g), similar as described for the conversion of compound 187 to compound 188. Compound 204 was crystallised from Et₂O, filtered off, washed with 3×Et₂O, and dried at 50° C. in vacuo. Method F; Rt: 0.94 min. m/z: 409.1 (M−H)⁻ Exact mass: 410.1. ¹H NMR (400 MHz, DMSO-d₆) δ ppm 1.46 (s, 3H), 2.24 (d, J=1.8 Hz, 3H), 2.38 (s, 3H), 4.18 (d, J=6.6 Hz, 2H), 4.62 (d, J=6.2 Hz, 2H), 7.14 (dd, J=9.1 Hz, 1H), 7.33 (d, J=8.1 Hz, 1H), 7.45-7.53 (m, 1H), 7.63 (dd, J=7.0, 2.2 Hz, 1H), 7.77 (t, J=7.9 Hz, 1H), 8.61 (br. s., 1H), 10.72 (s, 1H).

Compound 205

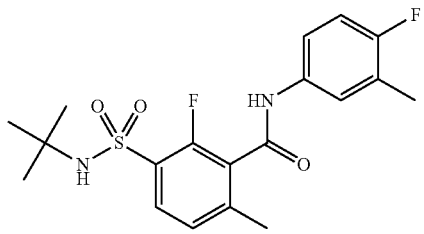

3-(tert-butylsulfamoyl)-2-fluoro-6-methyl-benzoic acid was prepared similarly as described for 2-fluoro-6-methyl-3-[(3-methyloxetan-3-yl)sulfamoyl]benzoic acid, using tert-butylamine instead of 3-methyloxetan-3-amine. Compound 205 was prepared similar as described for compound 194, using 4-fluoro-3-methylaniline instead of 3,4-difluoroaniline and starting from 3-(tert-butylsulfamoyl)-2-fluoro-6-methyl-benzoic acid instead of 2-fluoro-6-methyl-3-[(3-methyloxetan-3-yl)sulfamoyl]benzoic acid. Method F; Rt: 1.08 min. m/z: 395.2 (M−H)⁻ Exact mass: 396.1. ¹H NMR (400 MHz, DMSO-d$_6$) δ ppm 1.16 (s, 9H), 2.24 (d, J=1.8 Hz, 3H), 2.37 (s, 3H), 7.14 (t, J=9.2 Hz, 1H), 7.30 (d, J=8.1 Hz, 1H), 7.50 (ddd, J=9.0, 4.7, 2.3 Hz, 1H), 7.64 (dd, J=6.9, 2.3 Hz, 1H), 7.73-7.84 (m, 2H), 10.70 (br. s, 1H).

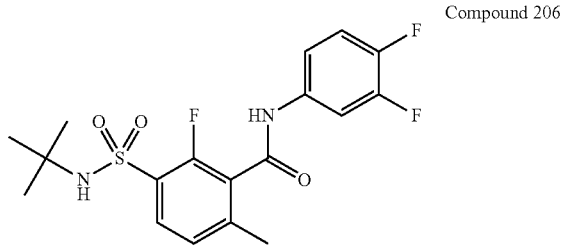 [SMILES: Cc1ccc(S(=O)(=O)NC(C)(C)C)c(F)c1C(=O)Nc1ccc(F)c(F)c1]

Compound 206

Compound 206 was prepared similar as described for for compound 194, starting from 3-(tert-butylsulfamoyl)-2-fluoro-6-methyl-benzoic acid instead of 2-fluoro-6-methyl-3-[(3-methyloxetan-3-yl)sulfamoyl]benzoic acid. Method F; Rt: 1.08 min. m/z: 399.1 (M–H)⁻ Exact mass: 400.1. $^1$H NMR (400 MHz, DMSO-d$_6$) δ ppm 1.16 (s, 9H), 2.31 (s, 3H), 7.32 (d, J=8.1 Hz, 1H), 7.40-7.51 (m, 2H), 7.76-7.82 (m, 2H), 7.88 (ddd, J=13.0, 7.5, 2.4 Hz, 1H), 10.97 (br. s., 1H)

Synthesis of 6-chloro-2-fluoro-3-[(3-methyloxetan-3-yl)sulfamoyl]benzoic acid and 2-chloro-6-fluoro-3-[(3-methyloxetan-3-yl)sulfamoyl]benzoic acid 2-chloro-6-fluorobenzoic acid (2 g, 11.46 mmol) was treated with chlorosulfonic acid (10 mL, 150.44 mmol) and this was heated to 100° C. and stirred for 5 hours. The resulting mixture was cooled to room temperature and added dropwise to ice-water (1 liter). This was then extracted using dichloromethane (2×500 mL). The combined organics were dried on Na$_2$SO$_4$, filtered and concentrated in vacuo yielding an isomeric mixture of 2-chloro-3-chlorosulfonyl-6-fluoro-benzoic acid and 6-chloro-3-chlorosulfonyl-2-fluoro-benzoic acid (3.1 gram) as a slightly yellow powder which was used as such. Method F, Rt: 0.47 min and 0.49 min. m/z: 270.9 (M–H)– Exact mass: 271.9. Sodium carbonate (1.21 g, 11.4 mmol) was dissolved in distilled water (22 mL). To this was added 3-methyl-3-oxetanamine (1.19 g, 13.68 mmol) at once followed by THF (20 mL). The obtained solution was stirred and cooled in an ice bath. An isomeric mixture of 2-chloro-3-chlorosulfonyl-6-fluoro-benzoic acid and 6-chloro-3-chlorosulfonyl-2-fluoro-benzoic acid (3.1 g, 11.4 mmol) was dissolved in THF (30 mL) and this was added drop wise to the stirring solution. The resulting mixture was stirred for 30 minutes while cooling was continued. Then, the mixture was stirred for 3 hours at room temperature. The mixture was concentrated in vacuo until only water remained. Then water (20 mL) was added and the mixture was acidified with HCl (46 mL, 1M/aq). This was extracted using Me-THF (3×50 mL). The combined organics were dried on Na$_2$SO$_4$, filtered and concentrated in vacuo. The residue was purified, and isomers were separated using preparative HPLC (Stationary phase: Uptisphere C18 ODB –10 μm, 200 g, 5 cm), Mobile phase: 0.25% NH$_4$HCO$_3$ solution in water, MeOH), yielding 6-chloro-2-fluoro-3-[(3-methyloxetan-3-yl)sulfamoyl]benzoic acid as a white powder. Method G, Rt: 0.40 min. m/z: 322.0 (M–H)⁻ Exact mass: 323.0. 1H NMR (400 MHz, DMSO-d) ppm 1.42 (s, 3H), 4.15 (d, J=6.6 Hz, 2H), 4.61 (d, J=5.9 Hz, 13H), 7.29 (dd, J=8.5, 0.8 Hz, 1H), 7.36-7.73 (m, 5H). and 2-chloro-6-fluoro-3-[(3-methyloxetan-3-yl)sulfamoyl]benzoic acid as a white powder. Method G, Rt: 0.34 min. m/z: 321.9 (M–H)⁻ Exact mass: 323.0

Compound 207 to 210 were prepared similarly as described for compound 196 using 6-chloro-2-fluoro-3-[(3-methyloxetan-3-yl)sulfamoyl]benzoic acid instead of 2,6-difluoro-3-[[(3S)-tetrahydrofuran-3-yl]sulfamoyl]benzoic acid and the corresponding aniline instead of 3,4-difluoroaniline.

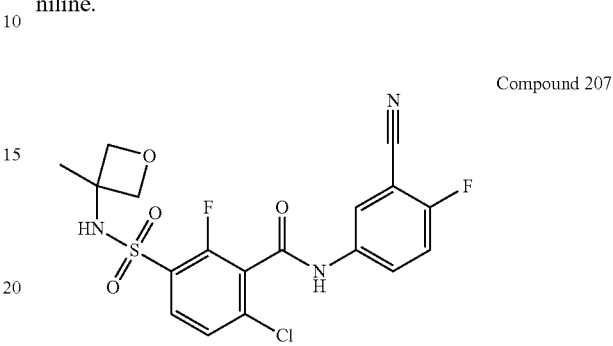

Compound 207

Using 5-amino-2-fluorobenzonitrile as aniline. Method F, Rt: 0.92 min. m/z: 440.0 (M–H)⁻ Exact mass: 441.0. $^1$H NMR (400 MHz, DMSO-d$_6$) δ ppm 1.46 (s, 2H), 4.21 (d, J=6.4 Hz, 2H), 4.61 (d, J=6.2 Hz, 2H), 7.59 (t, J=9.1 Hz, 1H), 7.66 (d, J=8.8 Hz, 1H), 7.89-7.99 (m, 2H), 8.18 (dd, J=5.6, 2.8 Hz, 1H), 8.93 (br. s, 1H), 11.37 (br. s., 1H)

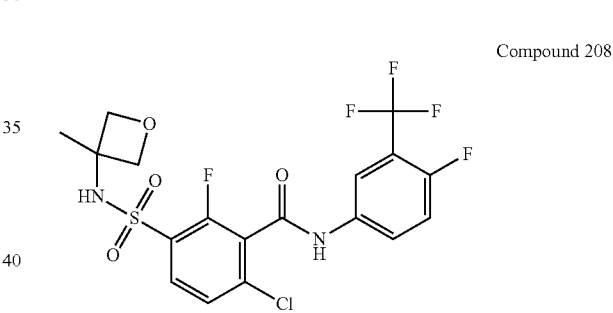

Compound 208

Using 4-fluoro-3-(trifluoromethyl)aniline as aniline. Method F, Rt: 1.06 min. m/z: 483 (M–H)⁻ Exact mass: 484.0. $^1$H NMR (400 MHz, DMSO-d$_6$) δ ppm 1.46 (s, 2H), 4.20 (d, J=6.2 Hz, 2H), 4.61 (d, J=6.2 Hz, 2H), 7.58 (t, J=9.9 Hz, 1H), 7.66 (d, J=8.6 Hz, 1H), 7.94 (m, J=8.1, 8.1 Hz, 2H), 8.07-8.25 (m, 1H), 8.91 (br. s, 1H), 11.34 (br. s., 1H)

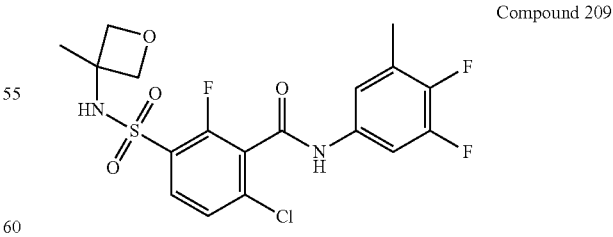

Compound 209

Using 3,4-difluoro-5-methyl-aniline as aniline. Method F, Rt: 1.03 min. m/z: 447.1 (M–H)⁻ Exact mass: 448.1. $^1$H NMR (400 MHz, DMSO-d$_6$) δ ppm 1.45 (s, 3H), 2.30 (d, J=2.0 Hz, 3H), 4.20 (d, J=6.4 Hz, 2H), 4.61 (d, J=6.2 Hz, 2H), 7.32 (m, J=5.9 Hz, 1H), 7.54-7.69 (m, 2H), 7.91 (t, J=8.3 Hz, 1H), 8.92 (br. s, 1H), 11.09 (br. s, 1H)

Compound 210

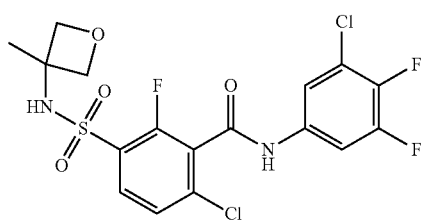

Using 3-chloro-4,5-difluoro-aniline hydrochloride as aniline. Method F, Rt: 1.07 min. m/z: 467.0 (M−H)⁻ Exact mass: 468.0. ¹H NMR (400 MHz, DMSO-d$_6$) δ ppm 1.45 (s, 3H), 4.20 (d, J=6.6 Hz, 2H), 4.60 (d, J=6.2 Hz, 2H), 7.64 (d, J=8.6 Hz, 1H), 7.67-7.79 (m, 2H), 7.93 (t, J=8.1 Hz, 1H), 9.08 (br. s, 1H), 11.34 (br. s., 1H)

Compound 211

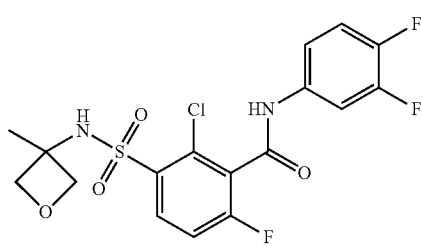

Compound 211 was prepared similarly as described for compound 196 using 2-chloro-6-fluoro-3-[(3-methyloxetan-3-yl)sulfamoyl]benzoic acid instead of 2,6-difluoro-3-[[(3S)-tetrahydrofuran-3-yl]sulfamoyl]benzoic acid. Method F, Rt: 0.94 min. m/z: 433.1 (M−H)⁻ Exact mass: 434.0. ¹H NMR (400 MHz, DMSO-d$_6$) δ ppm 1.46 (s, 3H), 4.20 (d, J=6.6 Hz, 2H), 4.62 (d, J=6.4 Hz, 2H), 7.30-7.43 (m, 1H), 7.43-7.54 (m, 1H), 7.61 (t, J=8.6 Hz, 1H), 7.84 (ddd, J=12.7, 7.4, 2.3 Hz, 1H), 8.17 (dd, J=9.0, 5.9 Hz, 1H), 8.75 (br. s, 1H), 11.18 (br. s, 1H).

2-bromo-6-fluoro-3-[(3-methyloxetan-3-yl)sulfamoyl]benzoic acid and 6-bromo-2-fluoro-3-[(3-methyloxetan-3-yl)sulfamoyl]benzoic acid were prepared similarly as described for 2-chloro-6-fluoro-3-[(3-methyloxetan-3-yl)sulfamoyl]benzoic acid and 6-chloro-2-fluoro-3-[(3-methyloxetan-3-yl)sulfamoyl]benzoic acid, starting from 2-bromo-6-fluorobenzoic acid instead of 2-chloro-6-fluorobenzoic acid.

Compound 212

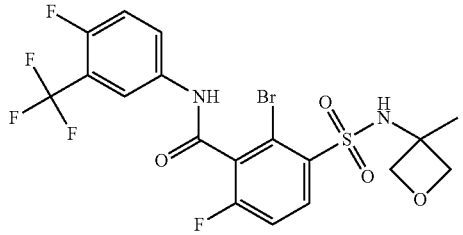

Compound 212 was prepared similarly as described for compound 196 using 2-bromo-6-fluoro-3-[(3-methyloxetan-3-yl)sulfamoyl]benzoic acid instead of 2,6-difluoro-3-[[(3S)-tetrahydrofuran-3-yl]sulfamoyl]benzoic acid and 4-fluoro-3-(trifluoromethyl)aniline instead of 3,4-difluoroaniline. ¹H NMR (400 MHz, DMSO-d$_6$) δ ppm 1.48 (s, 3H), 4.20 (d, J=6.6 Hz, 2H), 4.64 (d, J=6.2 Hz, 2H), 7.57 (t, J=9.7 Hz, 1H), 7.65 (t, J=8.6 Hz, 1H), 7.93 (dt, J=8.4, 3.7 Hz, 1H), 8.08-8.31 (m, 2H), 8.70 (br. s., 1H), 11.29 (br. s., 1H).

Compound 213 to 216 were prepared similarly as described for compound 196 using 6-bromo-2-fluoro-3-[(3-methyloxetan-3-yl)sulfamoyl]benzoic acid instead of 2,6-difluoro-3-[[(3S)-tetrahydrofuran-3-yl]sulfamoyl]benzoic acid the corresponding aniline instead of 3,4-difluoroaniline.

Compound 213

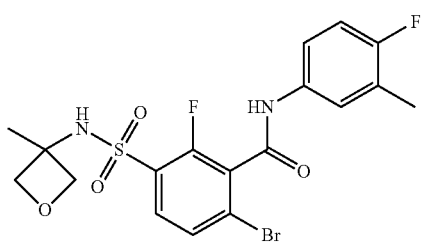

Using 4-fluoro-3-methylaniline as aniline. Method F, Rt: 0.99 min. m/z: 473.0 (M−H)⁻ Exact mass: 474.0. ¹H NMR (400 MHz, DMSO-d$_6$) δ ppm 1.46 (s, 3H), 2.25 (d, J=1.5 Hz, 3H), 4.20 (d, J=6.4 Hz, 2H), 4.62 (d, J=6.2 Hz, 2H), 7.16 (t, J=9.1 Hz, 1H), 7.42-7.52 (m, 1H), 7.60 (dd, J=7.0, 2.4 Hz, 1H), 7.68-7.93 (m, 2H), 8.65 (br. s, 1H), 10.82 (br. s, 1H).

Compound 214

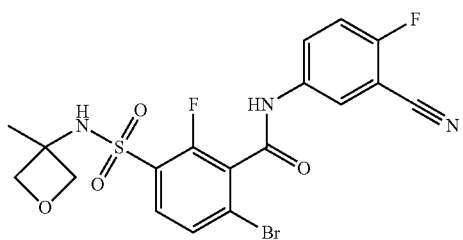

Using 5-amino-2-fluorobenzonitrile as aniline. Method F, Rt: 0.92 min. m/z: 484.0 (M−H)⁻ Exact mass: 485.0. ¹H NMR (400 MHz, DMSO-d$_6$) δ ppm 1.39-1.55 (m, 3H), 4.20 (d, J=6.6 Hz, 2H), 4.61 (d, J=6.4 Hz, 2H), 7.59 (t, J=9.1 Hz, 1H), 7.77-7.89 (m, 2H), 7.95 (ddd, J=9.2, 4.8, 2.8 Hz, 1H), 8.18 (dd, J=5.7, 2.6 Hz, 1H), 8.90 (br. s, 1H), 11.34 (br. s., 1H).

Compound 215

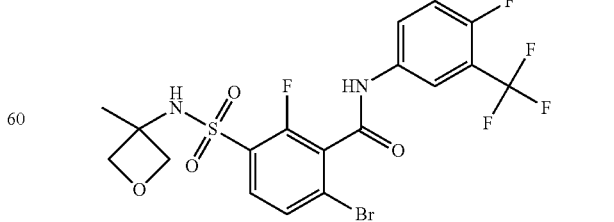

Using 4-fluoro-3-(trifluoromethyl)aniline as aniline. Method F, Rt: 1.07 min. m/z: 527.0 (M−H)⁻ Exact mass:

528.0. ¹H NMR (400 MHz, DMSO-d₆) δ ppm 1.46 (s, 3H), 4.20 (d, J=6.6 Hz, 2H), 4.61 (d, J=6.2 Hz, 2H), 7.58 (t, J=9.8 Hz, 1H), 7.74-7.89 (m, 2H), 7.90-7.98 (m, 1H), 8.16 (dd, J=6.3, 2.5 Hz, 1H), 8.84 (br. s, 1H), 11.31 (br. s., 1H).

Compound 216

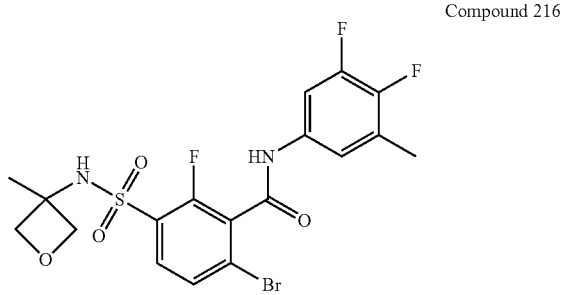

Using 3,4-difluoro-5-methyl-aniline as aniline. Method F, Rt: 1.03 min. m/z: 491.0 (M−H)⁻ Exact mass: 492.0. ¹H NMR (400 MHz, DMSO-d₆) δ ppm 1.46 (s, 3H), 2.30 (d, J=1.8 Hz, 3H), 4.20 (d, J=6.6 Hz, 2H), 4.61 (d, J=6.4 Hz, 2H), 7.32 (m, J=5.7 Hz, 1H), 7.61 (ddd, J=12.3, 6.9, 2.6 Hz, 1H), 7.72-7.89 (m, 2H), 8.86 (br. s., 1H), 11.07 (br. s, 1H).

Compound 217

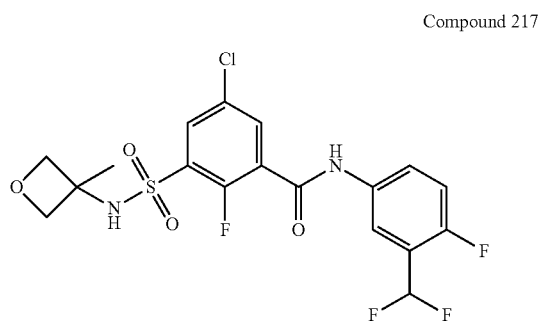 [SMILES: CC1(NS(=O)(=O)c2cc(Cl)cc(C(=O)Nc3ccc(F)c(C(F)F)c3)c2F)COC1]

A solution of 3-(difluoromethyl)-4-fluoro-aniline (1.02 mL, 8.58 mmol) in dry toluene (10 mL) was added dropwise (over 15 min) to a refluxing solution of 5-chloro-3-chlorosulfonyl-2-fluoro-benzoyl chloride (2500 mg, 8.576 mmol) in dry toluene (100 mL). After the addition, the reaction mixture was left to stir at reflux for 1 h. The reaction mixture was left to cool to room temperature under nitrogen atmosphere while stirring. The brown solution containing 5-chloro-3-[[3-(difluoromethyl)-4-fluoro-phenyl]carbamoyl]-2-fluoro-benzenesulfonyl chloride was used without further purification. 3-methyl-3-oxetanamine (580 mg, 6.66 mmol) was added dropwise to the above solution at room temperature. Et₃N (2.10 mL 15.14 mmol) was then added dropwise to the reaction mixture and the reaction mixture was stirred at room temperature for 45 minutes. The solvent was evaporated and the residue was taken up in EtOAc. HCl (0.5 N, 30 mL) was added to the reaction mixture and the layers were separated. The organic layer was washed again with NaOH (0.5 N, 30 mL).

The organic layer was dried on MgSO₄ and was evaporated. The obtained residue was purified by silica gel column chromatography (eluent: CH₂Cl₂:MeOH 100:0→95:5), resulting in compound 217 (1.8 g). ¹H NMR (360 MHz, DMSO-d₆) δ ppm 1.45 (s, 3H) 4.23 (d, J=6.6 Hz, 2H) 4.63 (d, J=6.2 Hz, 2H) 7.27 (t, J=54.3 Hz, 1H) 7.43 (t, J=9.7 Hz, 1H) 7.83 (dt, J=8.1, 4.0 Hz, 1H) 7.95 (dd, J=5.9, 2.6 Hz, 1H) 8.04 (dd, J=6.0, 2.4 Hz, 1H) 8.13 (dd, J=5.3, 2.7 Hz, 1H) 8.98 (s, 1H) 10.98 (s, 1H) Method F, Rt: 1.03 min. m/z: 465.1 (M−H)⁻ Exact mass: 466.0.

Compound 218

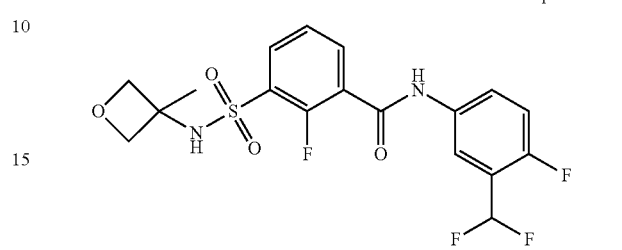

Pd/C (10%) (716 mg) was suspended in a solution of compound 217 (345 mg, 0.673 mmol) and Et₃N (0.467 mL) in MeOH (100 mL) at room temperature under nitrogen atmosphere. The reaction mixture was next stirred at room temperature under an atmosphere of hydrogen until one equivalent of hydrogen was absorbed. The reaction mixture was filtered on decalite and the solvent was evaporated. The obtained residue was purified by silica gel column chromatography (CH₂Cl₂:MeOH 100:0 →95:5) resulting in compound 218 (206 mg) as a white solid, dried in vacuo at 50° C.

¹H NMR (360 MHz, DMSO-d₆) δ ppm 1.44 (s, 3H) 4.19 (d, J=6.6 Hz, 2H) 4.63 (d, J=6.2 Hz, 2H) 7.26 (t, J=54.3 Hz, 1H) 7.42 (t, J=9.5 Hz, 1H) 7.52 (t, J=7.7 Hz, 1H) 7.86 (dd, J=8.1, 3.7 Hz, 1H) 7.93-8.01 (m, 2H) 8.06 (dd, J=6.4, 2.4 Hz, 1H) 8.77 (s, 1H) 10.92 (s, 1H). Method F, Rt: 0.92 min. m/z: 431.1 (M−H)⁻ Exact mass: 432.1.

Compound 219

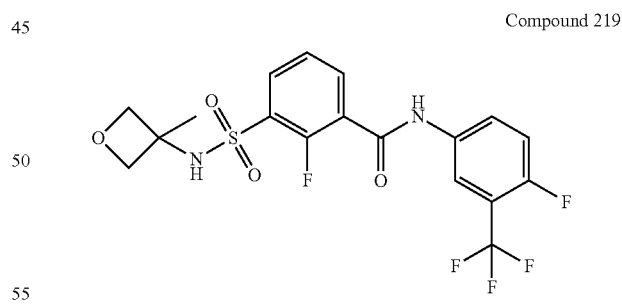

Compound 219 (828 mg), was prepared similar as described for compound 217 and 218. Using 4-fluoro-3-(trifluoromethyl)aniline instead of 3-(difluoromethyl)-4-fluoro-aniline. Method F, Rt: 1.00 min. m/z: 449.1 (M−H)⁻ Exact mass: 450.1.

¹H NMR (360 MHz, DMSO-d₆) δ ppm 1.44 (s, 3H) 4.19 (d, J=5.9 Hz, 2H) 4.62 (d, J=6.2 Hz, 2H) 7.53 (t, J=7.9 Hz, 1H) 7.57 (t, J=9.9 Hz, 1H) 7.94-8.02 (m, 3H) 8.20 (dd, J=6.4, 2.7 Hz, 1H) 8.78 (s, 1H) 11.02 (s, 1H).

Compound 220

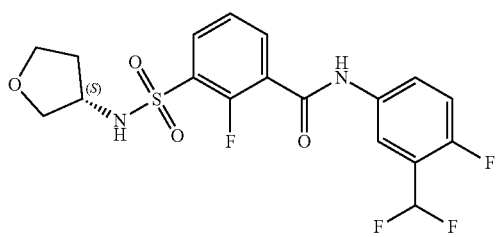

Compound 220 was prepared similar as described for compound 217 and 218, using (S)-3-aminotetrahydrofuran instead of 3-methyl-3-oxetanamine. Method F, Rt: 0.90 min. m/z: 431.1 (M−H)⁻ Exact mass: 432.1. $^1$H NMR (360 MHz, DMSO-d$_6$) δ ppm 1.66-1.77 (m, 1H) 1.91-2.03 (m, 1H) 3.43 (dd, J=8.8, 4.8 Hz, 1H) 3.57-3.70 (m, 2H) 3.70-3.78 (m, 1H) 3.79-3.90 (m, 1H) 7.26 (t, J=54.2 Hz, 1H) 7.42 (t, J=9.5 Hz, 1H) 7.53 (t, J=7.7 Hz, 1H) 7.81-7.88 (m, 1H) 7.94-8.00 (m, 2H) 8.07 (dd, J=6.4, 2.4 Hz, 1H) 8.45 (d, J=6.6 Hz, 1H) 10.92 (s, 1H).

Compound 221

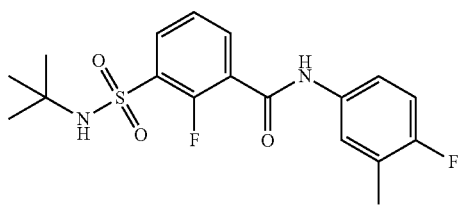

Compound 221 was prepared similar as described for compound 217 and 218, using 2-methylpropan-2-amine instead of 3-methyl-3-oxetanamine, and 4-fluoro-3-methyl-aniline instead of 3-(difluoromethyl)-4-fluoro-aniline Method F, Rt: 1.06 min. m/z: 381.2 (M−H)⁻ Exact mass: 382.1. 1 H NMR (360 MHz, DMSO-d$_6$) δ ppm 1.15 (s, 9H) 2.24 (d, J=1.5 Hz, 3H) 7.15 (t, J=9.1 Hz, 1H) 7.47 (t, J=7.7 Hz, 1H) 7.43-7.55 (m, 1H) 7.65 (dd, J=7.0, 2.6 Hz, 1H) 7.87 (ddd, J=7.8, 6.1, 1.8 Hz, 1H) 7.93 (s, 1H) 7.90-7.99 (m, 1H) 10.63 (s, 1H).

Compound 243

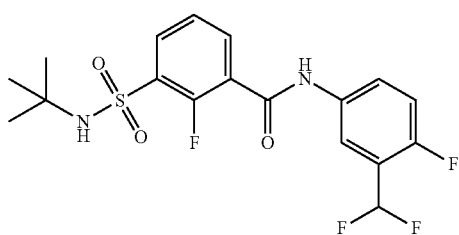

Compound 243 was prepared similar as described for compound 217 and 218, using tert-butylamine instead of 3-methyl-3-oxetanamine. Method G, Rt: 1.76 min. m/z: 417.1 (M−H)⁻ Exact mass: 418.1. $^1$H NMR (360 MHz, DMSO-d$_6$) δ ppm 1.15 (s, 9H) 7.41 (t, J=9.7 Hz, 1H) 7.26 (t, J=54.5 Hz, 1H) 7.49 (t, J=7.7 Hz, 1H) 7.85 (ddd, J=8.6, 4.4, 3.1 Hz, 1H) 7.88-8.01 (m, 3H) 8.08 (dd, J=6.2, 2.6 Hz, 1H) 10.90 (s, 1H).

Compound 222

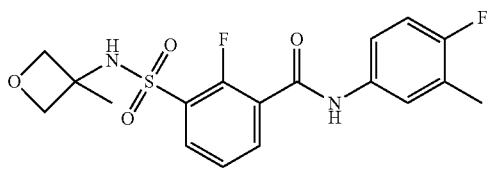

Compound 222 was prepared similar as described for compound 221, using 3-methyl-3-oxetanamine instead of 2-methylpropan-2-amine. Method F, Rt: 0.91 min. m/z: 395.1 (M−H)⁻ Exact mass: 396.1. $^1$H NMR (360 MHz, DMSO-d$_6$) δ ppm 1.44 (s, 3H) 2.24 (d, J=1.5 Hz, 3H) 4.19 (d, J=6.6 Hz, 2H) 4.62 (d, J=6.2 Hz, 2H) 7.15 (t, J=9.3 Hz, 1H) 7.46-7.55 (m, 2H) 7.63 (dd, J=7.0, 2.6 Hz, 1H) 7.88-7.99 (m, 2H) 8.75 (s, 1H) 10.65 (s, 1H).

Compound 223

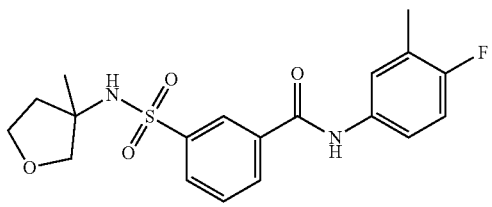

3-methyloxolan-3-amine hydrochloride (165.9 mg, 1.21 mmol) was added to a solution of 3-[(4-fluoro-3-methyl-phenyl)carbamoyl]benzenesulfonyl chloride (499 mg, 1.096 mmol) in dry CH$_2$Cl$_2$ (20 mL) at room temperature. Et$_3$N (381 µL) was then added dropwise to the reaction mixture and the reaction mixture was stirred at room temperature for 1 hour. The reaction mixture was diluted with EtOAc (250 mL). HCl 0.5 N (50 mL) was added and the layers were separated. The organic layer was washed again with NaOH 0.5 N (30 mL). The organic layer was dried on MgSO$_4$ and was evaporated. The obtained residue was purified t by silica gel column chromatography (CH$_2$Cl$_2$:MeOH 100:0 →95:5) and by preparative HPLC (Stationary phase: RP XBridge Prep C18 OBD-10 µm, 30×150 mm), Mobile phase: 0.25% NH$_4$HCO$_3$ solution in water, MeOH) resulting in compound 223 (257 mg) as a white solid after drying in vacuo at 50° C. Method F, Rt: 0.93 min. m/z: 391.2 (M−H)⁻ Exact mass: 392.1. $^1$H NMR (360 MHz, DMSO-d$_6$) ppm 1.17 (s, 3H) 1.72 (dt, J=12.8, 7.7 Hz, 1H) 2.14 (ddd, J=12.8, 7.1, 6.0 Hz, 1H) 2.25 (d, J=1.8 Hz, 3H) 3.30-3.40 (m, 1H) 3.61-3.77 (m, 3H) 7.15 (t, J=9.3 Hz, 1H) 7.55-7.64 (m, 1H) 7.69 (dd, J=7.0, 2.2 Hz, 1H) 7.75 (t, J=7.9 Hz, 1H) 8.04 (d, J=8.0 Hz, 1H) 8.10 (br. s., 1H) 8.18 (dt, J=7.7, 1.3 Hz, 1H) 8.39 (t, J=1.6 Hz, 1H) 10.49 (br. s., 1H).

Compound 225

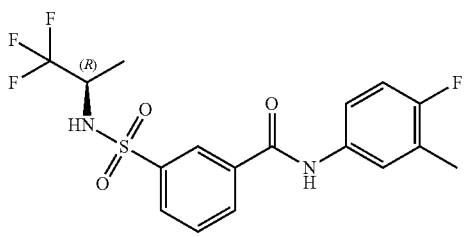

3-[(4-fluoro-3-methyl-phenyl)carbamoyl]benzenesulfonyl chloride (0.5 g, 1.53 mmol) and (R)-1,1,1-trifluoro-2-propylamine (0.38 g, 3.36 mmol) were dissolved in of dichloromethane (10 mL). Then diisopropylethylamine (0.66 mL, 3.81 mmol) was added and the resulting mixture was stirred for two hours. Then 1M HCl (5 mL) was added and the organic layer was separated, loaded on silica and subjected to silica gel column chromatography using gradient elution from heptane to EtOAc. (100:0 to 0:100). The desired fractions were concentrated in vacuo and dried in a vacuum oven at 55° C. for 24 hours compound 225 (233 mg) as a white powder. Method F, Rt: 1.05 min. m/z: 403.1 (M−H)⁻ Exact mass: 404.1. ¹H NMR (400 MHz, DMSO-d₆) δ ppm 1.01 (d, J=6.8 Hz, 3H), 2.25 (d, J=1.8 Hz, 3H), 4.06-4.22 (m, 1H), 7.15 (t, J=9.2 Hz, 1H), 7.51-7.63 (m, 1H), 7.67 (dd, J=7.2, 2.3 Hz, 1H), 7.78 (t, J=7.8 Hz, 1H), 8.00-8.10 (m, 1H), 8.16-8.28 (m, 1H), 8.40 (t, J=1.7 Hz, 1H), 8.66 (br. s., 1H), 10.46 (s, 1H).

Compound 226

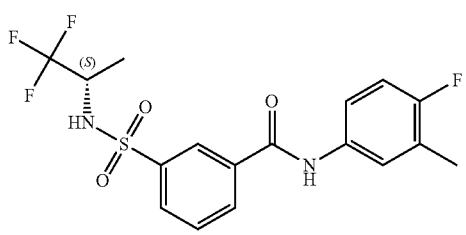

Compound 226 (416 mg) was prepared as described for compound 225, using (S)-1,1,1-trifluoro-2-propylamine instead of (R)-1,1,1-trifluoro-2-propylamine. Method F, Rt: 1.05 min. m/z: 403.1 (M−H)⁻ Exact mass: 404.1.

Compound 227

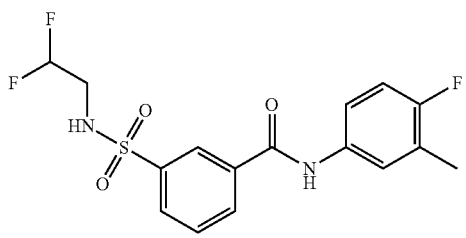

Compound 227 (444 mg) was prepared similarly as described in synthetic procedure S3 (using 2,2-difluoroethylamine as amine), workup W4. Method F, Rt: 0.93 min. m/z: 371.1 (M−H)⁻ Exact mass: 372.1. ¹H NMR (400 MHz, DMSO-d₆) δ ppm 2.25 (d, J=1.8 Hz, 3H), 3.26 (td, J=15.8, 3.7 Hz, 2H), 6.00 (tt, J=55.2, 3.5 Hz, 1H), 7.14 (t, J=9.0 Hz, 1H), 7.52-7.62 (m, 1H), 7.63-7.70 (m, 1H), 7.77 (t, J=7.9 Hz, 1H), 7.96-8.06 (m, 1H), 8.14-8.25 (m, 1H), 8.30-8.45 (m, 2H), 10.46 (s, 1H)

Compound 228

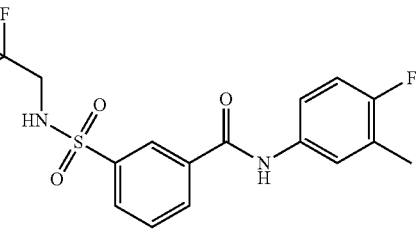

Compound 228 (238 mg) was prepared similarly as described in synthetic procedure S3 (using 2,2-difluoroethylamine as amine), workup W4, followed by preparative HPLC (SunFire Prep C18 OBD-10 μm, 30×150 mm). Mobile phase (0.25% NH₄HCO₃ solution in water, MeOH). Method F, Rt: 0.97 min. m/z: 389.1 (M−H)⁻ Exact mass: 390.1.
¹H NMR (400 MHz, DMSO-d₆) δ ppm 2.25 (d, J=1.8 Hz, 3H), 3.74 (q, J=9.5 Hz, 2H), 7.15 (t, J=9.2 Hz, 1H), 7.48-7.62 (m, 1H), 7.64-7.71 (m, 1H), 7.77 (t, J=7.8 Hz, 1H), 7.94-8.10 (m, 1H), 8.20 (m, J=8.1 Hz, 1H), 8.37 (t, J=1.7 Hz, 1H), 8.49-9.15 (bs, 1H), 10.45 (s, 1H)

Compound 229

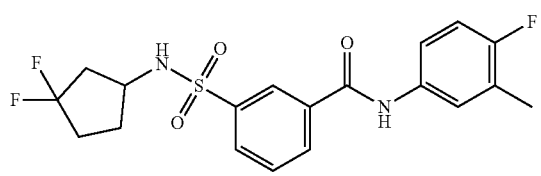

Compound 243 (239 mg) was prepared similar to synthetic procedure S2 (using 3,3-difluoro-cyclopentanamine as amine), workup W4. Method F, Rt: 1.03 min. m/z: 411.2 (M−H)⁻ Exact mass: 412.1. ¹H NMR (400 MHz, DMSO-d₆) δ ppm 1.50-1.165 (m, 1H), 1.81-2.04 (m, 3H), 2.04-2.23 (m, 2H), 2.25 (s, 3H), 3.63-3.76 (m, 1H), 7.14 (t, J=9.1 Hz, 1H), 7.59 (dt, J=8.1, 3.9 Hz, 1H), 7.65-7.72 (m, 1H), 7.78 (t, J=7.8 Hz, 1H), 8.02 (d, J=7.9 Hz, 1H), 8.14 (d, J=6.8 Hz, 1H), 8.22 (d, J=7.7 Hz, 1H), 8.37 (s, 1H), 10.47 (s, 1H).

Compound 230

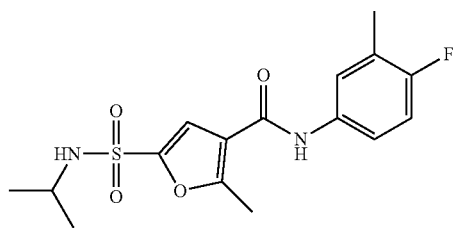

2-methyl-3-furoic acid (4.2 g, 32.6 mmol) was dissolved in CH₂Cl₂ (100 mL) and cooled with an ice-bath to −5° C. Then chlorosulfonic acid (10.85 mL, 163.2 mmol) was added dropwise at a rate of 0.250 mL/min. The reaction mixture was allowed to warm to room temperature and stirred overnight. The reaction mixture was quenched on ice and extracted with 2-MeTHF. The organic layer was washed with brine, dried over MgSO₄ and evaporated to dryness yielding crude 5-chlorosulfonyl-2-methyl-furan-3-carboxylic acid (420 mg) as a brown oil. 5-chlorosulfonyl-2-methyl-furan-3-carboxylic acid (420 mg) was dissolved in CH₂Cl₂ (10 mL). Hunig's base (0.64 mL, 3.74 mmol) and isopropylamine (0.478 mL, 5.61 mmol) were added and the reaction mixture was stirred overnight at room temperature. The volatiles were removed under reduced pressure and the residue was used as such in the next step. The above residue was dissolved in CH₂Cl₂ (20 mL), 4-fluoro-3-methylaniline (228 mg, 1.82 mmol), HATU (830 mg, 2.18 mmol) and N,N-diisopropylethylamine (0.94 mL, 5.46 mmol) were added and the reaction mixture was stirred for 30 minutes. The volatiles were removed under reduced pressure and the residue was purified on silica using a heptane to EtOAc gradient resulting in compound 230 (174 mg) as a white powder. Method F, Rt: 1.00 min. m/z: 353.1 (M−H)⁻ Exact mass: 354.1. ¹H NMR (400 MHz, DMSO-d₆) δ ppm 1.03 (d, J=6.4 Hz, 6H), 2.23 (s, 3H), 2.64 (s, 3H), 3.35-3.43 (m, 1H), 7.11 (t, J=9.2 Hz, 1H), 7.53 (dd, J=7.9, 4.0 Hz, 1H), 7.59-7.69 (m, 1H), 7.72 (s, 1H), 8.06 (d, J=5.5 Hz, 1H), 9.87 (s, 1H).

Compound 231

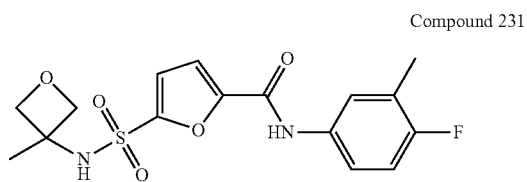 [SMILES: Cc1cc(NC(=O)c2ccc(S(=O)(=O)NC3(C)COC3)o2)ccc1F]

3-methyl-3-oxetanamine hydrochloride (302.6 mg, 2.45 mmol) and Hunig's base (1.15 mL, 6.68 mmol) dissolved in CH₂Cl₂ (2 mL) were added to a solution of methyl 5-(chlorosulfonyl)-2-furoate (thermo scientific, 500 mg, 2.23 mmol) in CH₂Cl₂ (10 mL). The reaction mixture was stirred overnight at room temperature. The volatiles were removed under reduced pressure and the obtained residue was used as such.

The residue was dissolved in THF (10 mL). LiOH (60.2 mg, 2.514 mmol), dissolved in H₂O (1 mL), was added to the reaction mixture, MeOH (1 mL) was added and this was stirred overnight at room temperature. The volatiles were removed under reduced pressure and the residue was dissolved water (25 mL). 1M HCl (2.5 mL) was added and then 2-MeTHF (50 mL) was added. The aqueous layer was removed and the organic layer was washed with brine (50 mL). The organic layer was dried over MgSO₄, filtered and evaporated to dryness yielding an oil which was used as such in the next step. The oil and HATU (573 mg, 1.51 mmol) were stirred in CH₂Cl₂ (5 mL) and 4-fluoro-3-methylaniline (157.3 mg, 1.26 mmol) and N,N-diisopropylethylamine (0.65 mL, 3.77 mmol) were added. The reaction mixture was stirred overnight at room temperature. The volatiles were removed under reduced pressure and the residue was purified on silica using a heptane to EtOAc gradient followed by by preparative HPLC (Stationary phase: RP Vydac Denali C18-10 μm, 200 g, 5 cm), Mobile phase: 0.25% NH₄HCO₃ solution in water, CH₃CN), the desired fractions were collected, evaporated, dissolved in MeOH and evaporated again. This fraction was triturated in MeOH (4 mL), filtered and dried in the oven yielding compound 231 (305 mg) as a white solid. Method F, Rt: 0.89 min. m/z: 367.1 (M−H)⁻ Exact mass: 368.1. ¹H NMR (400 MHz, DMSO-d₆) δ ppm 1.53 (s, 3H), 2.24 (d, J=1.8 Hz, 3H), 4.21 (d, J=6.6 Hz, 2H), 4.61 (d, J=6.2 Hz, 2H), 7.14 (t, J=9.2 Hz, 1H), 7.26 (d, J=3.7 Hz, 1H), 7.50 (d, J=3.7 Hz, 1H), 7.51-7.57 (m, 1H), 7.60 (dd, J=7.0, 2.4 Hz, 1H), 8.92 (s, 1H), 10.34 (s, 1H).

Compound 232 to 239 were prepared by slow addition of an aniline to a refluxing toluene solution of a 3-chlorosulfonylbenzoyl chloride derivative, followed by reaction with an amine in the presence of a base like NEt₃ or DIPEA, as described above.

| | Structure | Aniline | Amine | 3-chlorosulfonyl benzoyl chloride derivative |
|---|---|---|---|---|
| 232 | 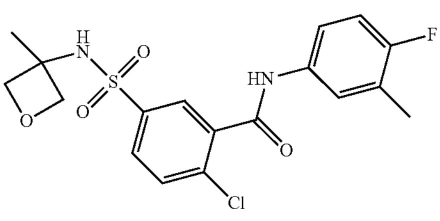 | 4-fluoro-3-methylaniline | 3-methyl-3-oxetanamine | 2-chloro-5-(chlorosulfonyl) benzoyl chloride |
| 233 | 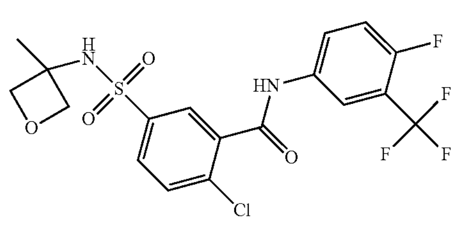 [SMILES: CC1(NS(=O)(=O)c2ccc(Cl)c(C(=O)Nc3ccc(F)c(C(F)(F)F)c3)c2)COC1] | 4-fluoro-3-(trifluoromethyl) aniline | 3-methyl-3-oxetanamine | 2-chloro-5-(chlorosulfonyl) benzoyl chloride |

-continued

| | Structure | Aniline | Amine | 3-chlorosulfonyl benzoyl chloride derivative |
|---|---|---|---|---|
| 234 | 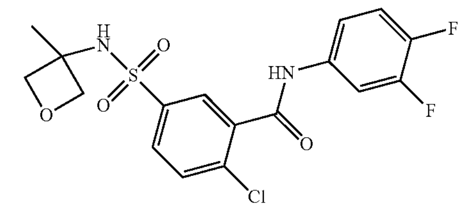 | 3,4-difluoroaniline | 3-methyl-3-oxetanamine | 2-chloro-5-(chlorosulfonyl) benzoyl chloride |
| 235 | 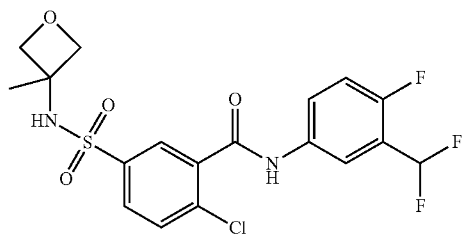 [SMILES: CC1(NS(=O)(=O)c2ccc(Cl)c(C(=O)Nc3ccc(F)c(C(F)F)c3)c2)COC1] | 3-(difluoromethyl)-4-fluoro-aniline | 3-methyl-3-oxetanamine | 2-chloro-5-(chlorosulfonyl) benzoyl chloride |
| 236 | 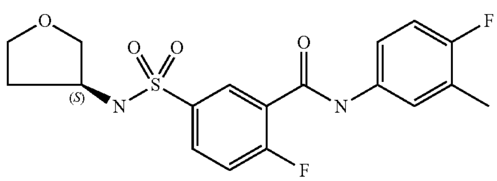 | 4-fluoro-3-methylaniline | (S)-3-aminotetrahydro furan tosylate | 5-chlorosulfonyl-2-fluoro-benzoyl chloride |
| 237 | 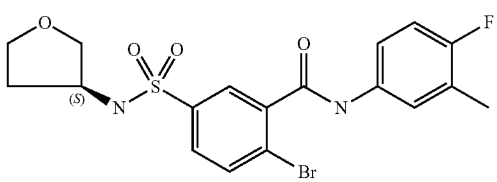 | 4-fluoro-3-methylaniline | (S)-3-aminotetrahydro furan tosylate | 2-bromo-5-chlorosulfonyl-benzoyl chloride |
| 238 | 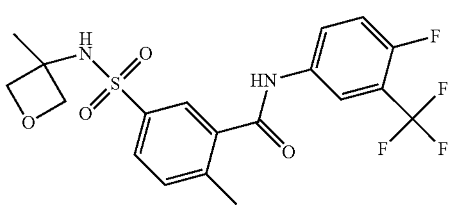 [SMILES: Cc1ccc(S(=O)(=O)NC2(C)COC2)cc1C(=O)Nc1ccc(F)c(C(F)(F)F)c1] | 4-fluoro-3-(trifluoromethyl) aniline | 3-methyl-3-oxetanamine | 5-chlorosulfonyl-2-methyl-benzoyl chloride |
| 239 | 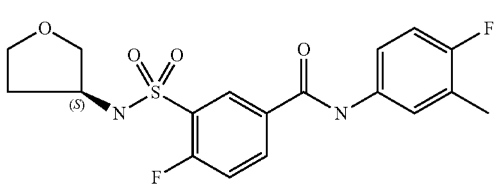 | 4-fluoro-3-methylaniline | (S)-tetrahydrofuran-3-amine hydrochloride | 3-chlorosulfonyl-4-fluoro-benzoyl chloride |

| Compound | LC method | Rt (min) | m/z (M − H)⁻ | Exact mass |
|---|---|---|---|---|
| 232 | G | 1.67 | 410.8 | 412.1 |
| 233 | G | 1.83 | 464.9 | 466.0 |
| 234 | G | 1.68 | 414.9 | 416.0 |
| 235 | G | 1.69 | 446.9 | 448.1 |
| 236 | F | 0.90 | 395.1 | 396.1 |

-continued

| Compound | LC method | Rt (min) | m/z (M − H)⁻ | Exact mass |
|---|---|---|---|---|
| 237 | F | 0.93 | 457.1 | 458.0 |
| 238 | F | 1.03 | 445.1 | 446.1 |
| 239 | G | 1.64 | 394.9 | 396.1 |

| Compound | ¹H-NMR |
|---|---|
| 232 | ¹H NMR (360 MHz, DMSO-d₆) δ ppm 10.67 (s, 1 H), 8.57 (s, 1 H), 7.96-7.88 (m, 2 H), 7.84-7.79 (m, 1 H), 7.62 (dd, J = 2.6, 7.0 Hz, 1 H), 7.54-7.46 (m, 1 H), 7.15 (t, J = 9.1 Hz, 1 H), 4.56 (d, J = 6.2 Hz, 2 H), 4.17 (d, J = 6.2 Hz, 2 H), 2.24 (d, J = 1.8 Hz, 3 H), 1.43 (s, 3 H) |
| 233 | ¹H NMR (360 MHz, DMSO-d₆) δ ppm 1.44 (s, 3 H) 4.18 (d, J = 6.6 Hz, 2 H) 4.57 (d, J = 6.0 Hz, 2 H) 7.57 (t, J = 9.9 Hz, 1 H) 7.85 (d, J = 8.4 Hz, 1 H) 7.91-7.98 (m, 2 H) 8.02 (d, J = 2.2 Hz, 1 H) 8.20 (dd, J = 6.2, 2.6 Hz, 1 H) 8.58 (s, 1 H) 11.06 (s, 1H) |
| 234 | ¹H NMR (360 MHz, CHLOROFORM-d) δ ppm 1.64 (s, 3 H) 4.37 (d, J = 6.5 Hz, 2 H) 4.66 (d, J = 6.5 Hz, 2 H) 5.74 (s, 1 H) 7.09-7.24 (m, 2 H) 7.59 (d, J = 8.2 Hz, 1 H) 7.70 (ddd, J = 11.8, 7.0, 2.4 Hz, 1 H) 7.88 (dd, J = 8.4, 2.2 Hz, 1 H) 8.19 (d, J = 2.2 Hz, 1 H) 8.30 (s, 1 H) |
| 235 | ¹H NMR (360 MHz, DMSO-d₆) δ ppm 1.44 (s, 3 H) 4.18 (d, J = 6.2 Hz, 2 H) 4.57 (d, J = 6.2 Hz, 2 H) 7.26 (t, J = 54.2 Hz, 1 H) 7.36-7.46 (m, 1 H) 7.84 (d, J = 8.4 Hz, 2 H) 7.91 (d, J = 2.2 Hz, 1 H) 8.00 (d, J = 2.2 Hz, 1 H) 8.03-8.10 (m, 1 H) 8.58 (s, 1 H) 10.95 (s, 1 H) |
| 236 | ¹H NMR (400 MHz, DMSO-d₆) δ ppm 1.57-1.70 (m, 1 H), 1.87-2.04 (m, 1 H), 2.25 (d, J = 1.0 Hz, 3 H), 3.38 (m, 1 H), 3.54-3.81 (m, 4 H), 7.15 (t, J = 9.1 Hz, 1 H), 7.47-7.56 (m, 1 H), 7.57-7.72 (m, 2 H), 7.95-8.20 (ddd, J = 8.6, 4.6, 2.4 Hz, 1 H), 8.06-8.19 (m, 2 H), 10.60 (s, 1 H) |
| 237 | ¹H NMR (400 MHz, DMSO-d₆) δ ppm 1.60-1.70 (m, 1 H), 1.89-2.00 (m, 1 H), 2.24 (d, J = 1.6 Hz, 3 H), 3.38 (dd, J = 8.9, 4.4 Hz, 1 H), 3.55-3.62 (m, 1 H), 3.63-3.67 (m, 1 H), 3.68-3.72 (m, 1 H), 3.73-3.80 (m, 1 H), 7.14 (t, J = 9.3 Hz, 1 H), 7.49 (ddd, J = 8.9, 4.4, 2.8 Hz, 1 H), 7.63 (dd, J = 6.9, 2.4 Hz, 1 H), 7.80 (dd, J = 8.3, 2.2 Hz, 1 H), 7.89 (d, J = 2.4 Hz, 1 H), 7.97 (d, J = 8.5 Hz, 1 H), 8.12 (br. s., 1 H), 10.63 (s, 1 H) |
| 238 | ¹H NMR (360 MHz, DMSO-d₆) δ ppm 1.42 (s, 3 H) 2.46 (s, 3 H) 4.14 (d, J = 6.2 Hz, 2 H) 4.56 (d, J = 6.2 Hz, 2 H) 7.51-7.59 (m, 2 H) 7.84 (dd, J = 8.1, 1.8 Hz, 1 H) 7.89 (d, J = 1.8 Hz, 1 H) 7.95-8.02 (m, 1 H) 8.24 (dd, J = 6.6, 2.6 Hz, 1 H) 8.42 (s, 1 H) 10.87 (s, 1 H) |
| 239 | ¹H NMR (400 MHz, DMSO-d₆) δ ppm 1.65-1.74 (m, 1 H), 1.90-2.00 (m, 1 H), 2.25 (d, J = 1.5 Hz, 3 H), 3.41 (dd, J = 8.9, 4.7 Hz, 1 H), 3.57-3.77 (m, 3 H), 3.83-3.91 (m, 1 H), 7.14 (dd, J = 9.2 Hz, 1 H), 7.54-7.61 (m, 1 H), 7.61-7.69 (m, 2 H), 8.29 (ddd, J = 8.5, 4.6, 2.3 Hz, 1 H), 8.40 (dd, J = 7.0, 2.2 Hz, 1 H), 8.44 (br. s., 1 H), 10.47 (s, 1 H) |

Differential scanning calorimetry From 30 to 300° C. at 10° C./min:

Compound 232: Peak at 169.6° C.

Optical Rotation:

Compound 236: $[\alpha]_D^{20} = -5.83$ (c 0.67 w/v %, MeOH).

Compound 240

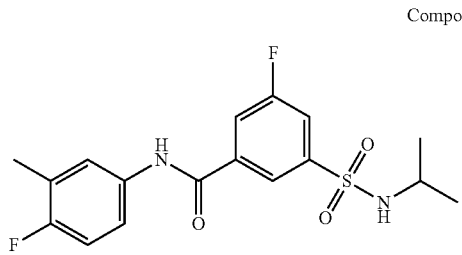

SOCl₂ (20.1 mL, 277.2 mmol) was added slowly to water (125 mL) cooled to 5° C., maintaining the temperature between 4 and 7° C. (addition took about 1.5 hour).

The solution was then kept stirring overnight while the temperature was allowed to slowly reach room temperature. Copper(I) chloride (76.6 mg, 0.774 mmol) was then added to the solution and it was cooled to −10° C. (dry ice/acetone bath), (resulting in solution A). In another flask cooled to 0° C., HCl (37% in H₂O, 65 mL) was added dropwise to 3-amino-5-fluorobenzoic acid (10 g, 64.46 mmol), keeping the temperature below 20° C. This slurry was cooled to −10° C. (dry ice/acetone bath) and a solution of sodium nitrite (4.803 g, 69.62 mmol) in H₂O (20 mL) was added very slowly (1 drop/5 sec) to the slurry, keeping the temperature below −5° C.

After addition, the orange mixture was allowed to warm to −2° C. for 5 min before cooling back to −15° C. (solution B). Solution B was then added portionwise (plastic pipette) to solution A, cooled to −10° C. After addition (~30 min), the reaction mixture was stirred at 0° C. for 2 h. The resulting orange solid was filtered and rinsed with water (2×25 mL) resulting in 3-chlorosulfonyl-5-fluoro-benzoic acid as an orange solid (dried at 35° C. in vacuo). Et₃N (1.22 mL, 8.8 mmol) was slowly added to a solution of 3-chlorosulfonyl-5-fluoro-benzoic acid (525 mg, 2.2 mmol) in dry CH₂Cl₂ (10 mL). Isopropylamine (198 µL, 2.42 mmol) was then added dropwise at room temperature to the reaction mixture. The reaction mixture was stirred at room temperature for 30 min. The brown reaction mixture was diluted with CH₂Cl₂ and water. HCl 1N was added to pH 2. The layers were separated and the aqueous layer was extracted twice with CH₂Cl₂. The organic layer was dried on MgSO₄, filtered, and evaporated resulting in 3-fluoro-5-(isopropylsulfamoyl)benzoic acid as an orange solid, which was used without further purification. HATU (356.7 mg, 0.94 mmol) was added to a solution of crude 3-fluoro-5-(isopropylsulfamoyl)benzoic acid (190 mg), 4-fluoro-3-methylaniline (78.3 mg, 0.625 mmol) and N,N-diisopropylethylamine (326.8 µL, 1.88 mmol) in CH₂Cl₂ (30 mL) at room temperature. The mixture was stirred at room temperature for 1 h. The reaction mixture was diluted with CH₂Cl₂, washed with HCl 0.5 N, filtered on Extrelut NT3 and evaporated. The obtained residue was purified by column chromatography on silica gel (Grace Resolv 12 g, eluent: CH₂Cl₂:MeOH 100:0 →95:5) resulting in compound 240 (136 mg) as a white solid, dried at 50° C. in vacuo. Method G, Rt: 1.87 min. m/z: 366.9 (M–H)⁻ Exact mass: 368.1. ¹H NMR (360 MHz, DMSO-d₆) δ ppm 0.97 (d, J=6.2 Hz, 6H) 2.25 (d, J=1.5 Hz, 3H) 3.30-3.39 (m, 1H), 7.16 (t, J=9.3 Hz, 1H) 7.55-7.62 (m, 1H) 7.67 (dd, J=7.1, 2.4 Hz, 1H) 7.83 (dt, J=8.0, 1.9 Hz, 1H) 7.88 (d, J=7.0 Hz, 1H) 8.08 (dt, J=9.3, 1.7 Hz, 1H) 8.22 (s, 1H) 10.52 (s, 1H).

Compound 241

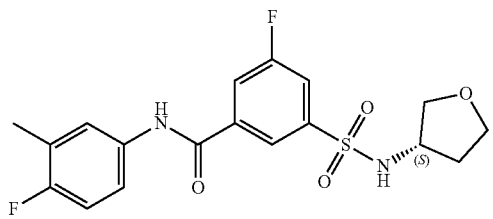

Compound 241 was prepared similarly as described for compound 240 using (S)-3-aminotetrahydrofuran tosylate instead of isopropylamine. Method G, Rt: 1.70 min. m/z: 394.9 (M–H)⁻ Exact mass: 396.1. ¹H NMR (360 MHz, DMSO-d₆) δ ppm 1.55-1.67 (m, 1H) 1.93 (dq, J=12.8, 7.4 Hz, 1H) 2.25 (d, J=1.8 Hz, 3H) 3.37 (dd, J=9.0, 4.2 Hz, 1H) 3.55-3.75 (m, 3H) 3.75-3.85 (m, 1H) 7.16 (t, J=9.1 Hz, 1H) 7.56-7.62 (m, 1H) 7.67 (dd, J=7.3, 2.6 Hz, 1H) 7.82-7.88 (m, 1H) 8.08-8.13 (m, 1H) 8.20-8.25 (m, 2H) 10.53 (s, 1H).

Compound 242

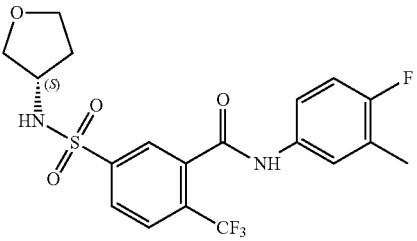

Compound 237 (400 mg, 0.87 mmol) was dissolved in a mixture of DMF (2.5 mL) and N-methylpyrrolidine (0.12 mL) containing Copper(I)iodide (45.43 mg, 0.24 mmol) and 2,2-difluoro-2-fluorosulfonyl acetic acid methylester (0.21 g, 1.09 mmol). The resulting mixture was stirred at room temperature for 2 hours. An extra amount of 2,2-difluoro-2-fluorosulfonyl acetic acid methylester (0.21 g, 1.09 mmol) was added and the mixture was stirred at 60° C. for 1 hour. The mixture was stirred at 60° C. for 18 hours. Saturated ammonium chloride solution (10 mL) was added to the reaction mixture. Then this was extracted using EtOAc (3×15 mL). The combined extracts were dried on Na₂SO₄, filtered and concentrated in vacuo. The obtained residue was purified using column chromatography on silica (gradient elution: ethylacetate: heptane from 0 to 100%). All desired fractions were combined and concentrated under reduced pressure and then dried at 50° C. in a vacuum oven overnight yielding compound 242 (314 mg) as a white powder. Method G, Rt: 1.73 min. m/z: 445.0 (M–H)⁻ Exact mass: 446.1.

Biological Examples—Anti-HBV Activity of Compounds of Formula (I)

The anti-HBV activity was measured using a stable transfected cell line, HepG2.2.15. This cell line was described to secrete relatively consistent high levels of HBV virion particles, which have been shown to cause both acute and chronic infection and disease in chimpanzees.

For the antiviral, assay cells were treated twice for three days with serially diluted compound in 96-well plates in duplicate. After 6 days of tretament the antiviral activity was determined by quantification of purified HBV DNA from secreted virions using realtime PCR and an HBV specific primer set and probe.

Cytotoxicity of the compounds was tested in HepG2 cells using CellTiter-Blue, with the same incubation period and dose range as in the HepG2.2.15 assay.

The anti HBV activity was also measured using the HepG2.117 cell line, a stable, inducibly HBV producing cell line, which replicates HBV in the absence of doxicycline (Tet-off system). For the antiviral assay, HBV replication was induced, followed by a treatment with serially diluted compound in 96-well plates in duplicate. After 3 days of treatment, the antiviral activity was determined by quantification of intracellular HBV DNA using realtime PCR and an HBV specific primer set and probe.

Cytotoxicity of the compounds was tested using HepG2 cells, incubated for 4 days in the presence of compounds. The viability of the cells was assessed using a Resazurin assay. Results are displayed in Table 1.

TABLE 1

| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| (structure) | 1 | 0.93 | | 1.67 | >100 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
| --- | --- | --- | --- | --- | --- |
| 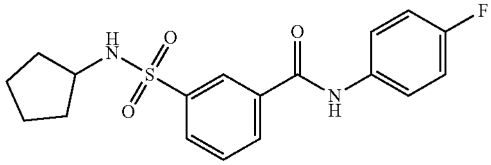 [SMILES: O=C(Nc1ccc(F)cc1)c1cccc(S(=O)(=O)NC2CCCC2)c1] | 2 | 0.47 | | 0.56 | 32.7 |
| 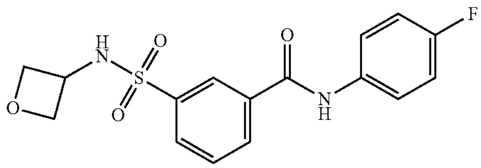 [SMILES: O=C(Nc1ccc(F)cc1)c1cccc(S(=O)(=O)NC2COC2)c1] | 3 | 2.10 | | 3.05 | >100 |
| 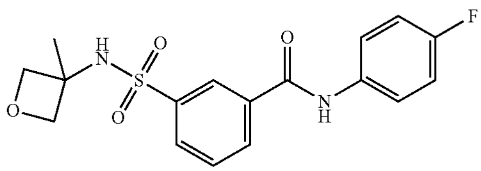 [SMILES: CC1(NS(=O)(=O)c2cccc(C(=O)Nc3ccc(F)cc3)c2)COC1] | 4 | 0.96 | | 0.93 | >100 |
| 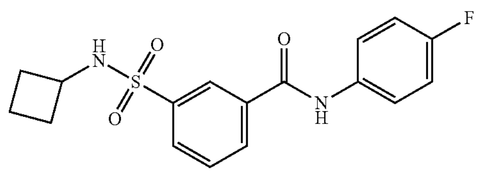 [SMILES: O=C(Nc1ccc(F)cc1)c1cccc(S(=O)(=O)NC2CCC2)c1] | 5 | 0.83 | | 0.90 | 57.7 |
| 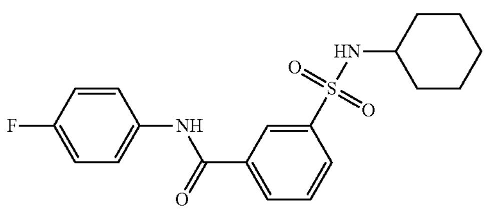 [SMILES: O=C(Nc1ccc(F)cc1)c1cccc(S(=O)(=O)NC2CCCCC2)c1] | 6 | | | 0.58 | >25 |
| 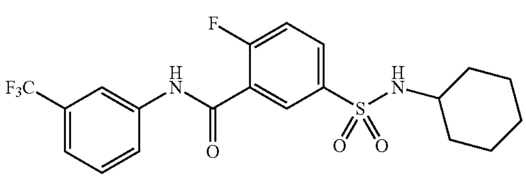 [SMILES: O=C(Nc1cccc(C(F)(F)F)c1)c1cc(S(=O)(=O)NC2CCCCC2)ccc1F] | 7 | 0.66 | — | 0.56 | 11.4 |
| 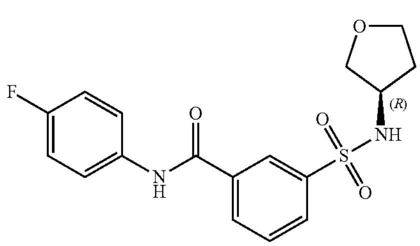 | 8 | 1.18 | | 2.03 | >100 |
| 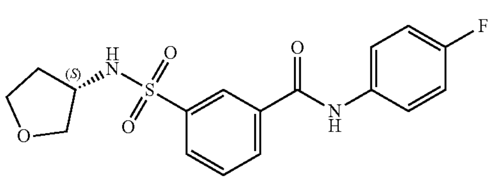 | 9 | 0.54 | | 1.36 | >100 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 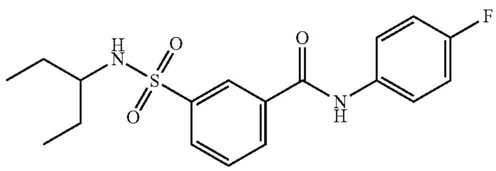 [SMILES: CCC(CC)NS(=O)(=O)c1cccc(C(=O)Nc2ccc(F)cc2)c1] | 10 | 0.75 | | 3.63 | 40.3 |
| 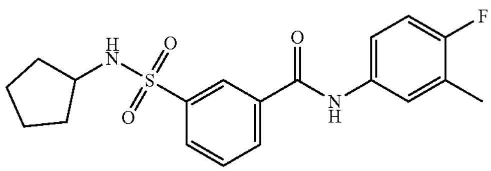 [SMILES: Cc1cc(NC(=O)c2cccc(S(=O)(=O)NC3CCCC3)c2)ccc1F] | 11 | 0.10 | | 0.42 | 19.6 |
| 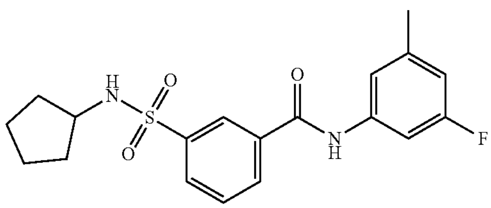 [SMILES: Cc1cc(F)cc(NC(=O)c2cccc(S(=O)(=O)NC3CCCC3)c2)c1] | 12 | 0.11 | | 1.51 | 13.3 |
| 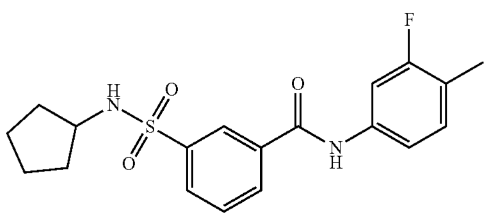 [SMILES: Cc1ccc(NC(=O)c2cccc(S(=O)(=O)NC3CCCC3)c2)cc1F] | 13 | 1.99 | | 15.31 | 13.8 |
| 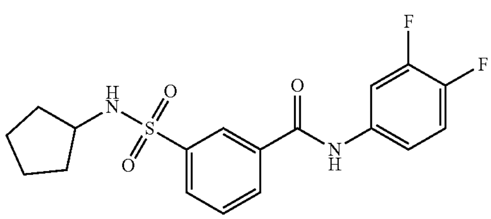 [SMILES: O=C(Nc1ccc(F)c(F)c1)c1cccc(S(=O)(=O)NC2CCCC2)c1] | 14 | 0.09 | | 0.36 | 11.7 |
| 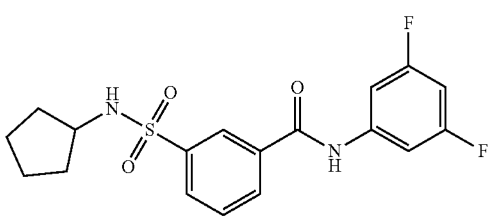 [SMILES: O=C(Nc1cc(F)cc(F)c1)c1cccc(S(=O)(=O)NC2CCCC2)c1] | 15 | 0.28 | | 0.78 | 10.1 |
| 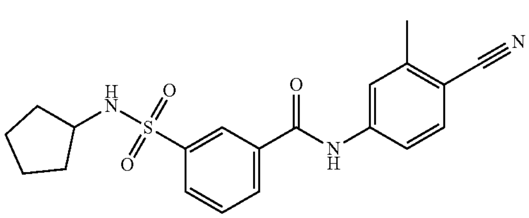 [SMILES: Cc1cc(NC(=O)c2cccc(S(=O)(=O)NC3CCCC3)c2)ccc1C#N] | 16 | 1.21 | | 2.8 | 10.3 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 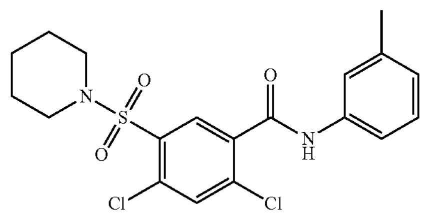 [SMILES: Cc1cccc(NC(=O)c2cc(S(=O)(=O)N3CCCCC3)c(Cl)cc2Cl)c1] | 17 | 0.56 | | 2.65 | >100 |
| 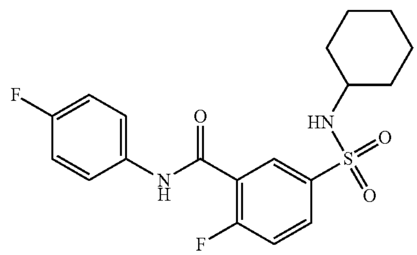 [SMILES: O=C(Nc1ccc(F)cc1)c1cc(S(=O)(=O)NC2CCCCC2)ccc1F] | 18 | 0.78 | 51.6 | 1.30 | >50 |
| 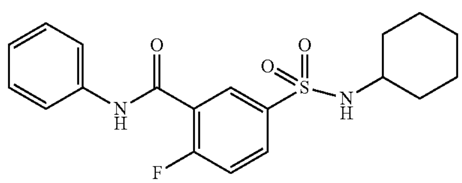 [SMILES: O=C(Nc1ccccc1)c1cc(S(=O)(=O)NC2CCCCC2)ccc1F] | 19 | 0.66 | 42.5 | 0.60 | >25 |
| 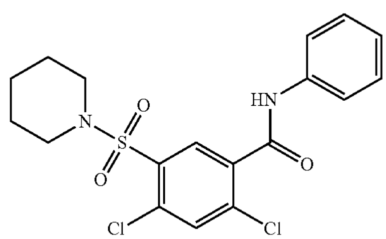 [SMILES: O=C(Nc1ccccc1)c1cc(S(=O)(=O)N2CCCCC2)c(Cl)cc1Cl] | 20 | 0.50 | >25 | 1.00 | 79.6 |
| 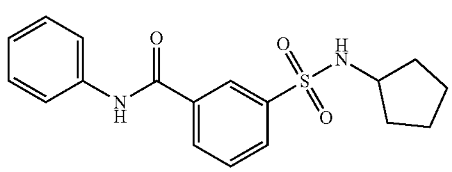 [SMILES: O=C(Nc1ccccc1)c1cccc(S(=O)(=O)NC2CCCC2)c1] | 21 | 0.60 | 27.2 | 0.76 | 41.1 |
| 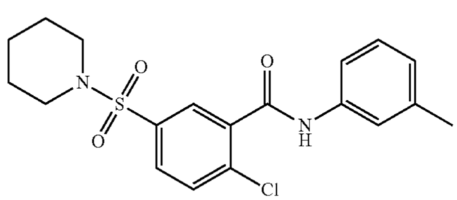 [SMILES: Cc1cccc(NC(=O)c2cc(S(=O)(=O)N3CCCCC3)ccc2Cl)c1] | 22 | 0.52 | >25 | | |
| 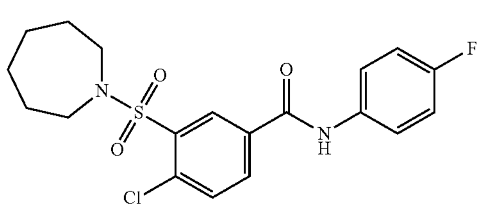 [SMILES: O=C(Nc1ccc(F)cc1)c1ccc(Cl)c(S(=O)(=O)N2CCCCCC2)c1] | 23 | 0.66 | 17.0 | 1.30 | 19.6 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 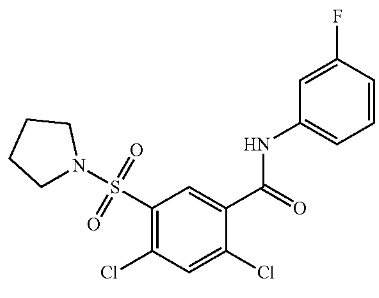 [SMILES: O=C(Nc1cccc(F)c1)c1cc(S(=O)(=O)N2CCCC2)c(Cl)cc1Cl] | 24 | 0.79 | >25 | | |
| 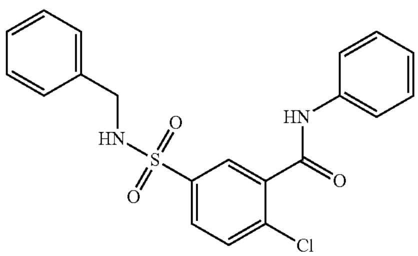 [SMILES: O=C(Nc1ccccc1)c1cc(S(=O)(=O)NCc2ccccc2)ccc1Cl] | 25 | 0.80 | >25 | 1.02 | >6.25 |
| 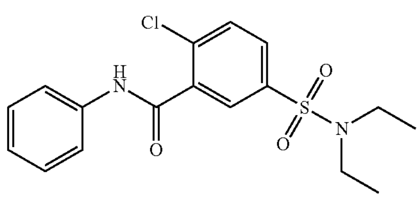 [SMILES: CCN(CC)S(=O)(=O)c1ccc(Cl)c(C(=O)Nc2ccccc2)c1] | 26 | 1.04 | >25 | | |
| 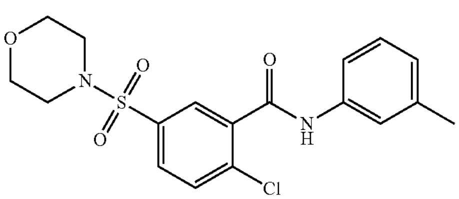 [SMILES: Cc1cccc(NC(=O)c2cc(S(=O)(=O)N3CCOCC3)ccc2Cl)c1] | 27 | 1.13 | >25 | | |
| 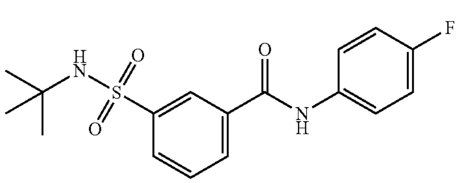 [SMILES: CC(C)(C)NS(=O)(=O)c1cccc(C(=O)Nc2ccc(F)cc2)c1] | 28 | 1.24 | | 2.28 | 52.5 |
| 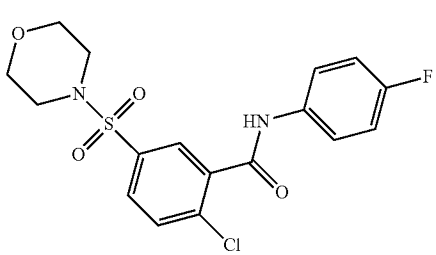 [SMILES: O=C(Nc1ccc(F)cc1)c1cc(S(=O)(=O)N2CCOCC2)ccc1Cl] | 29 | 1.39 | >25 | | |

TABLE 1-continued
| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 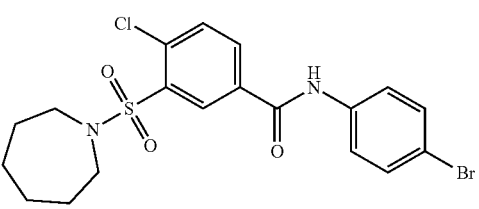 [SMILES: O=C(Nc1ccc(Br)cc1)c1ccc(Cl)c(S(=O)(=O)N2CCCCCC2)c1] | 30 | 1.67 | >25 | | |
| 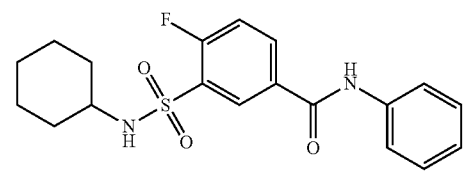 [SMILES: O=C(Nc1ccccc1)c1ccc(F)c(S(=O)(=O)NC2CCCCC2)c1] | 31 | 2.23 | 16.4 | | |
| 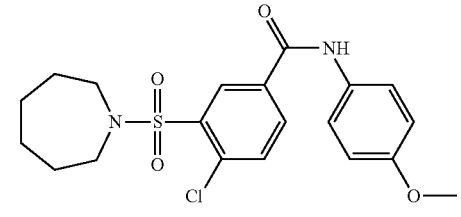 [SMILES: COc1ccc(NC(=O)c2ccc(Cl)c(S(=O)(=O)N3CCCCCC3)c2)cc1] | 32 | 2.59 | 9.9 | 4.58 | >25 |
| 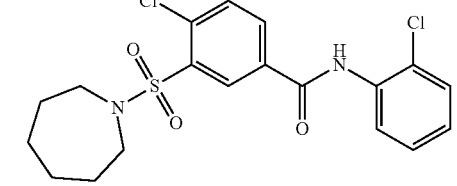 | 33 | 3.56 | >25 | | |
| 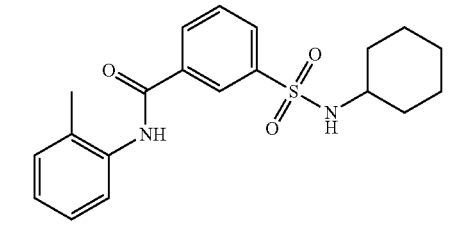 [SMILES: Cc1ccccc1NC(=O)c1cccc(S(=O)(=O)NC2CCCCC2)c1] | 34 | 4.18 | >25 | | |
| 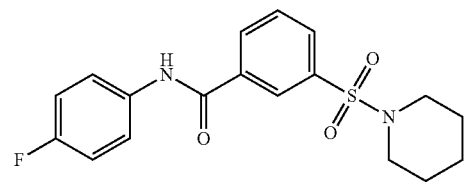 [SMILES: O=C(Nc1ccc(F)cc1)c1cccc(S(=O)(=O)N2CCCCC2)c1] | 35 | 4.50 | | 2.70 | 70.4 |
| 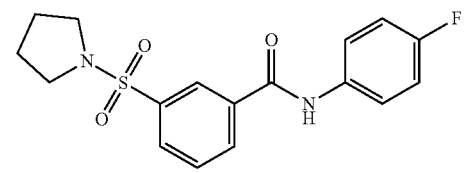 [SMILES: O=C(Nc1ccc(F)cc1)c1cccc(S(=O)(=O)N2CCCC2)c1] | 36 | 4.53 | | 3.03 | 97.0 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
| --- | --- | --- | --- | --- | --- |
| 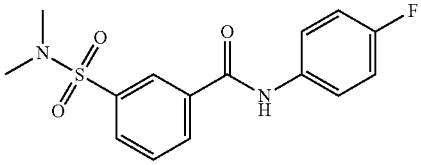 [SMILES: CN(C)S(=O)(=O)c1cccc(C(=O)Nc2ccc(F)cc2)c1] | 37 | 5.02 | | 2.99 | >100 |
| 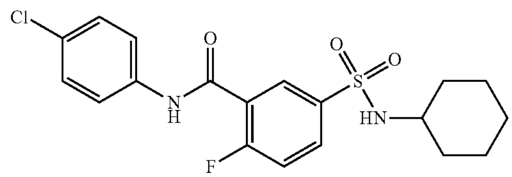 [SMILES: O=C(Nc1ccc(Cl)cc1)c1cc(S(=O)(=O)NC2CCCCC2)ccc1F] | 38 | <6.25 | 18.4 | 15.54 | 22.10 |
| 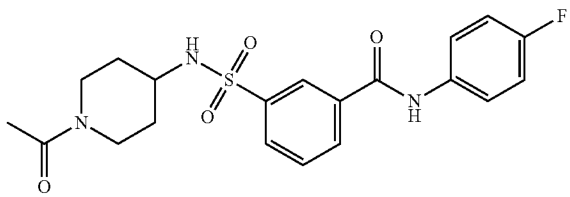 [SMILES: CC(=O)N1CCC(NS(=O)(=O)c2cccc(C(=O)Nc3ccc(F)cc3)c2)CC1] | 39 | 6.77 | | 4.68 | >100 |
| 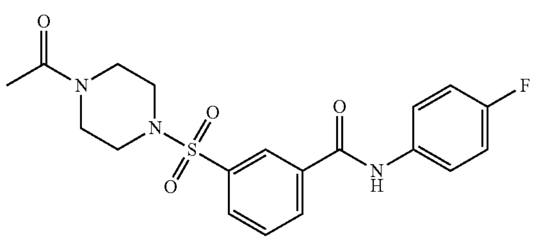 [SMILES: CC(=O)N1CCN(S(=O)(=O)c2cccc(C(=O)Nc3ccc(F)cc3)c2)CC1] | 40 | 7.10 | | 6.29 | >100 |
| 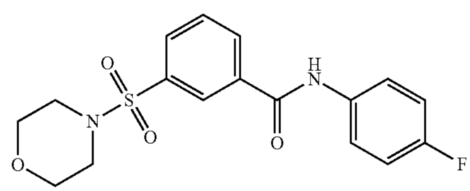 [SMILES: O=C(Nc1ccc(F)cc1)c1cccc(S(=O)(=O)N2CCOCC2)c1] | 41 | 8.49 | — | 10.95 | >100 |
| 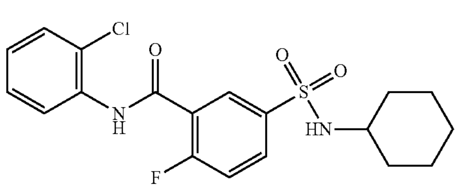 [SMILES: O=C(Nc1ccccc1Cl)c1cc(S(=O)(=O)NC2CCCCC2)ccc1F] | 42 | 11.64 | 37.2 | >25 | |
| 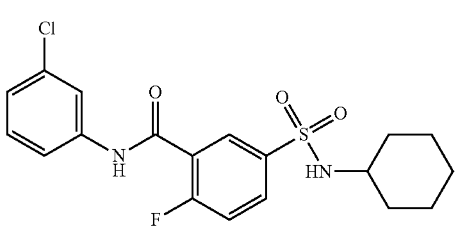 [SMILES: O=C(Nc1cccc(Cl)c1)c1cc(S(=O)(=O)NC2CCCCC2)ccc1F] | 43 | 15.13 | 36.3 | >25 | >25 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
| --- | --- | --- | --- | --- | --- |
| 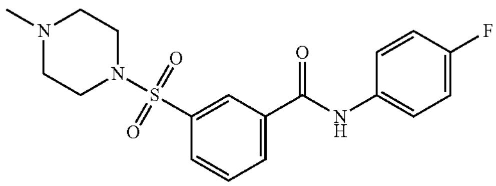 [SMILES: CN1CCN(S(=O)(=O)c2cccc(C(=O)Nc3ccc(F)cc3)c2)CC1] | 44 | 26.49 | | 11.08 | >100 |
| 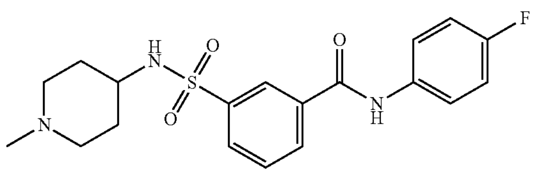 [SMILES: CN1CCC(NS(=O)(=O)c2cccc(C(=O)Nc3ccc(F)cc3)c2)CC1] | 45 | 59.33 | | 16.03 | >100 |
| 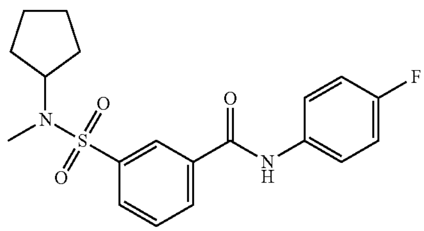 [SMILES: CN(C1CCCC1)S(=O)(=O)c1cccc(C(=O)Nc2ccc(F)cc2)c1] | 46 | 2.61 | | 11.09 | 23.8 |
| 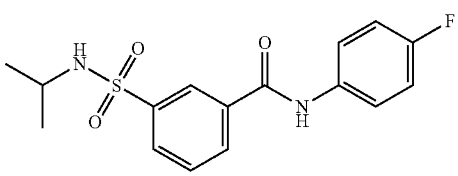 [SMILES: CC(C)NS(=O)(=O)c1cccc(C(=O)Nc2ccc(F)cc2)c1] | 47 | 0.74 | | 0.96 | 57.5 |
| 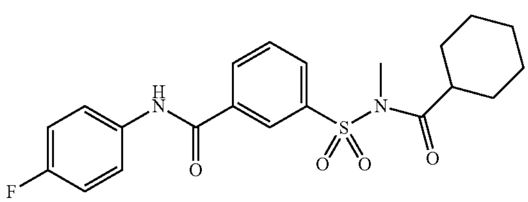 [SMILES: CN(C(=O)C1CCCCC1)S(=O)(=O)c1cccc(C(=O)Nc2ccc(F)cc2)c1] | 48 | 2.92 | | 1.88 | 97.2 |
| 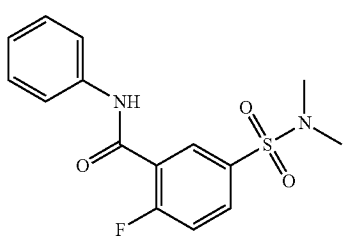 [SMILES: CN(C)S(=O)(=O)c1ccc(F)c(C(=O)Nc2ccccc2)c1] | 49 | 13.4 | | 9.15 | >100 |
| 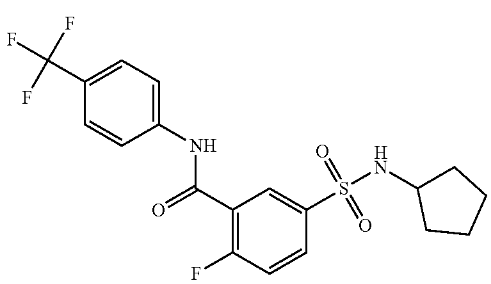 [SMILES: O=C(Nc1ccc(C(F)(F)F)cc1)c1cc(S(=O)(=O)NC2CCCC2)ccc1F] | 50 | 45.9 | | 15.80 | 11.3 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 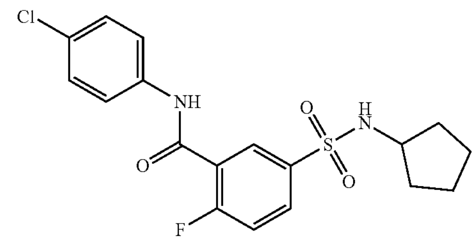 [SMILES: O=C(Nc1ccc(Cl)cc1)c1cc(S(=O)(=O)NC2CCCC2)ccc1F] | 51 | 3.98 | | 9.44 | 20.8 |
| 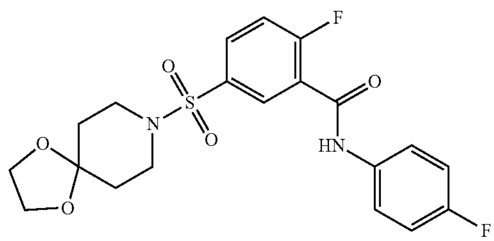 [SMILES: O=C(Nc1ccc(F)cc1)c1cc(S(=O)(=O)N2CCC3(CC2)OCCO3)ccc1F] | 52 | 1.94 | | 2.44 | >50 |
| 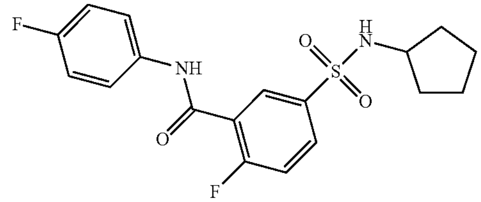 [SMILES: O=C(Nc1ccc(F)cc1)c1cc(S(=O)(=O)NC2CCCC2)ccc1F] | 53 | 0.36 | | 0.44 | >50 |
| 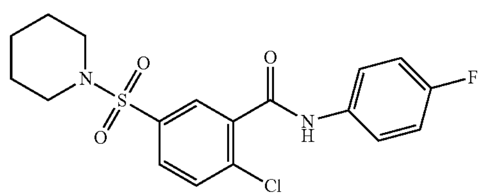 [SMILES: O=C(Nc1ccc(F)cc1)c1cc(S(=O)(=O)N2CCCCC2)ccc1Cl] | 54 | 1.63 | | 1.55 | >50 |
| 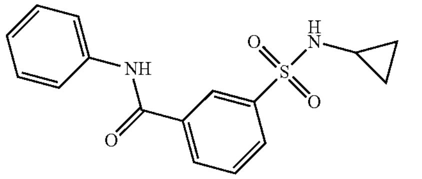 [SMILES: O=C(Nc1ccccc1)c1cccc(S(=O)(=O)NC2CC2)c1] | 55 | 3.06 | | 3.26 | >100 |
| 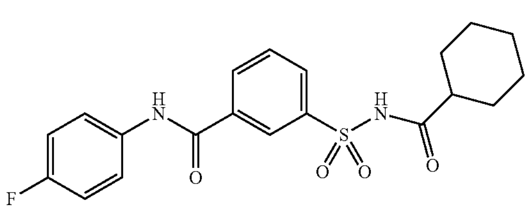 [SMILES: O=C(Nc1ccc(F)cc1)c1cccc(S(=O)(=O)NC(=O)C2CCCCC2)c1] | 56 | 1.64 | | 5.45 | >100 |
| 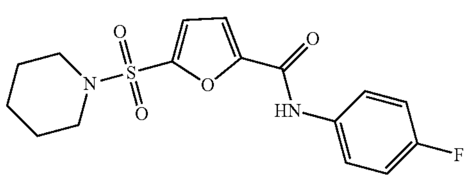 [SMILES: O=C(Nc1ccc(F)cc1)c1ccc(S(=O)(=O)N2CCCCC2)o1] | 57 | 15.53 | | 12.74 | 52.1 |

TABLE 1-continued
| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 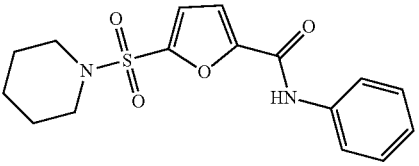 [SMILES: O=C(Nc1ccccc1)c1ccc(S(=O)(=O)N2CCCCC2)o1] | 58 | 14.62 | | 19.94 | 62.5 |
| 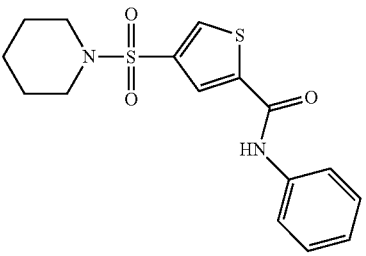 [SMILES: O=C(Nc1ccccc1)c1cc(S(=O)(=O)N2CCCCC2)cs1] | 59 | 12.79 | | 19.27 | 46.7 |
| 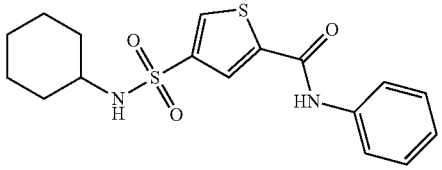 [SMILES: O=C(Nc1ccccc1)c1cc(S(=O)(=O)NC2CCCCC2)cs1] | 60 | 0.85 | | 0.67 | 29.1 |
| 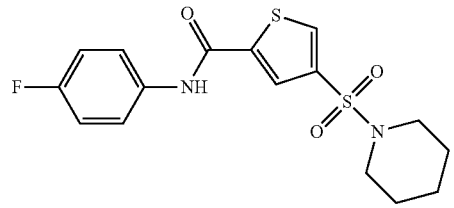 [SMILES: O=C(Nc1ccc(F)cc1)c1cc(S(=O)(=O)N2CCCCC2)cs1] | 61 | 7.07 | | 15.44 | 35.7 |
| 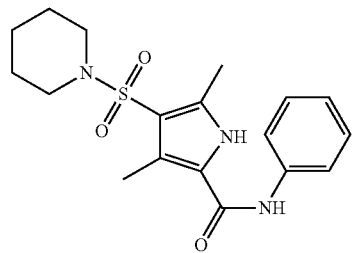 [SMILES: Cc1[nH]c(C(=O)Nc2ccccc2)c(C)c1S(=O)(=O)N1CCCCC1] | 62 | 7.06 | | 10.07 | >50 |
| 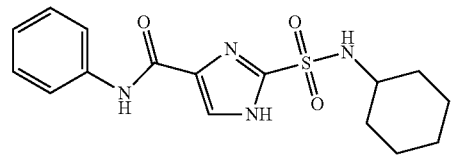 [SMILES: O=C(Nc1ccccc1)c1c[nH]c(S(=O)(=O)NC2CCCCC2)n1] | 63 | 9.94 | | 21.12 | >100 |
| 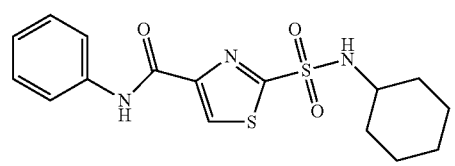 [SMILES: O=C(Nc1ccccc1)c1csc(S(=O)(=O)NC2CCCCC2)n1] | 64 | | | 7.83 | >25 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 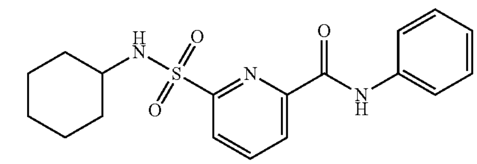 [SMILES: O=C(Nc1ccccc1)c1cccc(S(=O)(=O)NC2CCCCC2)n1] | 65 | 10.76 | >25 | | 35.3 |
| 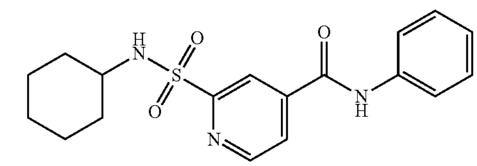 [SMILES: O=C(Nc1ccccc1)c1ccnc(S(=O)(=O)NC2CCCCC2)c1] | 66 | 4.27 | | 14.49 | >100 |
| 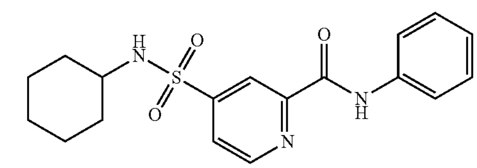 [SMILES: O=C(Nc1ccccc1)c1cc(S(=O)(=O)NC2CCCCC2)ccn1] | 67 | 11.10 | | 18.55 | >100 |
| 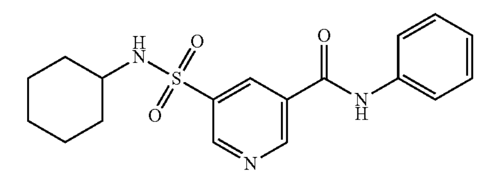 [SMILES: O=C(Nc1ccccc1)c1cncc(S(=O)(=O)NC2CCCCC2)c1] | 68 | 18.60 | >25 | | 68.0 |
| 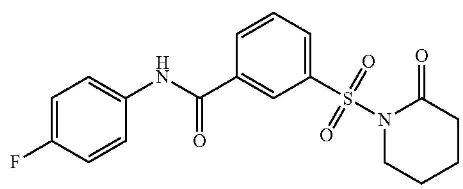 [SMILES: O=C(Nc1ccc(F)cc1)c1cccc(S(=O)(=O)N2CCCCC2=O)c1] | 69 | 3.90 | | 10.38 | >25 |
| 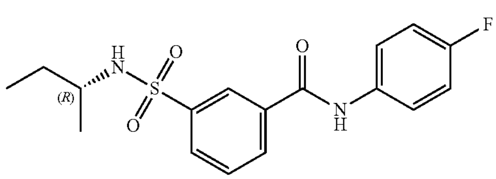 | 70 | 0.34 | | 0.89 | >25 |
| 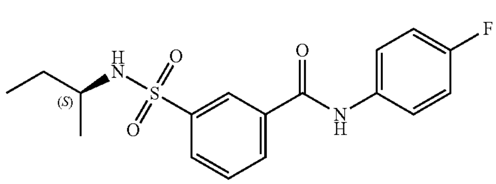 | 71 | 0.75 | | 8.63 | >25 |
| 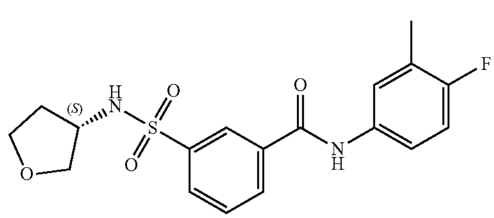 | 72 | 0.12 | | 0.37 | >25 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| (isopropyl-NH-SO2-phenyl-C(O)NH-(4-F,3-methylphenyl)) | 73 | 0.073 | | 0.15 | >25 |
| (isopropyl-NH-SO2-phenyl-C(O)NH-(4-F,3-CF3-phenyl)) | 74 | 0.64 | | 0.53 | >25 |
| (cyclopentyl-NH-SO2-phenyl-C(O)NH-(3-CN-phenyl)) | 75 | 0.39 | | 0.82 | >25 |
| (1-methylcyclopentyl-NH-SO2-phenyl-C(O)NH-(4-F-phenyl)) | 76 | 0.72 | | 2.5 | >25 |
| (cyclopentyl-NH-SO2-phenyl-C(O)NH-(3-F-phenyl)) | 77 | 0.27 | | 0.43 | >25 |
| (cyclopentyl-NH-SO2-(2,4-diCl-phenyl)-C(O)NH-(4-F-phenyl)) | 78 | 0.90 | | 0.65 | >25 |
| (tert-amyl-NH-SO2-phenyl-C(O)NH-(4-F-phenyl)) | 79 | 0.96 | | 1.69 | >25 |
| (cyclopentyl-NH-SO2-phenyl-C(O)NH-(4-CN-phenyl)) | 80 | 8.4 | | 17.9 | >25 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 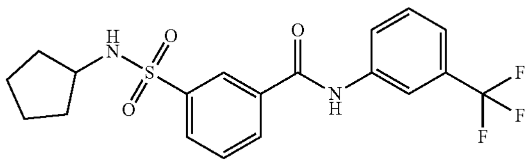 [SMILES: O=C(Nc1cccc(C(F)(F)F)c1)c1cccc(S(=O)(=O)NC2CCCC2)c1] | 81 | 0.24 | | 0.81 | 15.3 |
| 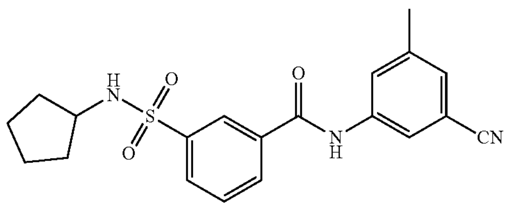 [SMILES: Cc1cc(C#N)cc(NC(=O)c2cccc(S(=O)(=O)NC3CCCC3)c2)c1] | 82 | 1.20 | | 3.13 | >25 |
| 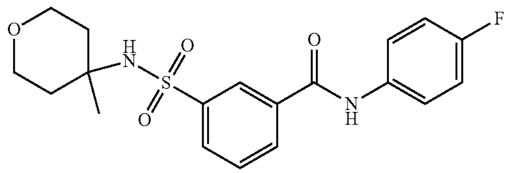 [SMILES: CC1(NS(=O)(=O)c2cccc(C(=O)Nc3ccc(F)cc3)c2)CCOCC1] | 83 | 1.04 | | 1.23 | >25 |
| 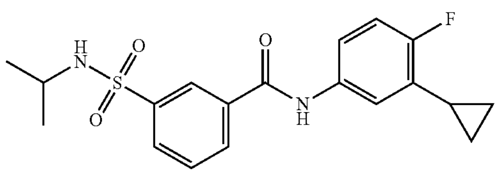 [SMILES: CC(C)NS(=O)(=O)c1cccc(C(=O)Nc2ccc(F)c(C3CC3)c2)c1] | 84 | 0.32 | | 0.91 | >25 |
| 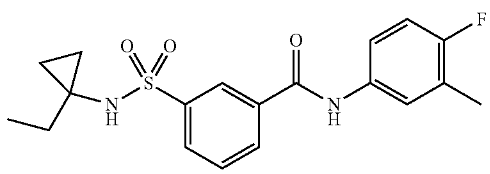 [SMILES: CCC1(NS(=O)(=O)c2cccc(C(=O)Nc3ccc(F)c(C)c3)c2)CC1] | 85 | 0.05 | | 0.38 | >25 |
| 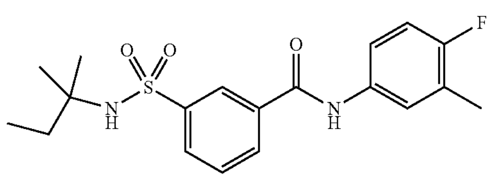 [SMILES: CCC(C)(C)NS(=O)(=O)c1cccc(C(=O)Nc2ccc(F)c(C)c2)c1] | 86 | 0.14 | | 0.11 | >25 |
| 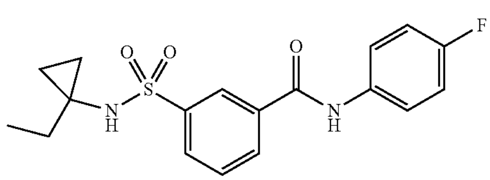 [SMILES: CCC1(NS(=O)(=O)c2cccc(C(=O)Nc3ccc(F)cc3)c2)CC1] | 87 | 0.41 | | 0.89 | >25 |
| 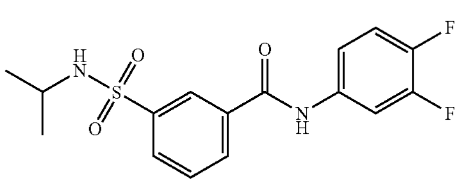 [SMILES: CC(C)NS(=O)(=O)c1cccc(C(=O)Nc2ccc(F)c(F)c2)c1] | 88 | 0.21 | | 0.40 | >25 |

TABLE 1-continued
| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 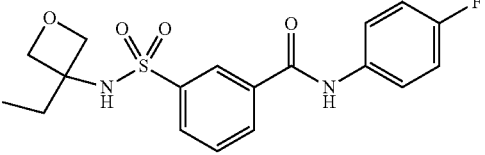 | 89 | 0.54 | | 0.72 | >25 |
| 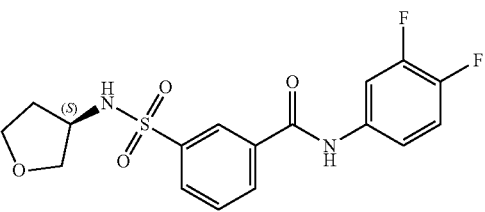 | 90 | 0.38 | | 0.51 | >25 |
| 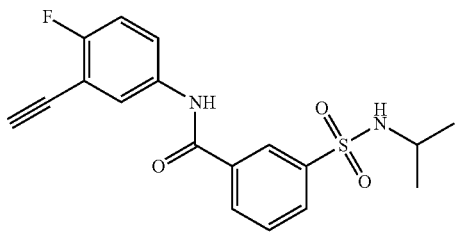 [SMILES: C#Cc1cc(NC(=O)c2cccc(S(=O)(=O)NC(C)C)c2)ccc1F] | 91 | 0.53 | | 0.77 | >25 |
| 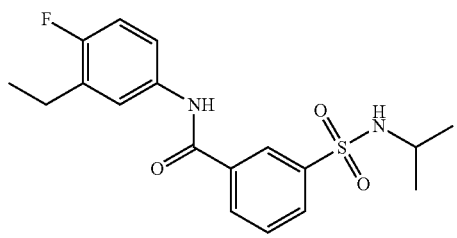 [SMILES: CCc1cc(NC(=O)c2cccc(S(=O)(=O)NC(C)C)c2)ccc1F] | 92 | 0.31 | | 2.59 | >25 |
| 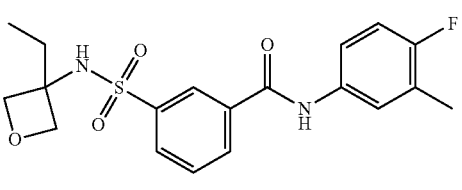 [SMILES: CCC1(NS(=O)(=O)c2cccc(C(=O)Nc3ccc(F)c(C)c3)c2)COC1] | 93 | 0.07 | | 0.22 | >25 |
| 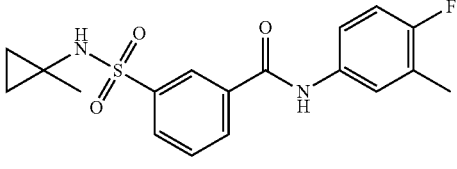 [SMILES: Cc1cc(NC(=O)c2cccc(S(=O)(=O)NC3(C)CC3)c2)ccc1F] | 94 | 0.15 | | 0.23 | >25 |
| 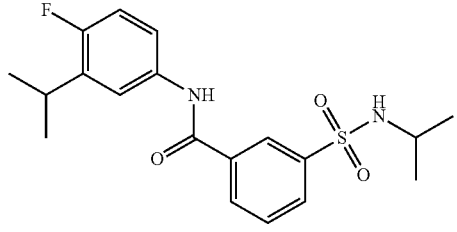 | 95 | 1.4 | | 2.79 | >25 |

TABLE 1-continued

| STRUCTURE | Co. No. | HepG2 2.15 EC50 (µM) | HepG2 6 days CC50 (µM) | HepG2 117 EC50 (µM) | HepG2 4 days CC50 (µM) |
| --- | --- | --- | --- | --- | --- |
| 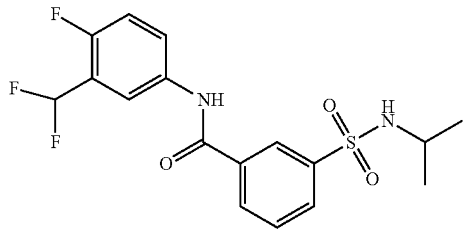 [SMILES: CC(C)NS(=O)(=O)c1cccc(C(=O)Nc2ccc(F)c(C(F)F)c2)c1] | 96 | 0.10 | | 0.29 | >25 |
| 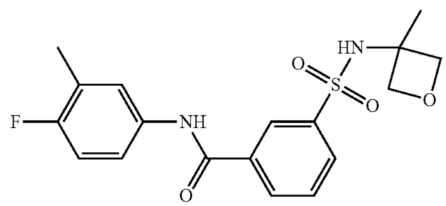 [SMILES: Cc1cc(NC(=O)c2cccc(S(=O)(=O)NC3(C)COC3)c2)ccc1F] | 97 | 0.12 | | 0.37 | >25 |
| 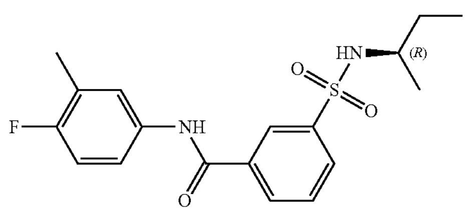 | 98 | 0.10 | | 0.31 | >25 |
| 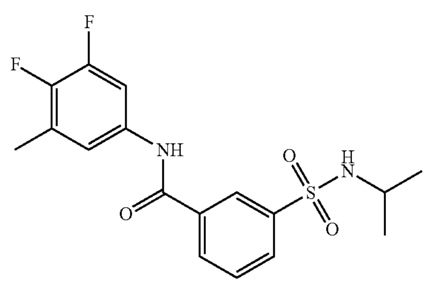 [SMILES: Cc1cc(NC(=O)c2cccc(S(=O)(=O)NC(C)C)c2)cc(F)c1F] | 99 | 0.09 | | 0.46 | >25 |
| 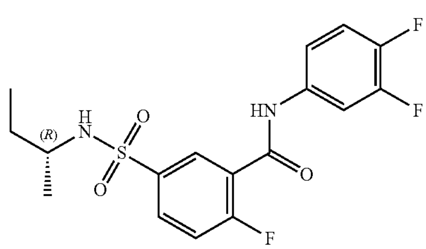 | 100 | 0.13 | | 0.43 | >25 |
| 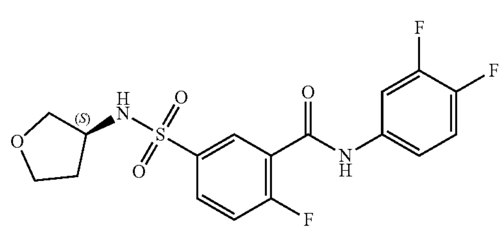 | 101 | 0.43 | | 1.51 | >25 |

TABLE 1-continued
| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 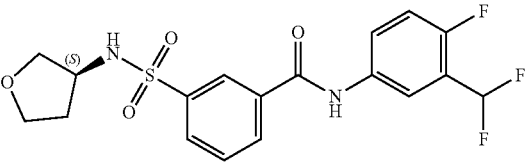 | 102 | 0.18 | | 0.33 | >25 |
| 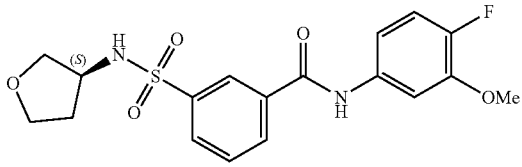 | 103 | 2.33 | | 2.66 | >25 |
| 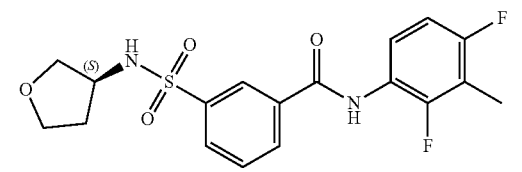 | 104 | 0.29 | | 0.78 | >25 |
| 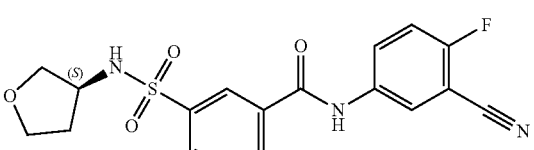 | 105 | 0.81 | | 0.98 | >25 |
| 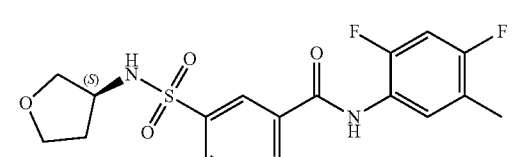 | 106 | 2.22 | | 3.30 | >25 |
| 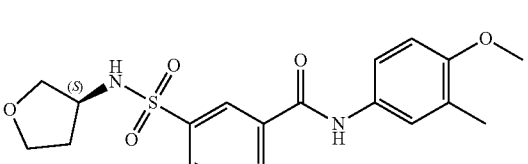 | 107 | 7.82 | | 13.82 | >25 |
| 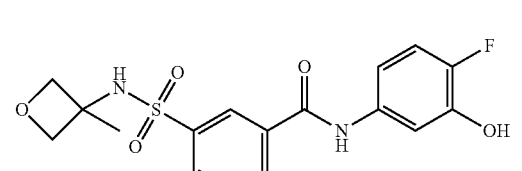 | 108 | 7.20 | | 9.27 | >25 |
| 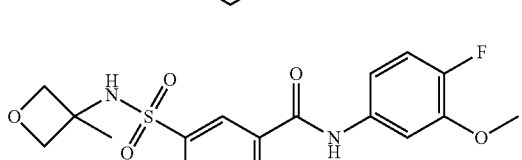 | 109 | 1.23 | | 2.53 | >25 |

TABLE 1-continued
| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 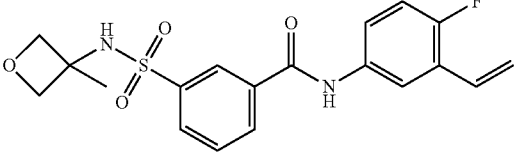 | 110 | 0.66 | | 0.85 | >25 |
| 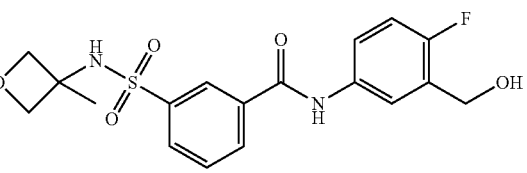 | 111 | 4.48 | | 1.48 | >25 |
| 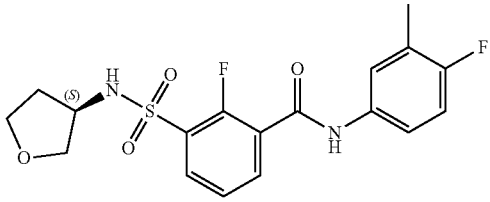 | 112 | 0.03 | | 0.14 | >25 |
| 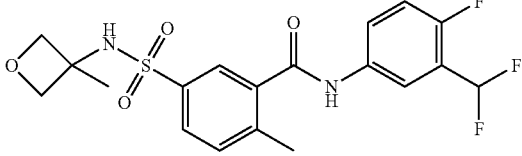 | 113 | 0.15 | | 0.18 | >25 |
| 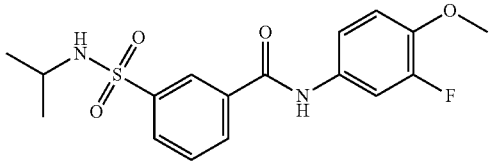 [SMILES: COc1ccc(NC(=O)c2cccc(S(=O)(=O)NC(C)C)c2)cc1F] | 114 | 1.35 | | 3.15 | >25 |
| 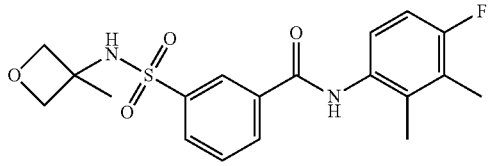 [SMILES: Cc1c(F)ccc(NC(=O)c2cccc(S(=O)(=O)NC3(C)COC3)c2)c1C] | 115 | 2.74 | | 1.65 | >25 |
| 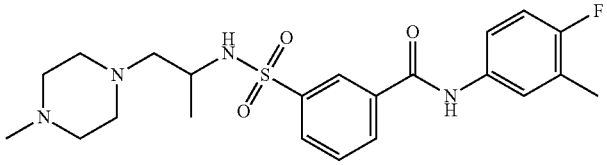 | 116 | 1.94 | | 0.90 | >25 |
| 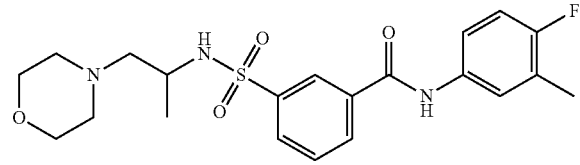 [SMILES: Cc1cc(NC(=O)c2cccc(S(=O)(=O)NC(C)CN3CCOCC3)c2)ccc1F] | 117 | 0.88 | | 0.50 | >25 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 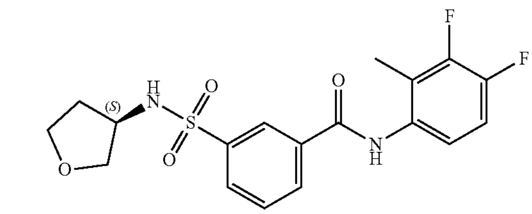 | 118 | 3.63 | | 1.91 | >25 |
| 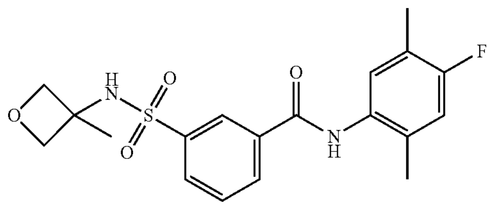 [SMILES: Cc1cc(NC(=O)c2cccc(S(=O)(=O)NC3(C)COC3)c2)c(C)cc1F] | 119 | 3.06 | | 1.91 | >25 |
| 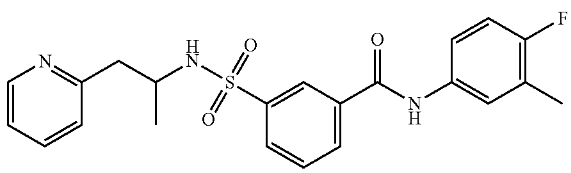 [SMILES: Cc1cc(NC(=O)c2cccc(S(=O)(=O)NC(C)Cc3ccccn3)c2)ccc1F] | 120 | 0.53 | | 0.51 | >25 |
| 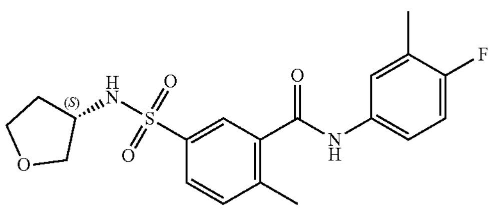 | 121 | 0.16 | | 0.13 | >25 |
| 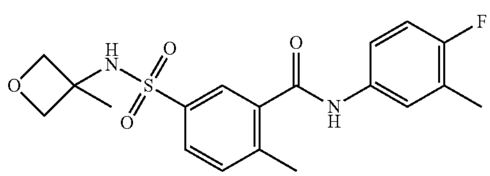 [SMILES: Cc1cc(NC(=O)c2cc(S(=O)(=O)NC3(C)COC3)ccc2C)ccc1F] | 122 | 0.13 | | 0.18 | >25 |
| 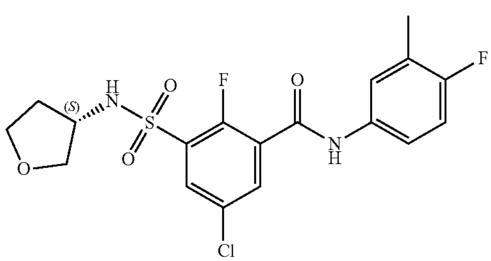 | 123 | 0.15 | | 0.3 | >25 |
| 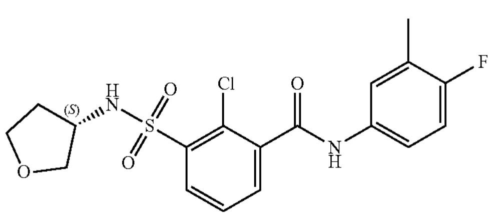 | 124 | 0.33 | | 0.68 | >25 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
| --- | --- | --- | --- | --- | --- |
| 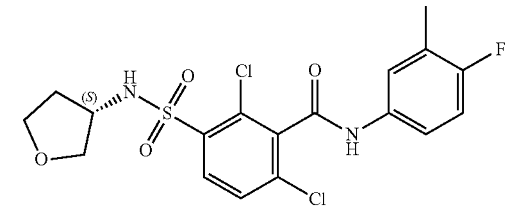 | 125 | 1.44 | | 1.15 | >25 |
| 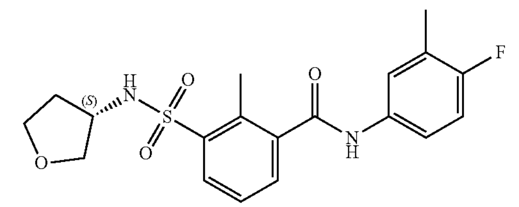 | 126 | 1.38 | | 0.89 | >25 |
| 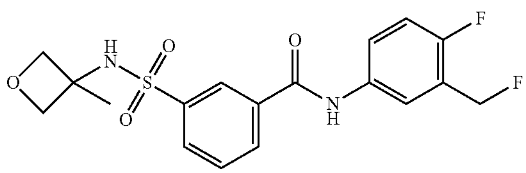 [SMILES: CC1(NS(=O)(=O)c2cccc(C(=O)Nc3ccc(F)c(CF)c3)c2)COC1] | 127 | 0.23 | | 0.58 | >25 |
| 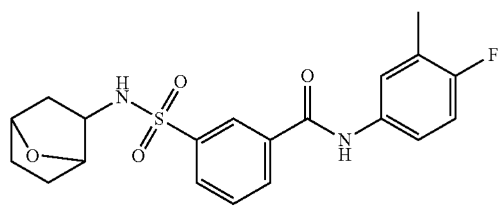 [SMILES: Cc1cc(NC(=O)c2cccc(S(=O)(=O)NC3CC4CCC3O4)c2)ccc1F] | 128 | 0.23 | | 0.54 | >25 |
| 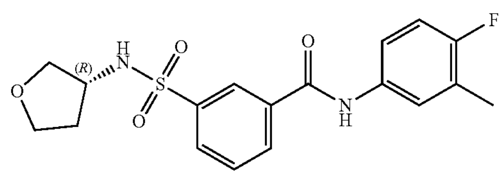 | 129 | 0.35 | | 0.78 | >25 |
| 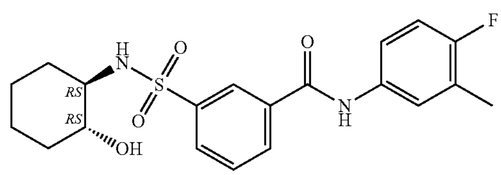 [SMILES: Cc1cc(NC(=O)c2cccc(S(=O)(=O)N[C@@H]3CCCC[C@H]3O)c2)ccc1F] | 130 | 0.88 | | 1.03 | >25 |
| 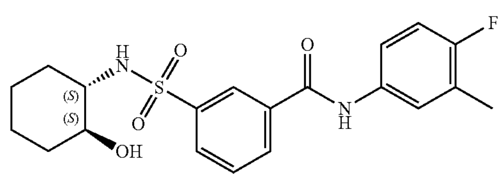 | 131 | 2.63 | | 1.74 | >25 |
| 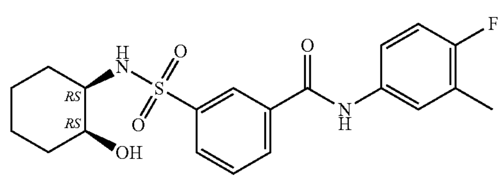 [SMILES: Cc1cc(NC(=O)c2cccc(S(=O)(=O)N[C@@H]3CCCC[C@@H]3O)c2)ccc1F] | 132 | 0.59 | | 0.73 | >25 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
| --- | --- | --- | --- | --- | --- |
| 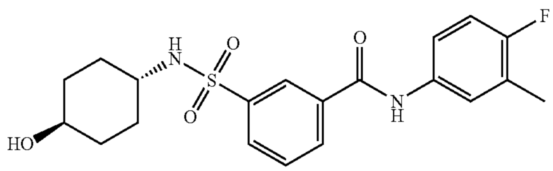 [SMILES: Cc1cc(NC(=O)c2cccc(S(=O)(=O)N[C@H]3CC[C@H](O)CC3)c2)ccc1F] | 133 | 0.60 | | 1.69 | >25 |
| 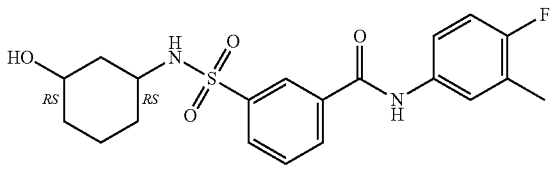 [SMILES: Cc1cc(NC(=O)c2cccc(S(=O)(=O)NC3CCCC(O)C3)c2)ccc1F] | 134 | 0.18 | | 0.57 | >25 |
| | 134a | 0.66 | | 0.72 | |
| | 134b | 0.57 | | 0.20 | |
| | 134c | 0.49 | | 0.38 | |
| | 134d | 0.25 | | 1.22 | |
| 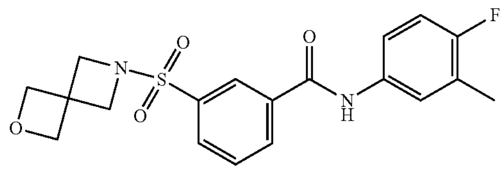 [SMILES: Cc1cc(NC(=O)c2cccc(S(=O)(=O)N3CC4(COC4)C3)c2)ccc1F] | 135 | 0.56 | | 0.36 | >25 |
| 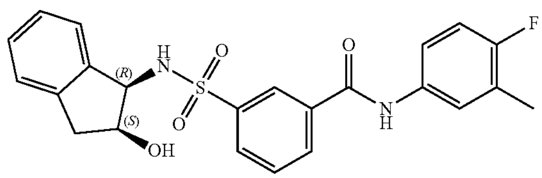 | 136 | 0.47 | | 0.81 | >25 |
| 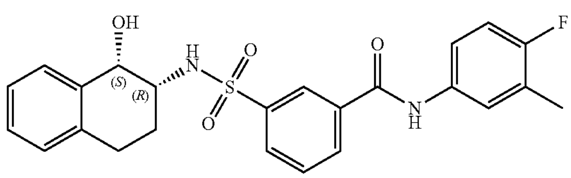 | 137 | 0.66 | | 0.92 | 23.7 |
| 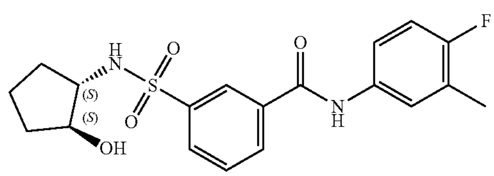 | 138 | 1.28 | | 2.27 | >25 |
| 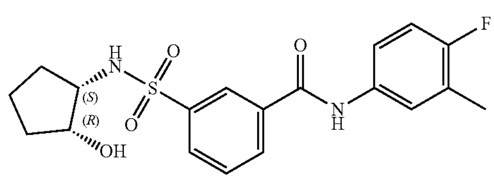 | 139 | 1.00 | | 1.75 | >25 |
| 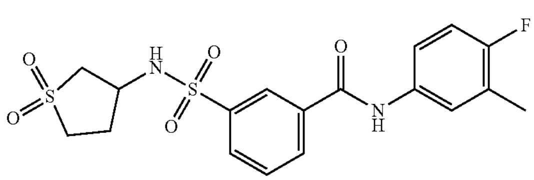 [SMILES: Cc1cc(NC(=O)c2cccc(S(=O)(=O)NC3CCS(=O)(=O)C3)c2)ccc1F] | 140 | 1.10 | | 1.12 | >25 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 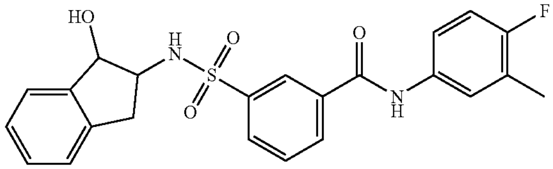 [SMILES: Cc1cc(NC(=O)c2cccc(S(=O)(=O)NC3Cc4ccccc4C3O)c2)ccc1F] | 141 | 0.36 | | 0.60 | >25 |
| | 141a | 0.70 | | 1.65 | >25 |
| | 141b | 0.27 | | 0.23 | >25 |
| | 141c | 0.17 | | 0.29 | >25 |
| | 141d | 0.56 | | 1.14 | >25 |
| 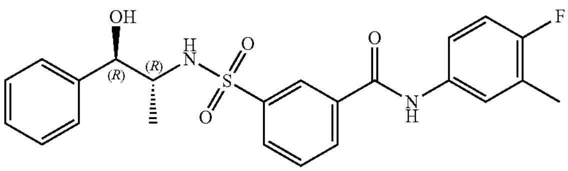 | 142 | 0.14 | | 0.56 | >25 |
| 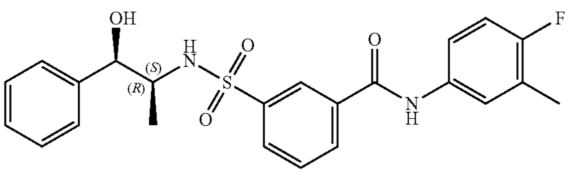 | 143 | 0.91 | | 2.66 | >25 |
| 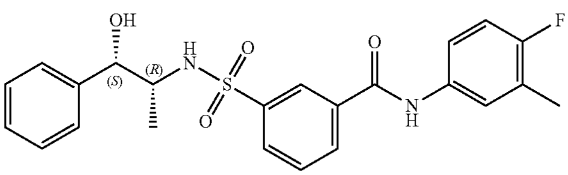 | 144 | 0.13 | | 0.24 | >25 |
| 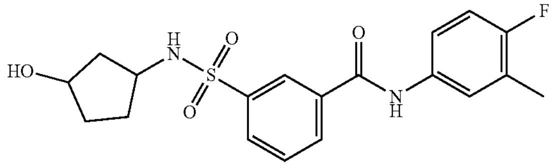 [SMILES: Cc1cc(NC(=O)c2cccc(S(=O)(=O)NC3CCC(O)C3)c2)ccc1F] | 145 | 0.22 | | 0.27 | >25 |
| | 145a | 0.14 | | 0.21 | >25 |
| | 145b | 0.44 | | 0.58 | >25 |
| | 145c | 0.34 | | 0.34 | >25 |
| | 145d | 0.40 | | 0.64 | >25 |
| 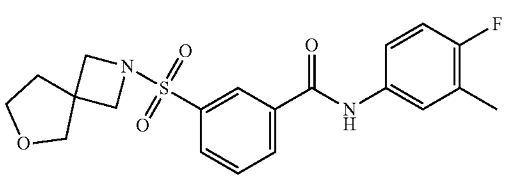 [SMILES: Cc1cc(NC(=O)c2cccc(S(=O)(=O)N3CC4(CCOC4)C3)c2)ccc1F] | 146 | 0.45 | | 0.42 | >25 |
| 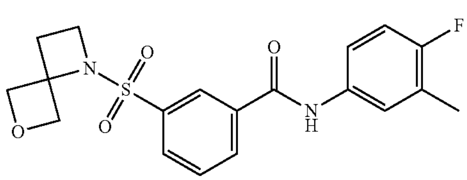 [SMILES: Cc1cc(NC(=O)c2cccc(S(=O)(=O)N3CCC34COC4)c2)ccc1F] | 147 | 0.26 | | 0.15 | >25 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
| --- | --- | --- | --- | --- | --- |
| 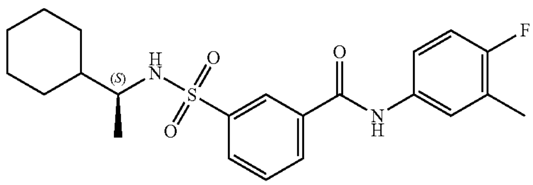 | 148 | 0.90 | | 3.11 | 18.2 |
| 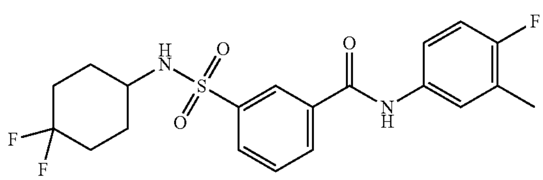 [SMILES: Cc1cc(NC(=O)c2cccc(S(=O)(=O)NC3CCC(F)(F)CC3)c2)ccc1F] | 149 | 0.22 | | 0.73 | 20.8 |
| 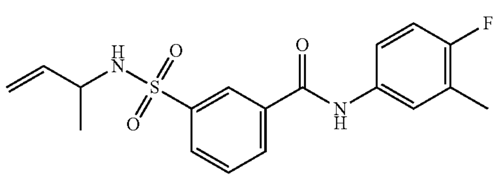 [SMILES: C=CC(C)NS(=O)(=O)c1cccc(C(=O)Nc2ccc(F)c(C)c2)c1] | 150 | 0.10 | | 0.73 | >25 |
| 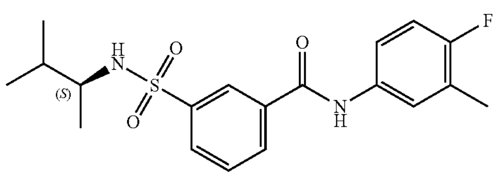 | 151 | 0.66 | | 2.74 | >25 |
| 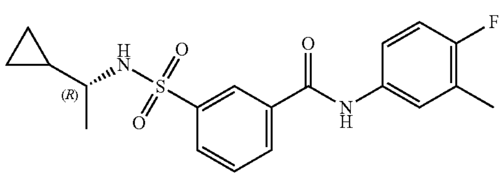 | 152 | <0.1 | | 0.57 | >25 |
| 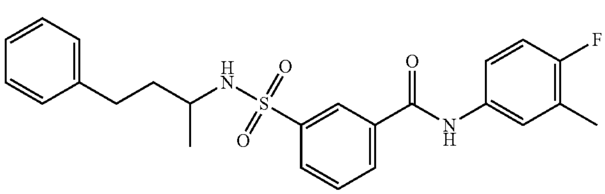 [SMILES: Cc1cc(NC(=O)c2cccc(S(=O)(=O)NC(C)CCc3ccccc3)c2)ccc1F] | 153 | 0.22 | | 0.25 | >25 |
| 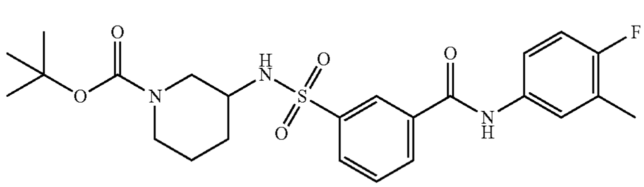 [SMILES: Cc1cc(NC(=O)c2cccc(S(=O)(=O)NC3CCCN(C(=O)OC(C)(C)C)C3)c2)ccc1F] | 155 | 0.36 | | 0.81 | >25 |
| 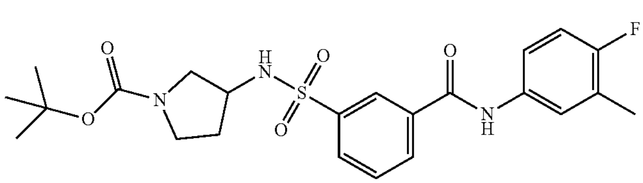 [SMILES: Cc1cc(NC(=O)c2cccc(S(=O)(=O)NC3CCN(C(=O)OC(C)(C)C)C3)c2)ccc1F] | 156 | 0.19 | | 0.21 | >25 |

TABLE 1-continued
| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 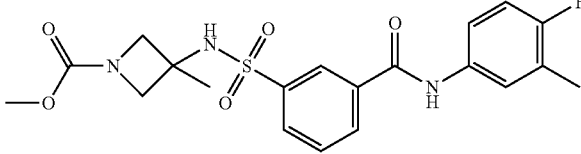 | 157 | 0.13 | | 0.23 | >25 |
| 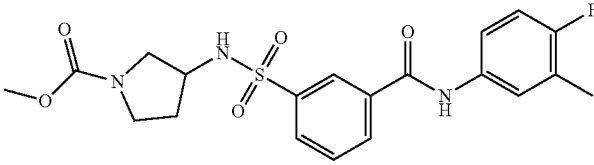 | 158 | 0.15 | | 0.50 | >25 |
| 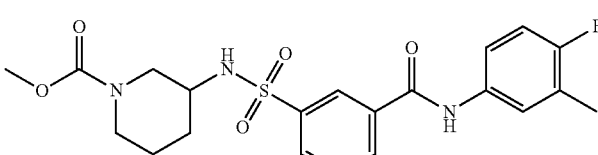 | 159 | 0.15 | | 0.30 | >25 |
| | 159a | 0.17 | | 0.86 | |
| | 159b | 0.16 | | 0.23 | |
| 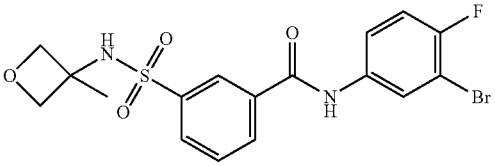 [SMILES: CC1(NS(=O)(=O)c2cccc(C(=O)Nc3ccc(F)c(Br)c3)c2)COC1] | 160 | 0.20 | | 0.69 | >25 |
| 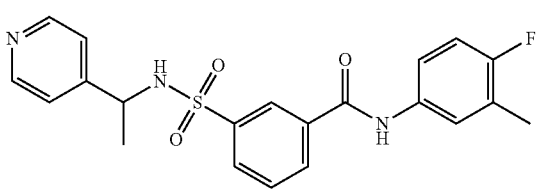 [SMILES: Cc1cc(NC(=O)c2cccc(S(=O)(=O)NC(C)c3ccncc3)c2)ccc1F] | 161 | 0.20 | | 0.35 | >25 |
| 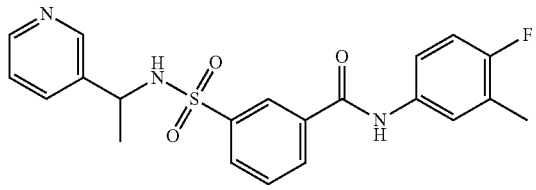 [SMILES: Cc1cc(NC(=O)c2cccc(S(=O)(=O)NC(C)c3cccnc3)c2)ccc1F] | 162 | 0.17 | | 1.26 | >25 |
| 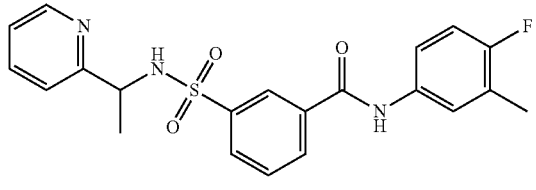 [SMILES: Cc1cc(NC(=O)c2cccc(S(=O)(=O)NC(C)c3ccccn3)c2)ccc1F] | 163 | 0.53 | | 8.53 | >25 |
| 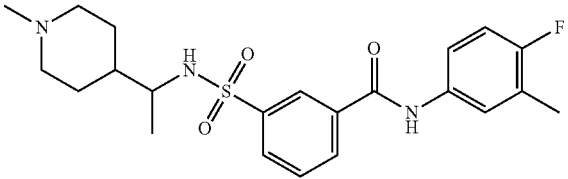 | 164 | 3.71 | | 0.97 | >25 |

TABLE 1-continued

| STRUCTURE | Co. No. | HepG2 2.15 EC50 (µM) | HepG2 6 days CC50 (µM) | HepG2 117 EC50 (µM) | HepG2 4 days CC50 (µM) |
|---|---|---|---|---|---|
| 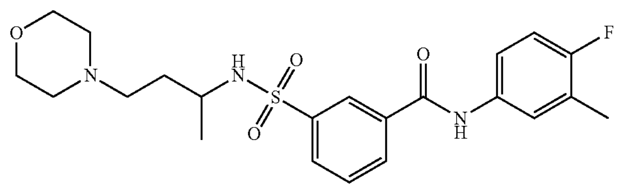 [SMILES: Cc1cc(NC(=O)c2cccc(S(=O)(=O)NC(C)CCN3CCOCC3)c2)ccc1F] | 165 | 0.71 | | 0.36 | >25 |
| 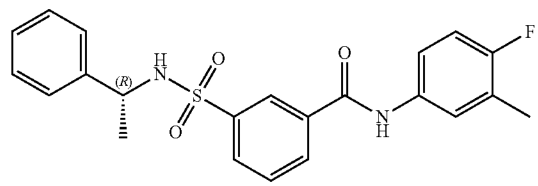 | 166 | 0.19 | | 2.39 | 14.6 |
| 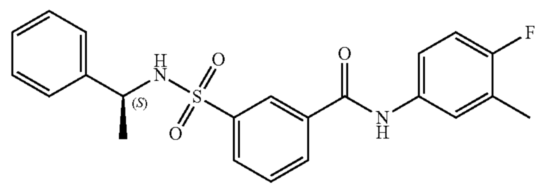 | 167 | 0.62 | | 9.84 | >25 |
| 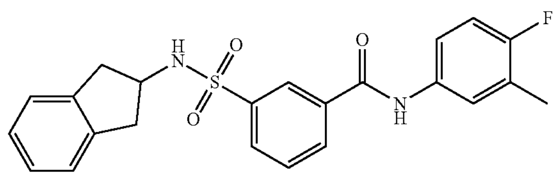 [SMILES: Cc1cc(NC(=O)c2cccc(S(=O)(=O)NC3Cc4ccccc4C3)c2)ccc1F] | 168 | 0.27 | | 0.37 | 11.8 |
| 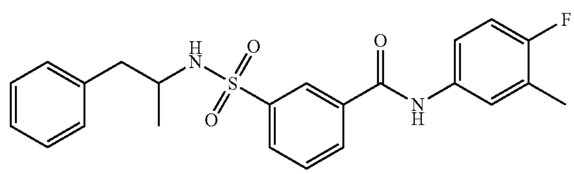 [SMILES: Cc1cc(NC(=O)c2cccc(S(=O)(=O)NC(C)Cc3ccccc3)c2)ccc1F] | 169 | 0.24 | | 1.41 | 14.9 |
| 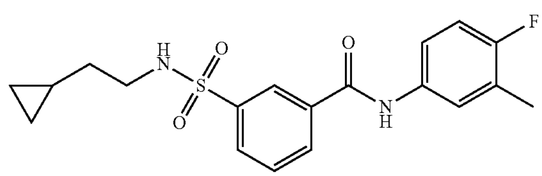 [SMILES: Cc1cc(NC(=O)c2cccc(S(=O)(=O)NCCC3CC3)c2)ccc1F] | 170 | 0.26 | | 0.45 | >25 |
| 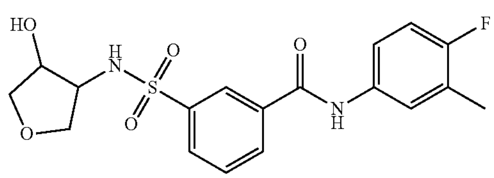 [SMILES: Cc1cc(NC(=O)c2cccc(S(=O)(=O)NC3COCC3O)c2)ccc1F] | 171 | 0.79 | | 4.39 | >25 |
| 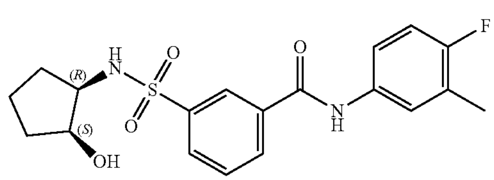 | 172 | 0.26 | | 0.61 | >25 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 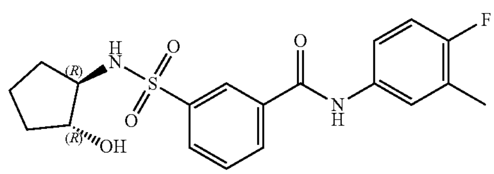 | 173 | 0.37 | | 0.36 | >25 |
| 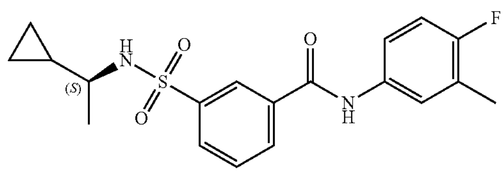 | 174 | 0.47 | | 2.84 | >25 |
| 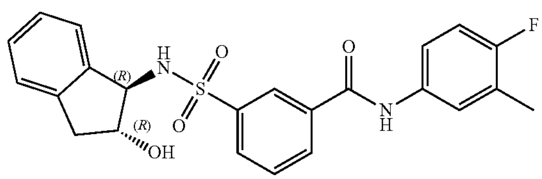 | 175 | 0.23 | | 0.15 | >25 |
| 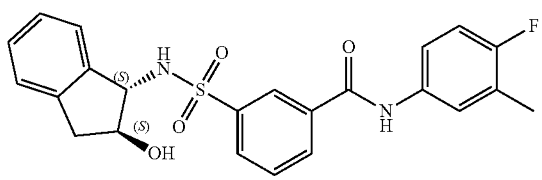 | 176 | 0.62 | | 0.56 | >25 |
| 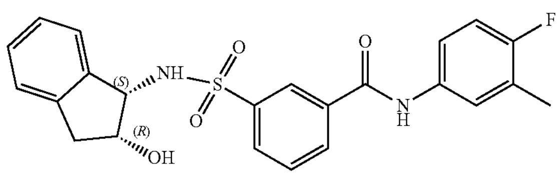 | 177 | 0.77 | | 0.72 | >25 |
| 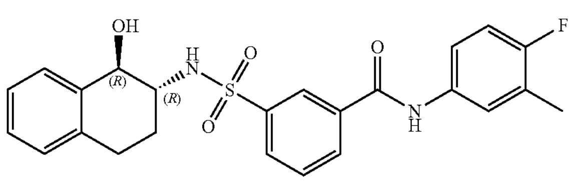 | 178 | 0.75 | | 2.54 | >25 |
| 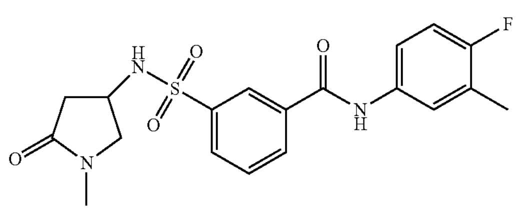 [SMILES: Cc1cc(NC(=O)c2cccc(S(=O)(=O)NC3CC(=O)N(C)C3)c2)ccc1F] | 179 | 0.21 | | 0.44 | >25 |
| | 179a | 0.38 | | 0.25 | >25 |
| | 179b | 1.11 | | 1.84 | >25 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 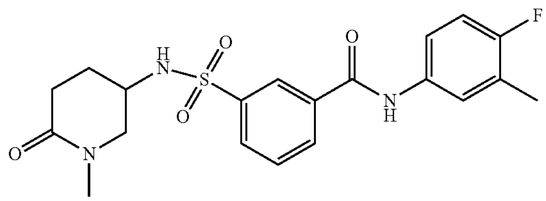 [SMILES: Cc1cc(NC(=O)c2cccc(S(=O)(=O)NC3CCC(=O)N(C)C3)c2)ccc1F] | 180 | 0.76 | | 1.30 | >25 |
| 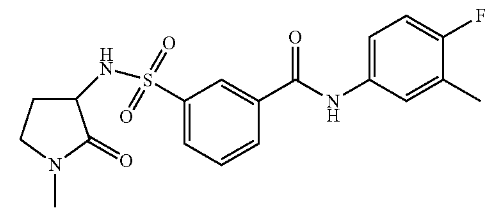 [SMILES: Cc1cc(NC(=O)c2cccc(S(=O)(=O)NC3CCN(C)C3=O)c2)ccc1F] | 181 | 2.59 | | 2.04 | >25 |
| 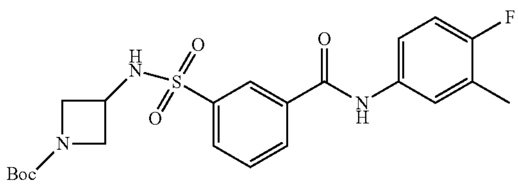 [SMILES: Cc1cc(NC(=O)c2cccc(S(=O)(=O)NC3CN(C(=O)OC(C)(C)C)C3)c2)ccc1F] | 182 | 0.31 | | 0.88 | >25 |
| 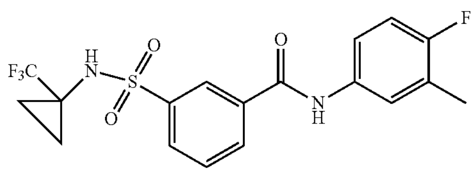 [SMILES: Cc1cc(NC(=O)c2cccc(S(=O)(=O)NC3(C(F)(F)F)CC3)c2)ccc1F] | 183 | 0.08 | | 0.84 | >25 |
| 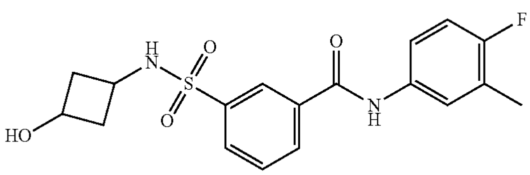 [SMILES: Cc1cc(NC(=O)c2cccc(S(=O)(=O)NC3CC(O)C3)c2)ccc1F] | 184 | 0.15 | | 0.40 | >25 |
| 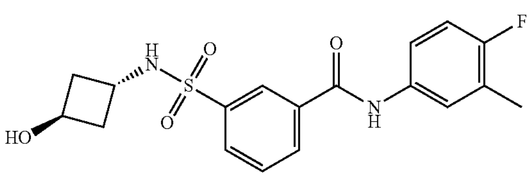 [SMILES: Cc1cc(NC(=O)c2cccc(S(=O)(=O)N[C@H]3C[C@H](O)C3)c2)ccc1F] | 184a | 0.31 | | 0.77 | >25 |
| 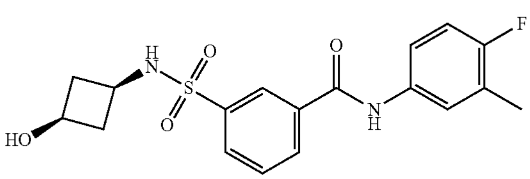 [SMILES: Cc1cc(NC(=O)c2cccc(S(=O)(=O)N[C@H]3C[C@@H](O)C3)c2)ccc1F] | 184b | 0.30 | | 0.33 | >25 |
| 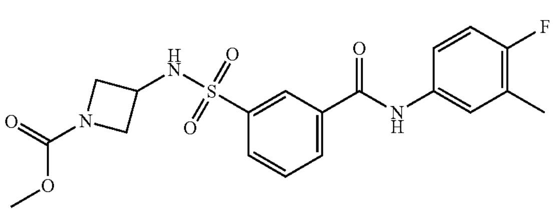 [SMILES: COC(=O)N1CC(NS(=O)(=O)c2cccc(C(=O)Nc3ccc(F)c(C)c3)c2)C1] | 185 | 0.22 | | 0.62 | >25 |

TABLE 1-continued
| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 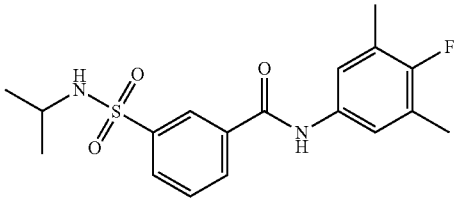 [SMILES: Cc1cc(NC(=O)c2cccc(S(=O)(=O)NC(C)C)c2)cc(C)c1F] | 186 | 0.20 | | 1.34 | >25 |
| 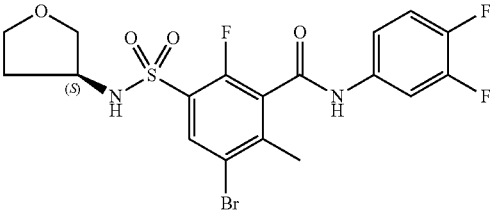 | 187 | | | 0.95 | >25 |
| 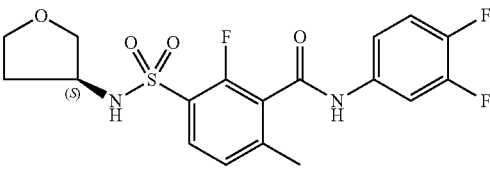 | 188 | | | 0.24 | >25 |
| 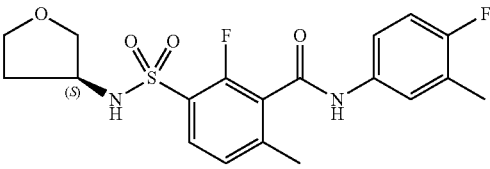 | 189 | | | 0.35 | >25 |
| 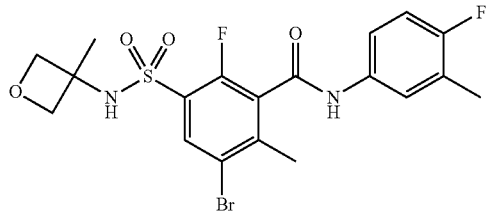 [SMILES: Cc1cc(NC(=O)c2c(C)c(Br)cc(S(=O)(=O)NC3(C)COC3)c2F)ccc1F] | 190 | | | 0.27 | >25 |
| 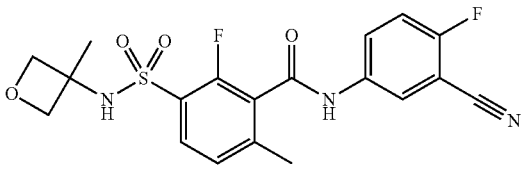 [SMILES: Cc1ccc(S(=O)(=O)NC2(C)COC2)c(F)c1C(=O)Nc1ccc(F)c(C#N)c1] | 191 | 0.33 | | 0.36 | >25 |
| 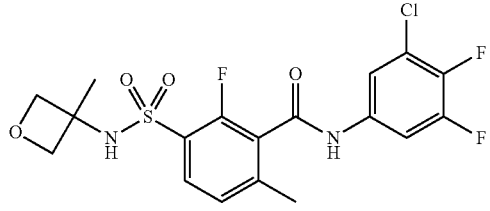 [SMILES: Cc1ccc(S(=O)(=O)NC2(C)COC2)c(F)c1C(=O)Nc1cc(F)c(F)c(Cl)c1] | 192 | | | 0.19 | >25 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| (structure) | 193 | | | 0.10 | 13.5 |
| (structure) | 194 | 0.38 | | 0.31 | >25 |
| (structure) | 195 | 0.27 | | 0.18 | >25 |
| (structure) | 196 | 0.13 | | 0.07 | >25 |
| (structure) | 197 | | | 0.09 | >25 |
| (structure) | 198 | | | 0.15 | >25 |
| (structure) | 199 | | | 0.43 | >25 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 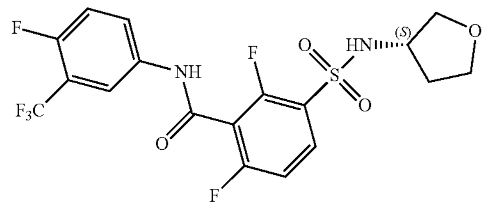 | 200 | | | 0.45 | >25 |
| 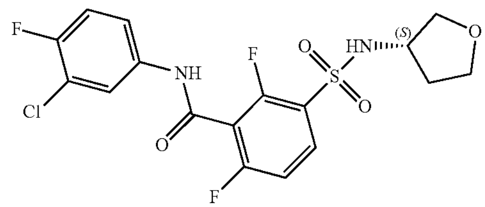 | 201 | 0.06 | | 0.06 | >25 |
| 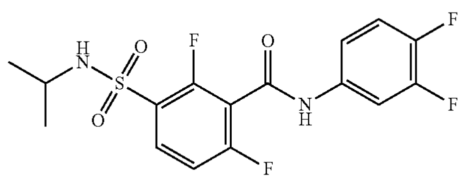 [SMILES: CC(C)NS(=O)(=O)c1ccc(F)c(C(=O)Nc2ccc(F)c(F)c2)c1F] | 202 | | | 0.11 | >25 |
| 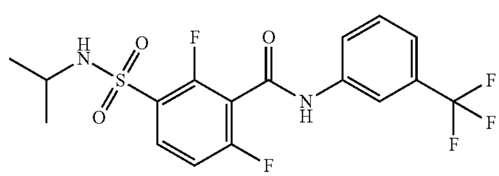 [SMILES: CC(C)NS(=O)(=O)c1ccc(F)c(C(=O)Nc2cccc(C(F)(F)F)c2)c1F] | 203 | | | 0.24 | 16.7 |
| 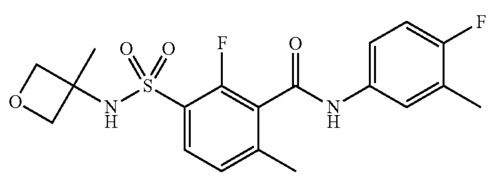 [SMILES: Cc1cc(NC(=O)c2c(C)ccc(S(=O)(=O)NC3(C)COC3)c2F)ccc1F] | 204 | | | 0.09 | >25 |
| 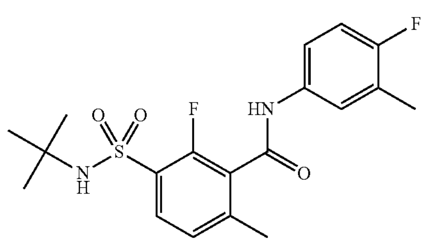 [SMILES: Cc1cc(NC(=O)c2c(C)ccc(S(=O)(=O)NC(C)(C)C)c2F)ccc1F] | 205 | | | 0.35 | >25 |
| 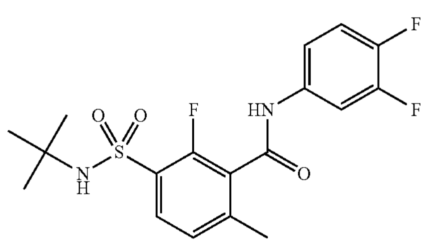 [SMILES: Cc1ccc(S(=O)(=O)NC(C)(C)C)c(F)c1C(=O)Nc1ccc(F)c(F)c1] | 206 | | | 0.64 | >25 |

TABLE 1-continued

| Co. No. | HepG2 2.15 EC50 (μM) | HepG2 6 days CC50 (μM) | HepG2 117 EC50 (μM) | HepG2 4 days CC50 (μM) |
|---|---|---|---|---|
| 207 | | | >1 | >25 |
| 208 | | | >1 | >25 |
| 209 | | | 0.15 | >25 |
| 210 | | | 0.46 | >25 |
| 211 | | | 0.65 | >25 |
| 212 | | | 7.3 | >25 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 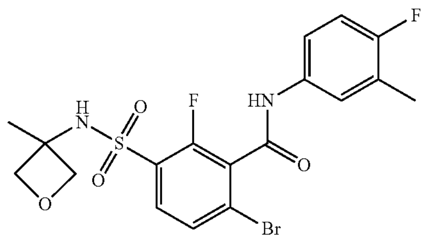 | 213 | | | 0.28 | >25 |
| 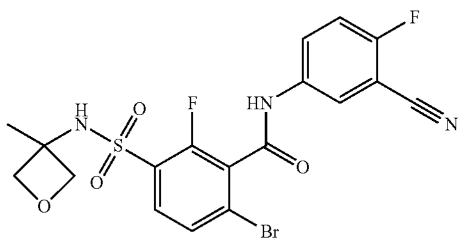 [SMILES: CC1(NS(=O)(=O)c2ccc(Br)c(C(=O)Nc3ccc(F)c(C#N)c3)c2F)COC1] | 214 | | | >1 | >25 |
| 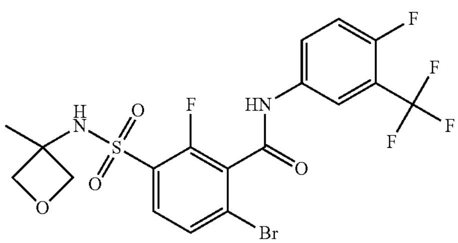 [SMILES: CC1(NS(=O)(=O)c2ccc(Br)c(C(=O)Nc3ccc(F)c(C(F)(F)F)c3)c2F)COC1] | 215 | | | >1 | >25 |
| 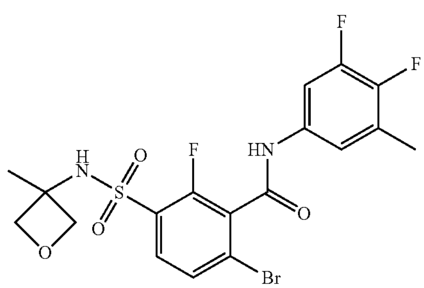 | 216 | | | 0.29 | >25 |
| 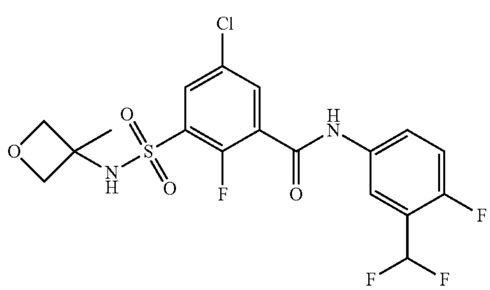 [SMILES: CC1(NS(=O)(=O)c2cc(Cl)cc(C(=O)Nc3ccc(F)c(C(F)F)c3)c2F)COC1] | 217 | 0.20 | | 0.60 | >25 |
| 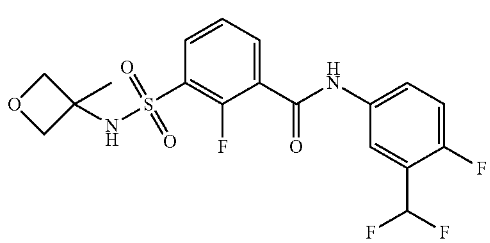 [SMILES: CC1(NS(=O)(=O)c2cccc(C(=O)Nc3ccc(F)c(C(F)F)c3)c2F)COC1] | 218 | 0.12 | | 0.10 | >25 |

TABLE 1-continued
| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 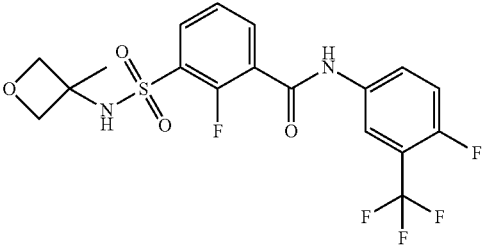 [SMILES: CC1(NS(=O)(=O)c2cccc(C(=O)Nc3ccc(F)c(C(F)(F)F)c3)c2F)COC1] | 219 | | | 0.46 | >25 |
| 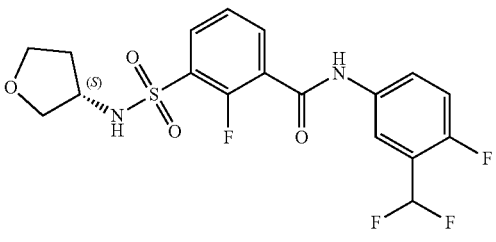 | 220 | 0.11 | | 0.09 | >25 |
| 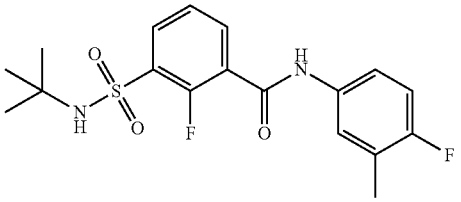 [SMILES: Cc1cc(NC(=O)c2cccc(S(=O)(=O)NC(C)(C)C)c2F)ccc1F] | 221 | | | 0.13 | >25 |
| 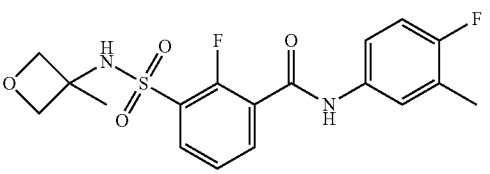 [SMILES: Cc1cc(NC(=O)c2cccc(S(=O)(=O)NC3(C)COC3)c2F)ccc1F] | 222 | 0.05 | | 0.10 | >25 |
| 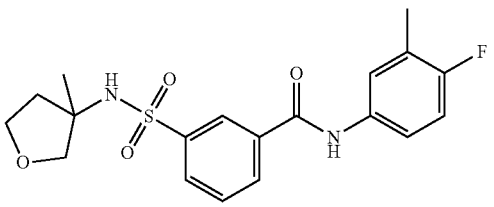 [SMILES: Cc1cc(NC(=O)c2cccc(S(=O)(=O)NC3(C)CCOC3)c2)ccc1F] | 223 | | | 0.21 | >25 |
| 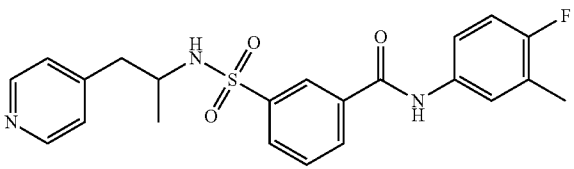 [SMILES: Cc1cc(NC(=O)c2cccc(S(=O)(=O)NC(C)Cc3ccncc3)c2)ccc1F] | 224 | 0.16 | | 0.76 | >25 |
| 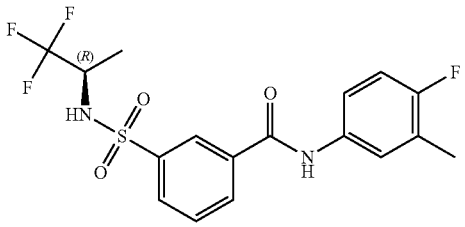 | 225 | 0.09 | | 1.34 | >25 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 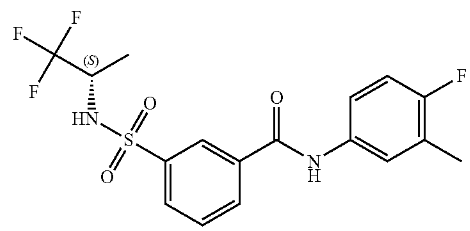 | 226 | 0.27 | | 1.9 | >25 |
| 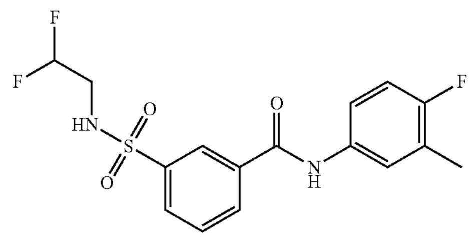 [SMILES: Cc1cc(NC(=O)c2cccc(S(=O)(=O)NCC(F)F)c2)ccc1F] | 227 | 0.16 | | 0.71 | >25 |
| 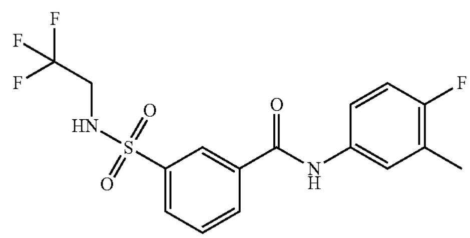 [SMILES: Cc1cc(NC(=O)c2cccc(S(=O)(=O)NCC(F)(F)F)c2)ccc1F] | 228 | 0.17 | | 1.19 | >25 |
| 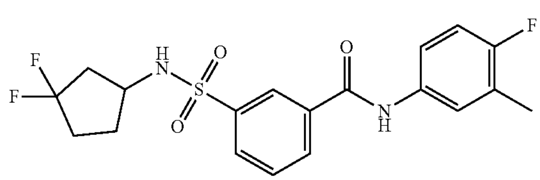 [SMILES: Cc1cc(NC(=O)c2cccc(S(=O)(=O)NC3CCC(F)(F)C3)c2)ccc1F] | 229 | 0.20 | | 0.49 | >25 |
| 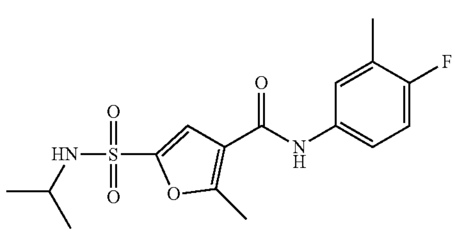 [SMILES: Cc1cc(NC(=O)c2cc(S(=O)(=O)NC(C)C)oc2C)ccc1F] | 230 | 0.73 | | 1.52 | >25 |
| 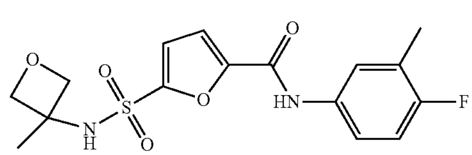 [SMILES: Cc1cc(NC(=O)c2ccc(S(=O)(=O)NC3(C)COC3)o2)ccc1F] | 231 | 0.21 | | 0.32 | >25 |
| 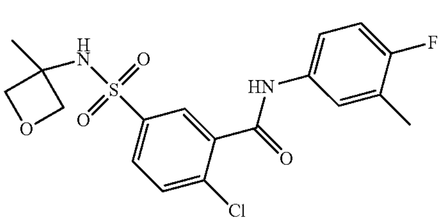 [SMILES: Cc1cc(NC(=O)c2cc(S(=O)(=O)NC3(C)COC3)ccc2Cl)ccc1F] | 232 | | | 0.31 | >25 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 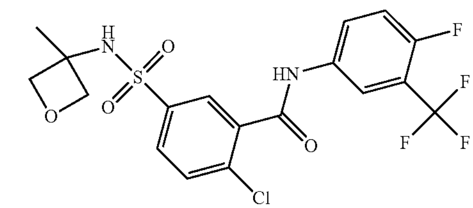 [SMILES: CC1(NS(=O)(=O)c2ccc(Cl)c(C(=O)Nc3ccc(F)c(C(F)(F)F)c3)c2)COC1] | 233 | >1 | | >1 | >25 |
| 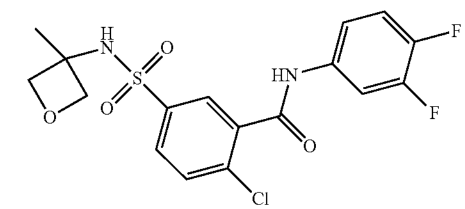 [SMILES: CC1(NS(=O)(=O)c2ccc(Cl)c(C(=O)Nc3ccc(F)c(F)c3)c2)COC1] | 234 | 0.72 | | 0.34 | >25 |
| 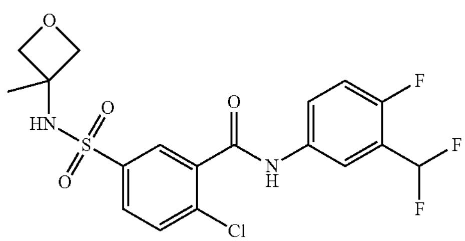 [SMILES: CC1(NS(=O)(=O)c2ccc(Cl)c(C(=O)Nc3ccc(F)c(C(F)F)c3)c2)COC1] | 235 | 0.83 | | 0.33 | >25 |
| 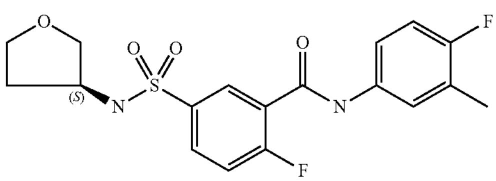 | 236 | 0.48 | | 1.58 | >25 |
| 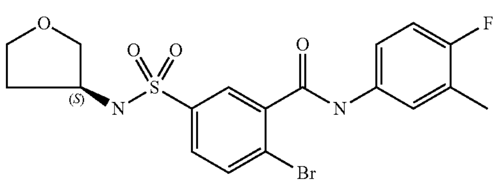 | 237 | 0.43 | | 0.13 | >25 |
| 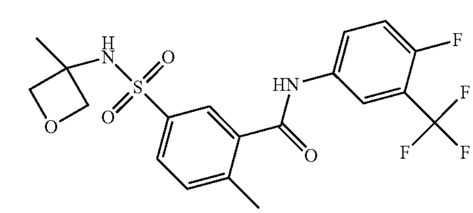 [SMILES: Cc1ccc(S(=O)(=O)NC2(C)COC2)cc1C(=O)Nc1ccc(F)c(C(F)(F)F)c1] | 238 | 0.61 | | 0.50 | >25 |
| 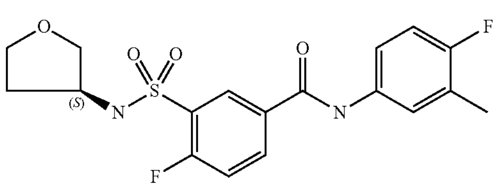 | 239 | 0.48 | | 0.53 | >25 |

TABLE 1-continued

| STRUCTURE | Co. No. | HepG2 2.15 EC50 (μM) | HepG2 6 days CC50 (μM) | HepG2 117 EC50 (μM) | HepG2 4 days CC50 (μM) |
|---|---|---|---|---|---|
| 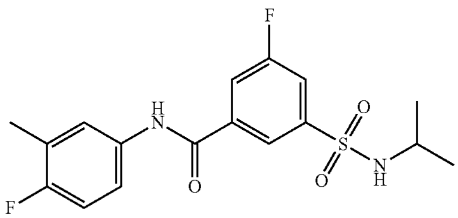 [SMILES: Cc1cc(NC(=O)c2cc(F)cc(S(=O)(=O)NC(C)C)c2)ccc1F] | 240 | 0.40 | | 2.86 | >25 |
| 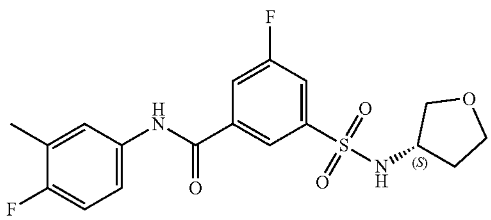 | 241 | 0.38 | | 1.79 | >25 |
| 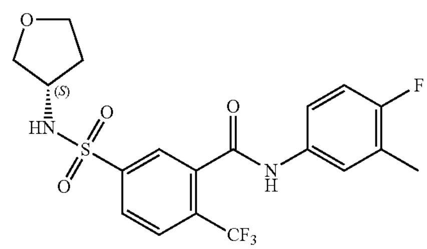 | 242 | 1.91 | | 1.80 | >25 |

The invention claimed is:

1. A compound of Formula (I)

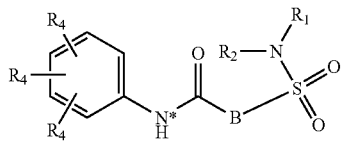

(I)

or a stereoisomer or tautomeric form thereof, wherein:

B is a monocyclic 5 membered aromatic ring containing two or more heteroatoms each independently selected from the group consisting of S and N, said 5 membered aromatic ring optionally substituted with one or more substituents each independently selected from the group consisting of hydrogen, $C_1$-$C_3$alkyl, $CFH_2$, $CF_2H$ and $CF_3$;

$R_1$ is hydrogen or $C_1$-$C_3$alkyl;

$R_2$ is $C_1$-$C_6$alkyl, $C_1$-$C_6$alkenyl, $C_1$-$C_6$alkyl-$R_5$, C(=O)—$R_5$, $CFH_2$, $CF_2H$, $CF_3$, a dihydroindenyl or tetrahydronaphthalenyl moiety optionally substituted with OH, or a 3-7 membered saturated ring optionally containing one or more heteroatoms each independently selected from the group consisting of O, S and N, said 3-7 membered saturated ring, $C_1$-$C_6$alkyl-$R_5$ or $C_1$-$C_6$alkyl optionally substituted with one or more substituents each independently selected from the group consisting of hydrogen, halogen, $C_1$-$C_4$alkyloxy, $C_1$-$C_4$alkyloxycarbonyl, oxo, C(=O)—$C_1$-$C_3$alkyl, $C_1$-$C_4$alkyl, OH, CN, $CFH_2$, $CF_2H$ and $CF_3$;

each $R_4$ is independently selected from the group consisting of hydrogen, halo, $C_1$-$C_4$alkyloxy, $C_1$-$C_4$alkenyl, OH, CN, $CFH_2$, $CF_2H$, $CF_3$, HC≡C and a 3-5 membered saturated ring optionally containing one or more heteroatoms each independently selected from the group consisting of O and N, said $C_1$-$C_4$alkyl optionally substituted with OH; and $R_5$ is selected from the group consisting of $C_1$-$C_6$alkyl, $CFH_2$, $CF_2H$, $CF_3$, phenyl, pyridyl and a 3-7 membered saturated ring optionally containing one or more heteroatoms each independently selected from the group consisting of O, S and N, said 3-7 membered saturated ring optionally substituted with one or more substituents each independently selected from the group consisting of hydrogen, halogen, $C_1$-$C_4$alkyloxy, $C_1$-$C_4$alkyloxycarbonyl, oxo, C(=O)—$C_1$-$C_3$alkyl, OH, CN, $CFH_2$, $CF_2H$ and $CF_3$;

or a pharmaceutically acceptable salt or a solvate thereof.

2. The compound of claim 1, wherein $R_1$ is hydrogen.

3. The compound of claim 1, wherein $R_2$ is a 4-7 membered saturated ring optionally containing one or more heteroatoms each independently selected from the group consisting of O, S and N, said 4-7 membered saturated ring optionally substituted with one or more substituents each independently selected from the group consisting of hydrogen, halogen, $C_1$-$C_4$alkyloxy, $C_1$-$C_4$alkyloxycarbonyl, C(=O)—$C_1$-$C_3$alkyl, $C_1$-$C_4$alkyl, OH, CN, $CFH_2$, $CF_2H$ and $CF_3$.

4. The compound of claim 1, wherein $R_2$ is $C_4$-$C_6$cycloalkyl.

5. The compound of claim 1, wherein B is imidazolyl or thiazolyl, each optionally substituted with one or more substituents each independently selected from the group consisting of hydrogen, $C_1$-$C_3$alkyl, $CFH_2$, $CF_2H$ and $CF_3$.

6. A compound of claim 1, wherein the compound is selected from the group consisting of

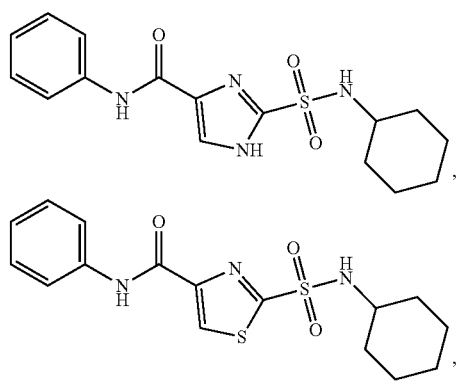

or pharmaceutically acceptable salts thereof.

7. A pharmaceutical composition comprising at least one compound of claim 1 and a pharmaceutically acceptable carrier.

8. A product containing (a) at least one compound of claim 1, and (b) an HBV inhibitor, as a combined preparation for simultaneous, separate or sequential use in the treatment of HBV infection.

9. A method of treating an HBV infection in a subject in need thereof, comprising administering to said subject an effective amount of at least one compound of claim 1.

10. A method of treating an HBV infection in a subject in need thereof, comprising administering to said subject the pharmaceutical composition of claim 7.

* * * * *